(12) United States Patent
Blackburn et al.

(10) Patent No.: US 8,946,223 B2
(45) Date of Patent: Feb. 3, 2015

(54) SUBSTITUTED HYDROXAMIC ACIDS AND USES THEREOF

(75) Inventors: Christopher Blackburn, Natick, MA (US); Janice Chin, Westborough, MA (US); Kenneth M. Gigstad, Westford, MA (US); He Xu, Needham, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 261 days.

(21) Appl. No.: 13/084,181

(22) Filed: Apr. 11, 2011

(65) Prior Publication Data
US 2011/0251184 A1 Oct. 13, 2011

Related U.S. Application Data

(60) Provisional application No. 61/323,082, filed on Apr. 12, 2010, provisional application No. 61/426,156, filed on Dec. 22, 2010.

(51) Int. Cl.
*A61K 31/4985* (2006.01)
*C07D 487/04* (2006.01)

(52) U.S. Cl.
CPC .................... *C07D 487/04* (2013.01)
USPC ........... 514/249; 514/250; 544/281; 544/349; 544/350

(58) Field of Classification Search
USPC .................. 514/249, 250; 544/281, 349, 350
See application file for complete search history.

(56) References Cited

U.S. PATENT DOCUMENTS

| | | | |
|---|---|---|---|
| 4,083,980 | A | 4/1978 | Schromm et al. |
| 6,541,661 | B1 | 4/2003 | Delorme et al. |
| 7,250,514 | B1 | 7/2007 | Xiao |
| RE39,850 | E | 9/2007 | Delorme et al. |
| 2003/0187009 | A1 | 10/2003 | Wentland |
| 2005/0148613 | A1 | 7/2005 | Van Emelen et al. |
| 2006/0004041 | A1 | 1/2006 | Cummings et al. |
| 2006/0058553 | A1 | 3/2006 | Leahy et al. |
| 2007/0213392 | A1 | 9/2007 | Miller et al. |
| 2009/0048228 | A1 | 2/2009 | Attenni et al. |
| 2010/0022514 | A1 | 1/2010 | Cho et al. |
| 2011/0039827 | A1 | 2/2011 | Blackburn et al. |
| 2011/0046157 | A1 | 2/2011 | Blackburn et al. |
| 2012/0053201 | A1 | 3/2012 | Blackburn et al. |
| 2012/0165316 | A1 | 6/2012 | Gould |

FOREIGN PATENT DOCUMENTS

| | | |
|---|---|---|
| WO | WO 2005/108367 A1 | 11/2005 |
| WO | WO 2006/023750 A2 | 3/2006 |
| WO | WO 2006/061638 A2 | 6/2006 |
| WO | WO 2007/115408 A1 | 10/2007 |
| WO | WO 2007/115410 A1 | 10/2007 |
| WO | WO 2009/037001 A4 | 3/2009 |
| WO | WO 2009/112550 A1 | 9/2009 |
| WO | WO 2009/129335 A2 | 10/2009 |
| WO | WO 2010/151317 A1 | 12/2010 |
| WO | WO 2010/151318 A1 | 12/2010 |
| WO | WO 2011/130163 A1 | 10/2011 |
| WO | WO 2012/027564 A1 | 3/2012 |
| WO | WO 2012/054332 A1 | 4/2012 |
| WO | WO 2012/088015 A2 | 6/2012 |

OTHER PUBLICATIONS

International Search Report and Written Opinion of the International Searching Authority dated Jun. 15, 2011 issued in International Application No. PCT/US2011/31933, which corresponds to U.S. Appl. No. 13/084,181.
Shinji, Chihiro, et al. "Design and synthesis of phthalimide-type histone deacetylase inhibitors," *Bioorganic &. Medicinal Chemistry Letters*, vol. 15, No. 20 (2005) pp. 4427-4431.
Yang, Xiang-Jiao, et al., "The Rpd3/Hda1 family of lysine deacetylases: from bacteria and yeast to mice and men," *Nature Reviews*, vol. 9 (Mar. 2008) pp. 206-218.
Kawaguchi, Yoshiharu, et al., "The deacetylase HDAC6 regulates aggresome formation and cell viability in response to misfolded protein stress," *Cell*, vol. 115 (Dec. 12, 2003) pp. 727-738.
Simms-Waldrip, Tiffany, et al., "The aggresome pathway as a target for therapy in hematologic malignancies," *Molecular Genetics and Metabolism*, vol. 94 (2008) pp. 283-286.
Kapoor, Shailendra, Letter to the Editor, "Inhibition of HDAC6-dependent carcinogenesis: emerging, new therapeutic options besides belinostat," *International Journal of Cancer*, vol. 124 (2009) p. 509.
Iwata, Atsushi, et al., "HDAC6 and microtubules are required for autophagic degradation of aggregated huntingtin," *The Journal of Biological Chemistry*, vol. 280, No. 48 (Dec. 2, 2005) pp. 40282-40292.
Ding, Wen-Xing, et al., "Linking of autophagy to ubiquitin-proteasome system is important for the regulation of endoplasmic reticulum stress and cell viability," *The American Journal of Pathology*, vol. 171, No. 2 (Aug. 2007) pp. 513-524.

(Continued)

*Primary Examiner* — Brenda Coleman
(74) *Attorney, Agent, or Firm* — Millennium Pharmaceuticals, Inc.

(57) ABSTRACT

This invention provides compounds of formula (I):

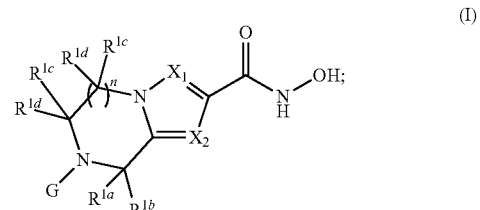

wherein $X_1$, $X_2$, $R^{1a}$, $R^{1b}$, $R^{1c}$, $R^{1d}$, n, and G have values as described in the specification, useful as inhibitors of HDAC6. The invention also provides pharmaceutical compositions comprising the compounds of the invention and methods of using the compositions in the treatment of proliferative, inflammatory, infectious, neurological or cardiovascular diseases or disorders.

28 Claims, No Drawings

(56) References Cited

OTHER PUBLICATIONS

Park, Jung-Hyun, et al. "Class II histone deacetylases play pivotal roles in heat shock protein 90-mediated proteasomal degradation of vascular endothelial growth factor receptors," *Biochemical and Biophysical Research Communications*, vol. 368 (2008) pp. 318-322.

Carta, Sonia, et al., "Histone deacetylase inhibitors prevent exocytosis of interleukin-1β-containing secretory lysosomes: role of microtubules," *Blood*, vol. 108, No. 5 (Sep. 1, 2006) pp. 1618-1626.

Mendrysa, Susan M., et al., "An integrated genetic-genomic approach for the identification of novel cancer loci in mice sensitized to c-Myc-induced apoptosis," *Genes & Cancer*, vol. 1, No. 5 (2010) pp. 465-479.

Namdar, Mandana, et al., "Selective inhibition of histone deacetylase 6 (HDAC6) induces DNA damage and sensitizes transformed cells to anticancer agents," *Proceedings of the National Academy of Sciences*, vol. 107, No. 46 (Nov. 16, 2010) (published on-line before print on Oct. 29, 2010 at: http://www.pnas.org/cgi/doi/10.1073/pnas.1013754107).

Tran, Andy Dong-Anh, et al., "HDAC6 deacetylation of tubulin modulates dynamics of cellular adhesions," *Journal of Cell Science*, vol. 120, No. 8 (2007) pp. 1469-1479.

Hubbert, Charlotte, et al., "HDAC6 is a microtubule-associated deacetylase," *Nature*, vol. 417, (May 23, 2002) pp. 455-458.

Kawada, Junichi, et al., "Tubacin kills Epstein-Barr virus (EBV)-Burkitt lymphoma cells by inducing reactive oxygen species and EBV lymphoblastoid cells by inducing apoptosis," *The Journal of Biological Chemistry*, vol. 284 (Jun. 19, 2009) pp. 17102-17109 (first published online on Apr. 22, 2009 at: http://www.jbc.org/cgi/doi/10.1074/jbc.M809090200).

Kaluza, David, et al., "Class IIb HDAC6 regulates endothelial cell migration and angiogenesis by deacetylation of cortactin," *The EMBO Journal* (2011) pp. 1-15.

d'Ydewalle, Constantin, et al., "HADC6 inhibitors reverse axonal loss in a mouse model of mutant HSPB1-induced Charcot-Marie-Tooth disease," *Nature Medicine*, vol. 17, No. 8 (Aug. 2011) pp. 968-974.

Haggarty, Stephen J., et al., "Domain-selective small-molecule inhibitor of histone deacetylase 6 (HDAC6)-mediated tubulin deacetylation," *Proceedings of the National Academy of Sciences*, vol. 100, No. 8 (Apr. 15, 2003) pp. 4389-4394.

Itoh, Yukihiro, et al., "Design, synthesis, structure-selectivity relationship, and effect on human cancer cells of a novel series of histone deacetylase 6-selective inhibitors," *Journal of Medicinal Chemistry*, vol. 50 (2007) pp. 5425-5438.

Butler, Kyle V., et al., "Rational design and simple chemistry yield a superior, neuroprotective HDAC6 inhibitor, tubastatin A," *Journal of the American Chemical Society*, vol. 132 (2010) pp. 10842-10846.

Yao, Tso-Pang, "The role of ubiquitin in autophagy-dependent protein aggregate processing," *Genes & Cancer*, vol. 1, No. 7 (2010) pp. 779-786.

Li, Guoyi, et al., "HDAC6 α-tubulin deacetylase: a potential therapeutic target in neurodegenerative diseases," *Journal of the Neurological Sciences*, vol. 304 (2011) pp. 1-8.

Lee, Joo-Yong, et al., "Quality control autophagy A joint effort of ubiquitin, protein deacetylase and actin cytoskeleton," *Autophagy*, vol. 6, No. 4 (May 16, 2010) pp. 555-557.

Tapia, Monica, et al., "Impaired Function of HDAC6 slows down axonal growth and interferes with axon initial segment development," *PLoS ONE*, vol. 5, No. 9 (Sep. 2010) e12908, pp. 1-13.

Cabrero, J. Roman, et al., "Lymphocyte chemotaxis is regulated by histone deacetylase 6, independently of its deacetylase activity," *Molecular Biology of the Cell*, vol. 17 (Aug. 2006) pp. 3435-3445.

Bobrowska, Anna, et al., "Hdac6 knock-out increases tubulin acetylation but does not modify disease progression in the R6/2 mouse model of Huntington's disease," *PLoS ONE*, vol. 6, No. 6 (Jun. 2011) e20696, pp. 1-11.

Fiesel, Fabienne C., et al., "TDP-43 knockdown impairs neurite outgrowth dependent on its target histone deacetylase 6," *Molecular Neurodegeneration*, vol. 6, No. 64 (2011) pp. 1-10.

Lemon, Douglas D., et al., "Cardiac HDAC6 catalytic activity is induced in response to chronic hypertension," *Journal of Molecular and Cellular Cardiology* (2011) doi:10.1016/j.yjmcc.2011.04.005.

Olzmann, J.A., et al., "Aggresome formation and neurodegenerative diseases: therapeutic implications," *Current Medicinal Chemistry*, vol. 15 (2008) pp. 47-60.

Zhu, Jianzhong, et al., "PKC alpha regulates Sendai virus-mediated interferon induction through HDAC6 and β-catenin," *The EMBO Journal*, vol. 30 (2011) pp. 4838-4849.

Zhang, Zhenhuan, et al., "HDAC6 expression is correlated with better survival in breast cancer," *Clinical Cancer Research*, vol. 10 (Oct. 5, 2004) pp. 6962-6968.

Fiesel, Fabienne C., et al., "Knockdown of transactive response DNA-binding protein (TDP-43) downregulates histone deacetylase 6," *The EMBO Journal*, vol. 29 (2010) pp. 209-221.

Beurel, Eleonore, "HDAC6 regulates LPS-tolerance in astrocytes," *PLoS ONE*, vol. 6, No. 10 (Oct. 2011) e25804, pp. 1-8.

Miki, Yasuo, et al., "Accumulation of histone deacetylase 6, an aggresome-related protein, is specific to Lewy bodies and glial cytoplasmic inclusions," *Neuropathology*, vol. 31, No. 6 (Dec. 2011) pp. 561-568 (first published online on Feb. 1, 2011: doi:10.1111/j.1440-1789.2011.01200.x.

Kim, In Ah, et al., "Epigenetic modulation of radiation response in human cancer cells with activated EGFR or HER-2 signaling: potential role of histone deacetylase 6," *Radiotherapy and Oncology*, vol. 92 (2009) pp. 125-132.

Mellado, Begona, et al., "Molecular biology of androgen-independent prostate cancer: the role of the androgen receptor pathway," *Clinical & Transational Oncology*, vol. 11 (2009) pp. 5-10.

Bhalla, K.N., et al., "Inhibition of histone deacetylase (HDAC) 6 sensitizes human leukemia and breast cancer cells to antagonists of heat shock protein (hsp) 90 and/or bortezomib (BZ)," *Journal of Clinical Oncology*, Abstract, 2006 ASCO Annual Meeting Proceedings (Post-Meeting Edition), vol. 24, No. 18S (Jun. 20, 2006 Supplement) (2006) p. 13039.

Dompierre, Jim P., "Histone deacetylase 6 inhibition compensates for the transport deficit in Huntington's disease by increasing tubulin acetylation," *The Journal of Neuroscience*, vol. 27, No. 13 (Mar. 28, 2007) pp. 3571-3583.

Kazantsev, Aleksey G., et al., "Therapeutic application of histone deacetylase inhibitors for central nervous system disorders," *Nature Reviews*, vol. 7 (Oct. 2008) pp. 854-868.

Dhakal, Bijaya K., et al., "Uropathogenic *Escherichia coli* invades host cells via an HDAC6-modulated microtubule-dependent pathway," *Journal of Biological Chemistry*, vol. 284, No. 1 (Jan. 2, 2009) pp. 446-454.

Perez, Mar, et al., "Tau—an inhibitor of deacetylase HDAC6 function," *Journal of Neurochemistry*, vol. 109 (2009) pp. 1756-1766.

Pugacheva, Elena N., et al., "HEF1-dependent aurora A activation induces disassembly of the primary cilium," *Cell*, vol. 129 (Jun. 29, 2007) pp. 1351-1363.

Gao, Ya-sheng, et al., "The microtubule-associated histone deacetylase 6 (HDAC6) regulates epidermal growth factor receptor (EGFR) endocytic trafficking and degradation," *Journal of Biological Chemistry*, vol. 285, No. 15 (Apr. 9, 2010) pp. 11219-11226.

Tannous, Paul, et al., "Intracellular protein aggregation is a proximal trigger of cardiomyocyte autophagy," *Circulation Journal of the American Heart Association*, vol. 117 (2008) pp. 3070-3078 (published online before print Jun. 9, 2008 at: doi:10.1161/Circulationaha.107.763870).

Rao, Rekha, et al., "HDAC6 inhibition enhances 17-AAG-mediated abrogation of hsp90 chaperone function in human leukemia cells," *Blood*, vol. 112, No. 5 (Sep. 1, 2008) pp. 1886-1893.

Zhou, Jun, et al., "The protein farnesyltransferase regulates HDAC6 activity in a microtubule-dependent manner," *Journal of Biological Chemistry*, vol. 284, No. 15 (Apr. 10, 2009) pp. 9648-9655.

Cha, Tai-Lung, et al., "Dual degradation of aurora A and B kinases by the histone deacetylase inhibitor LBH589 induces G2-M arrest and apoptosis of renal cancer cells," *Clinical Cancer Research*, vol. 15, No. 3 (Feb. 1, 2009) pp. 840-850.

Kozikowski, Alan P., "Functional differences in epigenetic modulators-superiority of mercaptoacetamide-based histone deacetylase

(56) References Cited

OTHER PUBLICATIONS inhibitors relative to hydroxamates in cortical neuron neuroprotection studies," *Journal of Medicinal Chemistry*, vol. 50 (2007) pp. 3054-3061.
Boyault, C., et al., "HDAC6, at the crossroads between cytoskeleton and cell signaling by acetylation and ubiquitination," *Oncogene*, vol. 26 (2007) pp. 5468-5476.
Saunders, L.R., et al., "Sirtuins: critical regulators at the crossroads between cancer and aging," *Oncogene*, vol. 26 (2007) pp. 5489-5504.
Li, Yu, et al., "HDAC6 is required for epidermal growth factor-induced β-catenin nuclear localization," *Journal of Biological Chemistry*, vol. 283, No. 19 (May 9, 2008) pp. 12686-12690.
Fiskus, Warren, et al., "Molecular and biologic characterization and drug sensitivity of pan-histone deacetylase inhibitor-resistant acute myeloid leukemia cells," *Blood*, vol. 112, No. 7 (Oct. 1, 2008) pp. 2896-2905.
Nawrocki, Steffan T., et al., "Aggresome disruption: a novel strategy to enhance bortezomib-induced apoptosis in pancreatic cancer cells," *Cancer Research*, vol. 66, No. 7 (Apr. 1, 2006) pp. 3773-3781.
Boyault, Cyril, et al., "HDAC6-p97/VCP controlled polyubiquitin chain turnover," *The EMBO Journal*, vol. 25 (2006) pp. 3357-3366.
Hideshima, Teru, et al., "Small-molecule inhibition of proteasome and aggresome function induces synergistic antitumor activity in multiple myeloma," *Proceedings of the National Academy of Sciences*, vol. 102, No. 24 (Jun. 14, 2005) pp. 8567-8572.
Rivieccio, Mark A., et al., "HDAC6 is a target for protection and regeneration following injury in the nervous system," *Proceedings of the National Academy of Sciences*, vol. 106, No. 46 (Nov. 17, 2009) pp. 19599-19604.
Parmigiani, R.B., et al., "HDAC6 is a specific deacetylase of peroxiredoxins and is involved in redox regulation," *Proceedings of the National Academy of Sciences*, vol. 105, No. 28 (Jul. 15, 2008) pp. 9633-9638.
Matthias, Patrick, et al., "HDAC6 a new cellular stress surveillance factor," *Cell Cycle*, vol. 7, No. 1 (Jan. 1, 2008) pp. 7-10.
Rodriguez-Gonzalez, Agustin, et al., "Role of the aggresome pathway in cancer: targeting histone deacetylase 6-dependent protein degradation," *Cancer Research*, vol. 68, No. 8 (Apr. 15, 2008) pp. 2557-2559.
Lee, Yi-Shan, et al., "The cytoplasmic deacetylase HDAC6 is required for efficient oncogenic tumorigenesis," Cancer Research, vol. 68, No. 18 (Sep. 15, 2008) pp. 7561-7569.
Lee, Joo-Yong, et al., "HDAC6 controls autophagosome maturation essential for ubiquitin-selective quality-control autophagy," *The EMBO Journal*, vol. 29 (2010) pp. 969-980.
Kamemura, Kazuo, et al., "Effects of downregulated HDAC6 expression on the proliferation of lung cancer cells," *Biochemical and Biophysical Research Communications*, vol. 374 (2008) pp. 84-89.
Crabbe, Tom, et al., "The P13K inhibitor arsenal: choose your weapon!" *TRENDS in Biochemical Sciences*, vol. 32, No. 10 (2007) pp. 45-456.
Pandey, Udai Bhan, et al., "HDAC6 rescues neurodegeneration and provides an essential link between autophagy and the UPS," *Nature*, vol. 447 (Jun. 14, 2007) pp. 859-863.
Zhang, Xiaochong, et al., "HDAC6 modulates cell motility by altering the acetylation level of cortactin," *Molecular Cell*, vol. 27 (Jul. 20, 2007) pp. 197-213.

Deribe, Yonathan Lissanu, et al., "Regulation of epidermal growth factor receptor trafficking by lysine deacetylase HDAC6," *Science Signaling*, vol. 2, No. 102 (Dec. 22, 2009) ra84 pp. 1-12 (published online at: DOI: 10.1126/scisignal.2000576).
Park, Jung-Hyun, et al., "Inhibitors of histone deacetylases induce tumor-selective cytotoxicity through modulating Aurora-A kinase," *Journal of Molecular Medicine*, vol. 86 (2008) pp. 117-128.
Bazzaro, Martina, et al., "Ubiquitin proteasome system stress underlies synergistic killing of ovarian cancer cells by bortezomib and novel HDAC6 inhibitor," *Clinical Cancer Research*, vol. 14, No. 22 (Nov. 15, 2008) pp. 7340-7347.
Shan, Bin, et al., "Requirement of HDAC6 for transforming growth factor-β1-induced epithelial-mesenchymal transition," *Journal of Biological Chemistry*, vol. 283, No. 30 (Jul. 25, 2008) pp. 21065-21073.
Kalveram, Birte, et al., "The ubiquitin-like modifier FAT10 interacts with HDAC6 and localizes to aggresomes under proteasome inhibition," *Journal of Cell Science*, vol. 121, No. 24 (2008) pp. 4079-4088.
Valenzuela-Fernandez, Agustin, et al., "HDAC6: a key regulator of cytoskeleton, cell migration and cell-cell interactions," *Trends in Cell Biology*, vol. 18, No. 6 (2008) pp. 291-297.
Du, Guiping, et al., "To prevent neurodegeneration HDAC6 uses different strategies for different challenges," *Communicative & Integrative Biology*, vol. 4, No. 2 (Mar./Apr. 2011) pp. 139-142.
Paris, Marielle, et al., "Histone deacetylase inhibitors: from bench to clinic," *Journal of Medicinal Chemistry*, vol. 51, No. 6 (Mar. 27, 2008) pp. 1505-1529.
Santo L. et al., "Selective Inhibition of HDAC6 with a New Prototype Inhibitor (ACY-1215) Overcomes Bortezomib Resistance in Multiple Myeloma (MM)," *Blood*, (ASH Annual Meeting Abstracts) (2010) 116: Abstract 2997.
Bosch, Lluis et al., "Synthesis of Benzo-, Pyrido-, Thieno- and Imidazo-Fused N-Hydroxy-4-Oxopyrimidine-2-Carboxylic Acid Derivatives," *Tetrahedron Letters*, vol. 52, (2011) pp. 753-756.
Langford, Marie H. et al., "Design and Synthesis of Substituted 4-oxo-4,5,6,7-Tetrahydropyrazolol[1,5-a]pyrazine-2-carboxamides, Novel HIV-1 Integrase Inhibitors," *Bioorganic & Medicinal Chemistry Letters*, vol. 18, (2008) pp. 721-725.
Wiscount, Catherine M. et al., "10-Hydroxy-7,8-dihydropyrazino[1,2:1,5]pyrrolo[2,3-d]pyridazine-1,9(2H,6H)-diones: Potent, Orally Bioavailable HIV-1 Integrase Strand-Transfer Inhibitors with Activity Against Integrase Mutants," *Bioorganic & Medicinal Chemistry Letters*, vol. 18, (2008) pp. 4581-4583.
"Pyrazolo[1,5-a]pyrazine-2-carboxamide, 5-[(3,5-dimethoxyphenyl)methyl]-N-ethoxy-4,5,6,7-tetrahydro-4-oxo-(CA Index Name)," CAS Registry No. 1047472-35-4, entered Sep. 8, 2008.
"Pyrazolo[1,5-a]pyrazine-2-carboxamide, 4,5,6,7-tetrahydro-N-hydroxy-4-oxo-5-[[3-(trifluoromethyl)phenyl]methyl]-(CA Index Name)," CAS Registry No. 1172870-02-8, entered Aug. 5, 2009.
"Pyrazolo[1,5-a]pyrazine-2-carboxamide, 4,5,6,7-tetrahydro-N-hydroxy-5-[(4-methoxyphenyl)methyl]-4-oxo-(CA Index Name)," CAS Registry No. 1172957-32-2, entered Aug. 5, 2009.
Braun, Matthew P. et al., "Suzuki Cross-Coupling for the Incorporation of Labeled Methyl Groups onto Aryl Halides. A Synthesis of [$^{14}$C]Tosyl Chloride and its use in the Synthesis of [$^{14}$C]L-738,167.," *Journal of Labelled Compounds & Radiopharmaceuticals*, vol. 42, No. 5 (1999) pp. 469-476.
Hamill, Terence G. et al., "Non-Peptide Fibrinogen Receptor Antagonists. The Synthesis of [$^{3}$H]L-738,167.," *Journal of Labelled Compounds & Radiopharmaceuticals*, vol. 41, No. 4 (1998) pp. 273-277.

SUBSTITUTED HYDROXAMIC ACIDS AND USES THEREOF

PRIORITY CLAIM

This application claims the benefit under 35 U.S.C. §119 (e) of U.S. Provisional Patent Application Ser. No. 61/323,082, filed Apr. 12, 2010, incorporated by reference in its entirety, and U.S. Provisional Patent Application Ser. No. 61/426,156, filed Dec. 22, 2010, incorporated by reference in its entirety.

FIELD OF THE INVENTION

The invention relates to compounds and methods for the selective inhibition of HDAC6. The present invention relates to compounds useful as HDAC6 inhibitors. The invention also provides pharmaceutical compositions comprising the compounds of the invention and methods of using the compositions in the treatment of various diseases.

BACKGROUND OF THE INVENTION

Histone deacetylase 6 (HDAC6) is a member of a family of amidohydrolases commonly referred as histone or lysine deacetylases (HDACs or KDACs) as they catalyze the removal of acetyl groups from the s-amino group of lysine residues from proteins. The family includes 18 enzymes which can be divided in 3 main classes based on their sequence homology to yeast enzymes Rpd3 (Class I), Hda1 (Class II) and Sir2 (Class III). A fourth class was defined with the finding of a distinct mammalian enzyme—HDAC 11 (reviewed in Yang, et al., *Nature Rev. Mol. Cell. Biol.* 2008, 9:206-218 and in Saunders and Verdin, *Oncogene* 2007, 26(37):5489-5504). Biochemically, Class I (HDAC1, 2, 3, 8) and Class II (HDAC4, 5, 6, 7, 9, 10) and Class IV (HDAC11) are $Zn^{2+}$-dependent enzymes, while Class III (SIRT1-7) are dependent on nicotinamide adenine dinucleotide ($NAD^+$) for activity. Unlike all other HDACs, HDAC6 resides primarily in the cytosol. It has 2 functional catalytic domains and a carboxy-terminal $Zn^{2+}$-finger ubiquitin binding domain that binds ubiquitinated misfolded proteins (Kawaguchi et al., *Cell* 2003, 115(6):727-738), ubiquitin (Boyaullt et al., *EMBO J.* 2006, 25(14): 3357-3366), as well as ubiquitin-like FAT10 modifier (Kalveram et al., *J. Cell Sci.* 2008, 121(24):4079-4088). Known substrates of HDAC6 include cytoskeletal proteins α-tubulin and cortactin; β-catenin which forms part of adherens junctions and anchors the actin cytoskeleton; the chaperone Hsp90; and the redox regulatory proteins peroxiredoxin (Prx) I and Prx II (reviewed in Boyault et al., *Oncogene* 2007, 26(37):5468-5476; Matthias et al., *Cell Cycle* 2008, 7(1):7-10; Li et al., *J Biol. Chem.* 2008, 283(19):12686-12690; Parmigiani et al., *Proc. Natl. Acad. Sci. USA* 2009, 105(28):9633-9638). Thus, HDAC6 mediates a wide range of cellular functions including microtubule-dependent trafficking and signaling, membrane remodeling and chemotactic motility, involvement in control of cellular adhesion, ubiquitin level sensing, regulation of chaperone levels and activity, and responses to oxidative stress. All of these functions may be important in tumorigenesis, tumor growth and survival as well as metastasis (Simms-Waldrip et al., *Mol. Genet. Metabolism* 2008, 94(3):283-286; Rodriguez-Gonzalez et al., *Cancer Res.* 2008, 68(8):2557-2560; Kapoor, *Int. J. Cancer* 2009, 124:509; Lee et al., *Cancer Res.* 2008, 68(18):7561-7569). Recent studies have shown HDAC6 to be important in autophagy, an alternative pathway for protein degradation that compensates for deficiencies in the activity of the ubiquitin proteasome system or expression of proteins prone to form aggregates and can be activated following treatment with a proteasome inhibitor (Kawaguchi et al., *Cell* 2003, 115(6):727-738; Iwata et al., *J. Biol. Chem.* 2005, 280(48): 40282-40292; Ding et al., *Am. J. Pathol.* 2007, 171:513-524, Pandey et al., *Nature* 2007, 447(7146):860-864). Although the molecular mechanistic details are not completely understood, HDAC6 binds ubiquitinated or ubiquitin-like conjugated misfolded proteins which would otherwise induce proteotoxic stress and then serves as an adaptor protein to traffic the ubiquitinated cargo to the microtubule organizing center using the microtubule network via its known association with dynein motor protein. The resulting perinuclear aggregates, known as aggresomes, are then degraded by fusion with lysosomes in an HDAC6- and cortactin-dependent process which induces remodeling of the actin cytoskeleton proximal to aggresomes (Lee et al., *EMBO J.* 2010, 29:969-980). In addition, HDAC6 regulates a variety of biological processes dependent on its association with the microtubular network including cellular adhesion (Tran et al., *J. Cell Sci.* 2007, 120(8):1469-1479) and migration (Zhang et al., *Mol. Cell.* 2007, 27(2):197-213; reviewed in Valenzuela-Fernandez et al., *Trends Cell. Biol.* 2008, 18(6):291-297), epithelial to mesenchymal transition (Shan et al., *J. Biol. Chem.* 2008, 283 (30):21065-21073), resistance to anoikis (Lee et al., *Cancer Res.* 2008, 68(18):7561-7569), epithelial growth factor-mediated Wnt signaling via β-catenin deacetylation (Li et al., *J. Biol. Chem.* 2008, 283(19):12686-12690) and epithelial growth factor receptor stabilization by endocytic trafficking (Lissanu Deribe et al., *Sci. Signal.* 2009, 2(102): ra84; Gao et al., *J. Biol. Chem.* 2010, 285:11219-11226); all events that promote oncogenesis and metastasis (Lee et al., *Cancer Res.* 2008, 68(18):7561-7569). HDAC6 activity is known to be upregulated by Aurora A kinase in cilia formation (Pugacheva et al., *Cell* 2007, 129(7):1351-1363) and indirectly by farnesyl transferase with which HDAC6 forms a complex with microtubules (Zhou et al., *J. Biol. Chem.* 2009, 284(15): 9648-9655). Also, HDAC6 is negatively regulated by tau protein (Perez et al., *J. Neurochem.* 2009, 109(6):1756-1766).

Diseases in which selective HDAC6 inhibition could have a potential benefit include cancer (reviewed in Simms-Waldrip et al., *Mol. Genet. Metabolism* 2008, 94(3):283-286 and Rodriguez-Gonzalez et al., *Cancer Res.* 2008, 68(8):2557-2560), specifically: multiple myeloma (Hideshima et al., *Proc. Natl. Acad. Sci. USA* 2005, 102(24):8567-8572); lung cancer (Kamemura et al., *Biochem. Biophys. Res. Commun.* 2008, 374(1):84-89); ovarian cancer (Bazzaro et al., *Clin. Cancer Res.* 2008, 14(22):7340-7347); breast cancer (Lee et al., *Cancer Res.* 2008, 68(18):7561-7569); prostate cancer (Mellado et al., *Clin. Trans. Onco.* 2009, 11(1):5-10); pancreatic cancer (Nawrocki et al., *Cancer Res.* 2006, 66(7): 3773-3781); renal cancer (Cha et al., *Clin. Cancer Res.* 2009, 15(3):840-850); and leukemias such as acute myeloid leukemia (AML) (Fiskus et al., *Blood* 2008, 112(7):2896-2905) and acute lymphoblastic leukemia (ALL) (Rodriguez-Gonzalez et al., *Blood* 2008, 112(11): Abstract 1923).

Inhibition of HDAC6 may also have a role in cardiovascular disease, i.e. cardiovascular stress, including pressure overload, chronic ischemia, and infarction-reperfusion injury (Tannous et al., *Circulation* 2008, 117(24):3070-3078); bacterial infection, including those caused by uropathogenic *Escherichia coli* (Dhakal and Mulve, *J. Biol. Chem.* 2008, 284(1):446-454); neurological diseases caused by accumulation of intracellular protein aggregates such as Huntington's disease (reviewed in Kazantsev et al., *Nat. Rev. Drug Disc.* 2008, 7(10):854-868; see also Dompierre et al., *J. Neurosci.* 2007, 27(13):3571-3583; Kozikowski et al., *J. Med. Chem.*

2007, 50:3054-3061) or central nervous system trauma caused by tissue injury, oxidative-stress induced neuronal or axomal degeneration (Rivieccio et al., *Proc. Natl. Acad. Sci. USA* 2009, 106(46):19599-195604); and inflammation, including reduction of pro-inflammatory cytokine IL-1β (Carta et al., *Blood* 2006, 108(5):1618-1626), increased expression of the FOXP3 transcription factor, which induces immunosuppressive function of regulatory T-cells resulting in benefits in chronic diseases such as rheumatoid arthritis, psoriasis, multiple sclerosis, lupus and organ transplant rejection (reviewed in Wang et al., *Nat. Rev. Drug Disc.* 2009, 8(12):969-981).

Given the complex function of HDAC6, selective inhibitors could have potential utility when used alone or in combination with other chemotherapeutics such as microtubule destabilizing agents (Zhou et al., *J. Biol. Chem.* 2009, 284 (15): 9648-9655); Hsp90 inhibitors (Rao et al., *Blood* 2008, 112(5)1886-1893); inhibitors of Hsp90 client proteins, including receptor tyrosine kinases such as Her-2 or VEGFR (Bhalla et al., *J. Clin. Oncol.* 2006, 24(18S): Abstract 1923; Park et al., *Biochem. Biophys. Res. Commun.* 2008, 368(2): 318-322), and signaling kinases such as Bcr-Abl, Akt, mutant FLT-3, c-Raf, and MEK (Bhalla et al., *J. Clin. Oncol.* 2006, 24(18S): Abstract 1923; Kamemura et al., *Biochem. Biophys. Res. Commun.* 2008, 374(1):84-89); inhibitors of cell cycle kinases Aurora A and Aurora B (Pugacheva et al., *Cell* 2007, 129(7):1351-1363; Park et al., *J. Mol. Med.* 2008, 86(1):117-128; Cha et al., *Clin. Cancer Res.* 2009, 15(3):840-850); EGFR inhibitors (Lissanu Deribe et al., *Sci. Signal.* 2009, 2(102): ra84; Gao et al., *J. Biol. Chem.* 2010, 285:11219-11226) and proteasome inhibitors (Hideshima et al., *Proc. Natl. Acad. Sci. USA* 2005, 102(24):8567-8572) or other inhibitors of the ubiquitin proteasome system such as ubiquitin and ubiqutin-like activating (E1), conjugation (E2), ligase enzymes (E3, E4) and deubiquitinase enzymes (DUBS) as well as modulators of autophagy and protein homeostasis pathways. In addition, HDAC6 inhibitors could be combined with radiation therapy (Kim et al., *Radiother. Oncol.* 2009, 92(1):125-132).

Clearly, it would be beneficial to provide novel HDAC6 inhibitors that possess good therapeutic properties, especially for the treatment of proliferative diseases or disorders.

DETAILED DESCRIPTION OF THE INVENTION

1. General Description of Compounds of the Invention

The present invention provides compounds that are effective inhibitors of HDAC6. These compounds are useful for inhibiting HDAC6 activity in vitro and in vivo, and are especially useful for the treatment of various cell proliferative diseases or disorders. The compounds of the invention are represented by formula (I):

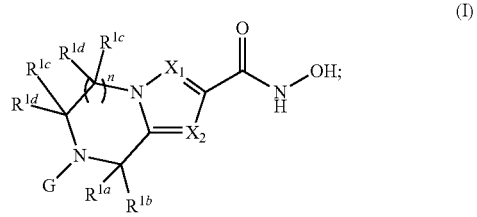

(I)

or a pharmaceutically acceptable salt thereof;
wherein:
$X_1$ is CH or N;
$X_2$ is CH or N;
n is 1-2;
$R^{1a}$ is hydrogen, fluoro, $C_{1-4}$ alkyl, or $C_{1-3}$fluoroalkyl;
$R^{1b}$ is hydrogen, fluoro, $C_{1-4}$ alkyl, or $C_{1-3}$fluoroalkyl; or $R^{1a}$ and $R^{1b}$ are taken together to form an oxo group;
each occurrence of $R^{1c}$ is independently hydrogen, fluoro, $C_{1-4}$ alkyl, or $C_{1-3}$fluoroalkyl;
each occurrence of $R^{1d}$ is independently hydrogen, fluoro, $C_{1-4}$ alkyl, or $C_{1-3}$fluoroalkyl;
G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$; or when $R^{1a}$ and $R^{1b}$ are taken together to form an oxo group, G is —$R^3$, or -$L_1$-$R^3$;
$L_1$ is an unsubstituted or substituted $C_{1-3}$ alkylene chain;
$L_2$ is an unsubstituted or substituted $C_{2-3}$ alkylene chain;
$V_1$ is —C(O)—, —C(S)—, —C(O)—$CR^A$=$CR^A$—, —C(O)—N($R^{4a}$)—, —C(O)—O—, or —S(O)$_2$—;
$V_2$ is —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—SO$_2$—N($R^{4a}$)—;
$R^3$ is unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each occurrence of $R^A$ is independently hydrogen, fluoro, or unsubstituted or substituted $C_{1-4}$ aliphatic; and
each occurrence of $R^{4a}$ is independently hydrogen, or unsubstituted or substituted $C_{1-4}$ aliphatic;
provided that the compound of formula (I) is other thaw N-hydroxy-5-(4-methoxybenzyl)-4-oxo-4,5,6,7-tetrahydropyrazolo[1,5-a]pyrazine-2-carboxamide; or
N-hydroxy-5-(3-(trifluoromethyl)benzyl)-4-oxo-4,5,6,7-tetrahydropyrazolo[1,5-a]pyrazine-2-carboxamide.

2. Compounds and Definitions

Compounds of this invention include those described generally for formula (I) above, and are further illustrated by the classes, subclasses, and species disclosed herein. As used herein, the following definitions shall apply unless otherwise indicated.

As described herein, compounds of the invention may be optionally substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient.

The phrase "one or more substituents", as used herein, refers to a number of substituents that equals from one to the maximum number of substituents possible based on the number of available bonding sites, provided that the above conditions of stability and chemical feasibility are met.

As used herein, the term "independently selected" means that the same or different values may be selected for multiple instances of a given variable in a single compound.

As used herein, the term "aromatic" includes aryl and heteroaryl groups as described generally below and herein.

The term "aliphatic" or "aliphatic group", as used herein, means an optionally substituted straight-chain or branched $C_{1-12}$ hydrocarbon. For example, suitable aliphatic groups include optionally substituted linear, branched or cyclic alkyl, alkenyl, alkynyl groups and hybrids thereof. Unless otherwise specified, in various embodiments, aliphatic groups have 1-12, 1-10, 1-8, 1-6, 1-4, 1-3, or 1-2 carbon atoms.

The term "alkyl", used alone or as part of a larger moiety, refers to an optionally substituted straight or branched chain hydrocarbon group having 1-12, 1-10, 1-8, 1-6, 1-4, 1-3, or 1-2 carbon atoms.

The term "alkenyl", used alone or as part of a larger moiety, refers to an optionally substituted straight or branched chain hydrocarbon group having at least one double bond and having 2-12, 2-10, 2-8, 2-6, 2-4, or 2-3 carbon atoms.

The term "alkynyl", used alone or as part of a larger moiety, refers to an optionally substituted straight or branched chain hydrocarbon group having at least one triple bond and having 2-12, 2-10, 2-8, 2-6, 2-4, or 2-3 carbon atoms.

The terms "cycloaliphatic", "carbocycle", "carbocyclyl", "carbocyclo", or "carbocyclic", used alone or as part of a larger moiety, refer to an optionally substituted saturated or partially unsaturated cyclic aliphatic ring system having from 3 to about 14 ring carbon atoms. In some embodiments, the cycloaliphatic group is an optionally substituted monocyclic hydrocarbon having 3-10, 3-8 or 3-6 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl. The terms "cycloaliphatic", "carbocycle", "carbocyclyl", "carbocyclo", or "carbocyclic" also include optionally substituted bridged or fused bicyclic rings having 6-12, 6-10, or 6-8 ring carbon atoms, wherein any individual ring in the bicyclic system has 3-8 ring carbon atoms.

The term "cycloalkyl" refers to an, optionally substituted saturated ring system of about 3 to about 10 ring carbon atoms. Exemplary monocyclic cycloalkyl rings include cyclopropyl, cyclobutyl, cyclopentyl, cyclohexyl, and cycloheptyl.

The term "cycloalkenyl" refers to an optionally substituted non-aromatic monocyclic or multicyclic ring system containing at least one carbon-carbon double bond and having about 3 to about 10 carbon atoms. Exemplary monocyclic cycloalkenyl rings include cyclopentyl, cyclohexenyl, and cycloheptenyl.

The terms "haloaliphatic", "haloalkyl", "haloalkenyl" and "haloalkoxy" refer to an aliphatic, alkyl, alkenyl or alkoxy group, as the case may be, which is substituted with one or more halogen atoms. As used herein, the term "halogen" or "halo" means F, Cl, Br, or I. The term "fluoroaliphatic" refers to a haloaliphatic wherein the halogen is fluoro, including perfluorinated aliphatic groups. Examples of fluoroaliphatic groups include, without limitation, fluoromethyl, difluoromethyl, trifluoromethyl, 2-fluoroethyl, 2,2,2-trifluoroethyl, 1,1,2-trifluoroethyl, 1,2,2-trifluoroethyl, and pentafluoroethyl.

The term "heteroatom" refers to one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

The terms "aryl" and "ar-", used alone or as part of a larger moiety, e.g., "aralkyl", "aralkoxy", or "aryloxyalkyl", refer to an optionally substituted $C_{6-14}$ aromatic hydrocarbon moiety comprising one to three aromatic rings. Preferably, the aryl group is a $C_{6-10}$ aryl group. Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

An "aralkyl" or "arylalkyl" group comprises an aryl group covalently attached to an alkyl group, either of which independently is optionally substituted. Preferably, the aralkyl group is $C_{6-10}$ aryl $C_{1-6}$ alkyl, including, without limitation, benzyl, phenethyl, and naphthylmethyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9, or 10 ring atoms; having 6, 10, or 14 π electrons shared in a cyclic array; and having, in addition to carbon atoms, from one to five heteroatoms. In some embodiments, the heteroaryl group has 5-10 ring atoms, having, in addition to carbon atoms, from one to five heteroatoms. A heteroaryl group may be mono-, bi-, tri-, or polycyclic, preferably mono-, bi-, or tricyclic, more preferably mono- or bicyclic. The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and refer to a stable 4-10 membered ring, preferably a 3- to 8-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR+ (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, piperidinyl, decahydroquinolinyl, oxazolidinyl, piperazinyl, dioxanyl, dioxolanyl, diazepinyl, oxazepinyl, thiazepinyl, morpholinyl, and thiomorpholinyl. A heterocyclyl group may be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted. Additionally, a heterocyclic ring also includes groups in which the heterocyclic ring is fused to one or more aryl rings.

As used herein, the term "partially unsaturated" refers to a ring moiety that includes at least one double or triple bond between ring atoms. The term "partially unsaturated" is intended to encompass rings having multiple sites of unsaturation, but is not intended to include aromatic (e.g., aryl or heteroaryl) moieties, as herein defined.

The term "alkylene" refers to a bivalent alkyl group. An "alkylene chain" is a polymethylene group, i.e., —(CH$_2$)$_{n'}$—, wherein n' is a positive integer, preferably from 1 to 6, from 1 to 4, from 1 to 3, from 1 to 2, or from 2 to 3. An optionally substituted alkylene chain is a polymethylene group in which one or more methylene hydrogen atoms is optionally replaced with a substituent. Suitable substituents include those described below for a substituted aliphatic group and also include those described in the specification herein. It will be appreciated that two substituents of the alkylene group may be taken together to form a ring system. In certain embodiments, two substituents can be taken together to form a 3-7-membered ring. The substituents can be on the same or different atoms.

An alkylene chain also can be optionally interrupted by a functional group. An alkylene chain is "interrupted" by a functional group when an internal methylene unit is interrupted by the functional group. Examples of suitable "interrupting functional groups" are described in the specification and claims herein.

For purposes of clarity, all bivalent groups described herein, including, e.g., the alkylene chain linkers described above, are intended to be read from left to right, with a corresponding left-to-right reading of the formula or structure in which the variable appears.

An aryl (including aralkyl, aralkoxy, aryloxyalkyl and the like) or heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl or heteroaryl group also include and are generally selected from -halo, —NO$_2$, —CN, —R$^+$, —C(R$^+$)=C(R$^+$)$_2$, —C≡C—R$^+$, —OR$^+$, —SR$^o$, —S(O)R$^o$, —SO$_2$R$^o$, —SO$_3$R$^+$, —SO$_2$N(R$^+$)$_2$, —N(R$^+$)$_2$, —NR$^+$C(O)R$^+$, —NR$^+$C(S)R$^+$, —NR$^+$C(O)N(R$^+$)$_2$, —NR$^+$C(S)N(R$^+$)$_2$, —N(R$^+$)C(=NR$^+$)—N(R$^+$)$_2$, —N(R$^+$)C(=NR$^+$)—R$^o$, —NR$^+$CO$_2$R$^+$, —NR$^+$SO$_2$R$^o$, —NR$^+$SO$_2$N(R$^+$)$^2$, —O—C(O)R$^+$, —O—CO$_2$R$^+$, —OC(O)N(R$^+$)$_2$, —C(O)R$^+$, —C(S)R$^o$, —CO$_2$R$^+$, —C(O)—C(O)R$^+$, —C(O)N(R$^+$)$_2$, —C(S)N(R$^+$)$_2$, —C(O)N(R$^+$)—OR$^+$, —C(O)N(R$^+$)C(=NR$^+$)—N(R$^+$)$_2$, —N(R$^+$)C(=NR$^+$)—N(R$^+$)—C(O)R$^+$, —C(=NR$^+$)—N(R$^+$)$_2$, —C(=NR$^+$)—OR$^+$, —N(R$^+$)—N(R$^+$)$_2$, —C(=NR$^+$)—N(R$^+$)—OR$^+$, —C(R$^o$)=N—OR$^+$, —P(O)(R$^+$)$_2$, —P(O)(OR$^+$)$_2$, —O—P(O)—OR$^+$, and —P(O)(NR$^+$)—N(R$^+$)$_2$, wherein R$^+$, independently, is hydrogen or an optionally substituted aliphatic, aryl, heteroaryl, cycloaliphatic, or heterocyclyl group, or two independent occurrences of R$^+$ are taken together with their intervening atom(s) to form an optionally substituted 5-7-membered aryl, heteroaryl, cycloaliphatic, or heterocyclyl ring. Each R$^o$ is an optionally substituted aliphatic, aryl, heteroaryl, cycloaliphatic, or heterocyclyl group.

An aliphatic or heteroaliphatic group, or a non-aromatic carbycyclic or heterocyclic ring may contain one or more substituents and thus may be "optionally substituted". Unless otherwise defined above and herein, suitable substituents on the saturated carbon of an aliphatic or heteroaliphatic group, or of a non-aromatic carbocyclic or heterocyclic ring are selected from those listed above for the unsaturated carbon of an aryl or heteroaryl group and additionally include the following: =O, =S, =C(R*)$_2$, =N—N(R*)$_2$, =N—OR*, =N—NHC(O)R*, =N—NHCO$_2$R$^o$=N—NHSO$_2$R$^o$ or =N—R* where R$^o$ is defined above, and each R* is independently selected from hydrogen or an optionally substituted C$_{1-6}$ aliphatic group.

In addition to the substituents defined above and herein, optional substituents on the nitrogen of a non-aromatic heterocyclic ring also include and are generally selected from —R$^+$, —N(R$^+$)$_2$, —C(O)R$^+$, —C(O)OR$^+$, —C(O)C(O)R$^+$, —C(O)CH$_2$C(O)R$^+$, —S(O)$_2$R$^+$, —S(O)$_2$N(R$^+$)$_2$, —C(S)N(R$^+$)$_2$, —C(=NH)—N(R$^+$)$_2$, or —N(R$^+$)S(O)$_2$R$^+$; wherein each R$^+$ is defined above. A ring nitrogen atom of a heteroaryl or non-aromatic heterocyclic ring also may be oxidized to form the corresponding N-hydroxy or N-oxide compound. A nonlimiting example of such a heteroaryl having an oxidized ring nitrogen atom is N-oxidopyridyl.

As detailed above, in some embodiments, two independent occurrences of R$^+$ (or any other variable similarly defined in the specification and claims herein), are taken together with their intervening atom(s) to form a monocyclic or bicyclic ring selected from 3-13-membered cycloaliphatic, 3-12-membered heterocyclyl having 1-5 heteroatoms independently selected from nitrogen, oxygen, or sulfur, 6-10-membered aryl, or 5-10-membered heteroaryl having 1-5 heteroatoms independently selected from nitrogen, oxygen, or sulfur.

Exemplary rings that are formed when two independent occurrences of R$^+$ (or any other variable similarly defined in the specification and claims herein), are taken together with their intervening atom(s) include, but are not limited to the following: a) two independent occurrences of R$^+$ (or any other variable similarly defined in the specification or claims herein) that are bound to the same atom and are taken together with that atom to form a ring, for example, N(R$^+$)$_2$, where both occurrences of R$^+$ are taken together with the nitrogen atom to form a piperidin-1-yl, piperazin-1-yl, or morpholin-4-yl group; and b) two independent occurrences of R+ (or any other variable similarly defined in the specification or claims herein) that are bound to different atoms and are taken together with both of those atoms to form a ring, for example where a phenyl group is substituted with two occurrences of OR+

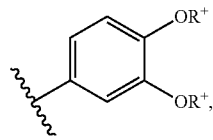

these two occurrences of R+ are taken together with the oxygen atoms to which they are bound to form a fused 6-membered oxygen containing ring:

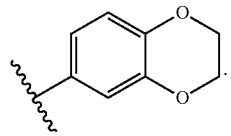 [SMILES: *c1ccc2c(c1)OCCO2]

It will be appreciated that a variety of other rings (e.g., spiro and bridged rings) can be formed when two independent occurrences of R+ (or any other variable similarly defined in the specification and claims herein) are taken together with their intervening atom(s) and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present Compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a 13C— or 14C-enriched carbon are within the scope of this invention. Such compounds are useful, for example, as analytical tools or probes in biological assays.

The terms "stereoisomer", "enantiomer", "diastereomer", "epimer", and "chiral center", are used herein in accordance with the meaning each is given in ordinary usage by those of ordinary skill in the art. Thus, stereoisomers are compounds that have the same atomic connectivity, but differ in the spatial arrangement of the atoms. Enantiomers are stereoisomers that have a mirror image relationship, that is, the stereochemical configuration at all corresponding chiral centers is opposite. Diastereomers are stereoisomers having more than one chiral center, which differ from one another in that the stereochemical configuration of at least one, but not all, of the corresponding chiral centers is opposite. Epimers are diastereomers that differ in stereochemical configuration at only one chiral center.

It is to be understood that, when a disclosed compound has at least one chiral center, the present invention encompasses one enantiomer of the compound, substantially free from the corresponding optical isomer, a racemic mixture of both optical isomers of the compound, and mixtures enriched in one enantiomer relative to its corresponding optical isomer. When a mixture is enriched in one enantiomer relative to its optical isomer, the mixture contains, for example, an enantiomeric excess of at least 50%, 75%, 90%, 95%, 99%, or 99.5%.

The enantiomers of the present invention may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. Where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a disclosed compound has at least two chiral centers, the present invention encompasses a diastereomer substantially free of other diastereomers, an enantiomeric pair of diastereomers substantially free of other stereoisomers, mixtures of diastereomers, mixtures of enantiomeric pairs of diastereomers, mixtures of diastereomers in which one diastereomer is enriched relative to the other diastereomer(s), and mixtures of enantiomeric pairs of diastereomers in which one enantiomeric pair of diastereomers is enriched relative to the other stereoisomers. When a mixture is enriched in one diastereomer or enantiomeric pair of diastereomers pairs relative to the other stereoisomers, the mixture is enriched with the depicted or referenced diastereomer or enantiomeric pair of diastereomers relative to other stereoisomers for the compound, for example, by a molar excess of at least 50%, 75%, 90%, 95%, 99%, or 99.5%.

As used herein, the term "diastereomeric ratio" refers to the ratio between diastereomers which differ in the stereochemical configuration at one chiral center, relative to a second chiral center in the same molecule. By way of example, a chemical structure with two chiral centers provides four possible stereoisomers: R*R, R*S, S*R, and S*S, wherein the asterisk denotes the corresponding chiral center in each stereoisomer. The diastereomeric ratio for such a mixture of stereoisomers is the ratio of one diastereomer and its enantiomer to the other diastereomer and its enantiomer =(R*R+S*S):(R*S+S*R).

One of ordinary skill in the art will recognize that additional stereoisomers are possible when the molecule has more than two chiral centers. For purposes of the present invention, the term "diastereomeric ratio" has identical meaning in reference to compounds with multiple chiral centers as it does in reference to compounds having two chiral centers. Thus, the term "diastereomeric ratio" refers to the ratio of all compounds having R*R or S*S configuration at the specified chiral centers to all compounds having R*S or S*R configuration at the specified chiral centers. For convenience, this ratio is referred to herein as the diastereomeric ratio at the asterisked carbon, relative to the second specified chiral center.

The diastereomeric ratio can be measured by any analytical method suitable for distinguishing between diastereomeric compounds having different relative stereochemical configurations at the specified chiral centers. Such methods include, without limitation, nuclear magnetic resonance (NMR), gas chromatography (GC), and high performance liquid chromatography (HPLC) methods.

The diastereoisomeric pairs may be separated by methods known to those skilled in the art, for example chromatography or crystallization and the individual enantiomers within each pair may be separated as described above. Specific procedures for chromatographically separating diastereomeric pairs of precursors used in the preparation of compounds disclosed herein are provided the examples herein.

3. Description of Exemplary Compounds

In some embodiments, the compound of formula (I) is represented by:

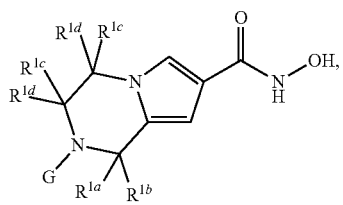
(I-a)

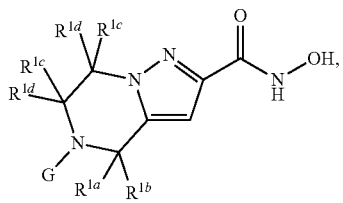
(I-b)

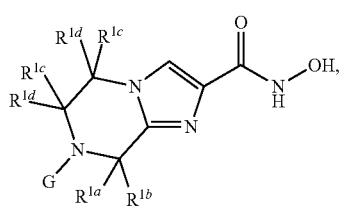
(I-c)

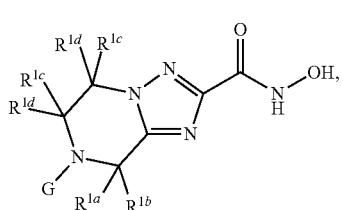
(I-d)

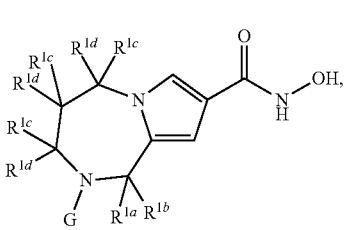
(I-e)

-continued

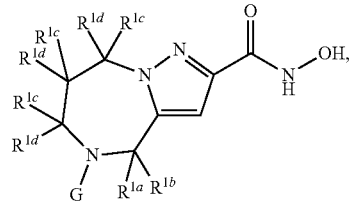
(I-f)

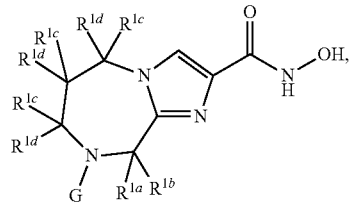
(I-g)

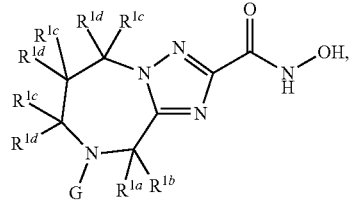
(I-h)

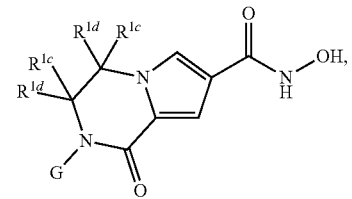
(I-i)

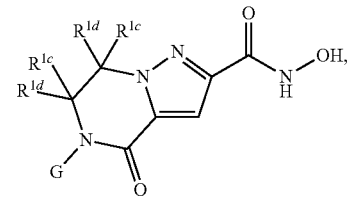
(I-j)

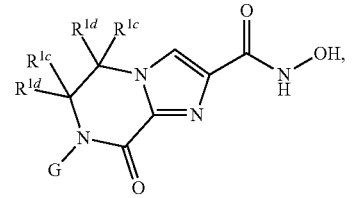
(I-k)

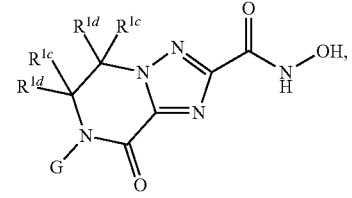
(I-l)

-continued

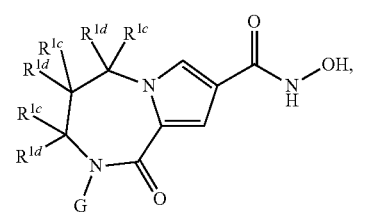
(I-m)

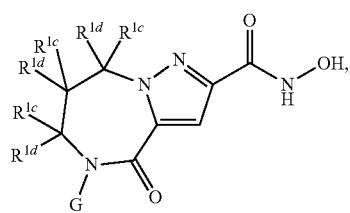
(I-n)

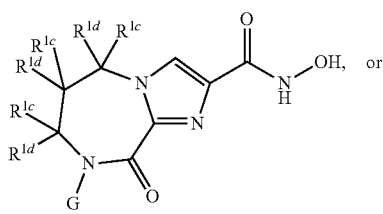
(I-o)

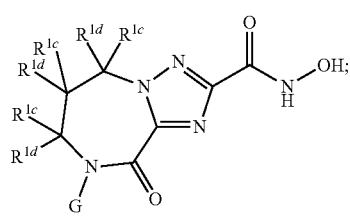
(I-p)

wherein $R^{1a}$, $R^{1b}$, $R^{1c}$, $R^{1d}$, and G have the values described herein. In certain embodiments, the compound of formula (I) is represented by formulas (I-a), (I-b), (I-c), or (I-l), wherein $R^{1a}$, $R^{1b}$, $R^{1c}$, $R^{1d}$, and G have the values described herein.

In some embodiments, the compound of formula (I) is represented by formula (II-i):

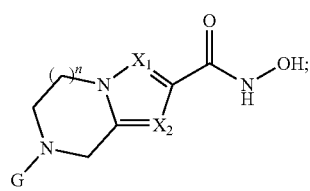
(II-i)

wherein $X_1$, $X_2$, n, and G have the values described herein.

In some embodiments, the compound of formula (II-i) is represented by:

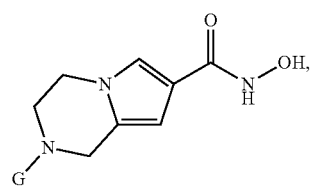
(II-i-a)

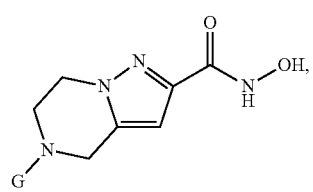
(II-i-b)

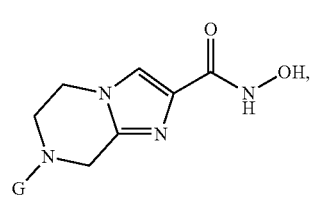
(II-i-c)

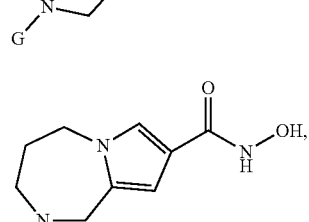
(II-i-d)

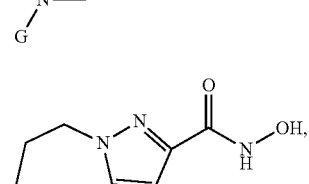
(II-i-e)

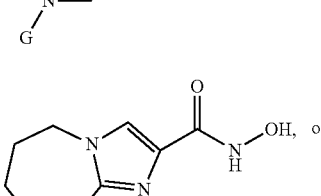
(II-i-f)

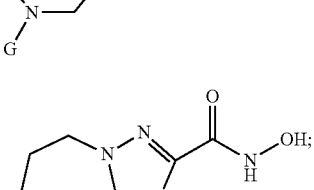
(II-i-g)

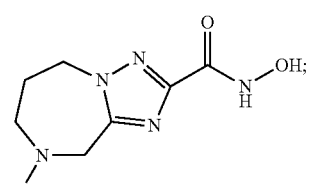
(II-i-h)

wherein G has the values described herein. In certain embodiments, the compound of formula (II-i) is represented by formulas (II-i-a), (II-i-b), or (II-i-c), wherein G has the values described herein.

In some embodiments, the compound of formula (I) is represented by formula (II-ii):

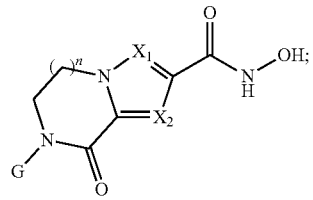
(II-ii)

wherein $X_1$, $X_2$, n, and G have the values described herein.

In some embodiments, the compound of formula (II-ii) is represented by:

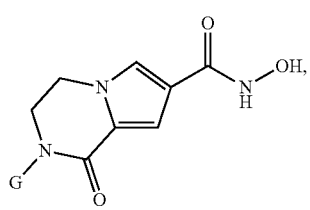
(II-ii-a)

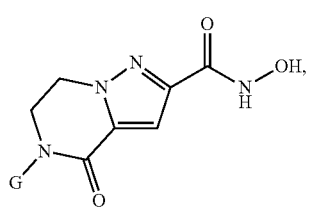
(II-ii-b)

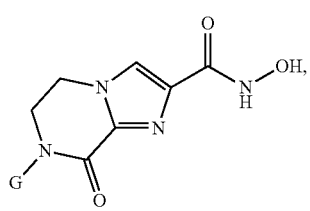
(II-ii-c)

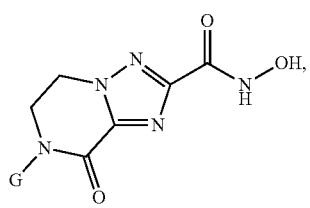
(II-ii-d)

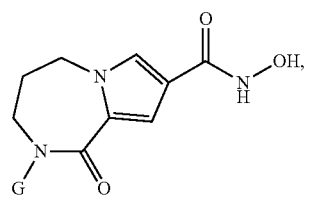
(II-ii-e)

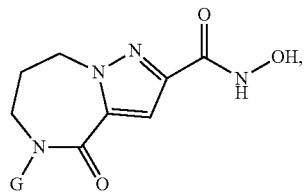
(II-ii-f)

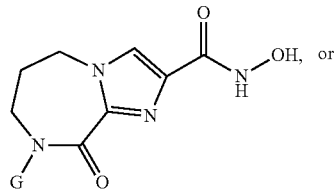
(II-ii-g)

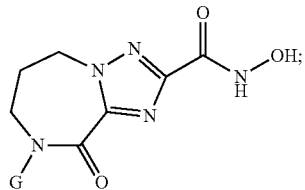
(II-ii-h)

wherein G has the values described herein. In certain embodiments, the compound of formula (II-ii) is represented by formula (II-ii-b) wherein G has the values described herein.

In some embodiments, the compound of formula (I) is represented by formula (III-a), (III-b), or (III-c):

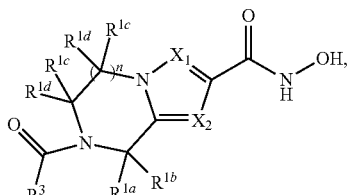
(III-a)

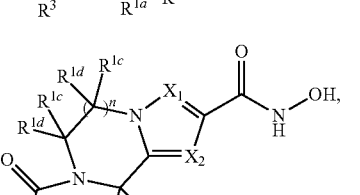
(III-b)

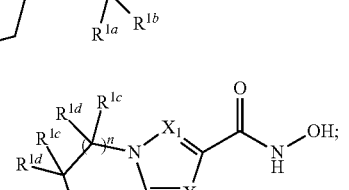
(III-c)

wherein $X_1$, $X_2$, $R^{1a}$, $R^{1b}$, $R^{1c}$, $R^{1d}$, n, and $R^3$ have the values described herein.

In some embodiments, the compound of formula (I) is represented by formula (IV-a), (IV-b), or (IV-c):

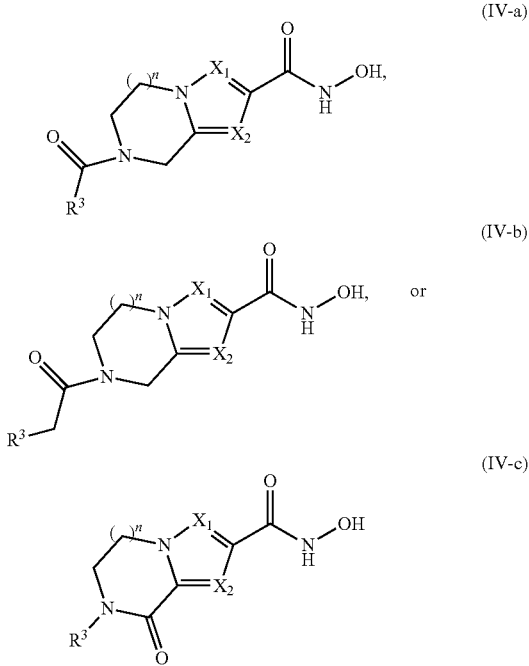

wherein $X_1$, $X_2$, n, and $R^3$ have the values described herein. In certain embodiments, the compound of formula (IV) is represented by formula (IV-a) wherein $X_1$, $X_2$, n, and $R^3$ have the values described herein. In certain embodiments, the compound of formula (IV) is represented by formula (IV-b) wherein $X_1$, $X_2$, n, and $R^3$ have the values described herein. In certain embodiments, the compound of formula (IV) is represented by formula (IV-c) wherein $X_1$, $X_2$, n, and $R^3$ have the values described herein.

The values described below for each variable are with respect to any of formulas (I), (II), (III), (IV), or their subformulas as described above.

The variable $X_1$ is CH or N. The variable $X_2$ is CH or N. In some embodiments, at least one of $X_1$ and $X_2$ is CH. In certain embodiments, $X_1$ is CH and $X_2$ is CH. In certain embodiments, $X_1$ is CH and $X_2$ is N. In certain embodiments, $X_1$ is N and $X_2$ is CH. In certain embodiments, $X_1$ is N and $X_2$ is N.

The variable $R^{1a}$ is hydrogen, fluoro, $C_{1-4}$ alkyl, or $C_{1-3}$ fluoroalkyl. In some embodiments, $R^{1a}$ is hydrogen, fluoro, or methyl. In certain embodiments, $R^{1a}$ is hydrogen or methyl. In certain embodiments, $R^{1a}$ is hydrogen.

The variable $R^{1b}$ is hydrogen, fluoro, $C_{1-4}$ alkyl, or $C_{1-3}$ fluoroalkyl. In some embodiments, $R^{1b}$ is hydrogen, fluoro, trifluoromethyl, methyl, ethyl, isopropyl, n-propyl, or tert-butyl. In certain embodiments, $R^{1b}$ is hydrogen, fluoro, or methyl. In certain embodiments, $R^{1b}$ is hydrogen.

In some embodiments, $R^{1a}$ and $R^{1b}$ are taken together to form an oxo group.

Each occurrence of the variable $R^{1c}$ is independently hydrogen, fluoro, $C_{1-4}$ alkyl, or $C_{1-3}$ fluoroalkyl. In some embodiments, each occurrence of $R^{1c}$ is independently hydrogen, fluoro, or methyl. In certain embodiments, each occurrence of $R^{1c}$ is independently hydrogen or methyl. In certain embodiments, $R^{1c}$ is hydrogen.

Each occurrence of the variable $R^{1d}$ is independently hydrogen, fluoro, $C_{1-4}$ alkyl, or $C_{1-3}$ fluoroalkyl. In some embodiments, each occurrence of $R^{1d}$ is independently hydrogen, fluoro, trifluoromethyl, methyl, ethyl, isopropyl, n-propyl, or tert-butyl. In certain embodiments, each occurrence of $R^{1d}$ is independently hydrogen, fluoro, or methyl. In certain embodiments, $R^{1d}$ is hydrogen.

The variable n is 1-2. In some embodiments, n is 1.

When $R^{1a}$ and $R^{1b}$ are not taken together to form an oxo group, the variable G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$, wherein $L_1$, $L_2$, $V_1$, $V_2$, and $R^3$ have the values described herein. In some such embodiments, G is —$V_1$—$R^3$, or —$V_1$-$L_1$-$R^3$, wherein $L_1$, $V_1$, and $R^3$ have the values described herein. In certain such embodiments, G is —$V_1$—$R^3$, wherein $V_1$, and $R^3$ have the values described herein.

When $R^{1a}$ and $R^{1b}$ are taken together to form an oxo group, G is —$R^3$, or -$L_1$-$R^3$, wherein $L_1$, and $R^3$ have the values described herein. In some such embodiments, G is —$R^3$, wherein $R^3$ has the values described herein.

The variable $L_1$ is an unsubstituted or substituted $C_{1-3}$ alkylene chain. In some embodiments, $L_1$ is —$CH_2$—, —$CH_2CH_2$—, or —$CH_2CH_2CH_2$—. In certain embodiments, $L_1$ is —$CH_2$—.

The variable $L_2$ is an unsubstituted or substituted $C_{2-3}$ alkylene chain. In some embodiments, $L_2$ is —$CH_2CH_2$— or —$CH_2CH_2CH_2$—.

The variable $V_1$ is —C(O)—, —C(S)—, —C(O)—$CR^A$=$CR^A$—, —C(O)—N($R^{4a}$)—, —C(O)—O—, or —S(O)$_2$—, wherein $R^A$ and $R^{4a}$ have the values described herein. In some embodiments, $V_1$ is —C(O)—, —C(O)—N($R^{4a}$)—, or —S(O)$_2$—, wherein $R^{4a}$ has the values described herein. In certain embodiments, $V_1$ is —C(O)—, —C(O)—NH—, or —S(O)$_2$—. In other certain embodiments, $V_1$ is —C(O)—.

Each occurrence of the variable $R^A$ is independently hydrogen, halo, or an optionally substituted $C_{1-4}$ aliphatic group. In some embodiments, each occurrence of $R^A$ is independently hydrogen, fluoro or methyl. In certain embodiments, $R^A$ is hydrogen.

Each occurrence of the variable $R^{4a}$ is independently hydrogen, or unsubstituted or substituted $C_{1-4}$ aliphatic. In certain embodiments, $R^{4a}$ is hydrogen.

The variable $V_2$ is —N($R^{4a}$)—, —N($R^{4a}$)—C(O)—, —$SO_2$—N($R^{4a}$)—, —N($R^{4a}$)—$SO_2$—, —O—, —S—, —S(O)—, —N($R^{4a}$)—C(O)—N($R^{4a}$)—, —N($R^{4a}$)—C(O)—O—, —O—C(O)—N($R^{4a}$)—, or —N($R^{4a}$)—$SO_2$—N($R^{4a}$)—, wherein $R^{4a}$ has the values described herein. In some embodiments, $V_2$ is —$NR^{4a}$—, —$NR^{4a}$—C(O)—, —$SO_2$—N($R^{4a}$)—, —N($R^{4a}$)—$SO_2$—, —O—, or —S—, wherein $R^{4a}$ has the values described herein. In certain embodiments, $V_2$ is —N($R^{4a}$)—, —O—, or —S—, wherein $R^{4a}$ has the values described herein. In certain embodiments, $V_2$ is —NH—, or —O—.

The variable $R^3$ is unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:

each substitutable carbon chain atom in $R^3$ is unsubstituted or substituted with 1-2 occurrences of —$R^{5dd}$;

each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;

each substitutable unsaturated ring carbon atom in $R^3$ is unsubstituted or is substituted with —$R^{5a}$; and each substitutable ring nitrogen atom in $R^3$ is unsubstituted or substituted with —$R^{9b}$;

wherein $R^{5dd}$, $R^4$, $R^5$, $R^6$, $R^{5a}$, and $R^{9b}$ have the values described herein.

In some embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein each substitutable carbon chain atom in $R^3$ is unsubstituted or substituted with 1-2 occurrences of —$R^{5dd}$;

each substitutable saturated ring carbon atom in $R^3$ is unsubstituted or substituted with =O, =S, =C($R^5$)$_2$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with —$R^{9b}$;

wherein $R^{5dd}$, $R^5$, $R^{5a}$, and $R^{9b}$ have the values described herein.

In certain embodiments, $R^3$ is unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; wherein:

each substitutable carbon chain atom in $R^3$ is unsubstituted or substituted with 1-2 occurrences of —$R^{5dd}$;

each substitutable saturated ring carbon atom in $R^3$ is unsubstituted or substituted with —$R^{5a}$;

each substitutable unsaturated ring carbon atom in $R^3$ is unsubstituted or is substituted with —$R^{5a}$;

the total number of $R^{5a}$ substituents is p; and each substitutable ring nitrogen atom in $R^3$ is unsubstituted or substituted with —$R^{9b}$;

wherein $R^{5dd}$, $R^{5a}$, $R^{9b}$ and p have the values described herein.

In some embodiments, each occurrence of $R^{5dd}$ is independently fluoro, hydroxy, —O($C_{1-3}$ alkyl), cyano, —N($R^4$)$_2$, —C(O)($C_{1-3}$ alkyl), —CO$_2$H, —C(O)NH$_2$, —N=C(O)—($C_{1-3}$ alkyl), —N=C(O)—O—($C_{1-3}$ alkyl), or —C(O)NH($C_{1-3}$ alkyl). In certain embodiments, each occurrence of $R^{5dd}$ is independently fluoro, hydroxy, methoxy, ethoxy, or —C(O)NHCH$_3$.

Each $R^4$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur.

Each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^6$ is independently unsubstituted or substituted $C_{1-6}$ aliphatic, or unsubstituted or substituted 6-10-membered aryl.

Each $R^{9b}$ is independently —C(O)$R^5$, —C(O)N($R^4$)$_2$, —CO$_2R^6$, —SO$_2R^6$, —SO$_2$N($R^4$)$_2$, unsubstituted $C_{1-4}$ aliphatic, or $C_{1-4}$ aliphatic substituted with 1-2 independent occurrences of $R^7$ or $R^8$, wherein $R^7$ and $R^8$ have the values described herein. In some embodiments, each $R^{9b}$ is independently unsubstituted —C(O)—$C_{1-4}$ aliphatic, unsubstituted —C(O)—$C_{3-10}$ cycloaliphatic, or unsubstituted $C_{1-4}$ aliphatic. In certain embodiments, each $R^{9b}$ is independently methyl, ethyl, isopropyl, isobutyl, n-propyl, n-butyl, tert-butyl, —C(O)-methyl, —C(O)-ethyl, —C(O)-cyclopropyl, or —C(O)-cyclobutyl.

Each $R^7$ is independently unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

Each $R^8$ is independently halogen, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl), wherein $R^4$ has the values described herein.

Each $R^{5a}$ is independently halogen, —NO$_2$, —CN, —C($R^5$)=C(R)$_2$, —C≡C—$R^5$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —OC(O)N($R^4$)$_2$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, —N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, —P(O)(O$R^5$)$_2$, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{5a}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur, wherein $R^5$, $R^6$, and $R^4$ have the values described herein.

In some embodiments, each $R^{5a}$ is independently halogen, cyano, hydroxy, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —C(O)NH$C_{1-3}$ alkyl, —NHC(O)NH$C_{1-3}$ alkyl, —NHS(O)$_2C_{1-3}$ alkyl, —NH$C_{1-3}$ alkyl, —N($C_{1-3}$ alkyl)$_2$, 3-10-membered cycloaliphatic substituted with 0-2 occurrences of —$R^{7a}$, 4-10-membered heterocyclyl having 1-4 heteroatoms independently selected from nitrogen, oxygen, and sulfur substituted with 0-2 occurrences of —$R^{7a}$, 6-10-membered aryl substituted with 0-2 occurrences of —$R^{7a}$, or 5-10-membered heteroaryl having 1-5 heteroatoms independently selected from nitrogen, oxygen, and sulfur substituted with 0-2 occurrences of —$R^{7a}$, wherein $R^{7a}$ has the values described herein.

In certain embodiments, each $R^{5a}$ is independently chloro, fluoro, hydroxy, methoxy, ethoxy, n-propoxy, isopropoxy, cyano, trifluoromethyl, methyl, ethyl, isopropyl, isobutyl, n-propyl, tert-butyl or phenyl.

Each occurrence of the variable $R^{7a}$ is independently halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —NH$C_{1-3}$ alkyl, —N($C_{1-3}$ alkyl)$_2$, —C(O)NH$C_{1-3}$ alkyl, —NHC(O)NH$C_{1-3}$ alkyl, or —NHS(O)$_2C_{1-3}$ alkyl.

The variable p is 1-2. In some embodiments, p is 1.

In certain embodiments, $R^3$ is unsubstituted or substituted $C_{1-6}$ aliphatic. In certain embodiments, each substitutable carbon chain atom in $R^3$ is unsubstituted or substituted with 1-2 occurrences of —$R^{5dd}$, wherein $R^{5dd}$ has the values described herein. In certain embodiments, $R^3$ is methyl, ethyl, n-propyl, isopropyl, tert-butyl, n-butyl, iso-butyl, pentyl, hexyl, butenyl, propenyl, pentenyl, or hexenyl, wherein each of the forementioned groups is unsubstituted or substituted. In certain embodiments, $R^3$ is methyl, ethyl, n-propyl, isopropyl, tert-butyl, n-butyl, iso-butyl, pentyl, hexyl, butenyl, propenyl, pentenyl, or hexenyl, wherein each substitutable carbon chain atom in $R^3$ is unsubstituted or substituted with 1-2 occurrences of —$R^{5dd}$, wherein $R^{5dd}$ has the values described herein.

In certain embodiments, $R^3$ is unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur.

In certain embodiments, $R^3$ is unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:

each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;

each substitutable unsaturated ring carbon atom in $R^3$ is unsubstituted or is substituted with —$R^{5a}$; and each substitutable ring nitrogen atom in $R^3$ is unsubstituted or substituted with —$R^{9b}$;

wherein $R^4$, $R^5$, $R^6$, $R^{5a}$, and $R^{9b}$ have the values described herein.

In certain embodiments, $R^3$ is unsubstituted or substituted 3-10-membered cycloaliphatic, unsubstituted or substituted 4-10-membered heterocyclyl having 1-5 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:

each substitutable saturated ring carbon atom in $R^3$ is unsubstituted or substituted with =O, =S, =C($R^5$)$_2$, =N—$R^5$ or —$R^{5a}$;

each substitutable unsaturated ring carbon atom in $R^3$ is unsubstituted or is substituted with —$R^{5a}$;

each substitutable ring nitrogen atom in $R^3$ is unsubstituted or substituted with —$R^{9b}$;

wherein $R^5$, $R^{5a}$, and $R^{9b}$ have the values described herein.

In certain embodiments, $R^3$ is unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur, wherein:

each substitutable saturated ring carbon atom in $R^3$ is unsubstituted or substituted with —$R^{5a}$;

each substitutable unsaturated ring carbon atom in $R^3$ is unsubstituted or is substituted with —$R^{5a}$;

the total number of $R^{5a}$ substituents is p; and each substitutable ring nitrogen atom in $R^3$ is unsubstituted or substituted with —$R^{9b}$;

wherein $R^{5a}$, $R^{9b}$ and p have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;

each substitutable unsaturated ring carbon atom in $R^3$ is unsubstituted or is substituted with —$R^{5a}$; and each substitutable ring nitrogen atom in $R^3$ is unsubstituted or substituted with —$R^{9b}$;

wherein $R^4$, $R^5$, $R^6$, $R^{5a}$, and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with $=O$, $=S$, $=C(R^5)_2$, $=N-R^5$ or $-R^{5a}$;

each substitutable unsaturated ring carbon atom in $R^3$ is unsubstituted or is substituted with $-R^{5a}$;

each substitutable ring nitrogen atom in $R^3$ is unsubstituted or substituted with $-R^{9b}$;

wherein $R^{5a}$ and $R^{9b}$ have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, naphthyl, pyranyl, pyridyl, pyridazinyl, pyrimidinyl, pyrazinyl, triazinyl, indolizinyl, imidazopyridyl, indolyl, isoindolyl, indazolyl, benzimidazolyl, benzthiazolyl, benzothienyl, benzofuranyl, benzoxazolyl, benzodioxolyl, benzthiadiazolyl, 2,3-dihydrobenzofuranyl, 4H-furo[3,2-b]pyrrolyl, pyrazolopyrimidinyl, purinyl, quinolyl, isoquinolyl, tetrahydroquinolinyl, tetrahydroisoquinolinyl, cinnolinyl, phthalazinyl, quinazolinyl, quinoxalinyl, naphthyridinyl, pteridinyl, tetrahydrofuranyl, tetrahydropyranyl, tetrahydrothienyl, indanyl, tetrahydroindazolyl, pyrrolidinyl, pyrrolidonyl, piperidinyl, pyrrolinyl, decahydroquinolinyl, oxazolidinyl, piperazinyl, dioxanyl, diazepinyl, oxazepinyl, thiazepinyl, morpholinyl, thiomorpholinyl, quinuclidinyl, phenanthridinyl, tetrahydronaphthyl, indolinyl, benzodioxanyl, chromanyl, cyclopropyl, cyclobutyl, cyclopentyl, cyclohexyl, cycloheptyl, cyclooctyl, cyclopentenyl, cyclohexenyl, cycloheptenyl, cyclooctenyl, bicycloheptanyl, bicyclooctanyl, or adamantyl; wherein:

each substitutable saturated ring carbon atom in $R^3$ is unsubstituted or substituted with $-R^{5a}$;

each substitutable unsaturated ring carbon atom in $R^3$ is unsubstituted or is substituted with $-R^{5a}$;

the total number of $R^{5a}$ substituents is p; and each substitutable ring nitrogen atom in $R^3$ is unsubstituted or substituted with $-R^{9b}$;

wherein $R^{5a}$, $R^{9b}$ and p have the values described herein.

In certain embodiments, $R^3$ is furanyl, thienyl, pyrrolyl, oxazolyl, thiazolyl, imidazolyl, pyrazolyl, isoxazolyl, isothiazolyl, oxadiazolyl, triazolyl, thiadiazolyl, phenyl, pyranyl, pyridyl, pyridazinyl, pyrimidinyl, pyrazinyl, or triazinyl, wherein:

each substitutable unsaturated ring carbon atom in $R^3$ is unsubstituted or is substituted with 1-2 occurrences of $-R^{5a}$;

each $R^{5a}$ is independently chloro, fluoro, hydroxy, methoxy, ethoxy, n-propoxy, isopropoxy, cyano, trifluoromethyl, methyl, ethyl, isopropyl, isobutyl, n-propyl, tert-butyl or phenyl;

each substitutable ring nitrogen atom in $R^3$ is unsubstituted or substituted with $-R^{9b}$; and each $R^{9b}$ is independently methyl, ethyl, isopropyl, isobutyl, n-propyl, n-butyl, tert-butyl, $-C(O)$-methyl, $-C(O)$-ethyl, $-C(O)$-cyclopropyl, or $-C(O)$-cyclobutyl.

In certain embodiments, $R^3$ is indolizinyl, imidazopyridyl, indolyl, indazolyl, benzimidazolyl, benzthiazolyl, benzothienyl, benzofuranyl, benzoxazolyl, benzthiadiazolyl, pyrazolopyrimidinyl, purinyl, quinolyl, isoquinolyl, cinnolinyl, phthalazinyl, quinazolinyl, quinoxalinyl, naphthyridinyl, naphthyl, or pteridinyl; wherein:

each substitutable unsaturated ring carbon atom in $R^3$ is unsubstituted or is substituted with 1-2 occurrences of $-R^{5a}$;

each $R^{5a}$ is independently chloro, fluoro, hydroxy, methoxy, ethoxy, n-propoxy, isopropoxy, cyano, trifluoromethyl, methyl, ethyl, isopropyl, isobutyl, n-propyl, tert-butyl or phenyl;

each substitutable ring nitrogen atom in $R^3$ is unsubstituted or substituted with $-R^{9b}$; and each $R^{9b}$ is independently methyl, ethyl, isopropyl, isobutyl, n-propyl, n-butyl, tert-butyl, $-C(O)$-methyl, $-C(O)$-ethyl, $-C(O)$-cyclopropyl, or $-C(O)$-cyclobutyl.

In certain embodiments, $R^3$ is tetrahydrofuranyl, tetrahydropyranyl, tetrahydrothienyl, pyrrolidinyl, pyrrolidonyl, piperidinyl, pyrrolinyl, oxazolidinyl, piperazinyl, dioxanyl, diazepinyl, oxazepinyl, thiazepinyl, morpholinyl, thiomorpholinyl, cyclopropyl, cyclobutyl, cyclopentyl, cyclohexyl, cycloheptyl, cyclooctyl, cyclopentenyl, cyclohexenyl, cycloheptenyl, or cyclooctenyl; wherein:

each substitutable saturated ring carbon atom in $R^3$ is unsubstituted or substituted with $-R^{5a}$;

each substitutable unsaturated ring carbon atom in $R^3$ is unsubstituted or is substituted with $-R^{5a}$;

the total number of $R^{5a}$ substituents is p;

p is 1-2;

each substitutable ring nitrogen atom in $R^3$ is unsubstituted or substituted with $-R^{9b}$;

each $R^{5a}$ is independently chloro, fluoro, hydroxy, methoxy, ethoxy, n-propoxy, isopropoxy, cyano, trifluoromethyl, methyl, ethyl, isopropyl, isobutyl, n-propyl, tert-butyl or phenyl; and each $R^{9b}$ is independently methyl, ethyl, isopropyl, isobutyl, n-propyl, n-butyl, tert-butyl, $-C(O)$-methyl, $-C(O)$-ethyl, $-C(O)$-cyclopropyl, or $-C(O)$-cyclobutyl.

In certain embodiments, $R^3$ is tetrahydroindazolyl, bicycloheptanyl, bicyclooctanyl, adamantyl, isoindolyl, benzodioxolyl, 2,3-dihydrobenzofuranyl, 4H-furo[3,2-b]pyrrolyl, quinuclidinyl, tetrahydroquinolinyl, tetrahydroisoquinolinyl, decahydroquinolinyl, tetrahydronaphthyl, indolinyl, benzodioxanyl, chromanyl, tetrahydroindazolyl, or indanyl; wherein:

each substitutable saturated ring carbon atom in $R^3$ is unsubstituted or substituted with $-R^{5a}$;

each substitutable unsaturated ring carbon atom in $R^3$ is unsubstituted or is substituted with $-R^{5a}$;

the total number of $R^{5a}$ substituents is p;

p is 1-2;

each substitutable ring nitrogen atom in $R^3$ is unsubstituted or substituted with $-R^{9b}$;

each $R^{5a}$ is independently chloro, fluoro, hydroxy, methoxy, ethoxy, n-propoxy, isopropoxy, cyano, trifluoromethyl, methyl, ethyl, isopropyl, isobutyl, n-propyl, tert-butyl or phenyl; and each $R^{9b}$ is independently methyl, ethyl, isopropyl, isobutyl, n-propyl, n-butyl, tert-butyl, $-C(O)$-methyl, $-C(O)$-ethyl, $-C(O)$-cyclopropyl, or $-C(O)$-cyclobutyl.

In some embodiments, when $R^{1a}$ and $R^{1b}$ are not taken together to form an oxo group, G is:

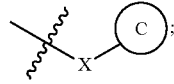

wherein X and Ring C have the values described herein.

In certain such embodiments, G is:

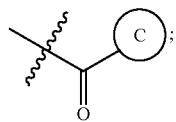

wherein Ring C has the values described herein.

The variable X is —C(O)— or -$L_{2a}$-$R^{3aa}$—$V_{2a}$—, wherein $L_{2a}$, $R^{3aa}$, and $V_{2a}$ have the values described herein. In some embodiments, X is —C(O)—. In some embodiments, X is -$L_{2a}$-$R^{3aa}$—$V_{2a}$—, wherein $L_{2a}$, $R^{3aa}$, and $V_{2a}$ have the values described herein. In some embodiments, X is —C(O)—,

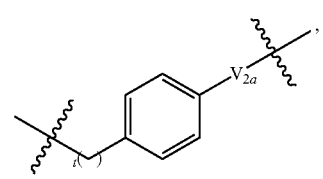 X-a

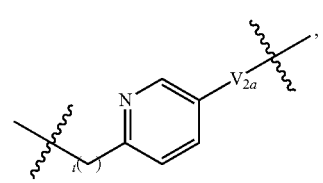 X-b

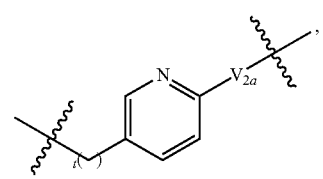 X-c

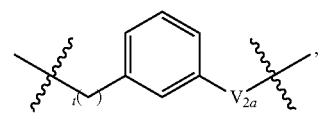 X-d

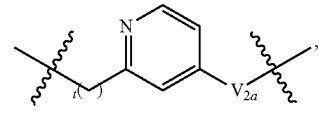 X-e

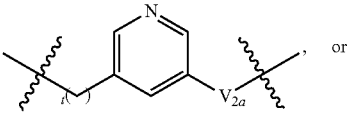 X-f, or

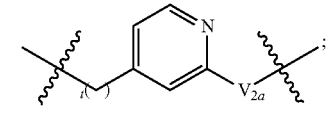 X-g wherein $V_{2a}$ and t have the values described herein.

In certain embodiments, X is —C(O)—,

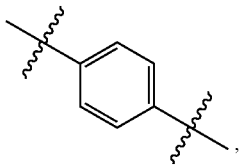 X-i

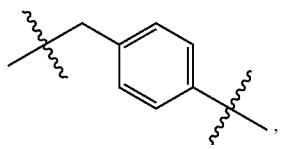 X-ii

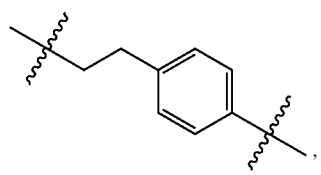 X-iii

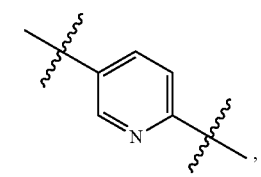 X-iv

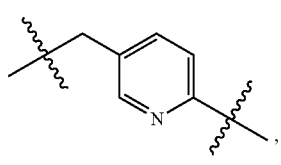 X-v

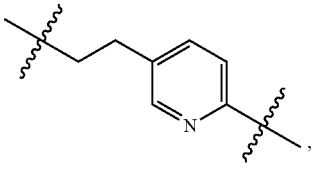 X-vi

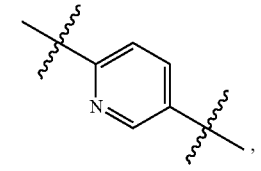 X-vii

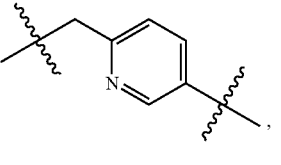 X-viii

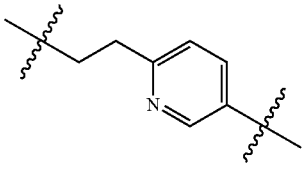 X-ix

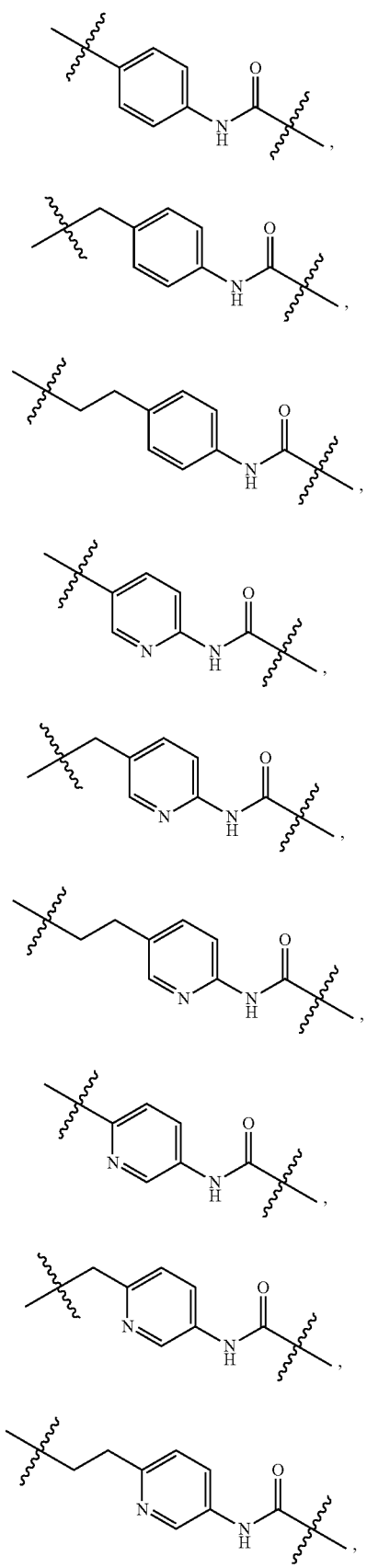

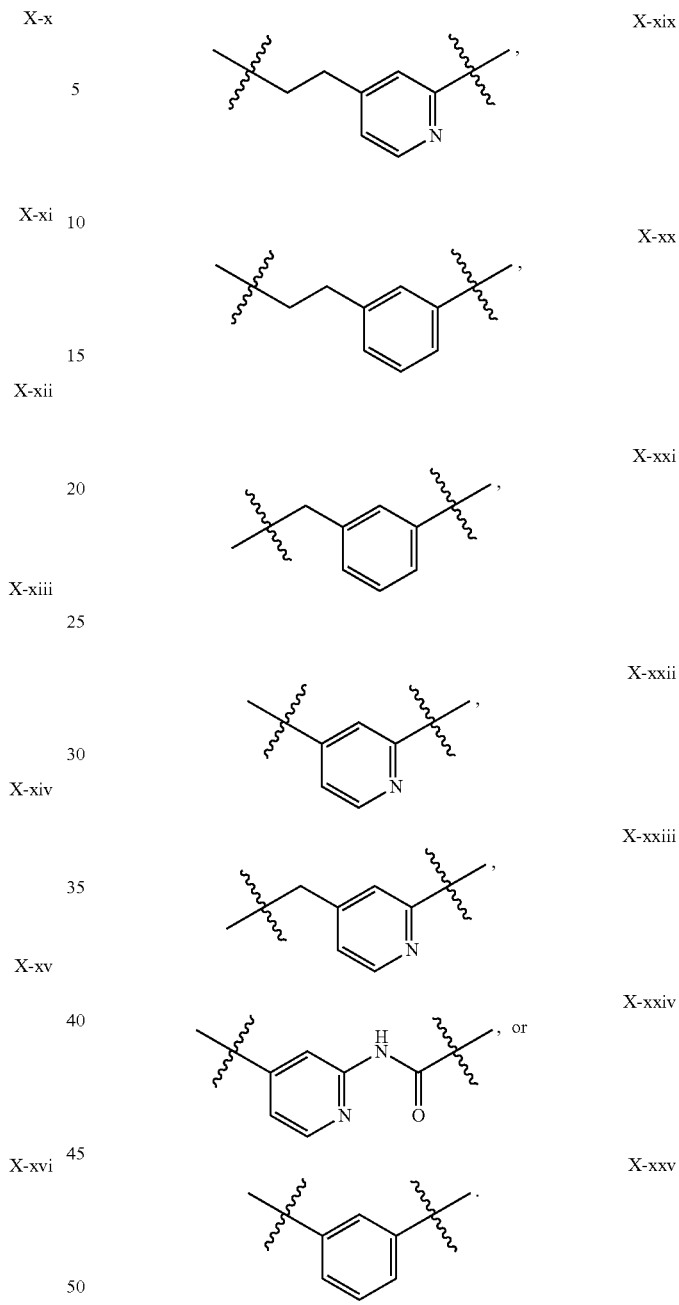

In certain embodiments, X is —C(O)—, X-ii, X-xi, X-xii, X-xxii, X-xxiv, or X-xxv.

Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-4 occurrences of $R^{5b}$; wherein $R^{9bb}$, X, and $R^{5b}$ have the values described herein. In some embodiments, Ring C is a 4-7 membered heterocyclic ring containing one nitrogen atom, wherein the nitrogen atom is not the atom bound to X, and wherein the nitrogen atom in Ring C is substituted with $R^{9bb}$ and Ring C is unsubstituted or substituted by 1-2 occurrences of $R^{5b}$; wherein $R^{9bb}$, X, and $R^{5b}$ have the values described herein.

In certain embodiments, Ring C is:

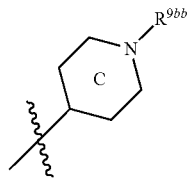

wherein Ring C is unsubstituted or substituted with 1 occurrence of $R^{5b}$, wherein $R^{9bb}$ and $R^{5b}$ have the values described herein. In certain embodiments, Ring C is:

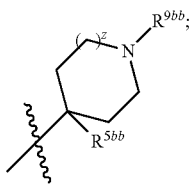

wherein $R^{9bb}$, z and $R^{5bb}$ have the values described herein.

The variable $V_{2a}$ is a bond, —NH—C(O)—, —NH—S(O)$_2$—, or —NH—C(O)—NH—. In some embodiments, $V_{2a}$ is a bond or —NH—C(O)—. In certain embodiments, $V_{2a}$ is a bond. In certain embodiments, $V_{2a}$ is —NH—C(O)—.

The variable t is 0-2. In some embodiments, t is 0-1. In certain embodiments, t is 0. In certain embodiments, t is 1. In certain embodiments, t is 2.

The variable $L_{2a}$ is a bond or unsubstituted or substituted $C_{1-3}$ alkylene chain. In some embodiments, $L_{2a}$ is a bond, —CH$_2$—, —CH$_2$CH$_2$—, or —CH$_2$CH$_2$CH$_2$—. In certain embodiments, $L_{2a}$ is a bond. In certain embodiments, $L_{2a}$ is —CH$_2$—. In certain embodiments, $L_{2a}$ is —CH$_2$CH$_2$—.

The variable $R^{3aa}$ is a 6-membered aromatic ring containing 0-2 nitrogen atoms which is unsubstituted or substituted with 1-2 independent occurrences of $R^{4c}$, wherein $R^{4c}$ has the values described herein. In some embodiments, $R^{3aa}$ is phenyl or pyridyl, each of which is unsubstituted or substituted with 1-2 independent occurrences of $R^{4c}$, wherein $R^{4c}$ has the values described herein. In some embodiments, $R^{3aa}$ is:

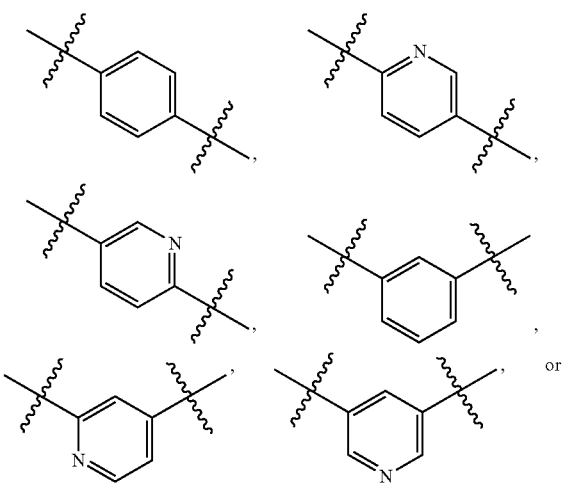

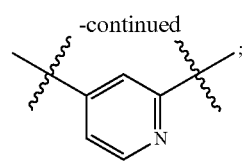

wherein each ring is unsubstituted or substituted with 1-2 independent occurrences of $R^{4c}$.

The variable $R^{4c}$ is chloro, fluoro, cyano, hydroxy, methoxy, ethoxy, trifluoromethoxy, trifluoromethyl, methyl, or ethyl. In some embodiments, $R^{4c}$ is chloro, fluoro, methyl or ethyl.

The variable z is 0-1. In some embodiments, z is 0. In some embodiments, z is 1.

Each occurrence of the variable $R^{5b}$ is independently chloro, fluoro, hydroxy, methyl, ethyl, methoxy, ethoxy, trifluoromethyl, trifluoromethoxy, —C(O)NH$_2$, or —CO$_2$H. In some embodiments, each occurrence of the variable $R^{5b}$ is independently chloro, fluoro, hydroxy, methyl, or ethyl. In certain embodiments, each occurrence of the variable $R^{5b}$ is methyl.

The variable $R^{5bb}$ is hydrogen or methyl. In some embodiments, $R^{5bb}$ is hydrogen. In some embodiments, $R^{5bb}$ is methyl.

The variable $R^{9bb}$ is hydrogen, unsubstituted C(O)—O—C$_{1-6}$ aliphatic, unsubstituted C(O)—C$_{1-5}$ aliphatic, unsubstituted C(O)—C$_{3-10}$ cycloaliphatic, or unsubstituted C$_{1-6}$ aliphatic. In some embodiments, $R^{9bb}$ is hydrogen, methyl, ethyl, isopropyl, or tert-butoxycarbonyl. In some embodiments, $R^{9bb}$ is methyl, ethyl, or isopropyl. In certain embodiments, $R^{9bb}$ is hydrogen.

In certain embodiments, the compound of formula (I) is represented by:

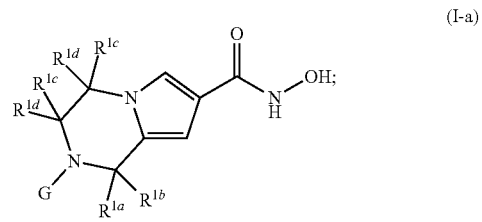

(I-a)

wherein:
$R^{1a}$ is hydrogen, fluoro, or methyl;
$R^{1b}$ is hydrogen, fluoro, trifluoromethyl, methyl, ethyl, isopropyl, n-propyl, or tert-butyl; or $R^{1a}$ and $R^{1b}$ are taken together to form an oxo group;
each occurrence of $R^{1c}$ is independently hydrogen, fluoro, or methyl; and
each occurrence of $R^{1d}$ is independently hydrogen, fluoro, trifluoromethyl, methyl, ethyl, isopropyl, n-propyl, or tert-butyl;
wherein G has the values described herein.
In such embodiments, when $R^{1a}$ and $R^{1b}$ are not taken together to form an oxo group;
G is —V$_1$—R$^3$, or —V$_1$-L$_1$-R$^3$;
V$_1$ is —C(O)—;
L$_1$ is —CH$_2$—;
$R^{1a}$ is hydrogen;
$R^{1b}$ is hydrogen, fluoro, or methyl;
$R^{1c}$ is hydrogen; and each occurrence of $R^{1d}$ is independently hydrogen, fluoro, or methyl;
wherein $R^3$ has the values described herein.
In such embodiments, where $R^{1a}$ and $R^{1b}$ are taken together to form an oxo group;
G is —$R^3$, or -$L_1$-$R^3$;
$R^{1c}$ is hydrogen; and
each occurrence of $R^{1d}$ is independently hydrogen, fluoro, or methyl;
wherein $L_1$ and $R^3$ have the values described herein.
In certain embodiments, the compound of formula (I) is represented by:

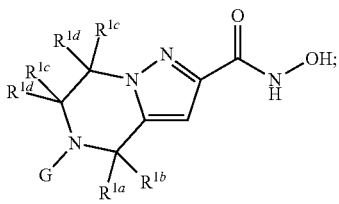
(I-b)

wherein:
$R^{1a}$ is hydrogen, fluoro, or methyl;
$R^{1b}$ is hydrogen, fluoro, trifluoromethyl, methyl, ethyl, isopropyl, n-propyl, or tert-butyl; or $R^{1a}$ and $R^{1b}$ are taken together to form an oxo group;
each occurrence of $R^{1c}$ is independently hydrogen, fluoro, or methyl; and
each occurrence of $R^{1d}$ is independently hydrogen, fluoro, trifluoromethyl, methyl, ethyl, isopropyl, n-propyl, or tert-butyl;
wherein G has the values described herein.
In such embodiments, when $R^{1a}$ and $R^{1b}$ are not taken together to form an oxo group;
G is —$V_1$—$R^3$, or —$V_1$-$L_1$-$R^3$;
$V_1$ is —C(O)—;
$L_1$ is —$CH_2$—;
$R^{1a}$ is hydrogen;
$R^{1b}$ is hydrogen, fluoro, or methyl;
$R^{1c}$ is hydrogen; and
each occurrence of $R^{1d}$ is independently hydrogen, fluoro, or methyl;
wherein $R^3$ has the values described herein.
In such embodiments, where $R^{1a}$ and $R^{1b}$ are taken together to form an oxo group;
G is —$R^3$, or -$L_1$-$R^3$;
$R^{1c}$ is hydrogen; and
each occurrence of $R^{1d}$ is independently hydrogen, fluoro, or methyl;
wherein $L_1$ and $R^3$ have the values described herein.
In certain embodiments, the compound of formula (I) is represented by:

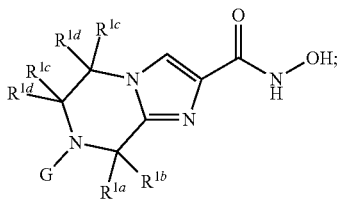
(I-c)

wherein:
$R^{1a}$ is hydrogen, fluoro, or methyl;
$R^{1b}$ is hydrogen, fluoro, trifluoromethyl, methyl, ethyl, isopropyl, n-propyl, or tert-butyl; or $R^{1a}$ and $R^{1b}$ are taken together to form an oxo group;
each occurrence of $R^{1c}$ is independently hydrogen, fluoro, or methyl; and
each occurrence of $R^{1d}$ is independently hydrogen, fluoro, trifluoromethyl, methyl, ethyl, isopropyl, n-propyl, or tert-butyl;
wherein G has the values described herein.
In such embodiments, when $R^{1a}$ and $R^{1b}$ are not taken together to form an oxo group;
G is —$V_1$—$R^3$, or —$V_1$-$L_1$-$R^3$;
$V_1$ is —C(O)—;
$L_1$ is —$CH_2$—;
$R^{1a}$ is hydrogen;
$R^{1b}$ is hydrogen, fluoro, or methyl;
$R^{1c}$ is hydrogen; and
each occurrence of $R^{1d}$ is independently hydrogen, fluoro, or methyl;
wherein $R^3$ has the values described herein.
In such embodiments, where $R^{1a}$ and $R^{1b}$ are taken together to form an oxo group;
G is —$R^3$, or -$L_1$-$R^3$;
$R^{1c}$ is hydrogen; and
each occurrence of $R^{1d}$ is independently hydrogen, fluoro, or methyl;
wherein $L_1$ and $R^3$ have the values described herein.
In certain embodiments, the compound of formula (I) is represented by:

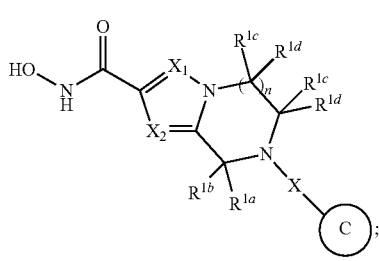
(V)

wherein:
$X_1$ is CH or N;
$X_2$ is CH or N;
n is 1-2;
$R^{1a}$ is hydrogen;
$R^{1b}$ is hydrogen, fluoro, or methyl;
$R^{1c}$ is hydrogen;
each occurrence of $R^{1d}$ is independently hydrogen, fluoro, or methyl; and
wherein Ring C and X have the values described herein.
In such embodiments:
n is 1;
$R^{1b}$ is hydrogen; and
$R^{1d}$ is hydrogen.
In certain embodiments, the compound of formula (I) is represented by:

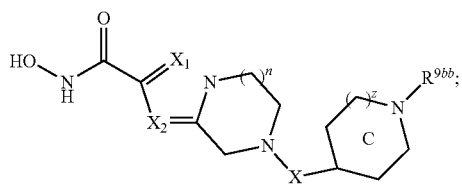

(VI)

wherein:
$X_1$ is CH or N;
$X_2$ is CH or N;
n is 1-2;
$R^{9bb}$ is hydrogen, methyl, ethyl, isopropyl, or tert-butoxycarbonyl;
X is —C(O)—, X-a, X-b, X-c, X-d, X-e, X-f, or X-g;
Ring C is unsubstituted or substituted with one occurrence of $R^{5b}$; and
z, $R^{5b}$, t, and $V_{2a}$ have the values described herein.
In certain such embodiments,
n is 1; and
$R^{5b}$ is methyl.
In certain embodiments, the compound of formula (I) is represented by:

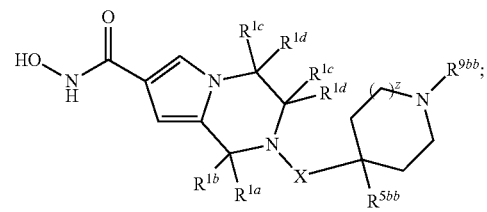

(VII-a)

wherein:
$R^{1a}$ is hydrogen;
$R^{1b}$ is hydrogen, fluoro, or methyl;
$R^{1c}$ is hydrogen;
each occurrence of $R^{1d}$ is independently hydrogen, fluoro, or methyl;
$R^{9bb}$ is hydrogen, methyl, ethyl, isopropyl, or tert-butoxycarbonyl;
X is —C(O)—, X-ii, X-xi, X-xii, X-xxiv, or X-xxv;
$R^{5bb}$ is hydrogen or methyl; and
z has the values described herein.
In certain such embodiments,
$R^{1b}$ is hydrogen;
$R^{1d}$ K is hydrogen;
$R^{5bb}$ is methyl; and
z is 1.
In certain embodiments, the compound of formula (I) is represented by:

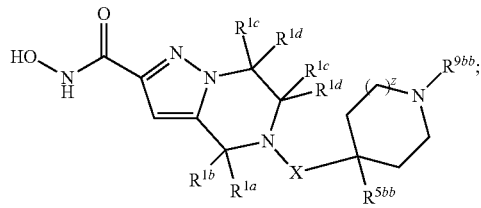

(VII-b)

wherein:
$R^{1a}$ is hydrogen;
$R^{1b}$ is hydrogen, fluoro, or methyl;
$R^{1c}$ is hydrogen;
each occurrence of $R^{1d}$ is independently hydrogen, fluoro, or methyl;
$R^{9bb}$ is hydrogen, methyl, ethyl, isopropyl, or tert-butoxycarbonyl;
X is —C(O)—, X-ii, X-xi, X-xii, X-xxii, X-xxiv, or X-xxv;
$R^{5bb}$ is hydrogen or methyl; and
z has the values described herein.
In certain such embodiments,
$R^{1b}$ is hydrogen;
$R^{1d}$ is hydrogen;
$R^{5bb}$ is methyl; and
z is 1.
In certain embodiments, the compound of formula (I) is represented by:

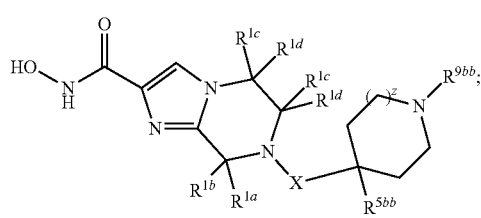

(VII-c)

wherein:
$R^{1a}$ is hydrogen;
$R^{1b}$ is hydrogen, fluoro, or methyl;
$R^{1c}$ is hydrogen;
each occurrence of $R^{1d}$ is independently hydrogen, fluoro, or methyl;
$R^{9bb}$ is hydrogen, methyl, ethyl, isopropyl, or tert-butoxycarbonyl;
X is —C(O)—, X-ii, X-xi, X-xii, X-xxii, X-xxiv, or X-xxv;
$R^{5bb}$ is hydrogen or methyl; and
z has the values described herein.
In certain such embodiments,
$R^{1b}$ is hydrogen;
$R^{1d}$ is hydrogen;
$R^{5bb}$ is methyl; and
z is 1.
In certain embodiments, the compound of formula (I) is represented by:

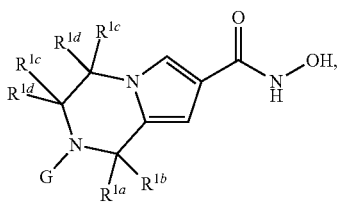
(I-a)

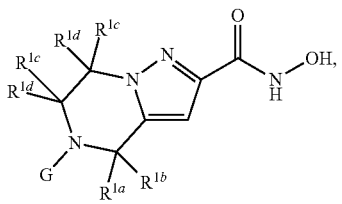
(I-b)

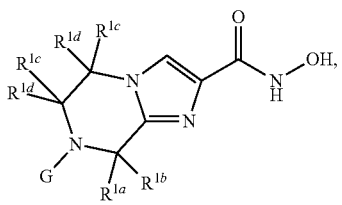
(I-c)

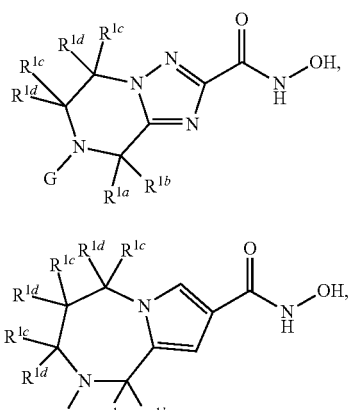
(I-d)

(I-e)

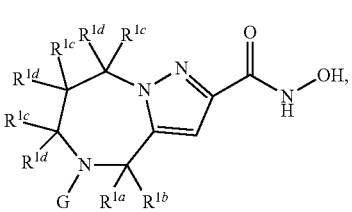
(I-f)

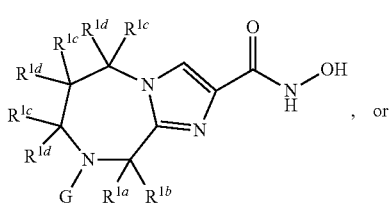
(I-g)

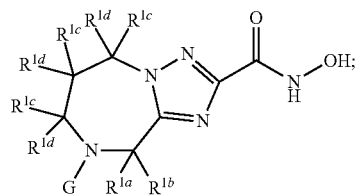
(I-h)

wherein:

G is —V$_1$—R$^3$, or —V$_1$-L$_1$-R$^3$;

V$_1$ is —C(O)—;

L$_1$ is —CH$_2$—;

R$^{1a}$ is hydrogen;

R$^{1b}$ is hydrogen, fluoro, or methyl;

R$^{1c}$ is hydrogen; and each occurrence of R$^{1d}$ is independently hydrogen, fluoro, or methyl;

wherein R$^3$ has the values described herein.

In certain such embodiments, the compound of formula (I) is represented by formula (I-a). In certain such embodiments, the compound of formula (I) is represented by formula (I-b). In certain such embodiments, the compound of formula (I) is represented by formula (I-c). In certain such embodiments, the compound of formula (I) is represented by formula (I-d). In certain such embodiments, the compound of formula (I) is represented by formula (I-e). In certain such embodiments, the compound of formula (I) is represented by formula (I-f). In certain such embodiments, the compound of formula (I) is represented by formula (I-g). In certain such embodiments, the compound of formula (I) is represented by formula (I-h).

In certain such embodiments, the compound of formula (I) is represented by formula (I-a), wherein R$^{1b}$ is hydrogen, and R$^{1d}$ is hydrogen. In certain such embodiments, the compound of formula (I) is represented by formula (I-b), wherein R$^{1b}$ is hydrogen, and R$^{1d}$ is hydrogen. In certain such embodiments, the compound of formula (I) is represented by formula (I-c), wherein R$^{1b}$ is hydrogen, and R$^{1d}$ is hydrogen. In certain such embodiments, the compound of formula (I) is represented by formula (I-d), wherein R$^{1b}$ is hydrogen, and R$^{1d}$ is hydrogen. In certain such embodiments, the compound of formula (I) is represented by formula (I-e), wherein R$^{1b}$ is hydrogen, and R$^{1d}$ is hydrogen. In certain such embodiments, the compound of formula (I) is represented by formula (I-f), wherein R$^{1b}$ is hydrogen, and R$^{1d}$ is hydrogen. In certain such embodiments, the compound of formula (I) is represented by formula (I-g), wherein R$^{1b}$ is hydrogen, and R$^{1d}$ is hydrogen. In certain such embodiments, the compound of formula (I) is represented by formula (I-h), wherein R$^{1b}$ is hydrogen, and R$^{1d}$ is hydrogen.

In certain such embodiments, the compound of formula (I) is represented by:

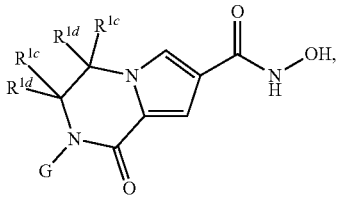
(I-i)

the compound of formula (I) is represented by formula (I-j). In certain such embodiments, the compound of formula (I) is represented by formula (I-k). In certain such embodiments, the compound of formula (I) is represented by formula (I-l). In certain such embodiments, the compound of formula (I) is represented by formula (I-m). In certain such embodiments, the compound of formula (I) is represented by formula (I-n). In certain such embodiments, the compound of formula (I) is represented by formula (I-o). In certain such embodiments, the compound of formula (I) is represented by formula (I-p).

In certain such embodiments, the compound of formula (I) is represented by formula (I-i), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-j), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-k), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-l), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-m), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-n), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-o), wherein $R^{1d}$ is hydrogen; and $L_1$ is —$CH_2$—, —$CH_2CH_2$—, or —$CH_2CH_2CH_2$—. In certain such embodiments, the compound of formula (I) is represented by formula (I-p), wherein $R^{1d}$ is hydrogen; and $L_1$ is —$CH_2$—, —$CH_2CH_2$—, or —$CH_2CH_2CH_2$—.

Representative examples of compounds of formula (I) are shown in Table 1:

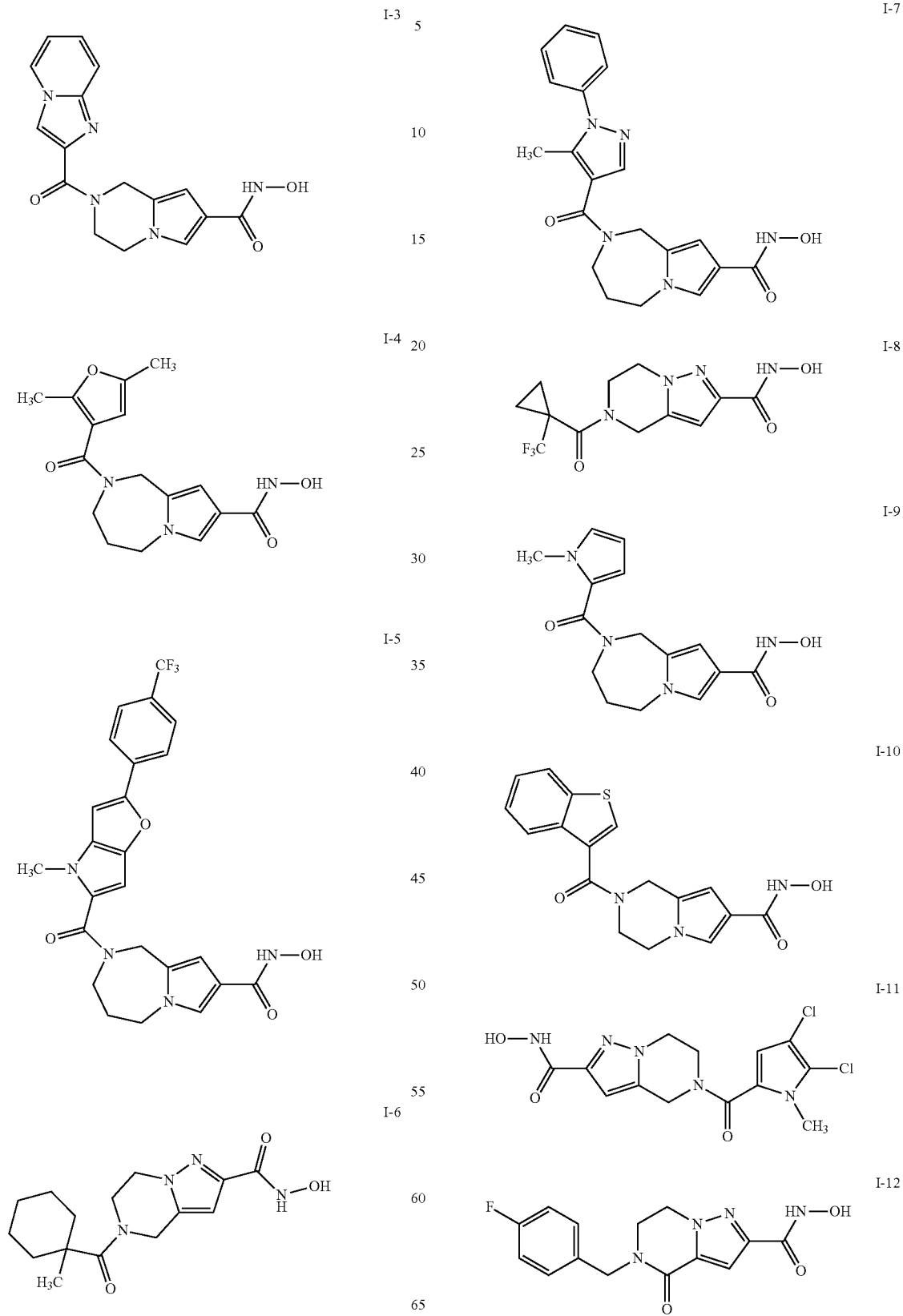

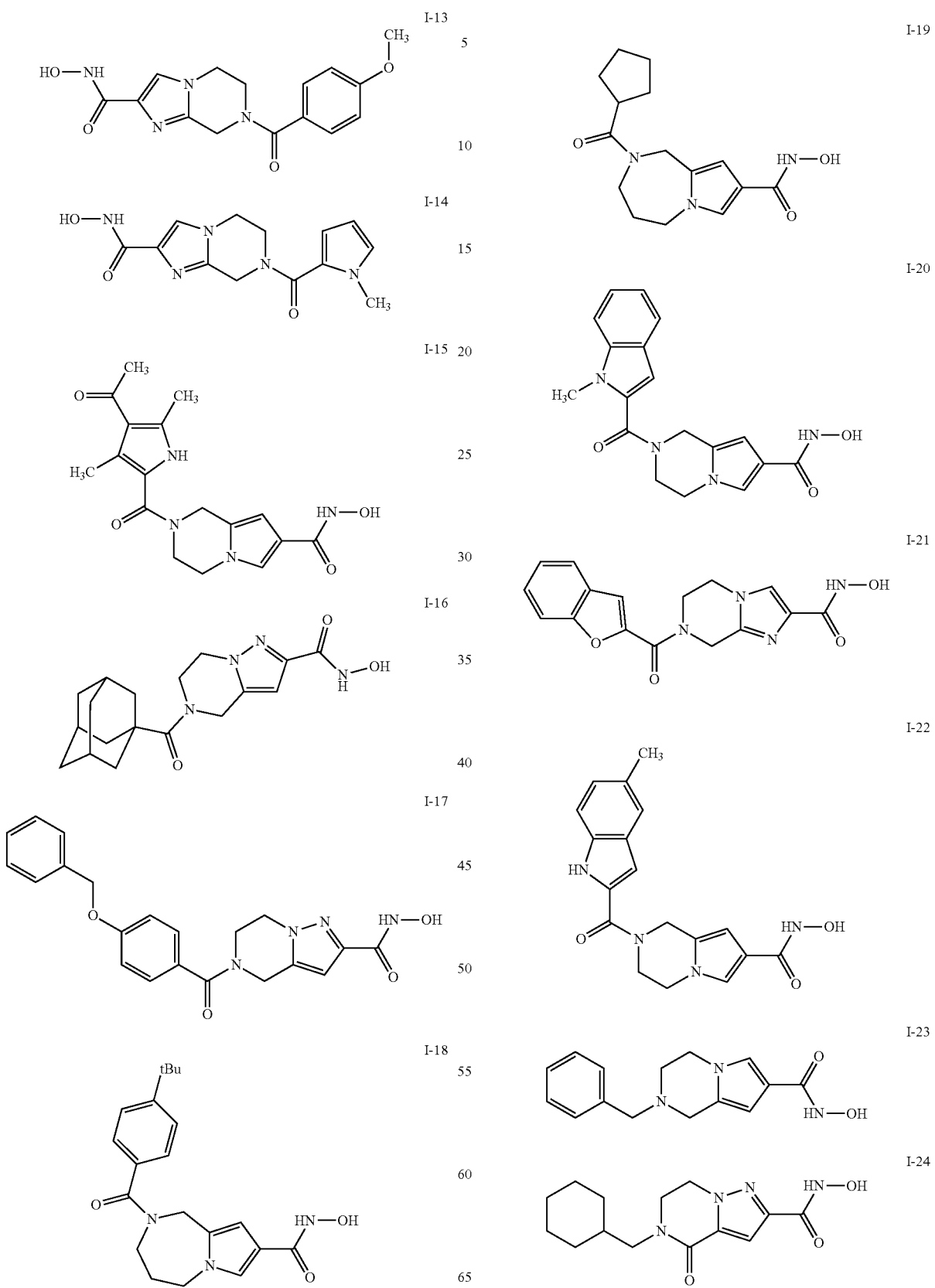

I-25 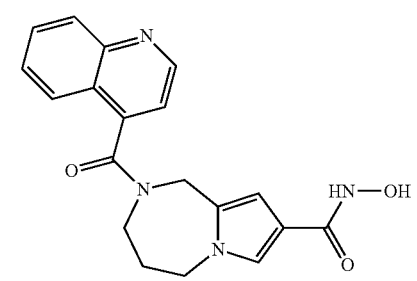 [SMILES: O=C(NO)c1cc2n(c1)CCCN(C(=O)c1ccnc3ccccc13)C2]
I-26 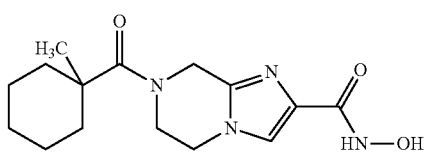 [SMILES: CC1(C(=O)N2CCn3cc(C(=O)NO)nc3C2)CCCCC1]
I-27 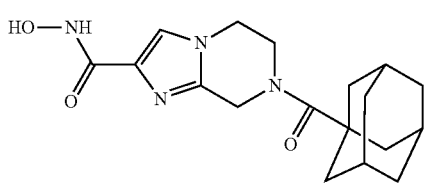 [SMILES: O=C(NO)c1cn2c(n1)CN(C(=O)C13CC4CC(CC(C4)C1)C3)CC2]
I-28 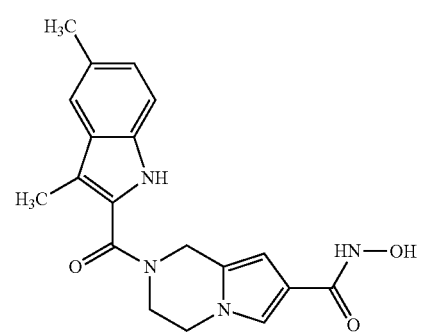 [SMILES: Cc1ccc2[nH]c(C(=O)N3CCn4cc(C(=O)NO)cc4C3)c(C)c2c1]
I-29 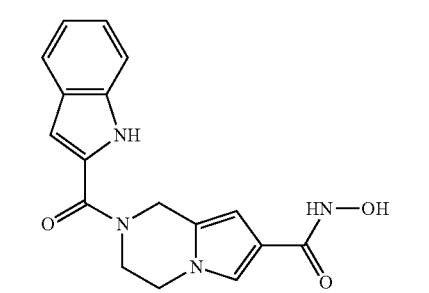 [SMILES: O=C(NO)c1cc2n(c1)CCN(C(=O)c1cc3ccccc3[nH]1)C2]
I-30 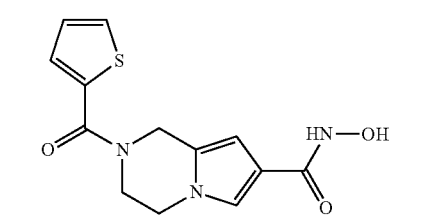 [SMILES: O=C(NO)c1cc2n(c1)CCN(C(=O)c1cccs1)C2]
I-31 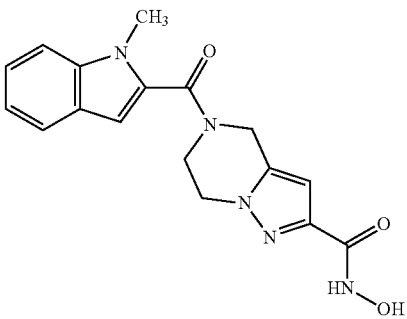 [SMILES: Cn1c(C(=O)N2CCn3nc(C(=O)NO)cc3C2)cc2ccccc21]
I-32 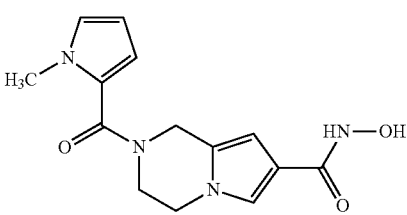 [SMILES: Cn1cccc1C(=O)N1CCn2cc(C(=O)NO)cc2C1]
I-33 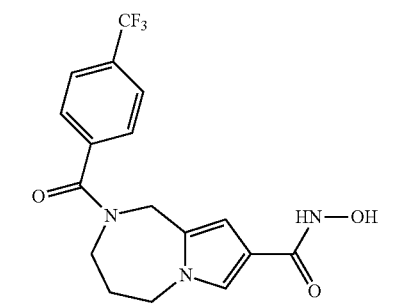 [SMILES: O=C(NO)c1cc2n(c1)CCCN(C(=O)c1ccc(C(F)(F)F)cc1)C2]
I-34 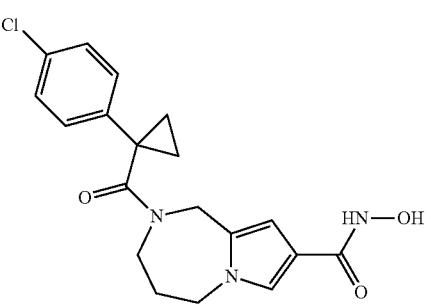 [SMILES: O=C(NO)c1cc2n(c1)CCCN(C(=O)C1(c3ccc(Cl)cc3)CC1)C2]
I-35 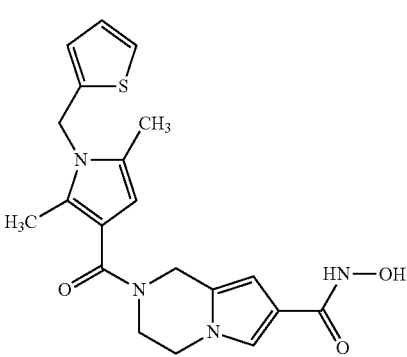 [SMILES: Cc1cc(C(=O)N2CCn3cc(C(=O)NO)cc3C2)c(C)n1Cc1cccs1]

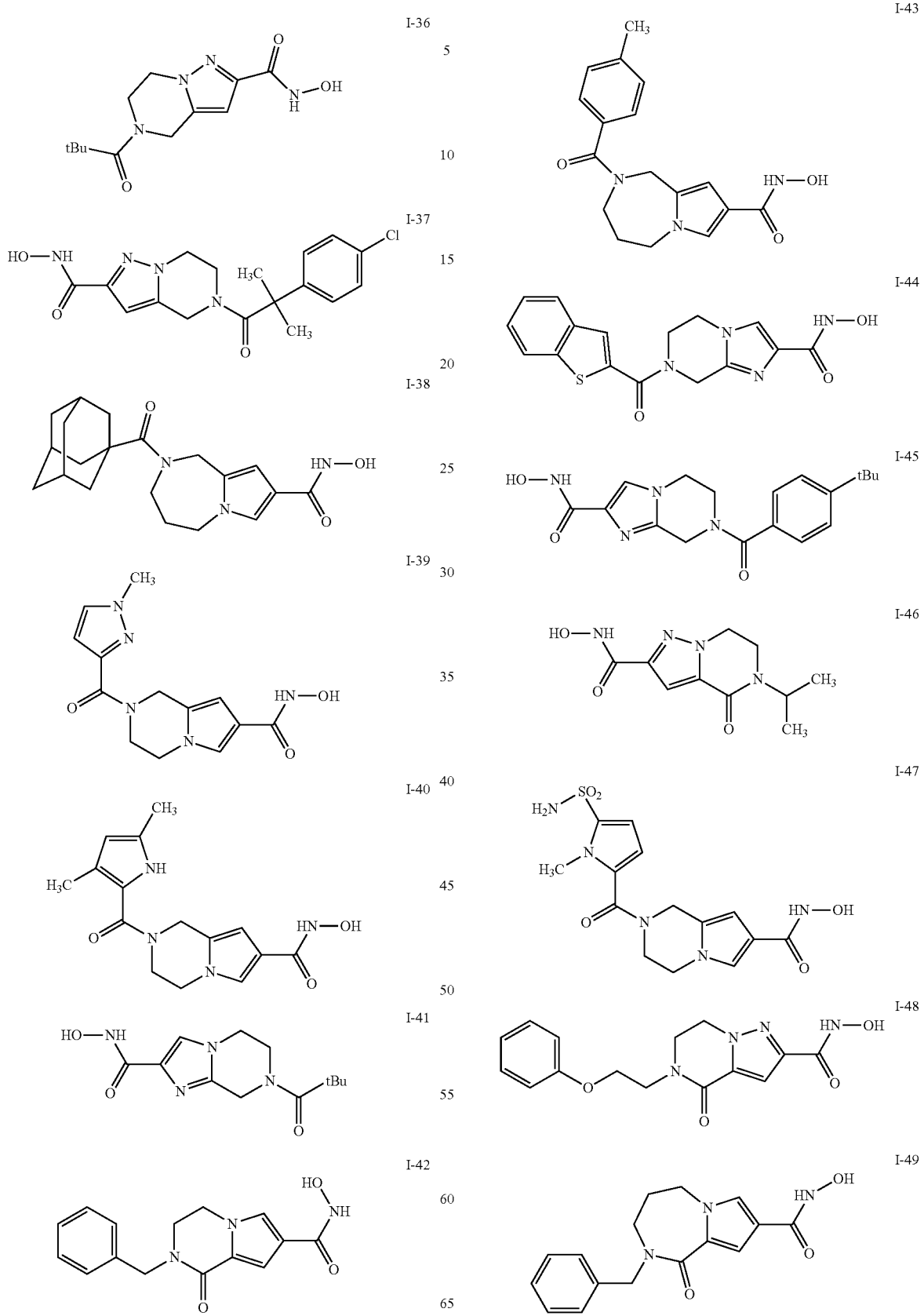

-continued
I-50
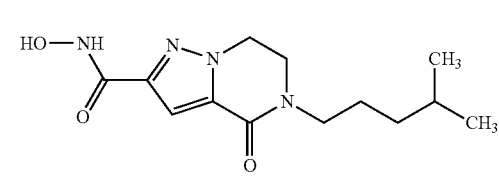 [SMILES: CC(C)CCCN1CCn2nc(C(=O)NO)cc2C1=O]
I-51
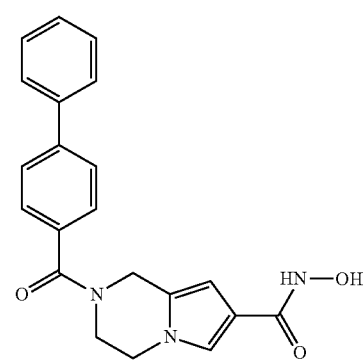 [SMILES: O=C(NO)c1cc2n(c1)CCN(C(=O)c1ccc(-c3ccccc3)cc1)C2]
I-52
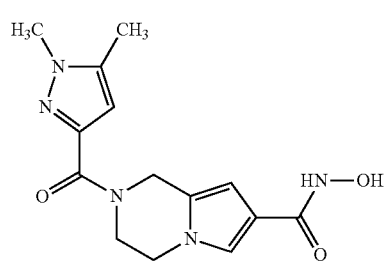 [SMILES: Cc1cc(C(=O)N2CCn3cc(C(=O)NO)cc3C2)nn1C]
I-53
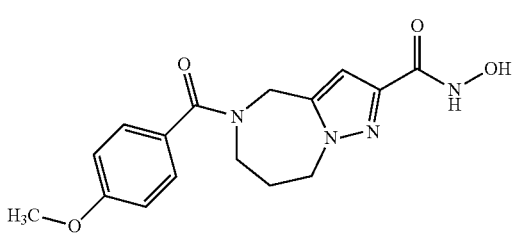 [SMILES: COc1ccc(C(=O)N2CCCn3nc(C(=O)NO)cc3C2)cc1]
I-54
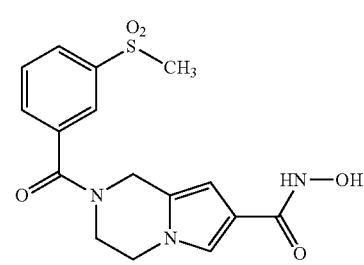 [SMILES: CS(=O)(=O)c1cccc(C(=O)N2CCn3cc(C(=O)NO)cc3C2)c1]
I-55
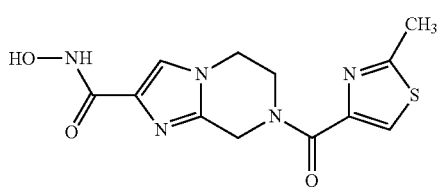 [SMILES: Cc1nc(C(=O)N2CCn3cc(C(=O)NO)nc3C2)cs1]
-continued
I-56
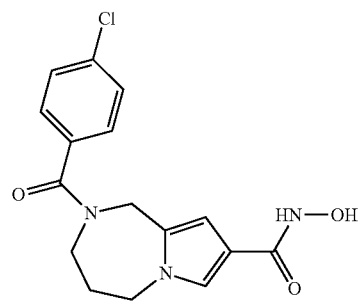 [SMILES: O=C(NO)c1cc2n(c1)CCCN(C(=O)c1ccc(Cl)cc1)C2]
I-57
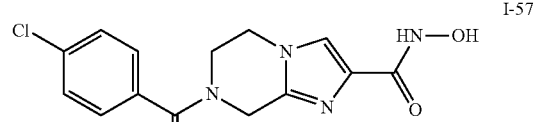
I-58
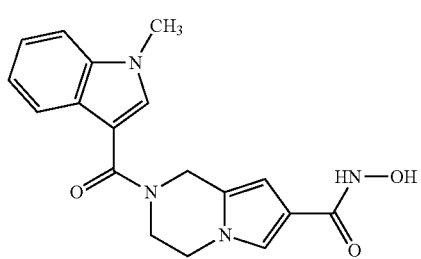 [SMILES: Cn1cc(C(=O)N2CCn3cc(C(=O)NO)cc3C2)c2ccccc21]
I-59
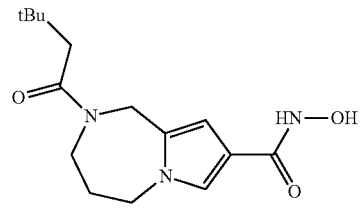 [SMILES: CC(C)(C)CC(=O)N1CCCn2cc(C(=O)NO)cc2C1]
I-60
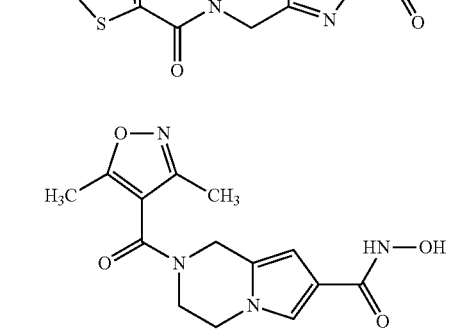
I-61
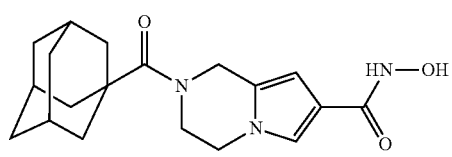 [SMILES: O=C(NO)c1cc2n(c1)CCN(C(=O)C13CC4CC(CC(C4)C1)C3)C2]
I-62

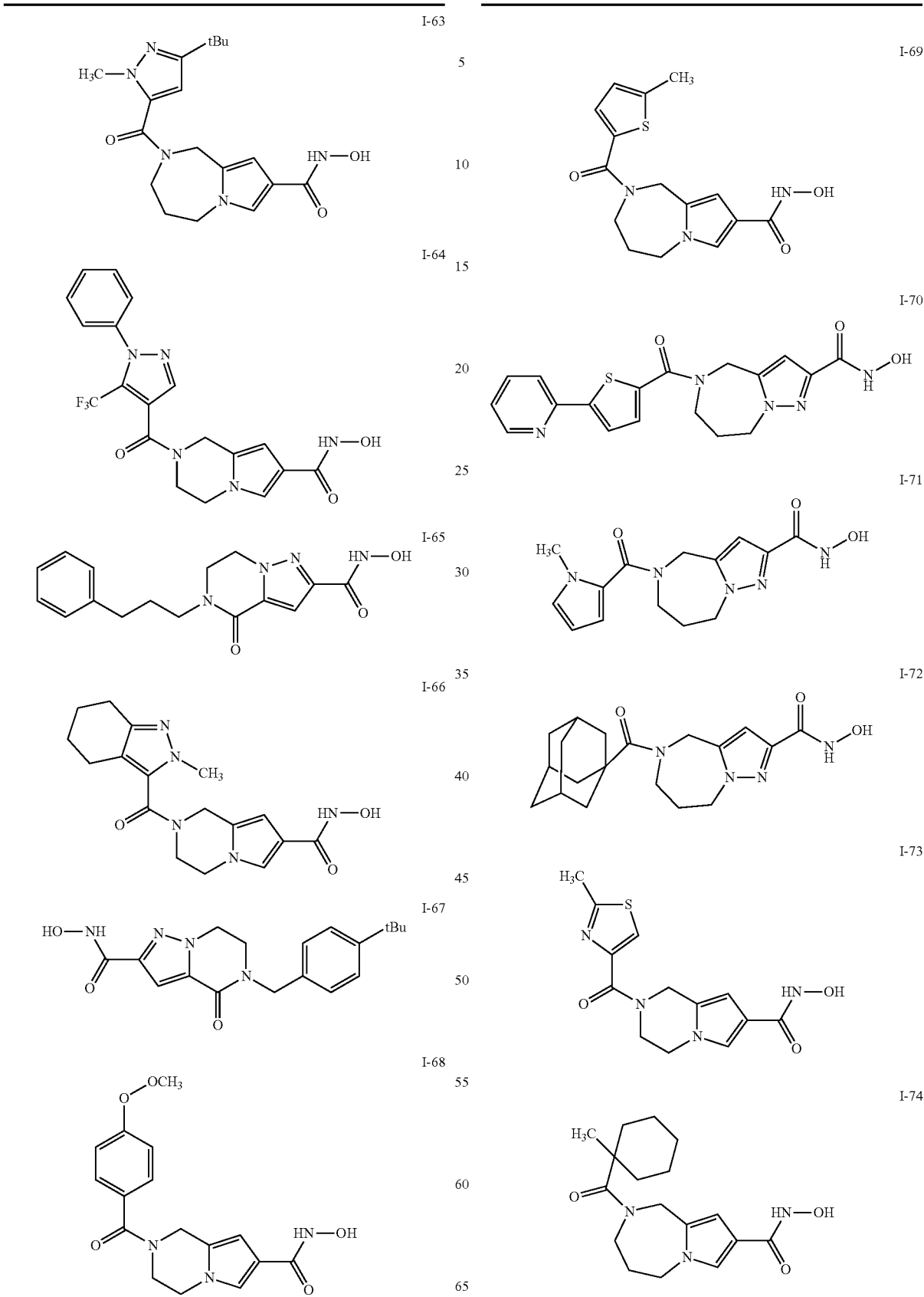

I-75 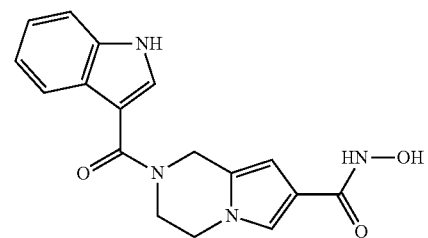 [SMILES: O=C(NO)c1cc2n(c1)CCN(C(=O)c1c[nH]c3ccccc13)C2]
I-76 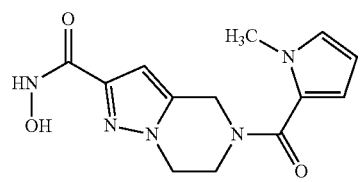 [SMILES: Cn1cccc1C(=O)N1CCn2nc(C(=O)NO)cc2C1]
I-77 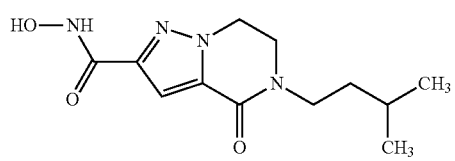
I-78 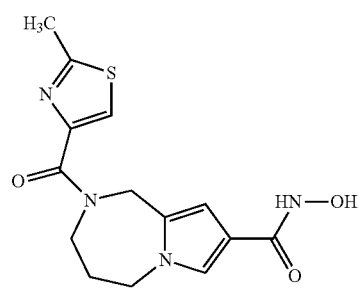 [SMILES: Cc1nc(C(=O)N2CCCn3cc(C(=O)NO)cc3C2)cs1]
I-79 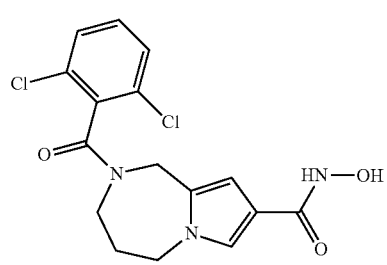 [SMILES: O=C(NO)c1cc2n(c1)CCCN(C(=O)c1c(Cl)cccc1Cl)C2]
I-80 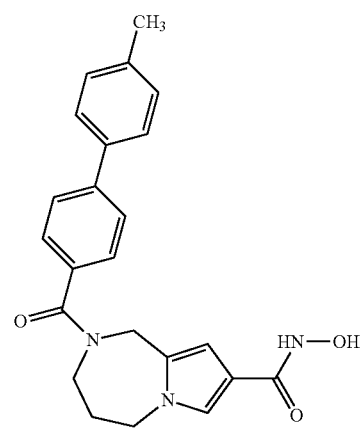 [SMILES: Cc1ccc(-c2ccc(C(=O)N3CCCn4cc(C(=O)NO)cc4C3)cc2)cc1]
I-81 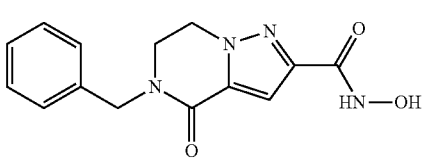 [SMILES: O=C(NO)c1cc2n(n1)CCN(Cc1ccccc1)C2=O]
I-82 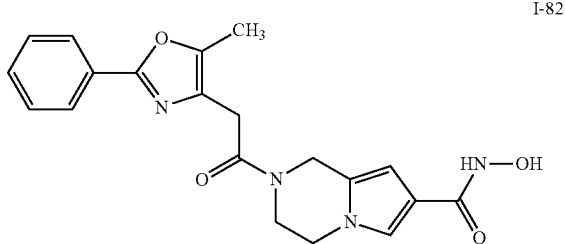
I-83 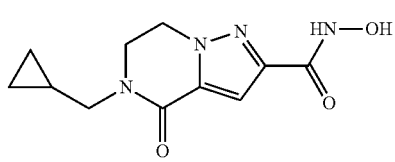 [SMILES: O=C(NO)c1cc2n(n1)CCN(CC1CC1)C2=O]
I-84 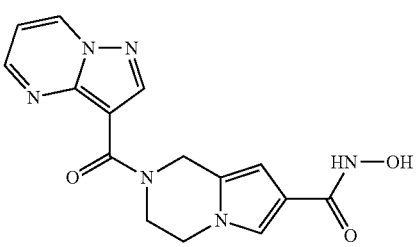 [SMILES: O=C(NO)c1cc2n(c1)CCN(C(=O)c1cnn3cccnc13)C2]
I-85 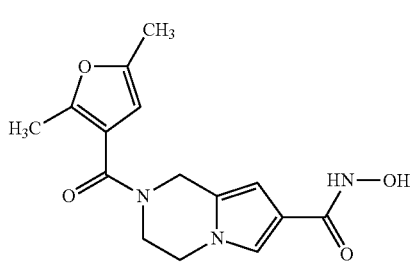 [SMILES: Cc1cc(C(=O)N2CCn3cc(C(=O)NO)cc3C2)c(C)o1]

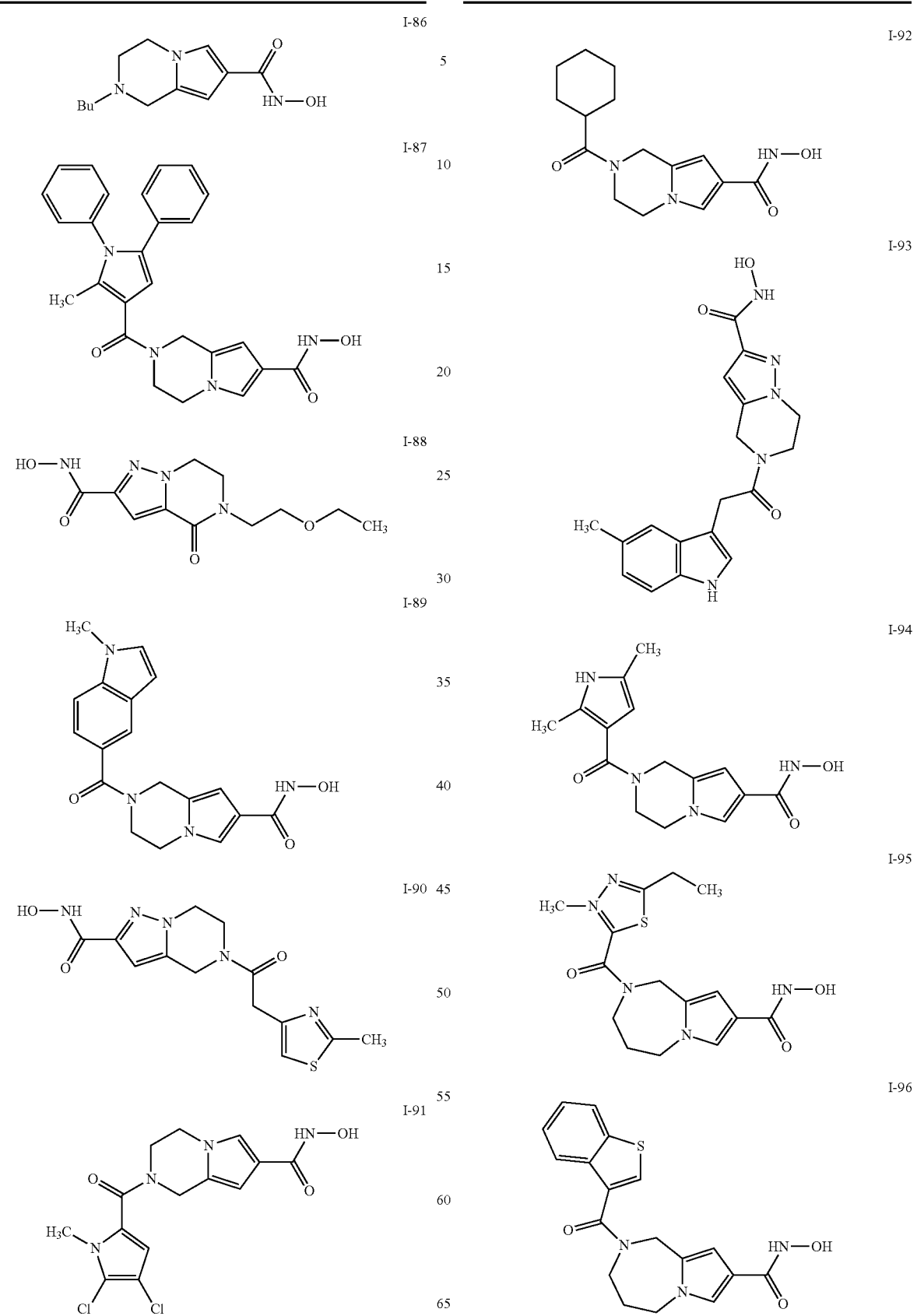

I-97
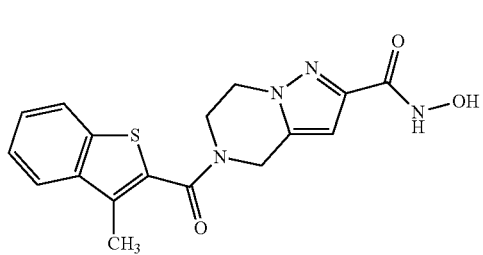 [SMILES: Cc1c(C(=O)N2CCn3nc(C(=O)NO)cc3C2)sc2ccccc12]
I-102
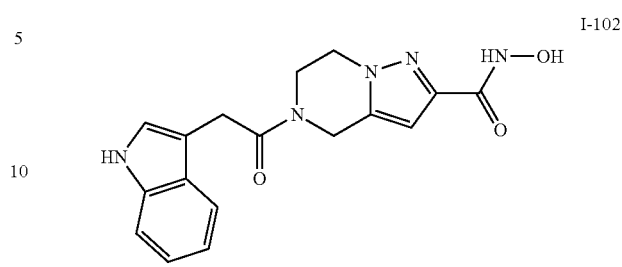
I-98
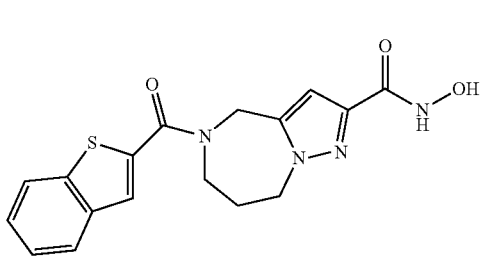 [SMILES: O=C(NO)c1cc2n(n1)CCCN(C(=O)c1cc3ccccc3s1)C2]
I-103
I-99
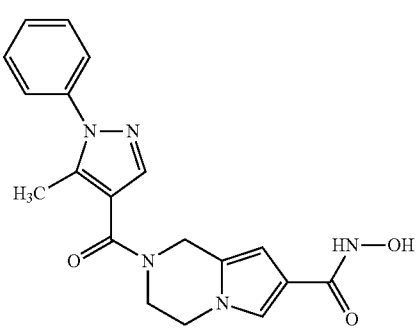 [SMILES: Cc1c(C(=O)N2CCn3cc(C(=O)NO)cc3C2)cnn1-c1ccccc1]
I-104
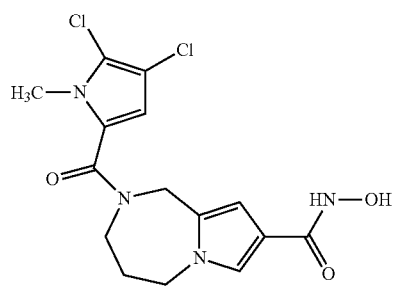
I-100
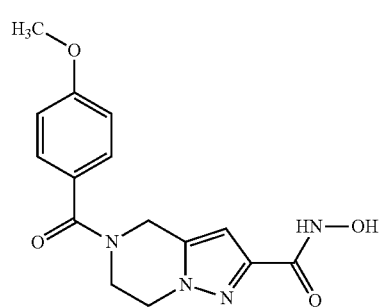 [SMILES: COc1ccc(C(=O)N2CCn3nc(C(=O)NO)cc3C2)cc1]
I-105
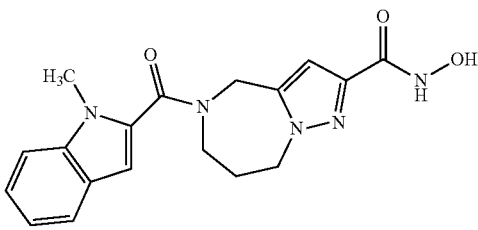
I-101
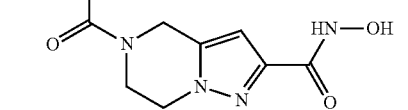
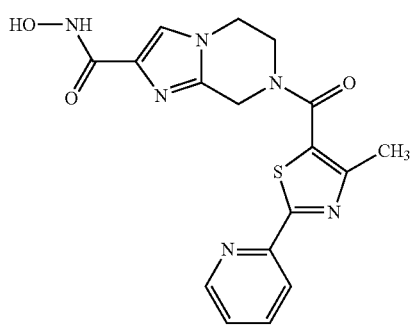 [SMILES: Cc1nc(-c2ccccn2)sc1C(=O)N1CCn2cc(C(=O)NO)nc2C1]
I-106
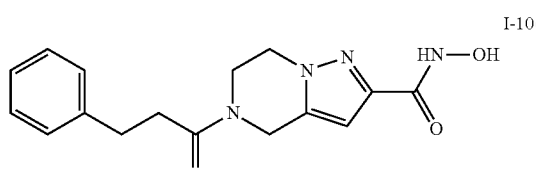
I-107
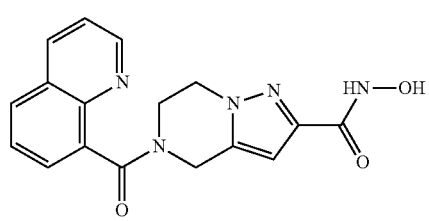 [SMILES: O=C(NO)c1cc2n(n1)CCN(C(=O)c1cccc3cccnc13)C2]

I-108 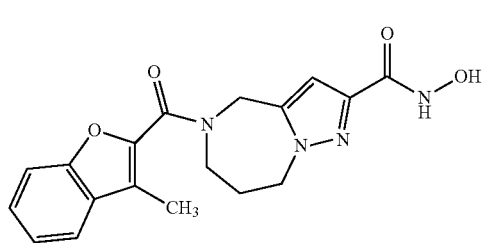 [SMILES: Cc1c(C(=O)N2CCCn3nc(C(=O)NO)cc3C2)oc2ccccc12]
I-109 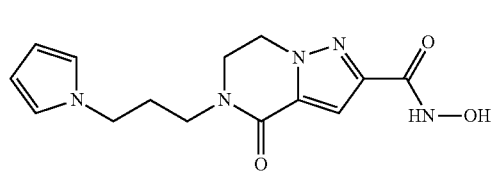 [SMILES: O=C(NO)c1cc2n(n1)CCN(CCCn1cccc1)C2=O]
I-110 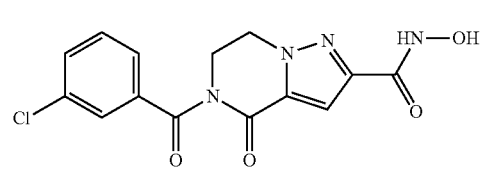 [SMILES: O=C(NO)c1cc2n(n1)CCN(C(=O)c1cccc(Cl)c1)C2=O]
I-111 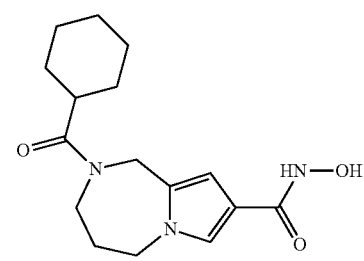 [SMILES: O=C(NO)c1cc2n(c1)CCCN(C(=O)C1CCCCC1)C2]
I-112 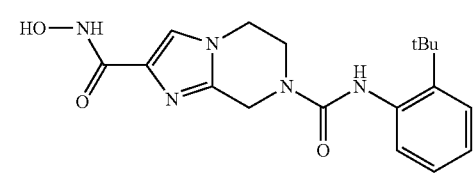 [SMILES: CC(C)(C)c1ccccc1NC(=O)N1CCn2cc(C(=O)NO)nc2C1]
I-113 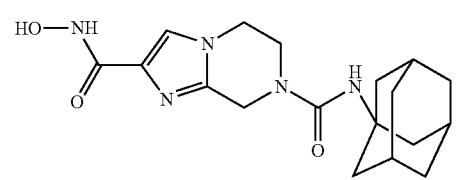 [SMILES: O=C(NO)c1cn2c(n1)CN(C(=O)NC13CC4CC(CC(C4)C1)C3)CC2]
I-114 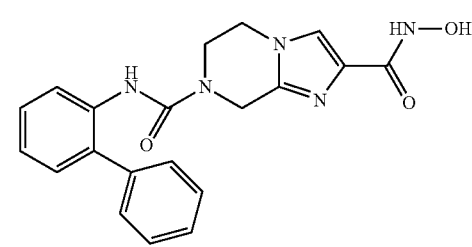 [SMILES: O=C(NO)c1cn2c(n1)CN(C(=O)Nc1ccccc1-c1ccccc1)CC2]
I-115 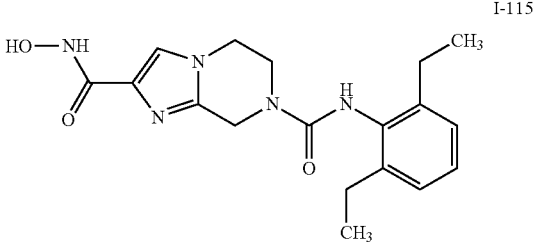
I-116 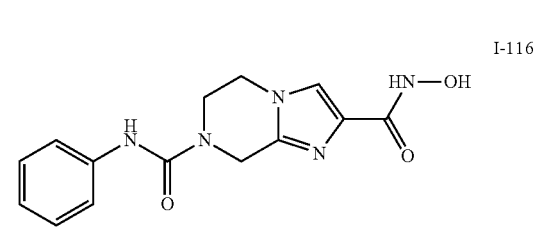
I-117 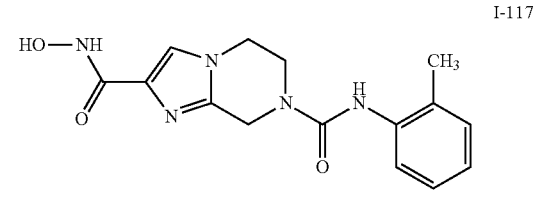
I-118 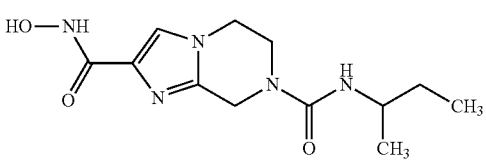 [SMILES: CCC(C)NC(=O)N1CCn2cc(C(=O)NO)nc2C1]
I-119 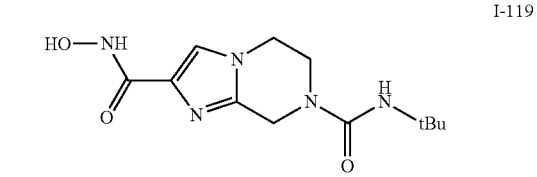
I-120 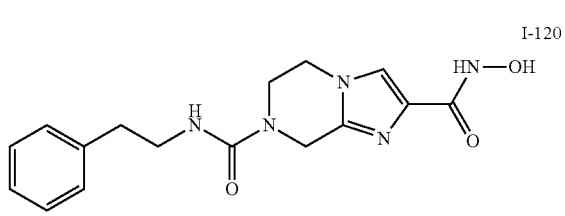
I-121 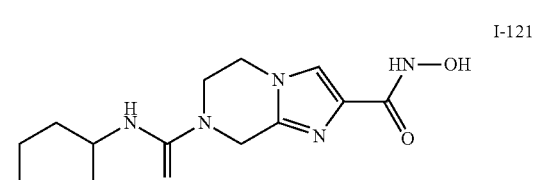

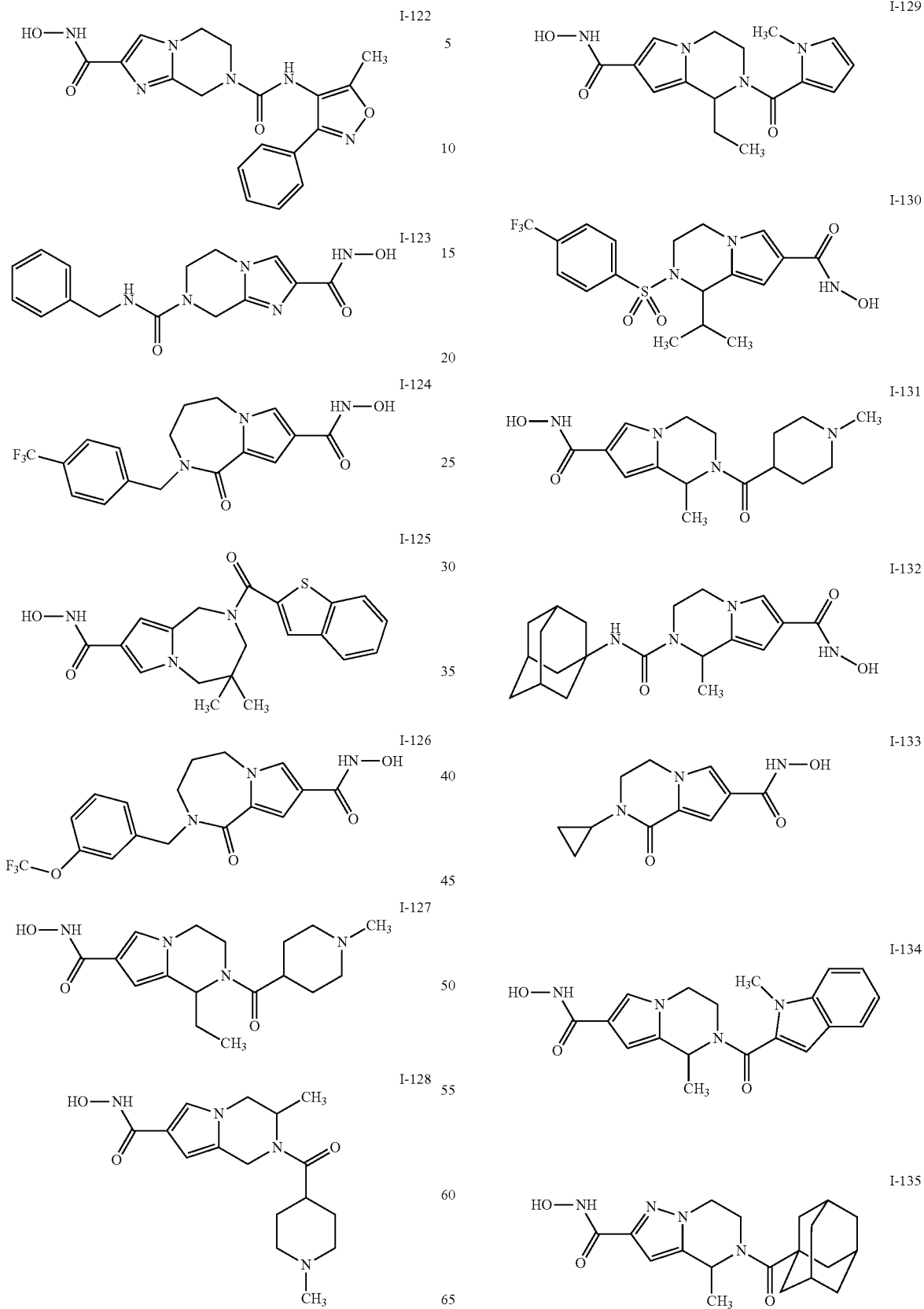

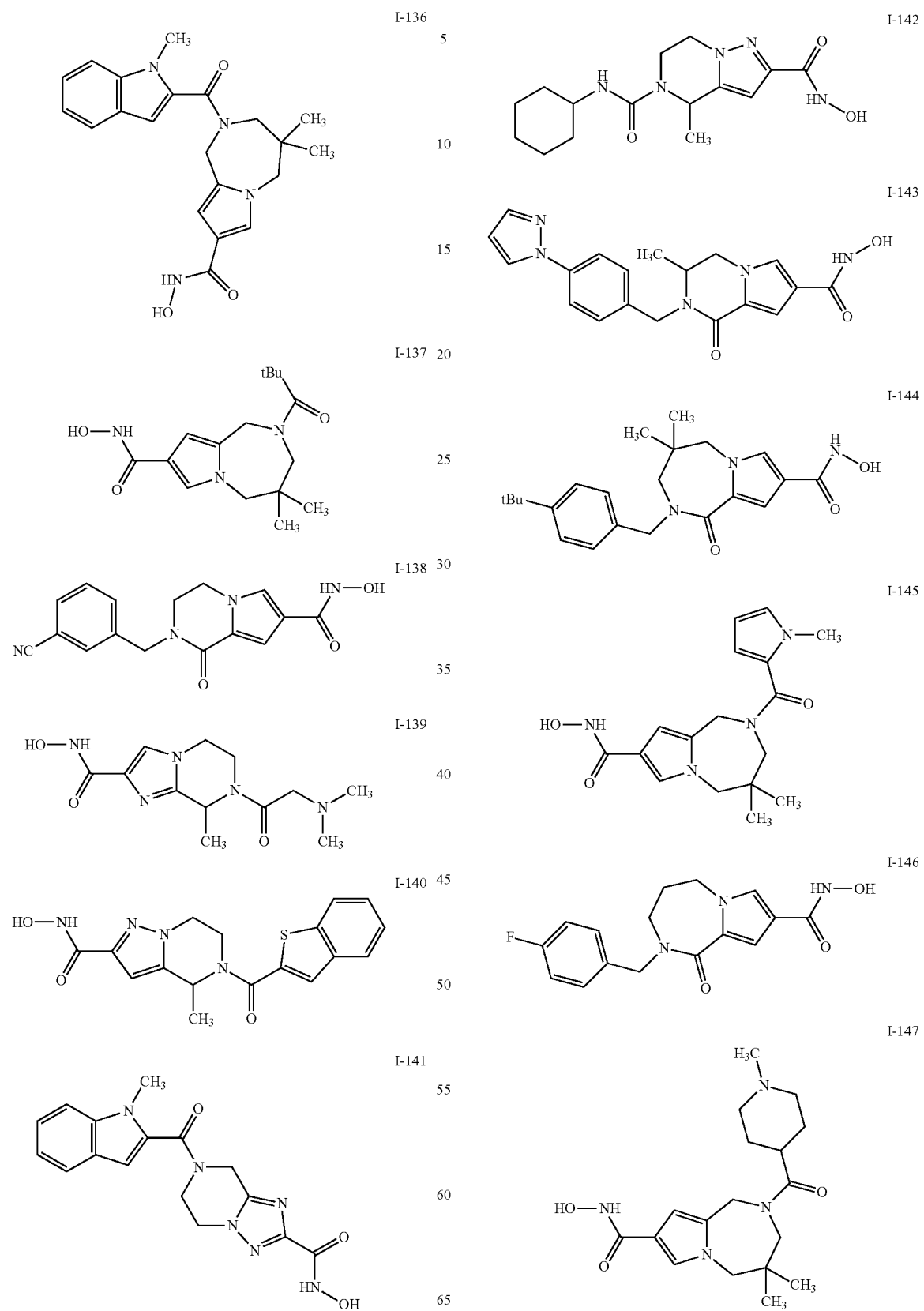

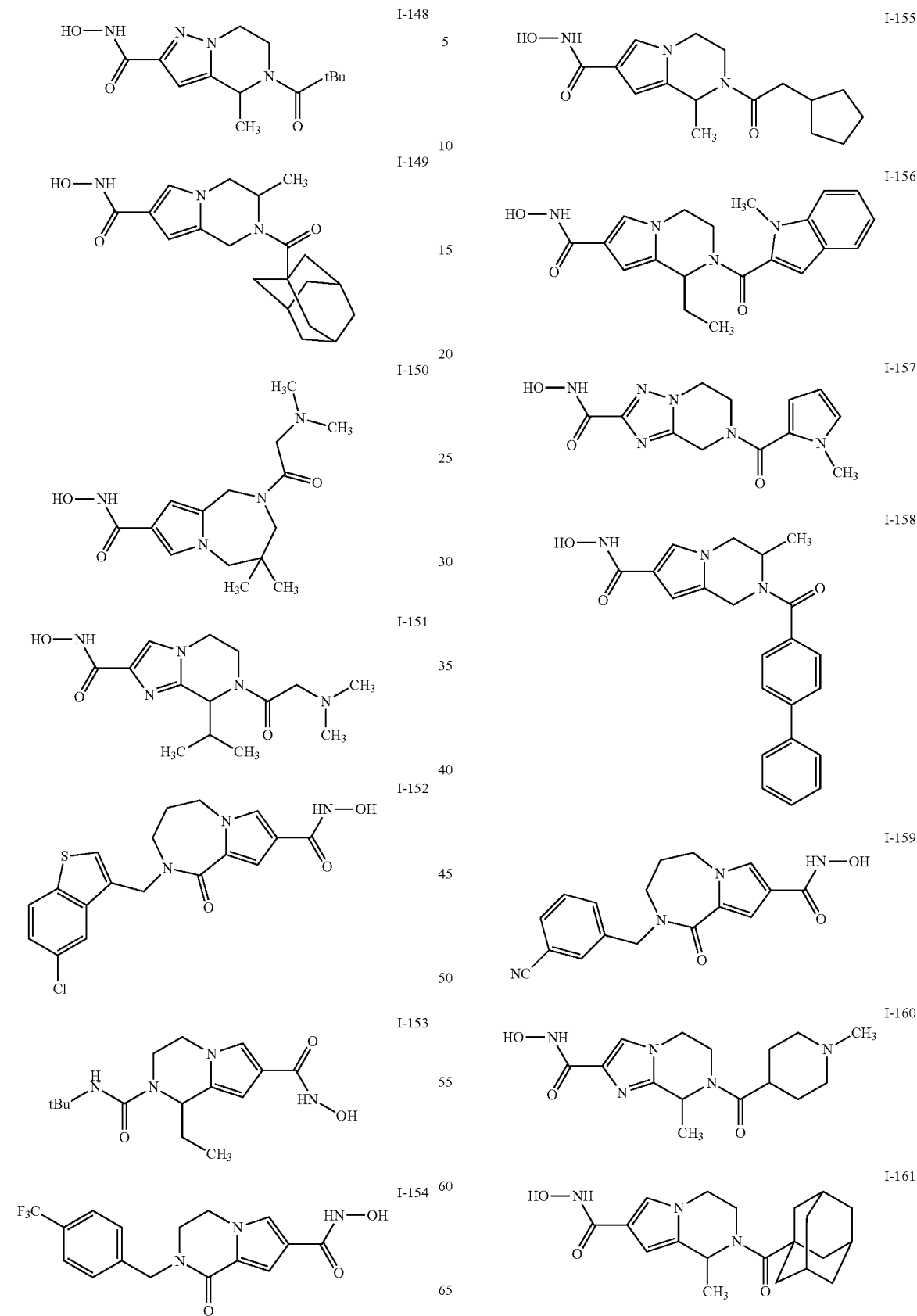

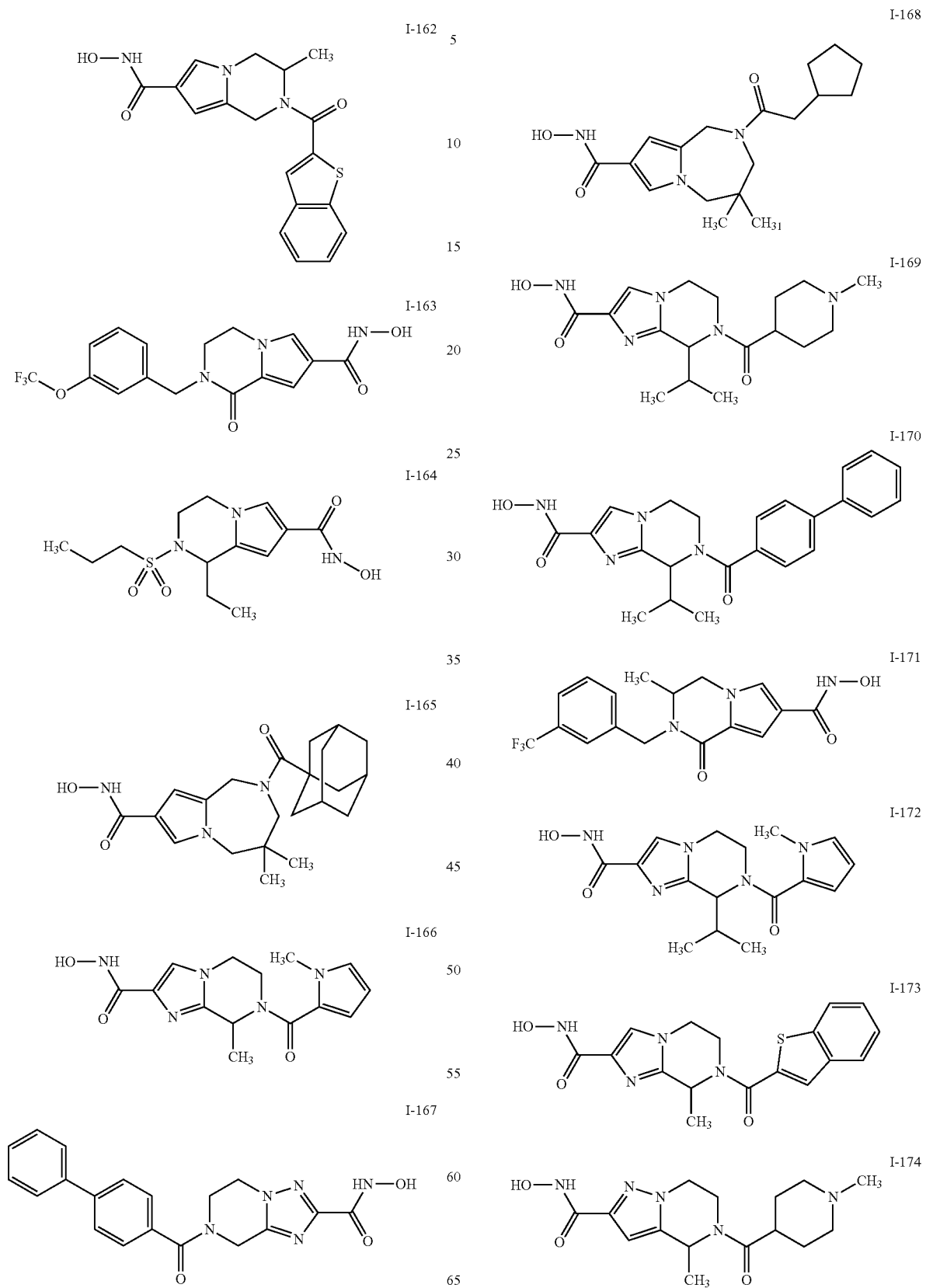

I-175 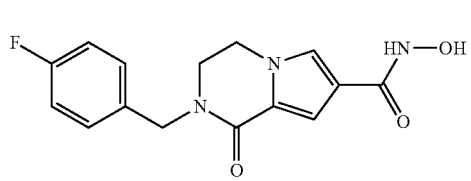
I-176 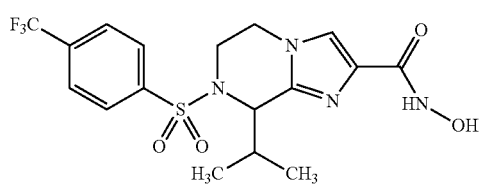 [SMILES: CC(C)C1c2cc(C(=O)NO)cn2CCN1S(=O)(=O)c1ccc(C(F)(F)F)cc1]
I-177 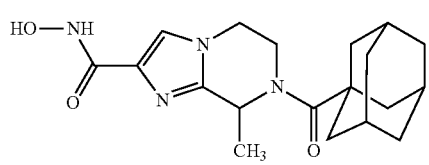 [SMILES: CC1c2nc(C(=O)NO)cn2CCN1C(=O)C12CC3CC(CC(C3)C1)C2]
I-178 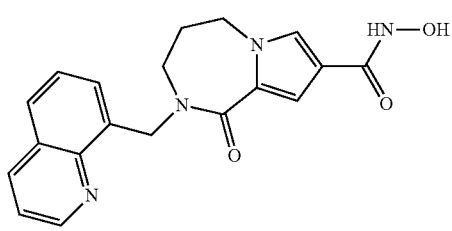 [SMILES: O=C(NO)c1cc2n(c1)CCCN(Cc1cccc3cccnc13)C2=O]
I-179 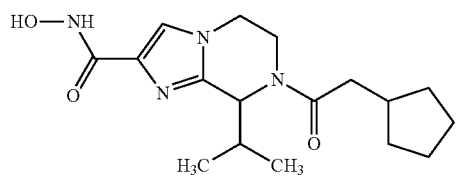 [SMILES: CC(C)C1c2nc(C(=O)NO)cn2CCN1C(=O)CC1CCCC1]
I-180 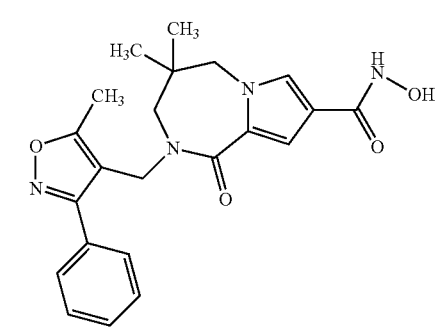 [SMILES: Cc1onc(-c2ccccc2)c1CN1CC(C)(C)Cn2cc(C(=O)NO)cc2C1=O]
I-181 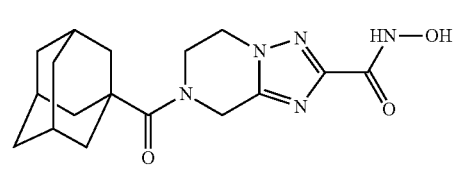 [SMILES: O=C(NO)c1nc2n(n1)CCN(C(=O)C13CC4CC(CC(C4)C1)C3)C2]
I-182 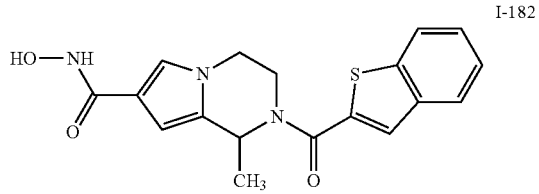
I-183 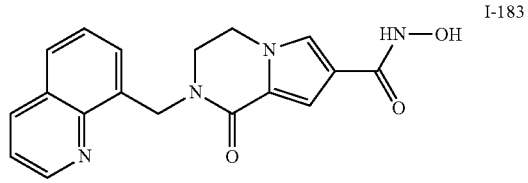
I-184 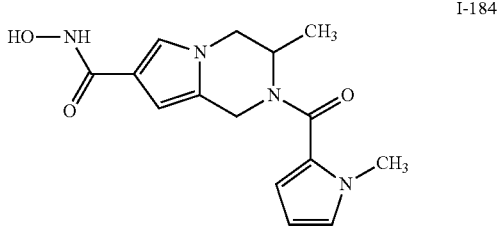
I-185 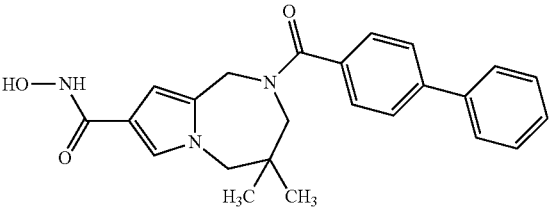 [SMILES: CC1(C)CN(C(=O)c2ccc(-c3ccccc3)cc2)Cc2cc(C(=O)NO)cn2C1]
I-186 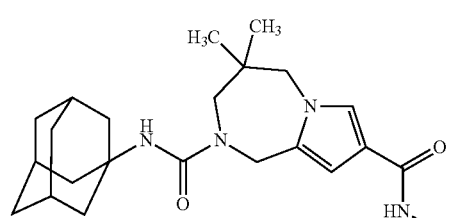
I-187 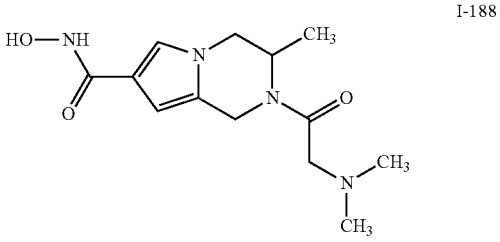
I-188

I-189 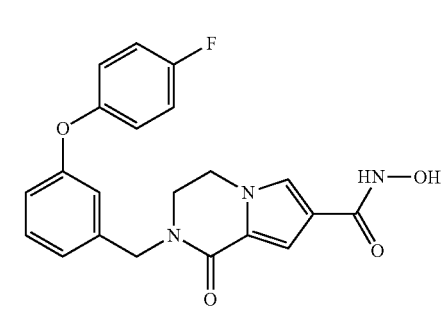 [SMILES: O=C(NO)c1cc2n(c1)CCN(Cc1cccc(Oc3ccc(F)cc3)c1)C2=O]
I-190 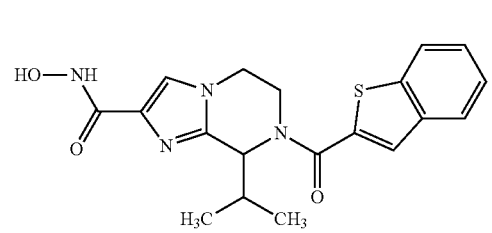 [SMILES: CC(C)C1c2nc(C(=O)NO)cn2CCN1C(=O)c1cc2ccccc2s1]
I-191 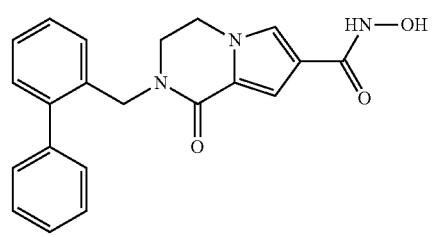 [SMILES: O=C(NO)c1cc2n(c1)CCN(Cc1ccccc1-c1ccccc1)C2=O]
I-192 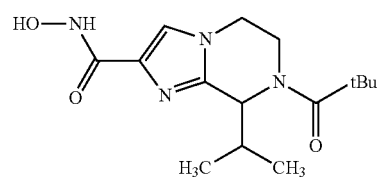 [SMILES: CC(C)C1c2nc(C(=O)NO)cn2CCN1C(=O)C(C)(C)C]
I-193 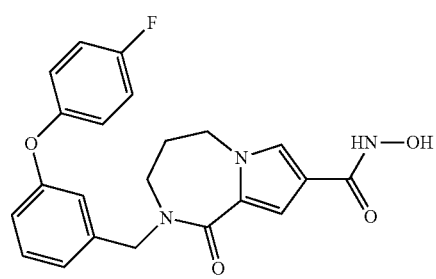 [SMILES: O=C(NO)c1cc2n(c1)CCCN(Cc1cccc(Oc3ccc(F)cc3)c1)C2=O]
I-194 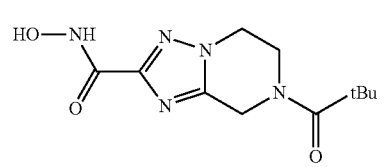 [SMILES: CC(C)(C)C(=O)N1CCn2nc(C(=O)NO)nc2C1]
I-195 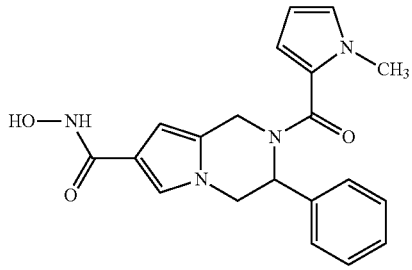 [SMILES: Cn1cccc1C(=O)N1Cc2cc(C(=O)NO)cn2CC1c1ccccc1]
I-196 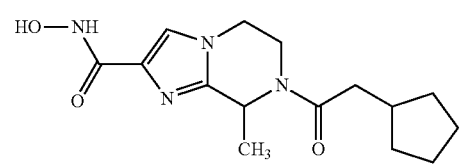 [SMILES: CC1c2nc(C(=O)NO)cn2CCN1C(=O)CC1CCCC1]
I-197 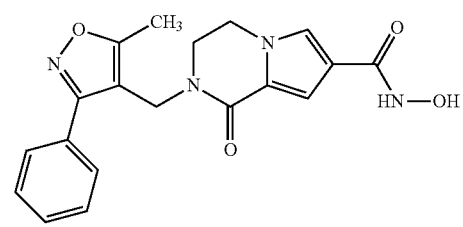 [SMILES: Cc1onc(-c2ccccc2)c1CN1CCn2cc(C(=O)NO)cc2C1=O]
I-198 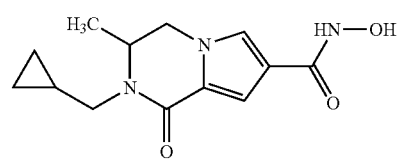 [SMILES: CC1Cn2cc(C(=O)NO)cc2C(=O)N1CC1CC1]
I-199 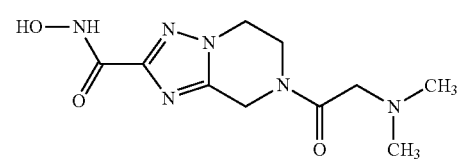
I-200 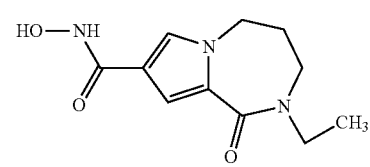 [SMILES: CCN1CCCn2cc(C(=O)NO)cc2C1=O]
I-201 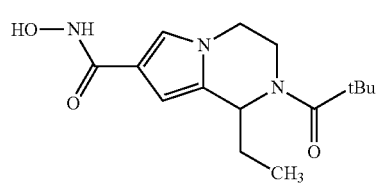 [SMILES: CCC1c2cc(C(=O)NO)cn2CCN1C(=O)C(C)(C)C]

| | |
|---|---|
| I-202 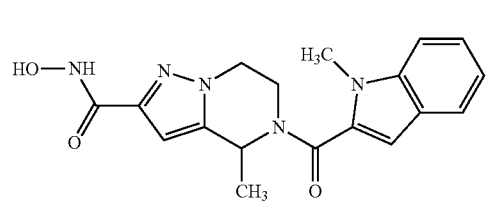 | I-210 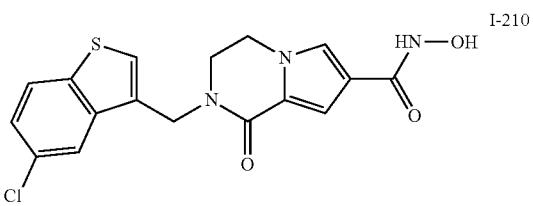 |
| I-203 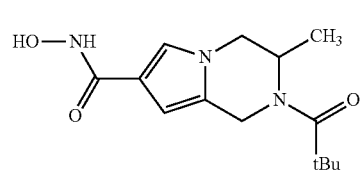 [SMILES: CC1Cn2cc(C(=O)NO)cc2CN1C(=O)C(C)(C)C] | I-211 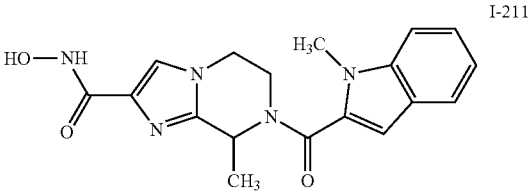 |
| I-204 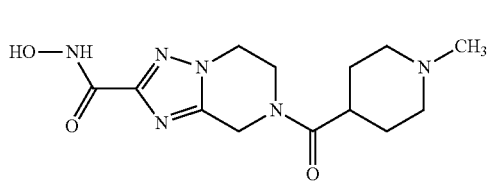 [SMILES: CN1CCC(C(=O)N2CCn3nc(C(=O)NO)nc3C2)CC1] | I-212 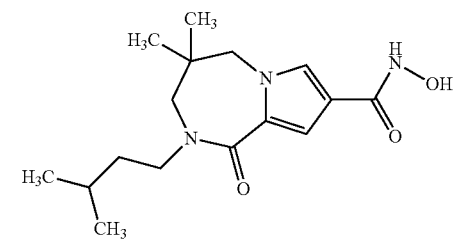 |
| I-205 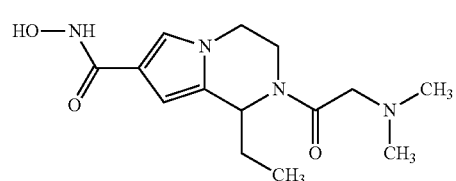 | I-213 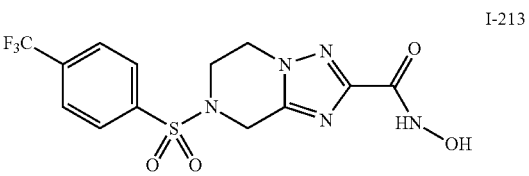 |
| I-206 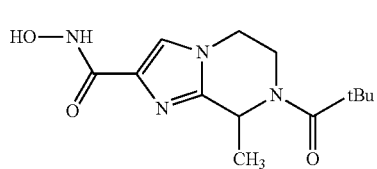 [SMILES: CC1c2nc(C(=O)NO)cn2CCN1C(=O)C(C)(C)C] | I-214 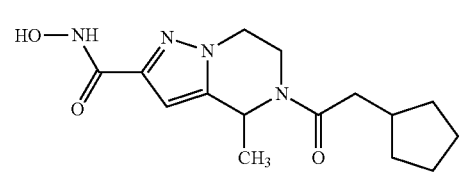 |
| I-207 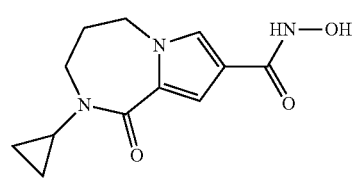 [SMILES: O=C(NO)c1cc2n(c1)CCCN(C1CC1)C2=O] | I-215 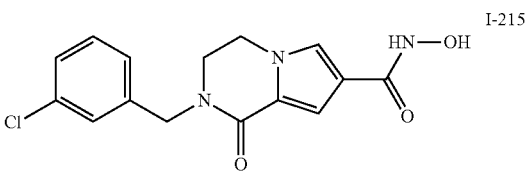 |
| I-208 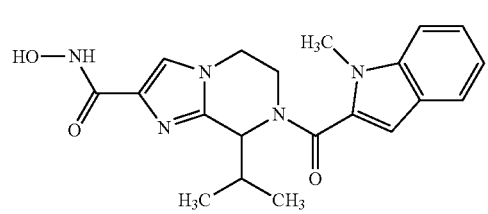 [SMILES: CC(C)C1c2nc(C(=O)NO)cn2CCN1C(=O)c1cc2ccccc2n1C] | I-216  |
| I-209 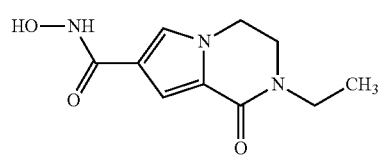 [SMILES: CCN1CCn2cc(C(=O)NO)cc2C1=O] | I-217 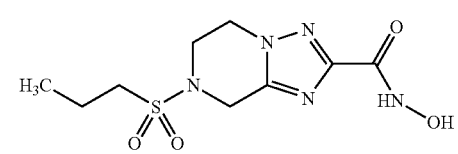 [SMILES: CCCS(=O)(=O)N1CCn2nc(C(=O)NO)nc2C1] |

-continued
I-218
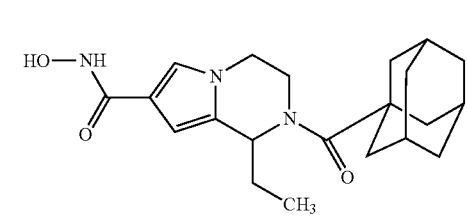 [SMILES: CCC1c2cc(C(=O)NO)cn2CCN1C(=O)C12CC3CC(CC(C3)C1)C2]
I-219
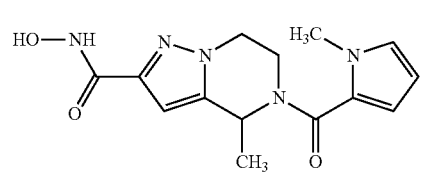
I-220
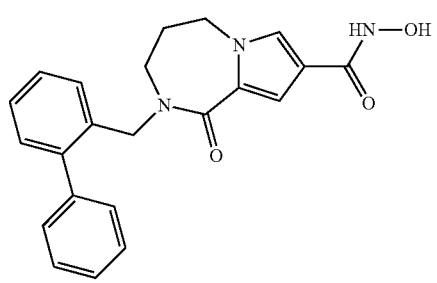 [SMILES: O=C(NO)c1cc2n(c1)CCCN(Cc1ccccc1-c1ccccc1)C2=O]
I-221
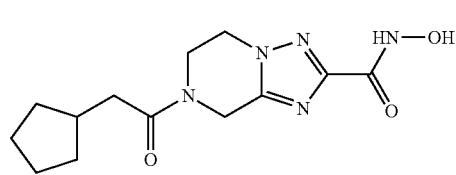 [SMILES: O=C(NO)c1nc2n(n1)CCN(C(=O)CC1CCCC1)C2]
I-222
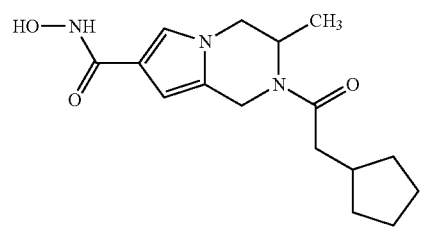 [SMILES: CC1Cn2cc(C(=O)NO)cc2CN1C(=O)CC1CCCC1]
I-223
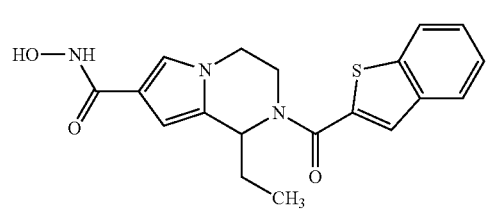 [SMILES: CCC1c2cc(C(=O)NO)cn2CCN1C(=O)c1cc2ccccc2s1]
-continued
I-224
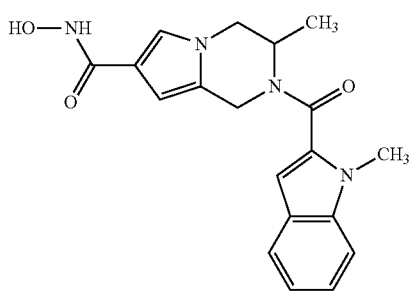 [SMILES: CC1Cn2cc(C(=O)NO)cc2CN1C(=O)c1cc2ccccc2n1C]
I-225
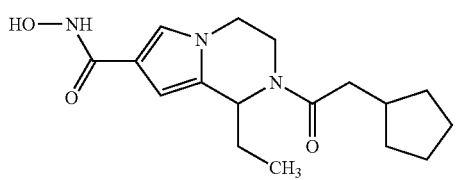 [SMILES: CCC1c2cc(C(=O)NO)cn2CCN1C(=O)CC1CCCC1]
I-226
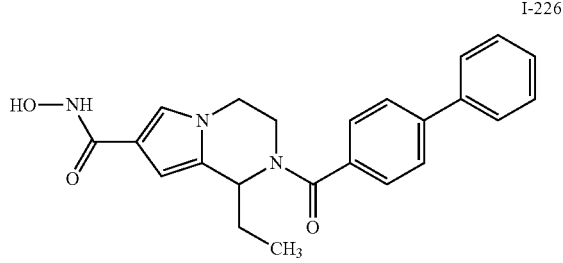
I-227
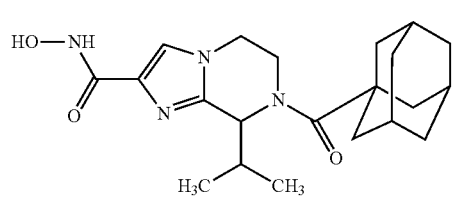 [SMILES: CC(C)C1c2nc(C(=O)NO)cn2CCN1C(=O)C12CC3CC(CC(C3)C1)C2]
I-228
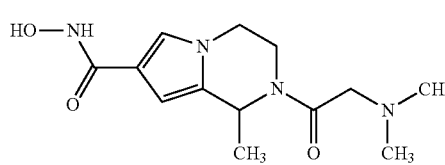
I-229
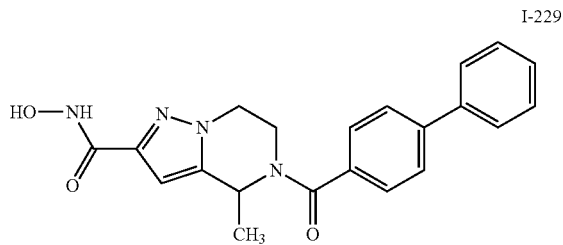

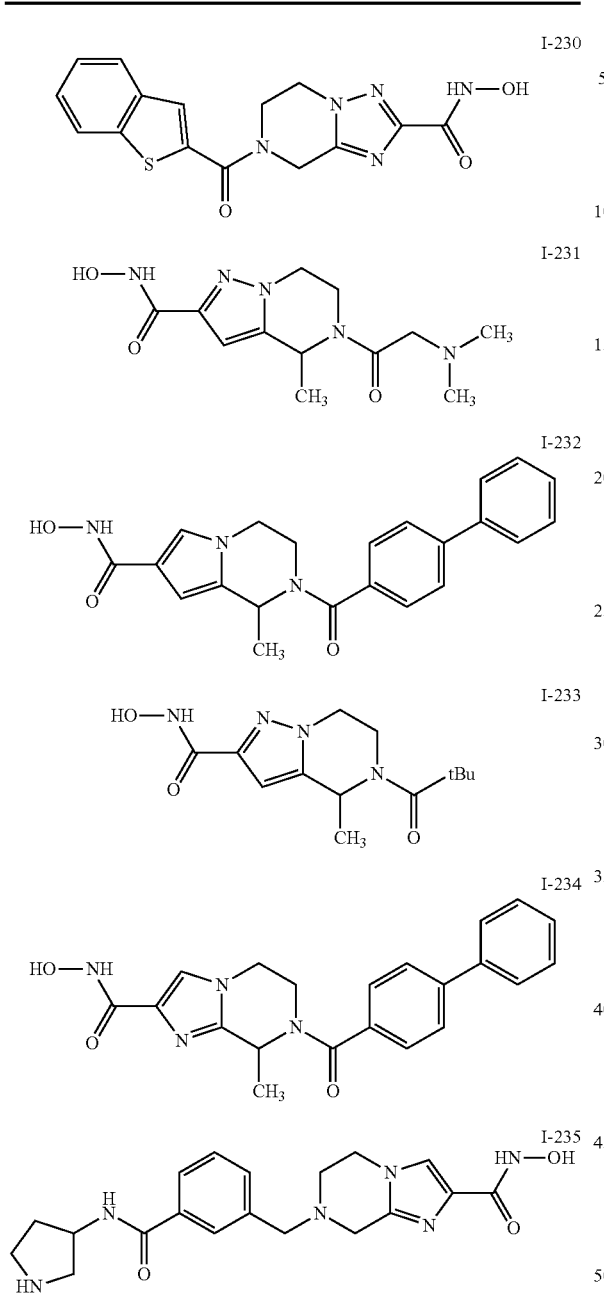
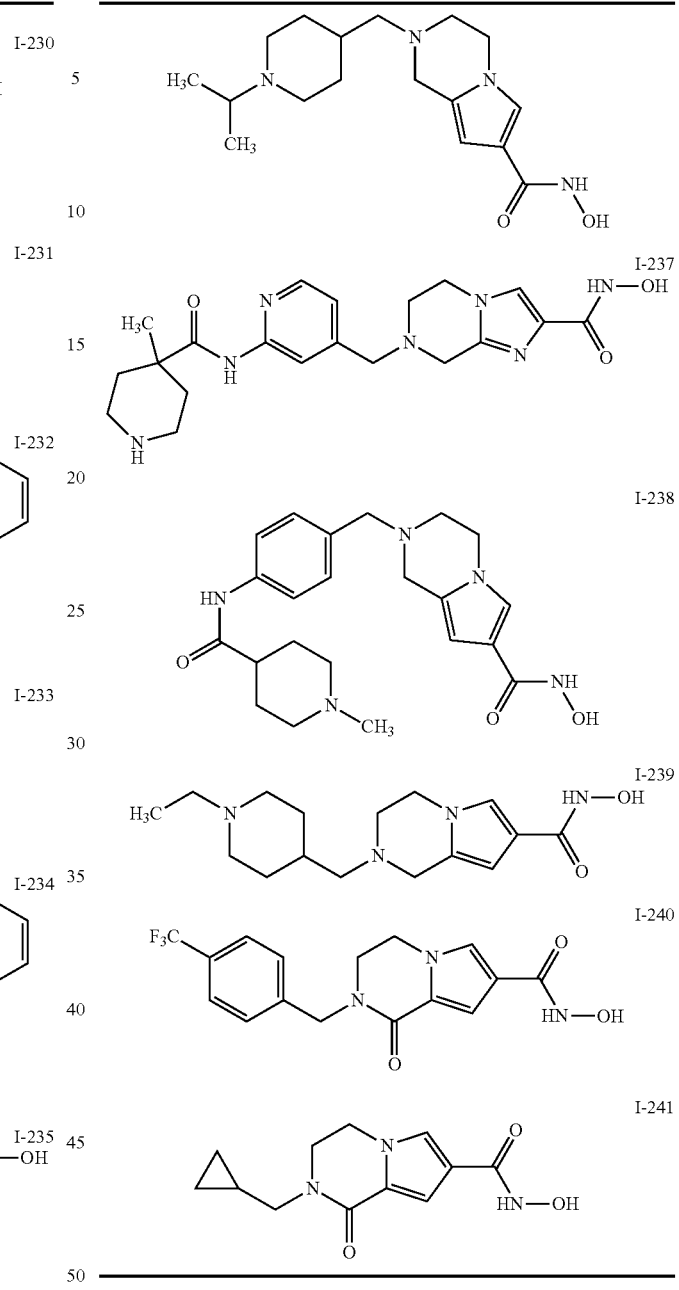

The compounds in Table 1 above may also be identified by the following chemical names:

| | |
|---|---|
| I-1 | 2-(4-tert-butylbenzoyl)-N-hydroxy-1,2,3,4-tetrahydropyrrolo[1,2-a]pyrazine-7-carboxamide |
| I-2 | 7-(biphenyl-4-ylcarbonyl)-N-hydroxy-5,6,7,8-tetrahydroimidazo[1,2-a]pyrazine-2-carboxamide |
| I-3 | N-hydroxy-2-(imidazo[1,2-a]pyridin-2-ylcarbonyl)-1,2,3,4-tetrahydropyrrolo[1,2-a]pyrazine-7-carboxamide |
| I-4 | 2-(2,5-dimethyl-3-furoyl)-N-hydroxy-2,3,4,5-tetrahydro-1H-pyrrolo[1,2-a][1,4]diazepine-8-carboxamide |
| I-5 | N-hydroxy-2-({4-methyl-2-[4-(trifluoromethyl)phenyl]-4H-furo[3,2-b]pyrrol-5-yl}carbonyl)-2,3,4,5-tetrahydro-1H-pyrrolo[1,2-a][1,4]diazepine-8-carboxamide |
| I-6 | N-hydroxy-5-[(1-methylcyclohexyl)carbonyl]-4,5,6,7-tetrahydropyrazolo[1,5-a]pyrazine-2-carboxamide |
| I-7 | N-hydroxy-2-[(5-methyl-1-phenyl-1H-pyrazol-4-yl)carbonyl]-2,3,4,5-tetrahydro-1H-pyrrolo[1,2-a][1,4]diazepine-8-carboxamide |
| I-8 | N-hydroxy-5-{[1-(trifluoromethyl)cyclopropyl]carbonyl}-4,5,6,7-tetrahydropyrazolo[1,5-a]pyrazine-2-carboxamide |

-continued

| | |
|---|---|
| I-9 | N-hydroxy-2-[(1-methyl-1H-pyrrol-2-yl)carbonyl]-2,3,4,5-tetrahydro-1H-pyrrolo[1,2-a][1,4]diazepine-8-carboxamide |
| I-10 | 2-(1-benzothien-3-ylcarbonyl)-N-hydroxy-1,2,3,4-tetrahydropyrrolo[1,2-a]pyrazine-7-carboxamide |
| I-11 | 5-[(4,5-dichloro-1-methyl-1H-pyrrol-2-yl)carbonyl]-N-hydroxy-4,5,6,7-tetrahydropyrazolo[1,5-a]pyrazine-2-carboxamide |
| I-12 | 5-(4-fluorobenzyl)-N-hydroxy-4-oxo-4,5,6,7-tetrahydropyrazolo[1,5-a]pyrazine-2-carboxamide |
| I-13 | N-hydroxy-7-(4-methoxybenzoyl)-5,6,7,8-tetrahydroimidazo[1,2-a]pyrazine-2-carboxamide |
| I-14 | N-hydroxy-7-[(1-methyl-1H-pyrrol-2-yl)carbonyl]-5,6,7,8-tetrahydroimidazo[1,2-a]pyrazine-2-carboxamide |
| I-15 | 2-[(4-acetyl-3,5-dimethyl-1H-pyrrol-2-yl)carbonyl]-N-hydroxy-1,2,3,4-tetrahydropyrrolo[1,2-a]pyrazine-7-carboxamide |
| I-16 | 5-(1-adamantylcarbonyl)-N-hydroxy-4,5,6,7-tetrahydropyrazolo[1,5-a]pyrazine-2-carboxamide |
| I-17 | 5-[4-(benzyloxy)benzoyl]-N-hydroxy-4,5,6,7-tetrahydropyrazolo[1,5-a]pyrazine-2-carboxamide |
| I-18 | 2-(4-tert-butylbenzoyl)-N-hydroxy-2,3,4,5-tetrahydro-1H-pyrrolo[1,2-a][1,4]diazepine-8-carboxamide |
| I-19 | 2-(cyclopentylcarbonyl)-N-hydroxy-2,3,4,5-tetrahydro-1H-pyrrolo[1,2-a][1,4]diazepine-8-carboxamide |
| I-20 | N-hydroxy-2-[(1-methyl-1H-indol-2-yl)carbonyl]-1,2,3,4-tetrahydropyrrolo[1,2-a]pyrazine-7-carboxamide |
| I-21 | 7-(1-benzofuran-2-ylcarbonyl)-N-hydroxy-5,6,7,8-tetrahydroimidazo[1,2-a]pyrazine-2-carboxamide |
| I-22 | N-hydroxy-2-[(5-methyl-1H-indol-2-yl)carbonyl]-1,2,3,4-tetrahydropyrrolo[1,2-a]pyrazine-7-carboxamide |
| I-23 | 2-benzyl-N-hydroxy-1,2,3,4-tetrahydropyrrolo[1,2-a]pyrazine-7-carboxamide |
| I-24 | 5-(cyclohexylmethyl)-N-hydroxy-4-oxo-4,5,6,7-tetrahydropyrazolo[1,5-a]pyrazine-2-carboxamide |
| I-25 | N-hydroxy-2-(quinolin-4-ylcarbonyl)-2,3,4,5-tetrahydro-1H-pyrrolo[1,2-a][1,4]diazepine-8-carboxamide |
| I-26 | N-hydroxy-7-[(1-methylcyclohexyl)carbonyl]-5,6,7,8-tetrahydroimidazo[1,2-a]pyrazine-2-carboxamide |
| I-27 | 7-[1-adamantylcarbonyl]-N-hydroxy-5,6,7,8-tetrahydroimidazo[1,2-a]pyrazine-2-carboxamide |
| I-28 | 2-[(3,5-dimethyl-1H-indol-2-yl)carbonyl]-N-hydroxy-1,2,3,4-tetrahydropyrrolo[1,2-a]pyrazine-7-carboxamide |
| I-29 | N-hydroxy-2-(1H-indol-2-ylcarbonyl)-1,2,3,4-tetrahydropyrrolo[1,2-a]pyrazine-7-carboxamide |
| I-30 | N-hydroxy-2-(2-thienylcarbonyl)-1,2,3,4-tetrahydropyrrolo[1,2-a]pyrazine-7-carboxamide |
| I-31 | N-hydroxy-5-[(1-methyl-1H-indol-2-yl)carbonyl]-4,5,6,7-tetrahydropyrazolo[1,5-a]pyrazine-2-carboxamide |
| I-32 | N-hydroxy-2-[(1-methyl-1H-pyrrol-2-yl)carbonyl]-1,2,3,4-tetrahydropyrrolo[1,2-a]pyrazine-7-carboxamide |
| I-33 | N-hydroxy-2-[4-(trifluoromethyl)benzoyl]-2,3,4,5-tetrahydro-1H-pyrrolo[1,2-a][1,4]diazepine-8-carboxamide |
| I-34 | 2-{[1-(4-chlorophenyl)cyclopropyl]carbonyl}-N-hydroxy-2,3,4,5-tetrahydro-1H-pyrrolo[1,2-a][1,4]diazepine-8-carboxamide |
| I-35 | 2-{[2,5-dimethyl-1-(2-thienylmethyl)-1H-pyrrol-3-yl]carbonyl}-N-hydroxy-1,2,3,4-tetrahydropyrrolo[1,2-a]pyrazine-7-carboxamide |
| I-36 | 5-(2,2-dimethylpropanoyl)-N-hydroxy-4,5,6,7-tetrahydropyrazolo[1,5-a]pyrazine-2-carboxamide |
| I-37 | 5-[2-(4-chlorophenyl)-2-methylpropanoyl]-N-hydroxy-4,5,6,7-tetrahydropyrazolo[1,5-a]pyrazine-2-carboxamide |
| I-38 | 2-[1-adamantylcarbonyl]-N-hydroxy-2,3,4,5-tetrahydro-1H-pyrrolo[1,2-a][1,4]diazepine-8-carboxamide |
| I-39 | N-hydroxy-2-[(1-methyl-1H-pyrazol-3-yl)carbonyl]-1,2,3,4-tetrahydropyrrolo[1,2-a]pyrazine-7-carboxamide |
| I-40 | 2-[(3,5-dimethyl-1H-pyrrol-2-yl)carbonyl]-N-hydroxy-1,2,3,4-tetrahydropyrrolo[1,2-a]pyrazine-7-carboxamide |
| I-41 | 7-(2,2-dimethylpropanoyl)-N-hydroxy-5,6,7,8-tetrahydroimidazo[1,2-a]pyrazine-2-carboxamide |
| I-42 | 2-benzyl-N-hydroxy-1-oxo-1,2,3,4-tetrahydropyrrolo[1,2-a]pyrazine-7-carboxamide |
| I-43 | N-hydroxy-2-(4-methylbenzoyl)-2,3,4,5-tetrahydro-1H-pyrrolo[1,2-a][1,4]diazepine-8-carboxamide |
| I-44 | 7-(1-benzothien-2-ylcarbonyl)-N-hydroxy-5,6,7,8-tetrahydroimidazo[1,2-a]pyrazine-2-carboxamide |
| I-45 | 7-(4-tert-butylbenzoyl)-N-hydroxy-5,6,7,8-tetrahydroimidazo[1,2-a]pyrazine-2-carboxamide |
| I-46 | N-hydroxy-5-isopropyl-4-oxo-4,5,6,7-tetrahydropyrazolo[1,5-a]pyrazine-2-carboxamide |
| I-47 | 2-{[5-(aminosulfonyl)-1-methyl-1H-pyrrol-2-yl]carbonyl}-N-hydroxy-1,2,3,4-tetrahydropyrrolo[1,2-a]pyrazine-7-carboxamide |
| I-48 | N-hydroxy-4-oxo-5-(2-phenoxyethyl)-4,5,6,7-tetrahydropyrazolo[1,5-a]pyrazine-2-carboxamide |
| I-49 | 2-benzyl-N-hydroxy-1-oxo-2,3,4,5-tetrahydro-1H-pyrrolo[1,2-a][1,4]diazepine-8-carboxamide |
| I-50 | N-hydroxy-5-(4-methylpentyl)-4-oxo-4,5,6,7-tetrahydropyrazolo[1,5-a]pyrazine-2-carboxamide |
| I-51 | 2-(biphenyl-4-ylcarbonyl)-N-hydroxy-1,2,3,4-tetrahydropyrrolo[1,2-a]pyrazine-7-carboxamide |
| I-52 | 2-[(1,5-dimethyl-1H-pyrazol-3-yl)carbonyl]-N-hydroxy-1,2,3,4-tetrahydropyrrolo[1,2-a]pyrazine-7-carboxamide |
| I-53 | N-hydroxy-5-(4-methoxybenzoyl)-5,6,7,8-tetrahydro-4H-pyrazolo[1,5-a][1,4]diazepine-2-carboxamide |
| I-54 | N-hydroxy-2-[3-(methylsulfonyl)benzoyl]-1,2,3,4-tetrahydropyrrolo[1,2-a]pyrazine-7-carboxamide |
| I-55 | N-hydroxy-7-[(2-methyl-1,3-thiazol-4-yl)carbonyl]-5,6,7,8-tetrahydroimidazo[1,2-a]pyrazine-2-carboxamide |
| I-56 | 2-(4-chlorobenzoyl)-N-hydroxy-2,3,4,5-tetrahydro-1H-pyrrolo[1,2-a][1,4]diazepine-8-carboxamide |

-continued

| | |
|---|---|
| I-57 | 7-(4-chlorobenzoyl)-N-hydroxy-5,6,7,8-tetrahydroimidazo[1,2-a]pyrazine-2-carboxamide |
| I-58 | N-hydroxy-2-[(1-methyl-1H-indol-3-yl)carbonyl]-1,2,3,4-tetrahydropyrrolo[1,2-a]pyrazine-7-carboxamide |
| I-59 | 2-(3,3-dimethylbutanoyl)-N-hydroxy-2,3,4,5-tetrahydro-1H-pyrrolo[1,2-a][1,4]diazepine-8-carboxamide |
| I-60 | 7-[(3-chloro-1-benzothien-2-yl)carbonyl]-N-hydroxy-5,6,7,8-tetrahydroimidazo[1,2-a]pyrazine-2-carboxamide |
| I-61 | 2-[(3,5-dimethylisoxazol-4-yl)carbonyl]-N-hydroxy-1,2,3,4-tetrahydropyrrolo[1,2-a]pyrazine-7-carboxamide |
| I-62 | 2-[1-adamantylcarbonyl]-N-hydroxy-1,2,3,4-tetrahydropyrrolo[1,2-a]pyrazine-7-carboxamide |
| I-63 | 2-[(3-tert-butyl-1-methyl-1H-pyrazol-5-yl)carbonyl]-N-hydroxy-2,3,4,5-tetrahydro-1H-pyrrolo[1,2-a][1,4]diazepine-8-carboxamide |
| I-64 | N-hydroxy-2-{[1-phenyl-5-(trifluoromethyl)-1H-pyrazol-4-yl]carbonyl}-1,2,3,4-tetrahydropyrrolo[1,2-a]pyrazine-7-carboxamide |
| I-65 | N-hydroxy-4-oxo-5-(3-phenylpropyl)-4,5,6,7-tetrahydropyrazolo[1,5-a]pyrazine-2-carboxamide |
| I-66 | N-hydroxy-2-[(2-methyl-4,5,6,7-tetrahydro-2H-indazol-3-yl)carbonyl]-1,2,3,4-tetrahydropyrrolo[1,2-a]pyrazine-7-carboxamide |
| I-67 | 5-(4-tert-butylbenzyl)-N-hydroxy-4-oxo-4,5,6,7-tetrahydropyrazolo[1,5-a]pyrazine-2-carboxamide |
| I-68 | N-hydroxy-2-(4-methoxybenzoyl)-1,2,3,4-tetrahydropyrrolo[1,2-a]pyrazine-7-carboxamide |
| I-69 | N-hydroxy-2-[(5-methyl-2-thienyl)carbonyl]-2,3,4,5-tetrahydro-1H-pyrrolo [1,2-a][1,4]diazepine-8-carboxamide |
| I-70 | N-hydroxy-5-[(5-pyridin-2-yl-2-thienyl)carbonyl]-5,6,7,8-tetrahydro-4H-pyrazolo[1,5-a][1,4]diazepine-2-carboxamide |
| I-71 | N-hydroxy-5-[(1-methyl-1H-pyrrol-2-yl)carbonyl]-5,6,7,8-tetrahydro-4H-pyrazolo[1,5-a][1,4]diazepine-2-carboxamide |
| I-72 | 5-(1-adamantylcarbonyl)-N-hydroxy-5,6,7,8-tetrahydro-4H-pyrazolo[1,5-a][1,4]diazepine-2-carboxamide |
| I-73 | N-hydroxy-2-[(2-methyl-1,3-thiazol-4-yl)carbonyl]-1,2,3,4-tetrahydropyrrolo[1,2-a]pyrazine-7-carboxamide |
| I-74 | N-hydroxy-2-[(1-methylcyclohexyl)carbonyl]-2,3,4,5-tetrahydro-1H-pyrrolo[1,2-a][1,4]diazepine-8-carboxamide |
| I-75 | N-hydroxy-2-(1H-indol-3-ylcarbonyl)-1,2,3,4-tetrahydropyrrolo[1,2-a]pyrazine-7-carboxamide |
| I-76 | N-hydroxy-5-[(1-methyl-1H-pyrrol-2-yl)carbonyl]-4,5,6,7-tetrahydropyrazolo[1,5-a]pyrazine-2-carboxamide |
| I-77 | N-hydroxy-5-(3-methylbutyl)-4-oxo-4,5,6,7-tetrahydropyrazolo[1,5-a]pyrazine-2-carboxamide |
| I-78 | N-hydroxy-2-[(2-methyl-1,3-thiazol-4-yl)carbonyl]-2,3,4,5-tetrahydro-1H-pyrrolo[1,2-a][1,4]diazepine-8-carboxamide |
| I-79 | 2-(2,6-dichlorobenzoyl)-N-hydroxy-2,3,4,5-tetrahydro-1H-pyrrolo[1,2-a][1,4]diazepine-8-carboxamide |
| I-80 | N-hydroxy-2-[(4'-methylbiphenyl-4-yl)carbonyl]-2,3,4,5-tetrahydro-1H-pyrrolo[1,2-a][1,4]diazepine-8-carboxamide |
| I-81 | 5-benzyl-N-hydroxy-4-oxo-4,5,6,7-tetrahydropyrazolo[1,5-a]pyrazine-2-carboxamide |
| I-82 | N-hydroxy-2-[(5-methyl-2-phenyl-1,3-oxazol-4-yl)acetyl]-1,2,3,4-tetrahydropyrrolo[1,2-a]pyrazine-7-carboxamide |
| I-83 | 5-(cyclopropylmethyl)-N-hydroxy-4-oxo-4,5,6,7-tetrahydropyrazolo[1,5-a]pyrazine-2-carboxamide |
| I-84 | N-hydroxy-2-(pyrazolo[1,5-a]pyrimidin-3-ylcarbonyl)-1,2,3,4-tetrahydropyrrolo[1,2-a]pyrazine-7-carboxamide |
| I-85 | 2-(2,5-dimethyl-3-furoyl)-N-hydroxy-1,2,3,4-tetrahydropyrrolo[1,2-a]pyrazine-7-carboxamide |
| I-86 | 2-butyl-N-hydroxy-1,2,3,4-tetrahydropyrrolo[1,2-a]pyrazine-7-carboxamide |
| I-87 | N-hydroxy-2-[(2-methyl-1,5-diphenyl-1H-pyrrol-3-yl)carbonyl]-1,2,3,4-tetrahydropyrrolo[1,2-a]pyrazine-7-carboxamide |
| I-88 | 5-(2-ethoxyethyl)-N-hydroxy-4-oxo-4,5,6,7-tetrahydropyrazolo[1,5-a]pyrazine-2-carboxamide |
| I-89 | N-hydroxy-2-[(1-methyl-1H-indol-5-yl)carbonyl]-1,2,3,4-tetrahydropyrrolo[1,2-a]pyrazine-7-carboxamide |
| I-90 | N-hydroxy-5-[(2-methyl-1,3-thiazol-4-yl)acetyl]-4,5,6,7-tetrahydropyrazolo[1,5-a]pyrazine-2-carboxamide |
| I-91 | 2-[(4,5-dichloro-1-methyl-1H-pyrrol-2-yl)carbonyl]-N-hydroxy-1,2,3,4-tetrahydropyrrolo[1,2-a]pyrazine-7-carboxamide |
| I-92 | 12-(cyclohexylcarbonyl)-N-hydroxy-1,2,3,4-tetrahydropyrrolo[1,2-a]pyrazine-7-carboxamide |
| I-93 | N-hydroxy-5-[(5-methyl-1H-indol-3-yl)acetyl]-4,5,6,7-tetrahydropyrazolo[1,5-a]pyrazine-2-carboxamide |
| I-94 | 2-[(2,5-dimethyl-1H-pyrrol-3-yl)carbonyl]-N-hydroxy-1,2,3,4-tetrahydropyrrolo[1,2-a]pyrazine-7-carboxamide |
| I-95 | 2-[(3-ethyl-1-methyl-1H-pyrazol-5-yl)carbonyl]-N-hydroxy-2,3,4,5-tetrahydro-1H-pyrrolo[1,2-a][1,4]diazepine-8-carboxamide |
| I-96 | 2-(1-benzothien-3-ylcarbonyl)-N-hydroxy-2,3,4,5-tetrahydro-1H-pyrrolo[1,2-a][1,4]diazepine-8-carboxamide |
| I-97 | N-hydroxy-5-[(3-methyl-1-benzothien-2-yl)carbonyl]-4,5,6,7-tetrahydropyrazolo[1,5-a]pyrazine-2-carboxamide |
| I-98 | 5-(1-benzothien-2-ylcarbonyl)-N-hydroxy-5,6,7,8-tetrahydro-4H-pyrazolo[1,5-a][1,4]diazepine-2-carboxamide |
| I-99 | N-hydroxy-2-[(5-methyl-1-phenyl-1H-pyrazol-4-yl)carbonyl]-1,2,3,4-tetrahydropyrrolo[1,2-a]pyrazine-7-carboxamide |
| I-100 | N-hydroxy-5-(4-methoxybenzoyl)-4,5,6,7-tetrahydropyrazolo[1,5-a]pyrazine-2-carboxamide |
| I-101 | N-hydroxy-7-[(4-methyl-2-pyridin-2-yl-1,3-thiazol-5-yl)carbonyl]-5,6,7,8-tetrahydroimidazo[1,2-a]pyrazine-2-carboxamide |
| I-102 | N-hydroxy-5-(1H-indol-3-ylacetyl)-4,5,6,7-tetrahydropyrazolo[1,5-a]pyrazine-2-carboxamide |

-continued

| | |
|---|---|
| I-103 | N-hydroxy-4-oxo-5-[3-(trifluoromethyl)benzyl]-4,5,6,7-tetrahydropyrazolo[1,5-a]pyrazine-2-carboxamide |
| I-104 | 2-[(4,5-dichloro-1-methyl-1H-pyrrol-2-yl)carbonyl]-N-hydroxy-2,3,4,5-tetrahydro-1H-pyrrolo[1,2-a][1,4]diazepine-8-carboxamide |
| I-105 | N-hydroxy-5-[(1-methyl-1H-indol-2-yl)carbonyl]-5,6,7,8-tetrahydro-4H-pyrazolo[1,5-a][1,4]diazepine-2-carboxamide |
| I-106 | N-hydroxy-5-(3-phenylpropanoyl)-4,5,6,7-tetrahydropyrazolo[1,5-a]pyrazine-2-carboxamide |
| I-107 | N-hydroxy-5-(quinolin-8-ylcarbonyl)-4,5,6,7-tetrahydropyrazolo[1,5-a]pyrazine-2-carboxamide |
| I-108 | N-hydroxy-5-[(3-methyl-1-benzofuran-2-yl)carbonyl]-5,6,7,8-tetrahydro-4H-pyrazolo[1,5-a][1,4]diazepine-2-carboxamide |
| I-109 | N-hydroxy-4-oxo-5-[3-(1H-pyrrol-1-yl)propyl]-4,5,6,7-tetrahydropyrazolo[1,5-a]pyrazine-2-carboxamide |
| I-110 | 5-(3-chlorobenzyl)-N-hydroxy-4-oxo-4,5,6,7-tetrahydropyrazolo[1,5-a]pyrazine-2-carboxamide |
| I-111 | 2-(cyclohexylcarbonyl)-N-hydroxy-2,3,4,5-tetrahydro-1H-pyrrolo[1,2-a][1,4]diazepine-8-carboxamide |
| I-112 | N7-(2-tert-butylphenyl)-N2-hydroxy-5,6-dihydroimidazo[1,2-a]pyrazine-2,7(8H)-dicarboxamide |
| I-113 | N7-[1-adamantyl]-N2-hydroxy-5,6-dihydroimidazo[1,2-a]pyrazine-2,7(8H)-dicarboxamide |
| I-114 | N7-biphenyl-2-yl-N2-hydroxy-5,6-dihydroimidazo[1,2-a]pyrazine-2,7(8H)-dicarboxamide |
| I-115 | N7-(2,6-diethylphenyl)-N2-hydroxy-5,6-dihydroimidazo[1,2-a]pyrazine-2,7(8H)-dicarboxamide |
| I-116 | N2-hydroxy-N7-phenyl-5,6-dihydroimidazo[1,2-a]pyrazine-2,7(8H)-dicarboxamide |
| I-117 | N2-hydroxy-N7-(2-methylphenyl)-5,6-dihydroimidazo[1,2-a]pyrazine-2,7(8H)-dicarboxamide |
| I-118 | N7-(sec-butyl)-N2-hydroxy-5,6-dihydroimidazo[1,2-a]pyrazine-2,7(8H)-dicarboxamide |
| I-119 | N7-(tert-butyl)-N2-hydroxy-5,6-dihydroimidazo[1,2-a]pyrazine-2,7(8H)-dicarboxamide |
| I-120 | N2-hydroxy-N7-(2-phenylethyl)-5,6-dihydroimidazo[1,2-a]pyrazine-2,7(8H)-dicarboxamide |
| I-121 | N7-cyclohexyl-N2-hydroxy-5,6-dihydroimidazo[1,2-a]pyrazine-2,7(8H)-dicarboxamide |
| I-122 | N2-hydroxy-N7-(5-methyl-3-phenylisoxazol-4-yl)-5,6-dihydroimidazo[1,2-a]pyrazine-2,7(8H)-dicarboxamide |
| I-123 | N7-benzyl-N2-hydroxy-5,6-dihydroimidazo[1,2-a]pyrazine-2,7(8H)-dicarboxamide |
| I-124 | N-hydroxy-1-oxo-2-[4-(trifluoromethyl)benzyl]-2,3,4,5-tetrahydro-1H-pyrrolo[1,2-a][1,4]diazepine-8-carboxamide |
| I-125 | 2-(1-benzothien-2-ylcarbonyl)-N-hydroxy-4,4-dimethyl-2,3,4,5-tetrahydro-1H-pyrrolo[1,2-a][1,4]diazepine-8-carboxamide |
| I-126 | N-hydroxy-1-oxo-2-[3-(trifluoromethoxy)benzyl]-2,3,4,5-tetrahydro-1H-pyrrolo[1,2-a][1,4]diazepine-8-carboxamide |
| I-127 | 1-ethyl-N-hydroxy-2-[(1-methylpiperidin-4-yl)carbonyl]-1,2,3,4-tetrahydropyrrolo[1,2-a]pyrazine-7-carboxamide |
| I-128 | N-hydroxy-3-methyl-2-[(1-methylpiperidin-4-yl)carbonyl]-1,2,3,4-tetrahydropyrrolo[1,2-a]pyrazine-7-carboxamide |
| I-129 | 1-ethyl-N-hydroxy-2-[(1-methyl-1H-pyrrol-2-yl)carbonyl]-1,2,3,4-tetrahydropyrrolo[1,2-a]pyrazine-7-carboxamide |
| I-130 | N-hydroxy-1-isopropyl-2-{[4-(trifluoromethyl)phenyl]sulfonyl}-1,2,3,4-tetrahydropyrrolo[1,2-a]pyrazine-7-carboxamide |
| I-131 | N-hydroxy-1-methyl-2-[(1-methylpiperidin-4-yl)carbonyl]-1,2,3,4-tetrahydropyrrolo[1,2-a]pyrazine-7-carboxamide |
| I-132 | N2-1-adamantyl-N7-hydroxy-1-methyl-3,4-dihydropyrrolo[1,2-a]pyrazine-2,7(1H)-dicarboxamide |
| I-133 | 2-cyclopropyl-N-hydroxy-1-oxo-1,2,3,4-tetrahydropyrrolo[1,2-a]pyrazine-7-carboxamide |
| I-134 | N-hydroxy-1-methyl-2-[(1-methyl-1H-indol-2-yl)carbonyl]-1,2,3,4-tetrahydropyrrolo[1,2-a]pyrazine-7-carboxamide |
| I-135 | 5-(1-adamantylcarbonyl)-N-hydroxy-4-methyl-4,5,6,7-tetrahydropyrazolo[1,5-a]pyrazine-2-carboxamide |
| I-136 | N-hydroxy-4,4-dimethyl-2-[(1-methyl-1H-indol-2-yl)carbonyl]-2,3,4,5-tetrahydro-1H-pyrrolo[1,2-a][1,4]diazepine-8-carboxamide |
| I-137 | 2-(2,2-dimethylpropanoyl)-N-hydroxy-4,4-dimethyl-2,3,4,5-tetrahydro-1H-pyrrolo[1,2-a][1,4]diazepine-8-carboxamide |
| I-138 | 2-(3-cyanobenzyl)-N-hydroxy-1-oxo-1,2,3,4-tetrahydropyrrolo[1,2-a]pyrazine-7-carboxamide |
| I-139 | 7-[(dimethylamino)acetyl]-N-hydroxy-8-methyl-5,6,7,8-tetrahydroimidazo[1,2-a]pyrazine-2-carboxamide |
| I-140 | 5-(1-benzothien-2-ylcarbonyl)-N-hydroxy-4-methyl-4,5,6,7-tetrahydropyrazolo[1,5-a]pyrazine-2-carboxamide |
| I-141 | N-hydroxy-7-[(1-methyl-1H-indol-2-yl)carbonyl]-5,6,7,8-tetrahydro[1,2,4]triazolo[1,5-a]pyrazine-2-carboxamide |
| I-142 | N5-cyclohexyl-N2-hydroxy-4-methyl-6,7-dihydropyrazolo[1,5-a]pyrazine-2,5(4H)-dicarboxamide |
| I-143 | N-hydroxy-3-methyl-1-oxo-2-[4-(1H-pyrazol-1-yl)benzyl]-1,2,3,4-tetrahydropyrrolo[1,2-a]pyrazine-7-carboxamide |
| I-144 | 2-(4-tert-butylbenzyl)-N-hydroxy-4,4-dimethyl-1-oxo-2,3,4,5-tetrahydro-1H-pyrrolo[1,2-a][1,4]diazepine-8-carboxamide |
| I-145 | N-hydroxy-4,4-dimethyl-2-[(1-methyl-1H-pyrrol-2-yl)carbonyl]-2,3,4,5-tetrahydro-1H-pyrrolo[1,2-a][1,4]diazepine-8-carboxamide |
| I-146 | 2-(4-fluorobenzyl)-N-hydroxy-1-oxo-2,3,4,5-tetrahydro-1H-pyrrolo[1,2-a][1,4]diazepine-8-carboxamide |
| I-147 | N-hydroxy-4,4-dimethyl-2-[(1-methylpiperidin-4-yl)carbonyl]-2,3,4,5-tetrahydro-1H-pyrrolo[1,2-a][1,4]diazepine-8-carboxamide |
| I-148 | 5-(2,2-dimethylpropanoyl)-N-hydroxy-4-methyl-4,5,6,7-tetrahydropyrazolo[1,5-a]pyrazine-2-carboxamide |
| I-149 | 2-(1-adamantylcarbonyl)-N-hydroxy-3-methyl-1,2,3,4-tetrahydropyrrolo[1,2-a]pyrazine-7-carboxamide |

-continued

| | |
|---|---|
| I-150 | 2-[(dimethylamino)acetyl]-N-hydroxy-4,4-dimethyl-2,3,4,5-tetrahydro-1H-pyrrolo[1,2-a][1,4]diazepine-8-carboxamide |
| I-151 | 7-[(dimethylamino)acetyl]-N-hydroxy-8-isopropyl-5,6,7,8-tetrahydroimidazo[1,2-a]pyrazine-2-carboxamide |
| I-152 | 2-[(5-chloro-1-benzothien-3-yl)methyl]-N-hydroxy-1-oxo-2,3,4,5-tetrahydro-1H-pyrrolo[1,2-a][1,4]diazepine-8-carboxamide |
| I-153 | N2-(tert-butyl)-1-ethyl-N7-hydroxy-3,4-dihydropyrrolo[1,2-a]pyrazine-2,7(1H)-dicarboxamide |
| I-154 | N-hydroxy-1-oxo-2-[4-(trifluoromethyl)benzyl]-1,2,3,4-tetrahydropyrrolo[1,2-a]pyrazine-7-carboxamide |
| I-155 | 2-(cyclopentylacetyl)-N-hydroxy-1-methyl-1,2,3,4-tetrahydropyrrolo[1,2-a]pyrazine-7-carboxamide |
| I-156 | 1-ethyl-N-hydroxy-2-[(1-methyl-1H-indol-2-yl)carbonyl]-1,2,3,4-tetrahydropyrrolo[1,2-a]pyrazine-7-carboxamide |
| I-157 | N-hydroxy-7-[(1-methyl-1H-pyrrol-2-yl)carbonyl]-5,6,7,8-tetrahydro[1,2,4]triazolo[1,5-a]pyrazine-2-carboxamide |
| I-158 | 2-(biphenyl-4-ylcarbonyl)-N-hydroxy-3-methyl-1,2,3,4-tetrahydropyrrolo[1,2-a]pyrazine-7-carboxamide |
| I-159 | 2-(3-cyanobenzyl)-N-hydroxy-1-oxo-2,3,4,5-tetrahydro-1H-pyrrolo[1,2-a][1,4]diazepine-8-carboxamide |
| I-160 | N-hydroxy-8-methyl-7-[(1-methylpiperidin-4-yl)carbonyl]-5,6,7,8-tetrahydroimidazo[1,2-a]pyrazine-2-carboxamide |
| I-161 | 2-(1-adamantylcarbonyl)-N-hydroxy-1-methyl-1,2,3,4-tetrahydropyrrolo[1,2-a]pyrazine-7-carboxamide |
| I-162 | 2-(1-benzothien-2-ylcarbonyl)-N-hydroxy-3-methyl-1,2,3,4-tetrahydropyrrolo[1,2-a]pyrazine-7-carboxamide |
| I-163 | N-hydroxy-1-oxo-2-[3-(trifluoromethoxy)benzyl]-1,2,3,4-tetrahydropyrrolo[1,2-a]pyrazine-7-carboxamide |
| I-164 | 1-ethyl-N-hydroxy-2-(propylsulfonyl)-1,2,3,4-tetrahydropyrrolo[1,2-a]pyrazine-7-carboxamide |
| I-165 | 2-(1-adamantylcarbonyl)-N-hydroxy-4,4-dimethyl-2,3,4,5-tetrahydro-1H-pyrrolo[1,2-a][1,4]diazepine-8-carboxamide |
| I-166 | N-hydroxy-8-methyl-7-[(1-methyl-1H-pyrrol-2-yl)carbonyl]-5,6,7,8-tetrahydroimidazo[1,2-a]pyrazine-2-carboxamide |
| I-167 | 7-(biphenyl-4-ylcarbonyl)-N-hydroxy-5,6,7,8-tetrahydro[1,2,4]triazolo[1,5-a]pyrazine-2-carboxamide |
| I-168 | 2-(cyclopentylacetyl)-N-hydroxy-4,4-dimethyl-2,3,4,5-tetrahydro-1H-pyrrolo[1,2-a][1,4]diazepine-8-carboxamide |
| I-169 | N-hydroxy-8-isopropyl-7-[(1-methylpiperidin-4-yl)carbonyl]-5,6,7,8-tetrahydroimidazo[1,2-a]pyrazine-2-carboxamide |
| I-170 | 7-(biphenyl-4-ylcarbonyl)-N-hydroxy-8-isopropyl-5,6,7,8-tetrahydroimidazo[1,2-a]pyrazine-2-carboxamide |
| I-171 | N-hydroxy-3-methyl-1-oxo-2-[3-(trifluoromethyl)benzyl]-1,2,3,4-tetrahydropyrrolo[1,2-a]pyrazine-7-carboxamide |
| I-172 | N-hydroxy-8-isopropyl-7-[(1-methyl-1H-pyrrol-2-yl)carbonyl]-5,6,7,8-tetrahydroimidazo[1,2-a]pyrazine-2-carboxamide |
| I-173 | 7-(1-benzothien-2-ylcarbonyl)-N-hydroxy-8-methyl-5,6,7,8-tetrahydroimidazo[1,2-a]pyrazine-2-carboxamide |
| I-174 | N-hydroxy-4-methyl-5-[(1-methylpiperidin-4-yl)carbonyl]-4,5,6,7-tetrahydropyrazolo[1,5-a]pyrazine-2-carboxamide |
| I-175 | 2-(4-fluorobenzyl)-N-hydroxy-1-oxo-1,2,3,4-tetrahydropyrrolo[1,2-a]pyrazine-7-carboxamide |
| I-176 | N-hydroxy-8-isopropyl-7-{[4-(trifluoromethyl)phenyl]sulfonyl}-5,6,7,8-tetrahydroimidazo[1,2-a]pyrazine-2-carboxamide |
| I-177 | 7-(1-adamantylcarbonyl)-N-hydroxy-8-methyl-5,6,7,8-tetrahydroimidazo[1,2-a]pyrazine-2-carboxamide |
| I-178 | N-hydroxy-1-oxo-2-(quinolin-8-ylmethyl)-2,3,4,5-tetrahydro-1H-pyrrolo[1,2-a][1,4]diazepine-8-carboxamide |
| I-179 | 7-(cyclopentylacetyl)-N-hydroxy-8-isopropyl-5,6,7,8-tetrahydroimidazo[1,2-a]pyrazine-2-carboxamide |
| I-180 | N-hydroxy-4,4-dimethyl-2-[(5-methyl-3-phenylisoxazol-4-yl)methyl]-1-oxo-2,3,4,5-tetrahydro-1H-pyrrolo[1,2-a][1,4]diazepine-8-carboxamide |
| I-181 | 7-(1-adamantylcarbonyl)-N-hydroxy-5,6,7,8-tetrahydro[1,2,4]triazolo[1,5-a]pyrazine-2-carboxamide |
| I-182 | 2-(1-benzothien-2-ylcarbonyl)-N-hydroxy-1-methyl-1,2,3,4-tetrahydropyrrolo[1,2-a]pyrazine-7-carboxamide |
| I-183 | N-hydroxy-1-oxo-2-(quinolin-8-ylmethyl)-1,2,3,4-tetrahydropyrrolo[1,2-a]pyrazine-7-carboxamide |
| I-184 | N-hydroxy-3-methyl-2-[(1-methyl-1H-pyrrol-2-yl)carbonyl]-1,2,3,4-tetrahydropyrrolo[1,2-a]pyrazine-7-carboxamide |
| I-185 | 2-(biphenyl-4-ylcarbonyl)-N-hydroxy-4,4-dimethyl-2,3,4,5-tetrahydro-1H-pyrrolo[1,2-a][1,4]diazepine-8-carboxamide |
| I-186 | 2-(3-chlorobenzyl)-N-hydroxy-1-oxo-2,3,4,5-tetrahydro-1H-pyrrolo[1,2-a][1,4]diazepine-8-carboxamide |
| I-187 | N2-1-adamantyl-N8-hydroxy-4,4-dimethyl-4,5-dihydro-1H-pyrrolo[1,2-a][1,4]diazepine-2,8(3H)-dicarboxamide |
| I-188 | 2-[(dimethylamino)acetyl]-N-hydroxy-3-methyl-1,2,3,4-tetrahydropyrrolo[1,2-a]pyrazine-7-carboxamide |
| I-189 | 2-[3-(4-fluorophenoxy)benzyl]-N-hydroxy-1-oxo-1,2,3,4-tetrahydropyrrolo[1,2-a]pyrazine-7-carboxamide |
| I-190 | 7-(1-benzothien-2-ylcarbonyl)-N-hydroxy-8-isopropyl-5,6,7,8-tetrahydroimidazo[1,2-a]pyrazine-2-carboxamide |

| | |
|---|---|
| I-191 | 2-(biphenyl-2-ylmethyl)-N-hydroxy-1-oxo-1,2,3,4-tetrahydropyrrolo[1,2-a]pyrazine-7-carboxamide |
| I-192 | 7-(2,2-dimethylpropanoyl)-N-hydroxy-8-isopropyl-5,6,7,8-tetrahydroimidazo[1,2-a]pyrazine-2-carboxamide |
| I-193 | 2-[3-(4-fluorophenoxy)benzyl]-N-hydroxy-1-oxo-2,3,4,5-tetrahydro-1H-pyrrolo[1,2-a][1,4]diazepine-8-carboxamide |
| I-194 | 7-(2,2-dimethylpropanoyl)-N-hydroxy-5,6,7,8-tetrahydro[1,2,4]triazolo[1,5-a]pyrazine-2-carboxamide |
| I-195 | N-hydroxy-2-[(1-methyl-1H-pyrrol-2-yl)carbonyl]-3-phenyl-1,2,3,4-tetrahydropyrrolo[1,2-a]pyrazine-7-carboxamide |
| I-196 | 7-(cyclopentylacetyl)-N-hydroxy-8-methyl-5,6,7,8-tetrahydroimidazo[1,2-a]pyrazine-2-carboxamide |
| I-197 | N-hydroxy-2-[(5-methyl-3-phenylisoxazol-4-yl)methyl]-1-oxo-1,2,3,4-tetrahydropyrrolo[1,2-a]pyrazine-7-carboxamide |
| I-198 | 2-(cyclopropylmethyl)-N-hydroxy-3-methyl-1-oxo-1,2,3,4-tetrahydropyrrolo[1,2-a]pyrazine-7-carboxamide |
| I-199 | 7-[(dimethylamino)acetyl]-N-hydroxy-5,6,7,8-tetrahydro[1,2,4]triazolo[1,5-a]pyrazine-2-carboxamide |
| I-200 | 2-ethyl-N-hydroxy-1-oxo-2,3,4,5-tetrahydro-1H-pyrrolo[1,2-a][1,4]diazepine-8-carboxamide |
| I-201 | 2-(2,2-dimethylpropanoyl)-1-ethyl-N-hydroxy-1,2,3,4-tetrahydropyrrolo[1,2-a]pyrazine-7-carboxamide |
| I-202 | N-hydroxy-4-methyl-5-[(1-methyl-1H-indol-2-yl)carbonyl]-4,5,6,7-tetrahydropyrazolo[1,5-a]pyrazine-2-carboxamide |
| I-203 | 2-(2,2-dimethylpropanoyl)-N-hydroxy-3-methyl-1,2,3,4-tetrahydropyrrolo[1,2-a]pyrazine-7-carboxamide |
| I-204 | N-hydroxy-7-[(1-methylpiperidin-4-yl)carbonyl]-5,6,7,8-tetrahydro[1,2,4]triazolo[1,5-a]pyrazine-2-carboxamide |
| I-205 | 2-[(dimethylamino)acetyl]-1-ethyl-N-hydroxy-1,2,3,4-tetrahydropyrrolo[1,2-a]pyrazine-7-carboxamide |
| I-206 | 7-(2,2-dimethylpropanoyl)-N-hydroxy-8-methyl-5,6,7,8-tetrahydroimidazo[1,2-a]pyrazine-2-carboxamide |
| I-207 | 2-cyclopropyl-N-hydroxy-1-oxo-2,3,4,5-tetrahydro-1H-pyrrolo[1,2-a][1,4]diazepine-8-carboxamide |
| I-208 | N-hydroxy-8-isopropyl-7-[(1-methyl-1H-indol-2-yl)carbonyl]-5,6,7,8-tetrahydroimidazo[1,2-a]pyrazine-2-carboxamide |
| I-209 | 2-ethyl-N-hydroxy-1-oxo-1,2,3,4-tetrahydropyrrolo[1,2-a]pyrazine-7-carboxamide |
| I-210 | 2-[(5-chloro-1-benzothien-3-yl)methyl]-N-hydroxy-1-oxo-1,2,3,4-tetrahydropyrrolo[1,2-a]pyrazine-7-carboxamide |
| I-211 | N-hydroxy-8-methyl-7-[(1-methyl-1H-indol-2-yl)carbonyl]-5,6,7,8-tetrahydroimidazo[1,2-a]pyrazine-2-carboxamide |
| I-212 | N-hydroxy-4,4-dimethyl-2-(3-methylbutyl)-1-oxo-2,3,4,5-tetrahydro-1H-pyrrolo[1,2-a][1,4]diazepine-8-carboxamide |
| I-213 | N-hydroxy-7-{[4-(trifluoromethyl)phenyl]sulfonyl}-5,6,7,8-tetrahydro[1,2,4]triazolo[1,5-a]pyrazine-2-carboxamide |
| I-214 | 5-(cyclopentylacetyl)-N-hydroxy-4-methyl-4,5,6,7-tetrahydropyrazolo[1,5-a]pyrazine-2-carboxamide |
| I-215 | 2-(3-chlorobenzyl)-N-hydroxy-1-oxo-1,2,3,4-tetrahydropyrrolo[1,2-a]pyrazine-7-carboxamide |
| I-216 | N-hydroxy-1-methyl-2-[(1-methyl-1H-pyrrol-2-yl)carbonyl]-1,2,3,4-tetrahydropyrrolo[1,2-a]pyrazine-7-carboxamide |
| I-217 | N-hydroxy-7-(propylsulfonyl)-5,6,7,8-tetrahydro[1,2,4]triazolo[1,5-a]pyrazine-2-carboxamide |
| I-218 | 2-(1-adamantylcarbonyl)-1-ethyl-N-hydroxy-1,2,3,4-tetrahydropyrrolo[1,2-a]pyrazine-7-carboxamide |
| I-219 | N-hydroxy-4-methyl-5-[(1-methyl-1H-pyrrol-2-yl)carbonyl]-4,5,6,7-tetrahydropyrazolo[1,5-a]pyrazine-2-carboxamide |
| I-220 | 2-(biphenyl-2-ylmethyl)-N-hydroxy-1-oxo-2,3,4,5-tetrahydro-1H-pyrrolo[1,2-a][1,4]diazepine-8-carboxamide |
| I-221 | 7-(cyclopentylacetyl)-N-hydroxy-5,6,7,8-tetrahydro[1,2,4]triazolo[1,5-a]pyrazine-2-carboxamide |
| I-222 | 2-(cyclopentylacetyl)-N-hydroxy-3-methyl-1,2,3,4-tetrahydropyrrolo[1,2-a]pyrazine-7-carboxamide |
| I-223 | 2-(1-benzothien-2-ylcarbonyl)-1-ethyl-N-hydroxy-1,2,3,4-tetrahydropyrrolo[1,2-a]pyrazine-7-carboxamide |
| I-224 | N-hydroxy-3-methyl-2-[(1-methyl-1H-indol-2-yl)carbonyl]-1,2,3,4-tetrahydropyrrolo[1,2-a]pyrazine-7-carboxamide |
| I-225 | 2-(cyclopentylacetyl)-1-ethyl-N-hydroxy-1,2,3,4-tetrahydropyrrolo[1,2-a]pyrazine-7-carboxamide |
| I-226 | 2-(biphenyl-4-ylcarbonyl)-1-ethyl-N-hydroxy-1,2,3,4-tetrahydropyrrolo[1,2-a]pyrazine-7-carboxamide |
| I-227 | 7-(1-adamantylcarbonyl)-N-hydroxy-8-isopropyl-5,6,7,8-tetrahydroimidazo[1,2-a]pyrazine-2-carboxamide |
| I-228 | 2-[(dimethylamino)acetyl]-N-hydroxy-1-methyl-1,2,3,4-tetrahydropyrrolo[1,2-a]pyrazine-7-carboxamide |
| I-229 | 5-(biphenyl-4-ylcarbonyl)-N-hydroxy-4-methyl-4,5,6,7-tetrahydropyrazolo[1,5-a]pyrazine-2-carboxamide |
| I-230 | 7-(1-benzothien-2-ylcarbonyl)-N-hydroxy-5,6,7,8-tetrahydro[1,2,4]triazolo[1,5-a]pyrazine-2-carboxamide |
| I-231 | 5-[(dimethylamino)acetyl]-N-hydroxy-4-methyl-4,5,6,7-tetrahydropyrazolo[1,5-a]pyrazine-2-carboxamide |
| I-232 | 2-(biphenyl-4-ylcarbonyl)-N-hydroxy-1-methyl-1,2,3,4-tetrahydropyrrolo[1,2-a]pyrazine-7-carboxamide |

-continued

| | |
|---|---|
| I-233 | 2-(2,2-dimethylpropanoyl)-N-hydroxy-1-methyl-1,2,3,4-tetrahydropyrrolo[1,2-a]pyrazine-7-carboxamide |
| I-234 | 7-(biphenyl-4-ylcarbonyl)-N-hydroxy-8-methyl-5,6,7,8-tetrahydroimidazo[1,2-a]pyrazine-2-carboxamide |
| I-235 | N-hydroxy-7-{-3-[(pyrrolidin-3-ylamino)carbonyl]benzyl}-5,6,7,8-tetrahydroimidazo[1,2-a]pyrazine-2-carboxamide |
| I-236 | N-hydroxy-2-[(1-isopropylpiperidin-4-yl)methyl]-1,2,3,4-tetrahydropyrrolo[1,2-a]pyrazine-7-carboxamide |
| I-237 | N-hydroxy-7-[(2-{[(4-methylpiperidin-4-yl)carbonyl]amino}pyridin-4-yl)methyl]-5,6,7,8-tetrahydroimidazo[1,2-a]pyrazine-2-carboxamide |
| I-238 | N-hydroxy-2-(4-{[(1-methylpiperidin-4-yl)carbonyl]amino}benzyl)-1,2,3,4-tetrahydropyrrolo[1,2-a]pyrazine-7-carboxamide |
| I-239 | 2-[(1-ethylpiperidin-4-yl)methyl]-N-hydroxy-1,2,3,4-tetrahydropyrrolo[1,2-a]pyrazine-7-carboxamide |
| I-240 | N-hydroxy-1-oxo-2-[4-(trifluoromethl)benzyl]-1,2,3,4-tetrahydropyrrolo[1,2-a]pyrazine-7-carboxamide |
| I-241 | 2-(cyclopropylmethyl)-N-hydroxy-1-oxo-1,2,3,4-tetrahydropyrrolo[1,2-a]pyrazine-7-carboxamide |

3. General Synthetic Methods and Intermediates

The compounds of the present invention can be prepared by methods known to one of ordinary skill in the art and/or by reference to the schemes shown below and the synthetic examples. Exemplary synthetic routes are set forth in Schemes below, and in the Examples.

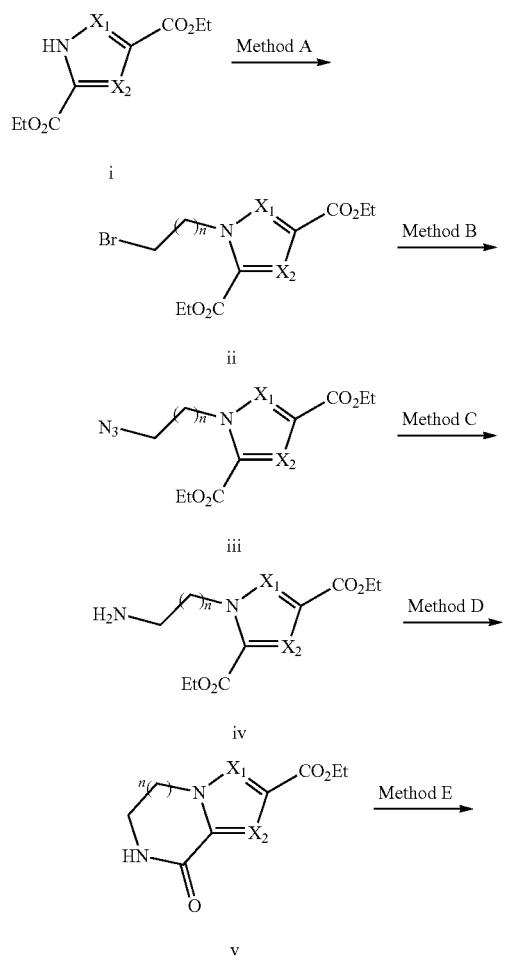

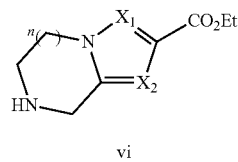

Scheme 1 shows a general route for preparing compounds represented by formula vi. Starting from one of the following: diethyl 1H-pyrrole-2,4-dicarboxylate (prepared as described by Bhattacharya et al., *Tetrahedron Lett.* 2006, 47(31):5481-5484); 1H-1,2,4-triazole-3,5-dicarboxylic acid, 3,5-diethyl ester (commercially available); diethyl 3,5-pyrazoledicarboxylate (commercially available); or diethyl 5-amino-1H-imidazole-2,4-dicarboxylate (commercially available) compounds of formula v can be prepared in a sequence analogous to that described by Askew et al., *Bioorg. Med. Chem. Lett.* 1995, 5(5):475.

Treatment of azole i with a dihaloalkane such as dibromoethane in the presence of a base with heating (Method A; see also Pratt, et al., *Bioorg. Med. Chem. Lett.* 2000, 10:2749) provides access to ii. Displacement of the pendant halide of ii with sodium azide (Method B, see Colombano et al., *J. Med. Chem.* 2010, 53: 616-623) affords iii which upon application of reducing conditions such as a palladium metal catalyst in a hydrogen atmosphere (Method C) provides access to the corresponding primary amine iv. Primary amine iv can be cyclized with heating in the presence of base (Method D) to generate lactam v. Removal of the amide carbonyl is accomplished via reduction in the presence of a suitable hydride delivery agent such as $BH_3 \cdot THF$ (Method E) as described by Di Fabio et al., *J. Med. Chem.* 2009, 52:3238-3247.

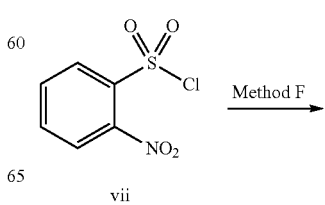

Scheme 2: General route for the preparation of N-fused pyrazoles

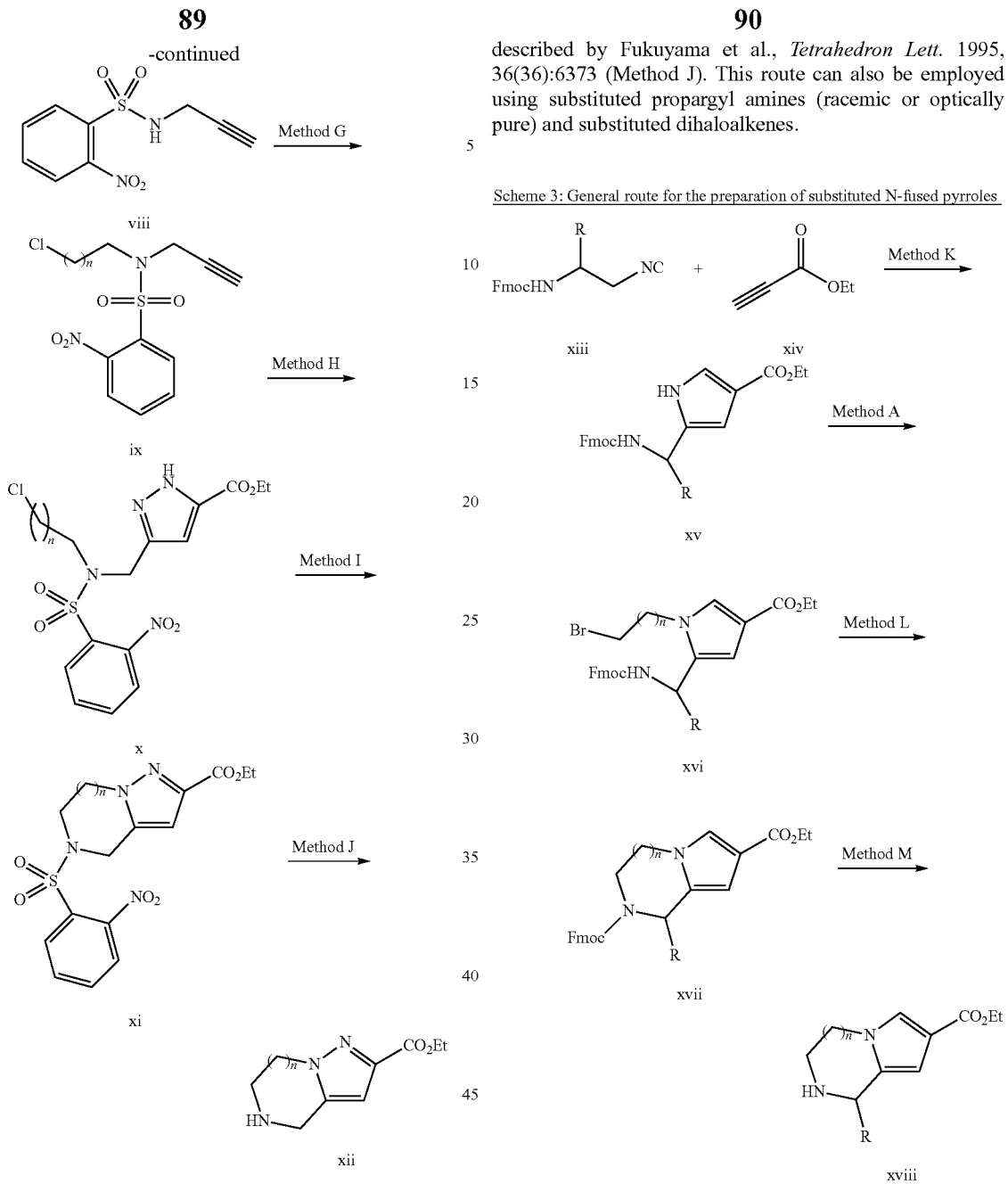

Scheme 2 shows a general route for preparing compounds represented by formula xii. Sulfonamide viii can be prepared from the reaction of propargyl amine with o-nitrobenzene sulfonyl chloride (Method F). Alkylation of the sulfonamide can be effected upon treatment with a dihaloalkane such as 1-bromo-2-chloroethane in the presence of a base such as cesium carbonate with heating (Method G). A 3+2 sigmatropic cyclization of the terminal acetylene with ethyl diazoacetate in a solvent such as benzene using a sealed tube with heating results in the construction of the pyrazole ring in compounds of formula x (Method H) in a fashion similar as described by Zrinski et al., *Heterocycles* 2006, 68(9):1961. An intramolecular cyclization onto the pendant aliphatic chlorine with a pyrazole nitrogen can be achieved through additional heating in the presence of a base such as cesium carbonate (Method I). Removal of the o-nitro sulfonamide protecting group is achieved by treatment with thiophenol as described by Fukuyama et al., *Tetrahedron Lett.* 1995, 36(36):6373 (Method J). This route can also be employed using substituted propargyl amines (racemic or optically pure) and substituted dihaloalkenes.

Scheme 3 shows a general route for the preparation of compounds of the type represented by formula xviii. Racemic or optically pure isonitriles (xiii) prepared from the corresponding β-amino acids (Sureshbabu et al., *J. Org. Chem.* 2009, 74:153) can be reacted with ethyl propiolate (xiv) to construct the pyrrole ring of xv through a 3+2 cycloaddition (Method K). Treatment of xv with a dihaloalkane such as dibromoethane in the presence of a base with heating (Method A) affords xvi. Formation of the tetrahydropyrrolopyrazine ring system of xvii can be carried out though the deprotonation of the carbamate nitrogen with sodium hydride, LDA or $Cs_2CO_3$ followed by cyclization onto the pendent bromide (Method L; Yamaguchi et al., *Chemistry Lett.* 1996, 8:621). Removal of the Fmoc protecting group using piperidine (Method M) provides compounds of formula xviii.

Scheme 4: General route for the preparation of N-fused imidazoles

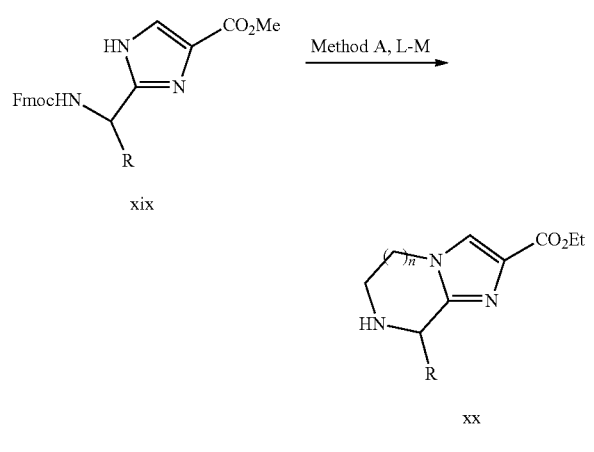

xix xx

Scheme 4 shows a general route for the preparation of substituted compounds of the type represented by formula xx. Racemic or optically pure substituted 2-(aminomethyl)-1H-imidazole-4-carboxylate esters depicted by xix (prepared as described by You et al., *Organic Letters* 2004, 6:1681, can be converted to the tetrahydroimidazopyrazine xx (Methods A, L and M) in a fashion analogous to that depicted in Scheme 3.

Scheme 5: General route for the preparation of N-fused triazoles

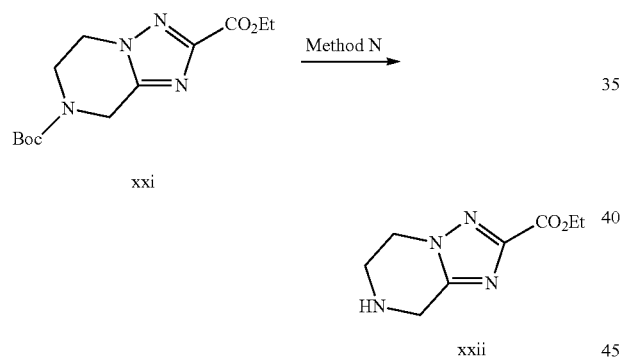

xxi xxii

Scheme 5 shows a general route for the preparation of compounds of the type represented by formula xxii. The Boc protecting group on 7-tert-butyl 2-ethyl 5,6-dihydro-[1,2,4]triazolo[1,5-a]pyrazine-2,7(8H)-dicarboxylate (xxi) (prepared as described by Carling et al., WO 00/023449) can be removed upon treatment with an acid such as HCl or TFA (Method N).

Scheme 6: General route for the preparation of amide bearing N-fused azole hydroxamates

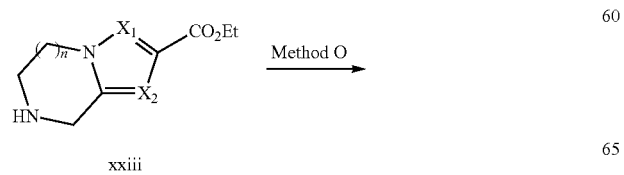

xxiii

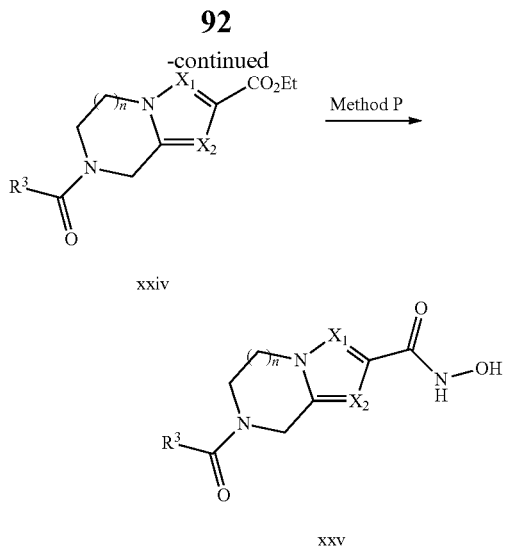

xxiv xxv

Scheme 6 shows a route for the preparation of substituted azole compounds of formula xxv. Reaction of the secondary amines represented by compounds of formula xxiii with carboxylic acids ($R^3$—$CO_2H$) employing coupling agents such as HBTU or HATU leads to the formation of the corresponding amide xiv (Method O). Conversion of the ethyl ester in xxiv to a hydroxamate is conducted by reaction with the potassium salt of hydroxylamine (Method P; Huang et al., *J. Med. Chem.* 2009, 52(21):6757) leading to the formation of compounds of formula xxv.

Scheme 7: General route for the preparation of sulfonamide bearing N-fused azole hydroxamates

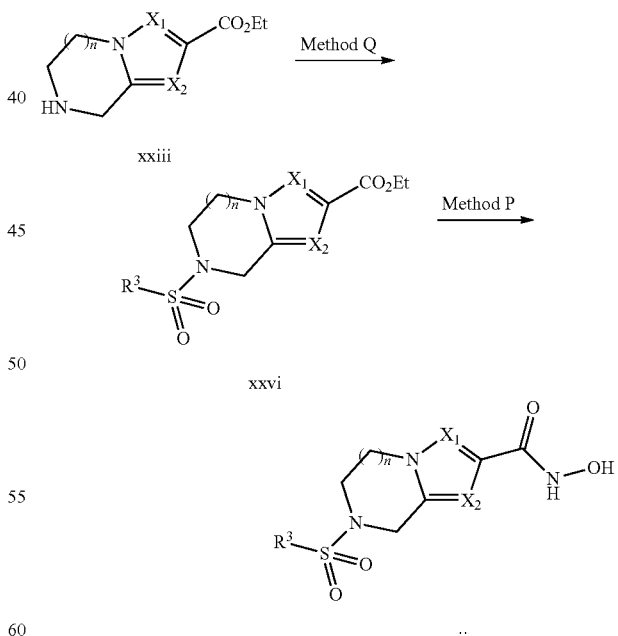

xxiii xxvi xxvii

Scheme 7 shows a route for the preparation of substituted azole compounds of formula xxvii. Reaction of the secondary amine in compounds represented by xxiii with sulfonyl chlorides (Method Q) leads to the formation of the corresponding sulfonamide xxvi. Conversion of xxvi to the corresponding hydroxamate is carried out in an analogous fashion as shown in Scheme 6 (Method P) leading to the formation of compounds of formula xxvii.

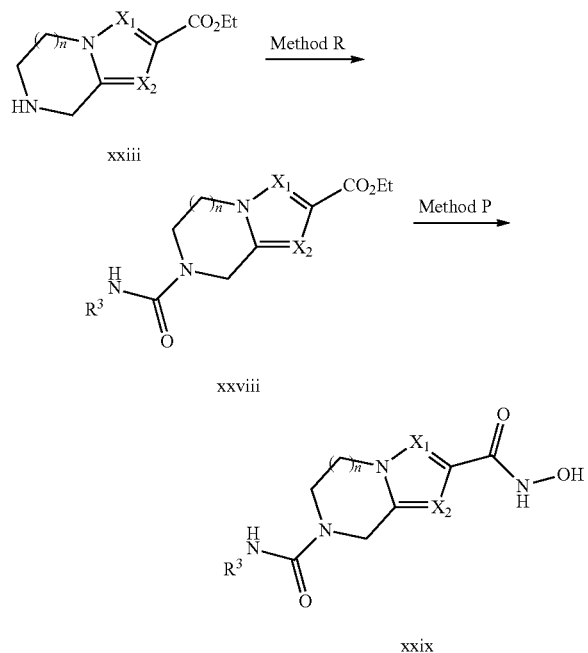

Scheme 8: General route for the preparation of urea bearing N-fused azole hydroxamates Scheme 8 shows a route for the preparation of substituted azole compounds of formula xxix. The reaction of the compounds of formula xxiii with the isocyanates ($R^3$—NCO; Method R) leads to the formation of the corresponding ureas of formula xxviii. Conversion of xxviii to the corresponding hydroxamate is carried out in an analogous fashion as shown in Scheme 6 (Method P) leading to the formation of compounds of formula xxix.

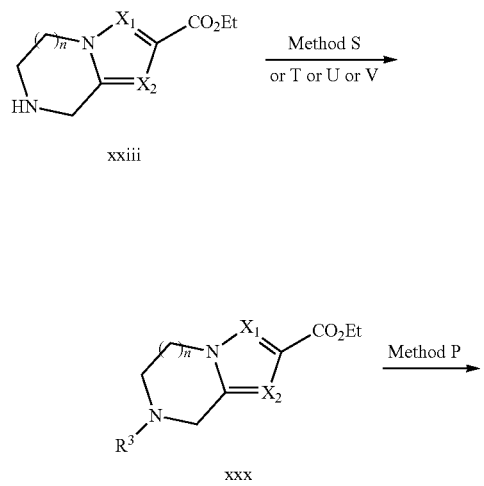

Scheme 9: General route for the preparation of N-alkyl or aryl bearing N-fused azole hydroxamates

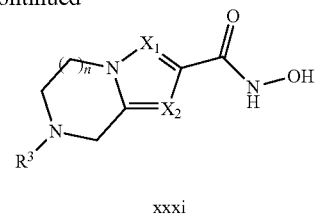

Scheme 9 shows a route for the preparation of substituted azole compounds of formula xxxi. Treatment of amine xxiii with either an aldehyde under standard reductive amination conditions, (i.e. in the presence of a borohydride such as sodium cyanoborohydride, Method S) or an alkyl halide in an $S_N2$ fashion (Method T) affords the tertiary amine xxx. The secondary amine xxiii may also be arylated using standard nucleophilic aromatic substitution of a suitable eletrophile such as 2-chloro-nitropyridine, in the presence of suitable base, such as DIPEA at elevated temperatures (Method U). Amine xxiii may also be N-arylated through a copper(II)-acetate mediated coupling with a suitable arylboronic acid (Method V; Chan et al. *Tetrahedron Lett.* 1998, 39(19):2933). Conversion of xxx to the corresponding hydroxamate is carried out in an analogous fashion as shown in Scheme 6 (Method P) leading to the formation of compounds of formula xxxi.

4. Uses, Formulation and Administration

As discussed above, the present invention provides compounds and pharmaceutical compositions that are useful as inhibitors of HDAC enzymes, particularly HDAC6, and thus the present compounds are useful for treating proliferative, inflammatory, infectious, neurological or cardiovascular disorders.

The compounds and pharmaceutical compositions of the invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

In some embodiments, therefore, the invention provides the compound of formula (I), or a pharmaceutically acceptable salt thereof, for use in treating cancer. In some embodiments, the invention provides a pharmaceutical composition (as described herein) for the treatment of cancer comprising the compound of formula (I), or a pharmaceutically acceptable salt thereof. In some embodiments, the invention provides the use of the compound of formula (I), or a pharmaceutically acceptable salt thereof, for the preparation of a pharmaceutical composition (as described herein) for the treatment of cancer. In some embodiments, the invention provides the use of an effective amount of the compound of formula (I), or a pharmaceutically acceptable salt thereof, for the treatment of cancer.

Non-limiting examples of solid tumors that can be treated with the disclosed inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

Non-limiting examples of hematologic malignancies that can be treated with the disclosed inhibitors include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma; T-cell lymphoma; multiple myeloma (MM); Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes.

In some embodiments, compounds of the invention are suitable for the treatment of breast cancer, lung cancer, ovarian cancer, multiple myeloma, acute myeloid leukemia or acute lymphoblastic leukemia.

In other embodiments, compounds of the invention are suitable for the treatment of inflammatory and cardiovascular disorders including, but not limited to, allergies/anaphylaxis, acute and chronic inflammation, rheumatoid arthritis; autoimmunity disorders, thrombosis, hypertension, cardiac hypertrophy, and heart failure.

Accordingly, in another aspect of the present invention, pharmaceutical compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of HDAC6.

Pharmaceutically acceptable salts are well known in the art. For example, S. M. Berge et al., describe pharmaceutically acceptable salts in detail in J Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for treating a proliferative, inflammatory, infectious, neurological or cardiovascular disorder is provided comprising administering an effective amount of a compound, or a pharmaceutical composition to a subject in need thereof. In certain embodiments of the present invention an "effective amount" of the compound or pharmaceutical composition is that amount effective for treating a proliferative, inflammatory, infectious, neurological or cardiovascular disorder, or is that amount effective for treating cancer. In other embodiments, an "effective amount" of a compound is an amount which inhibits binding of HDAC6, and thereby blocks the resulting signaling cascades that lead to the abnormal activity of growth factors, receptor tyrosine kinases, protein serine/threonine kinases, G protein coupled receptors and phospholipid kinases and phosphatases.

The compounds and compositions, according to the method of the present invention, may be administered using any amount and any route of administration effective for treating the disease. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disease being treated and the severity of the disease; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

In some embodiments, a compound of formula (I) or a pharmaceutical composition thereof is administered in conjunction with an anticancer agent. As used herein, the term "anticancer agent" refers to any agent that is administered to a subject with cancer for purposes of treating the cancer. Combination therapy includes administration of the therapeutic agents concurrently or sequentially. Alternatively, the therapeutic agents can be combined into one composition which is administered to the patient.

Non-limiting examples of DNA damaging chemotherapeutic agents include topoisomerase I inhibitors (e.g., irinotecan, topotecan, camptothecin and analogs or metabolites thereof, and doxorubicin); topoisomerase II inhibitors (e.g., etoposide, teniposide, and daunorubicin); alkylating agents (e.g., melphalan, chlorambucil, busulfan, thiotepa, ifosfamide, carmustine, lomustine, semustine, streptozocin, decarbazine, methotrexate, mitomycin C, and cyclophosphamide); DNA intercalators (e.g., cisplatin, oxaliplatin, and carboplatin); DNA intercalators and free radical generators such as bleomycin; and nucleoside mimetics (e.g., 5-fluorouracil, capecitibine, gemcitabine, fludarabine, cytarabine, mercaptopurine, thioguanine, pentostatin, and hydroxyurea).

Chemotherapeutic agents that disrupt cell replication include: paclitaxel, docetaxel, and related analogs; vincristine, vinblastin, and related analogs; thalidomide, lenalidomide, and related analogs (e.g., CC-5013 and CC-4047); protein tyrosine kinase inhibitors (e.g., imatinib mesylate and gefitinib); proteasome inhibitors (e.g., bortezomib); NF-κB inhibitors, including inhibitors of IκB kinase; antibodies which bind to proteins overexpressed in cancers and thereby downregulate cell replication (e.g., trastuzumab, rituximab, cetuximab, and bevacizumab); and other inhibitors of proteins or enzymes known to be upregulated, over-expressed or activated in cancers, the inhibition of which down-regulates cell replication. In certain embodiments, a compound of the invention is administered in conjunction with a proteasome inhibitor.

Another aspect of the invention relates to inhibiting HDAC6, activity in a biological sample or a patient, which method comprises administering to the patient, or contacting said biological sample with a compound of formula (I), or a composition comprising said compound. The term "biological sample", as used herein, generally includes in vivo, in vitro, and ex vivo materials, and also includes, without limitation, cell cultures or extracts thereof; biopsied material obtained from a mammal or extracts thereof; and blood, saliva, urine, feces, semen, tears, or other body fluids or extracts thereof.

Still another aspect of this invention is to provide a kit comprising separate containers in a single package, wherein the inventive pharmaceutical compounds, compositions and/or salts thereof are used in combination with pharmaceutically acceptable carriers to treat disorders, symptoms and diseases where HDAC6 plays a role.

5. Preparation of Exemplary Compounds

EXPERIMENTAL PROCEDURES

Definitions
ATP adenosine triphosphate
DCE dichloroethane
DCM dichloromethane
DIPEA diisopropylethyl amine
DMF N,N-dimethylformamide DMFDMA N,N-dimethylformamide dimethyl acetal
DMSO dimethylsulfoxide
EDCI   N-(3-dimethylaminopropyl)-N'-ethylcarbodiimide hydrochloride
EDTA ethylenediaminetetraacetic acid
EtOAc ethyl acetate
EtOH ethanol
FA formic acid
FBS fetal bovine serum
Fmoc 9H-fluoren-9-ylmethoxycarbonyl
h hours
HATU N,N, N',N'-tetramethyl-o-(7-azabenzotriazole-1-yl) uronium hexafluorophosphate
HBTU o-benzotriazol-1-yl-N,N, N',N'-tetramethyluronium hexafluorophosphate
HEPES N-(2-hydroxyethyl)piperazine-N'-(2-ethanesulfonic acid)
HOBT 1-hydroxybenztriazole hydrate
HRMS high resolution mass spectrum
IPA isopropyl alcohol
LAH lithium aluminum hydride
LC-MS liquid chromatography mass spectrum
m/z mass to charge
MTBE methyl tert-butyl ether
Me methyl
MeCN acetonitrile
MEM minimum essential media
MeOH methanol
min minutes
MS mass spectrum
MWI microwave irradiation
NMM N-methyl morpholine
PBS phosphate buffered saline
rt room temperature
TEA triethylamine
TFA trifluoroacetic acid
TFAA trifluoroacetic anhydride
TFFH  tetramethylfluoroformamidinium  hexafluorophosphate
THF tetrahydrofuran
THP tetrahydropyranyl Analytical Methods NMR: $^1$H NMR spectra are run on a 400 MHz Bruker unless otherwise stated.

LCMS: LC-MS spectra are run using an Agilent 1100 LC interfaced to a micromass Waters® Micromass® Zspray™ Mass Detector (ZMD).

HPLC: Preparative HPLC are conducted using 18×150 mm Sunfire C-18 columns eluting with water-MeCN gradients using a Gilson instrument operated by 322 pumps with the UV/visible 155 detector triggered fraction collection set to between 200 nm and 400 nm. Mass gated fraction collection is conducted on an Agilent 1100 LC/MSD instrument.

Example 1 ethyl 1,2,3,4-tetrahydropyrrolo[1,2-a]pyrazine-7-carboxylate 2,2,2-trifluoroacetate Intermediate 5

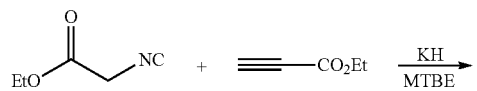

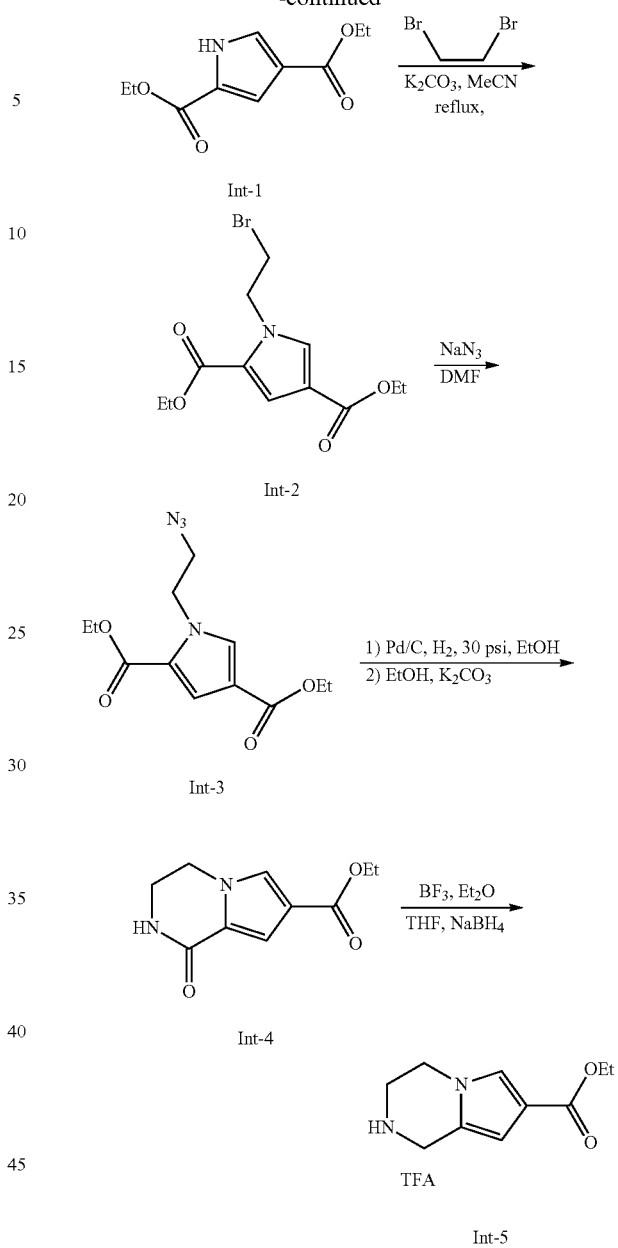

Step 1: diethyl 1H-pyrrole-2,4-dicarboxylate Intermediate 1

A suspension of potassium hydride (0.53 g, 13.26 mmol) in MTBE (10 mL) was added to a stirred solution of ethyl 2-isocyanoacetate (1 g, 8.84 mmol) and ethyl propiolate (1 g, 10.19 mmol) in MTBE (10 mL). The resulting mixture was stirred at rt for 4 h. The solution was then acidified with 1N HCl to pH≤3. The organic layer was washed with sat. NaHCO$_3$ solution (2 mL), brine (2 mL), dried (MgSO$_4$), and concentrated to give a solid residue. Purification via flash chromatography (petroleum ether:EtOAc, 15:1 to 10:1) afforded diethyl 1H-pyrrole-2,4-dicarboxylate (0.7 g, 37%). $^1$H NMR (CDCl$_3$, 300 MHz) δ9.75 (br, 1 H), 7.49 (s, 1 H), 7.24 (s, 1 H), 4.25 (m, 4 H), 1.29 (m, 6 H).

Step 2: diethyl 1-(2-bromoethyl)-1H-pyrrole-2,4-dicarboxylate Intermediate 2

To a stirred solution of diethyl 1H-pyrrole-2,4-dicarboxylate (0.7 g, 3.31 mmol), and 1,2-dibromoethane (2.8 mL, 32.5 mmol) in MeCN (30 mL) was added $K_2CO_3$ (0.55 g, 39.7 mmol). This reaction mixture was refluxed overnight then filtered. The filtrate was collected and concentrated to give diethyl 1-(2-bromoethyl)-1H-pyrrole-2,4-dicarboxylate (0.8 g, 76%). $^1$H NMR (CDCl$_3$, 300 MHz) δ7.42 (d, J=1.8 Hz, 1 H), 7.33 (d, J=1.8 Hz, 1 H), 4.60 (t, J=6.0 Hz, 2 H), 4.22 (q, J=7.2 Hz, 4 H), 3.62 (t, J=6.4 Hz, 2 H), 1.28 (m, 6 H).

Step 3: diethyl 1-(2-azidoethyl)-1H-pyrrole-2,4-dicarboxylate Intermediate 3

To a solution of diethyl 1-(2-bromoethyl)-1H-pyrrole-2,4-dicarboxylate (0.8 g) in DMF (10 mL) was added sodium azide (0.2 g, 3.07 mmol). The resulting mixture was stirred at rt overnight then diluted with water (10 mL) and EtOAc (100 mL). After separation, the aqueous layer was extracted with EtOAc (2×50 mL). The combined organic layers were washed with brine, dried (MgSO$_4$) and concentrated. Purification via flash chromatography (petroleum ether:EtOAc, 20:1 to 15:1) afforded diethyl 1-(2-azidoethyl)-1H-pyrrole-2,4-dicarboxylate (0.4 g, 57%). $^1$H NMR (CDCl$_3$, 300 MHz) δ7.49 (d, J=1.8 Hz, 1 H), 7.43 (d, J=1.8 Hz, 1 H), 4.88 (t, J=5.5 Hz, 2 H), 4.32 (q, J=7.2 Hz, 4 H), 3.70 (t, J=6.4 Hz, 2 H), 1.38 (m, 6 H).

Step 4: ethyl 1-oxo-1,2,3,4-tetrahydropyrrolo[1,2-a]pyrazine-7-carboxylate Intermediate 4

To a solution of diethyl 1-(2-azidoethyl)-1H-pyrrole-2,4-dicarboxylate (10 g, 35.68 mmol) in EtOH (1000 mL) was added 10% Pd/C (3 g). The resulting residue was stirred at rt under a 30 psi H$_2$ atmosphere for 2 h. The palladium catalyst was filtered. To the filtrate was added potassium carbonate (5 g, 36 mmol) and the mixture was refluxed overnight. All solids were removed by filtration, and the filtrate was concentrated. Purification via flash chromatography (DCM:methanol, 50:1 to 20:1) afforded ethyl 1-oxo-1,2,3,4-tetrahydropyrrolo[1,2-a]pyrazine-7-carboxylate (2.5 g, 41%). $^1$H NMR (DMSO-d$_6$, 300 MHz) δ7.91 (s, 1 H), 7.64 (s, 1H), 6.90 (s, 1 H), 4.18 (m, 4 H), 3.50 (m, 2 H), 1.25 (t, J=5.4 Hz, 3 H).

Step 5: ethyl 1,2,3,4-tetrahydropyrrolo[1,2-a]pyrazine-7-carboxylate 2,2,2-trifluoroacetate Intermediate 5

To a solution of ethyl 1-oxo-1,2,3,4-tetrahydropyrrolo[1,2-a]pyrazine-7-carboxylate (5 g, 24 mmol) in THF (1000 mL) was added sodium borohydride (40 g, 1.05 mol) under nitrogen. The mixture was cooled to 0° C. and boron trifluoride etherate (200 mL, 1.59 mmol) was added dropwise. The reaction mixture was stirred overnight at rt then EtOH (500 mL) was added. The solvent was then evaporated. To the resulting residue was added EtOH (850 mL), water (150 mL), and 10% aqueous HCl (75 mL). After the solution was stirred at rt for 4 h, the EtOH was removed by evaporation. The resulting solution was neutralized with sat. NaHCO$_3$ solution to pH≥8 then diluted with EtOAc (500 mL). After separation, the aqueous layer was extracted with EtOAc (2×500 mL). The combined organic layers were concentrated. Purification via prep-HPLC afforded ethyl 1,2,3,4-tetrahydropyrrolo[1,2-a] pyrazine-7-carboxylate 2,2,2-trifluoroacetate (3.1 g, 26%) as a solid. $^1$H NMR (DMSO-d$_6$, 300 MHz) δ9.34 (s, 1 H), 7.47 (s, 1H), 6.34 (s, 1 H), 4.29 (s, 2 H), 4.15 (m, 4 H), 3.54 (m, 2 H), 1.21 (t, J=7.1 Hz, 3 H).

Example 2 ethyl 2,3,4,5-tetrahydro-1H-pyrrolo[1,2-a][1,4]diazepine-8-carboxylate 2,2,2-trifluoroacetate Intermediate 9

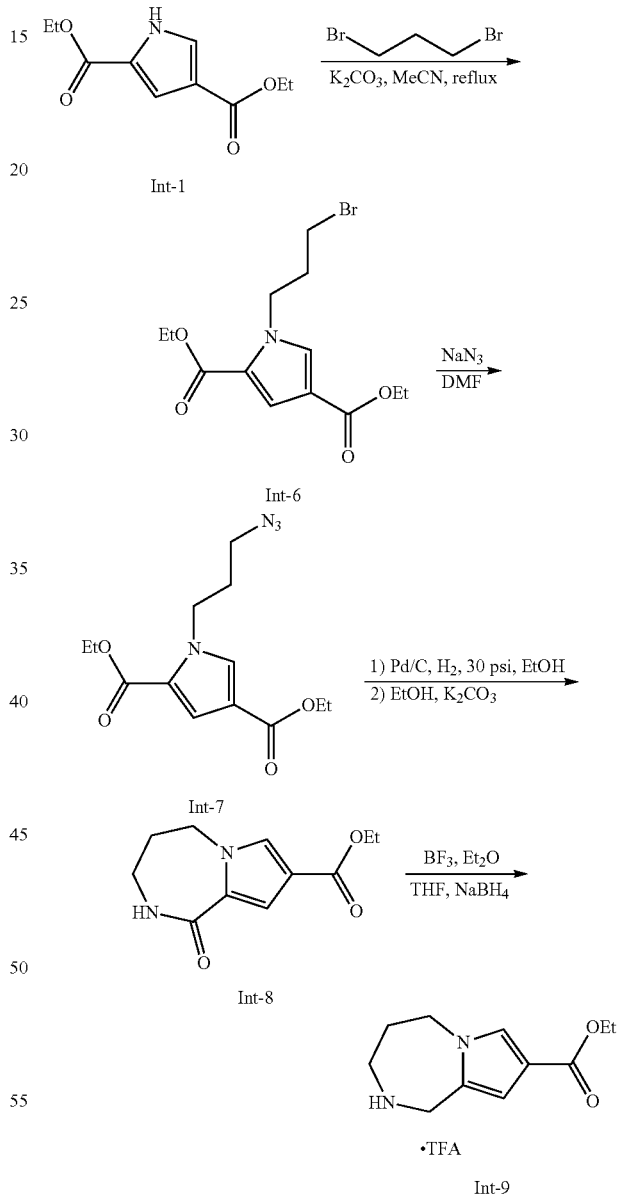

Step 1: diethyl 1-(3-bromopropyl)-1H-pyrrole-2,4-dicarboxylate Intermediate 6

To a stirred solution of diethyl 1H-pyrrole-2,4-dicarboxylate (2 g, 9.47 mmol) and 1,3-dibromopropane (10 mL, 98 mmol) in acetonitrile was added potassium carbonate (1.7 g, 12.3 mmol). The mixture was refluxed overnight, then filtered and concentrated to give crude diethyl 1-(3-bromopropyl)-1H-pyrrole-2,4-dicarboxylate. $^1$H NMR (CDCl$_3$, 300 MHz) δ7.47 (s, 1H), 7.36 (s, 1 H), 4.47 (t, J=6.6 Hz, 2 H), 4.27 (m, 4 H), 3.32 (t, J=6.2 Hz, 2 H), 2.32 (m, 2 H), 1.34 (m, 6 H).

Step 2: diethyl 1-(3-azidopropyl)-1H-pyrrole-2,4-dicarboxylate Intermediate 7

To a stirred solution of crude diethyl 1-(3-bromopropyl)-1H-pyrrole-2,4-dicarboxylate in DMF (30 mL) was added sodium azide (1 g, 15.4 mmol). The resulting mixture was stirred at rt overnight then diluted with water (30 mL) and EtOAc (150 mL). After separation, the aqueous layer was extracted with EtOAc (2×150 mL). The combined organic layers were washed with brine, dried (MgSO$_4$), and concentrated. Purification via flash chromatography (petroleum ether:EtOAc, 20:1 to 15:1) afforded diethyl 1-(3-azidopropyl)-1H-pyrrole-2,4-dicarboxylate (2 g, 75%). $^1$H NMR (CDCl$_3$, 300 MHz) δ7.42 (s, 1H), 7.36 (s, 1 H), 4.40 (t, J=6.6 Hz, 2 H), 4.26 (m, 4 H), 3.30 (m, J=6.2 Hz, 2 H), 2.04 (m, 2 H), 1.36 (m, 6 H).

Step 3: ethyl 1-oxo-2,3,4,5-tetrahydro-1H-pyrrolo[1,2-a][1,4]diazepine-8-carboxylate Intermediate 8

To a solution of diethyl 1-(3-azidopropyl)-1H-pyrrole-2,4-dicarboxylate Intermediate 7 (8 g, 27.2 mmol) in EtOH (800 mL) was added 10% Pd/C (2 g). The reaction was stirred at rt under a 30 psi H$_2$ atmosphere for 2 h then filtered. To the filtrate was added potassium carbonate (4 g, 28.9 mmol). The reaction was then refluxed overnight. All the solids were then removed by filtration and the filtrate was then concentrated to give a solid which was dissolved in DCM (200 mL) and 1N aqueous HCl. After separation, the aqueous layer was extracted with DCM (2×150 mL). The combined organic layers were washed with brine, dried (MgSO$_4$), and concentrated to give ethyl 1-oxo-2,3,4,5-tetrahydro-1H-pyrrolo[1,2-a][1,4]diazepine-8-carboxylate (4 g, 66%). $^1$H NMR (DMSO-d$_6$, 300 MHz) δ7.88 (s, 1 H), 7.61 (s, 1 H), 6.84 (s, 1 H), 4.19 (m, 4 H), 3.09 (m, 2 H), 1.99 (m, 2 H), 1.25 (t, J=7.1 Hz, 3 H).

Step 4: ethyl 2,3,4,5-tetrahydro-1H-pyrrolo[1,2-a][1,4]diazepine-8-carboxylate 2,2,2-trifluoroacetate Intermediate 9

To a solution of ethyl 1-oxo-2,3,4,5-tetrahydro-1H-pyrrolo[1,2-a][1,4]diazepine-8-carboxylate (4 g, 18 mmol) in THF (800 mL) was added sodium borohydride (32 g, 0.84 mol) under nitrogen. The mixture was cooled to 0° C. and boron trifluoride etherate (160 mL, 1.27 mmol) was added dropwise. The reaction mixture was stirred at rt overnight then EtOH (700 mL) was slowly added. The solvent was evaporated and to the resulting residue was added EtOH (1000 mL), water (240 mL), and 10% aqueous HCl (120 mL). After stirring at rt for 4 h, the EtOH was removed by evaporation. The remaining solution was neutralized with sat. NaHCO$_3$ solution to a pH of ≥8 and then diluted with EtOAc (500 mL). After separation, the aqueous layer was extracted with EtOAc (2×500 mL). The combined organic layers were concentrated. The residue obtained was dissolved in DMSO (1 mL) and purified via prep-HPLC afforded ethyl 2,3,4,5-tetrahydro-1H-pyrrolo[1,2-a][1,4]diazepine-8-carboxylate 2,2,2-trifluoroacetate (1.91 g, 33%) as a solid. $^1$H NMR (DMSO-d$_6$, 300 MHz) δ8.94 (s, 2 H), 7.51 (s, 1 H), 6.54 (s, 1 H), 4.28 (s, 2 H), 4.19 (m, 2 H), 4.12 (q, J=7.1 Hz, 2 H), 3.28 (m, 2 H), 1.92 (m, 2 H), 1.19 (t, J=7.1 Hz, 3 H).

Example 3

2-[1-adamantylcarbonyl]-N-hydroxy-1,2,3,4-tetrahydropyrrolo[1,2-a]pyrazine-7-carboxamide Compound I-62

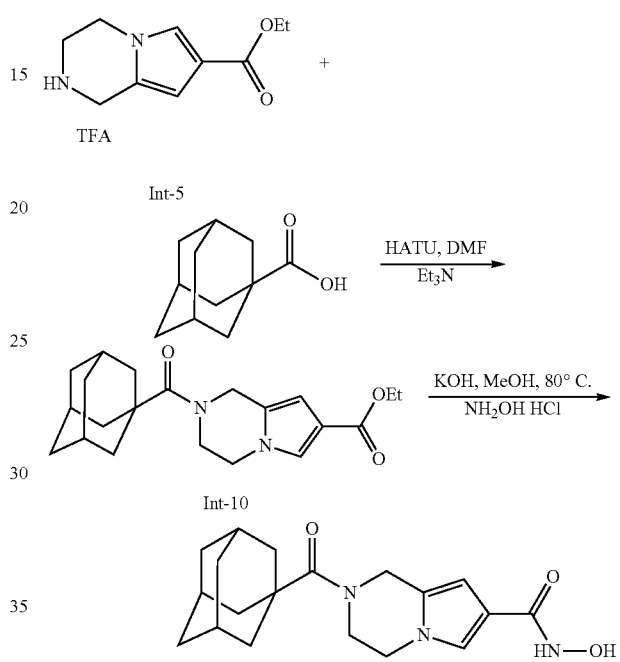

Step 1: ethyl 2-(1-adamantylcarbonyl)-1,2,3,4-tetrahydropyrrolo[1,2-a]pyrazine-7-carboxylate Intermediate 10

To a microwave vial containing 1-adamantanecarboxylic acid (0.05 g, 0.283 mmol) was added HATU (0.11 g, 0.283 mmol), triethylamine (0.11 mL, 0.772 mmol) and DMF (1.5 mL). The solution was allowed to stir at rt for 30 minutes before ethyl 1,2,3,4-tetrahydropyrrolo[1,2-a]pyrazine-7-carboxylate Intermediate 5 (0.05 g, 0.257 mmol) was added to the solution. The solution was then allowed to stir at rt overnight and then evaporated. To the resulting residue was added DCE (3 mL) and water (1 mL). After separation, the aqueous phase was extracted with DCE (2×3 mL). The combined organic phases were concentrated to give a crude ethyl 2-(1-adamantylcarbonyl)-1,2,3,4-tetrahydropyrrolo[1,2-a]pyrazine-7-carboxylate as a solid.

Step 2: 2-(1-adamantylcarbonyl)-N-hydroxy-1,2,3,4-tetrahydropyrrolo[1,2-a]pyrazine-7-carboxamide Compound I-62

To a vial with crude ethyl 2-(1-adamantylcarbonyl)-1,2,3,4-tetrahydropyrrolo[1,2-a]pyrazine-7-carboxylate from Step 1 was added potassium hydroxide (0.145 g, 2.59 mmol), hydroxylamine hydrochloride (0.054 g, 0.776 mmol), and methanol (1.63 mL). The vial was capped, heated at 80° C. for 1 h, and then cooled to rt. Acetic acid (0.147 mL, 2.59 mmol)

was slowly added to the solution to quench the excess base and then the solvent was completely evaporated. To the resulting residue was added DMSO (1.2 mL). The solution was purified by prep-HPLC purification after filtration to give the title compound (0.0011 g, 1.2%) as a white solid. LC-MS: (FA) ES+344; $^1$H NMR (CDCl$_3$, 300 MHz) δ7.21 (s, 1 H), 6.36 (s, 1 H), 4.85 (s, 2 H), 4.00 (m, 2 H), 3.79 (m, 2 H), 2.10-1.60 (m, 15 H).

Example 4

The following compounds were prepared in an analogous fashion to that described in Example 3 starting from the intermediates which were prepared as described above and the corresponding carboxylic acids.

| Compound | LC-MS (FA) |
|---|---|
| I-20 | ES+ 339 |
| I-47 | ES+ 368 |
| I-73 | ES+ 307 |
| I-64 | ES− 418 |
| I-85 | ES+ 304 |
| I-39 | ES+ 290 |
| I-66 | ES+ 344 |
| I-30 | ES+ 292 |
| I-58 | ES+ 339 |
| I-89 | ES+ 339 |
| I-15 | ES+ 345 |
| I-51 | ES+ 362 |
| I-10 | ES+ 342 |
| I-84 | ES+ 327 |
| I-68 | ES+ 316 |
| I-28 | ES+ 353 |
| I-3 | ES+ 326 |
| I-94 | ES+ 303 |
| I-1 | ES+ 342 |
| I-54 | ES+ 364 |
| I-61 | ES+ 305 |
| I-35 | ES+ 399 |
| I-22 | ES+ 339 |
| I-82 | ES+ 381 |
| I-75 | ES+ 325 |
| I-87 | ES+ 441 |
| I-52 | ES+ 304 |
| I-40 | ES+ 303 |
| I-29 | ES+ 325 |
| I-91 | ES+ 357 |
| I-99 | ES+ 366 |
| I-92 | ES+ 292 |
| I-32 | ES+ 289 |

Example 5

2-butyl-N-hydroxy-1,2,3,4-tetrahydropyrrolo[1,2-a]pyrazine-7-carboxamide Compound I-86

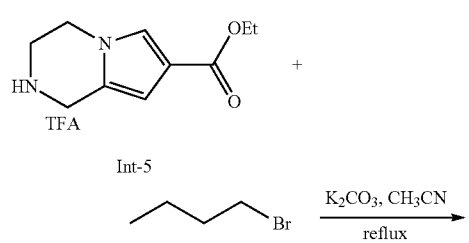

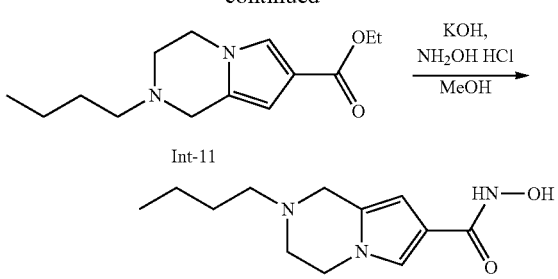

Step 1: ethyl 2-butyl-1,2,3,4-tetrahydropyrrolo[1,2-a]pyrazine-7-carboxylate Intermediate 11

To a solution of ethyl 1,2,3,4-tetrahydropyrrolo[1,2-a]pyrazine-7-carboxylate trifluoroacetate (2.6 g, 13.4 mmol) and 1-bromobutane (3.67 g, 26.8 mmol) in acetonitrile (26 mL) was added potassium carbonate (2.45 g, 17.7 mmol). The resulting mixture was refluxed overnight. The solvent was then evaporated to give a solid residue. Purification via flash chromatography (petroleum ether:EtOAc, 10:1) afforded ethyl 2-butyl-1,2,3,4-tetrahydropyrrolo[1,2-a]pyrazine-7-carboxylate Intermediate 11 (0.7 g, 21%). $^1$H NMR (CDCl$_3$, 300 MHz) δ7.11 (s, 1 H), 6.18 (s, 1 H), 4.25 (m, 2 H), 3.99 (m, 2 H), 3.53 (s, 2 H), 2.82 (t, J=5.6 Hz, 2 H), 2.46 (t, J=7.4 Hz, 2 H), 1.46 (m, 2 H), 1.30 (m, 2 H), 1.25 (t, J=7.1 Hz, 3 H), 0.87 (t, J=7.3 Hz, 2 H).

Step 2: 2-butyl-N-hydroxy-1,2,3,4-tetrahydropyrrolo[1,2-a]pyrazine-7-carboxamide Compound I-86

To a vial was added ethyl 2-butyl-1,2,3,4-tetrahydropyrrolo[1,2-a]pyrazine-7-carboxylate Intermediate 11 (0.075 g, 0.3 mmol), hydroxylamine hydrochloride (0.084 g, 1.2 mmol), potassium hydroxide (0.135 g, 2.4 mmol), and methanol (3 mL). The vial was capped and heated at 80° C. for 1 h. Upon cooling to rt, acetic acid (0.068 mL, 1.2 mmol) was added to neutralize the excess base. The solvent was then removed and to the resulting residue was added DMSO (1.2 mL). The solution was filtered and purified by Gilson prep-HPLC to give the title compound (0.0176 g, 25%) as a white solid. LC-MS: (FA) ES+238; $^1$H NMR (Methanol-d$_4$, 400 MHz) δ 7.45 (d, J=1.55 Hz, 1 H), 6.49 (s, 1 H), 4.50 (m, 2 H), 4.37 (t, J=5.8 Hz, 2 H), 3.79 (m, 2 H), 3.77 (s, 2 H), 1.81 (m, 2 H), 1.46 (m, 2 H), 1.02 (t, J=7.3 Hz, 3 H).

Example 6

2-benzyl-N-hydroxy-1,2,3,4-tetrahydropyrrolo[1,2-a]pyrazine-7-carboxamide Compound I-23

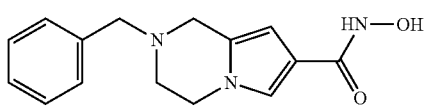 [SMILES: O=C(NO)c1cc2n(c1)CCN(Cc1ccccc1)C2]

The title compound was prepared in an analogous fashion to that described in Example 5 starting from the appropriate starting materials. Yield: 61%. LC-MS (FA): ES+272.

Example 7

2-benzyl-N-hydroxy-1-oxo-1,2,3,4-tetrahydropyrrolo[1,2-a]pyrazine-7-carboxamide Compound I-42

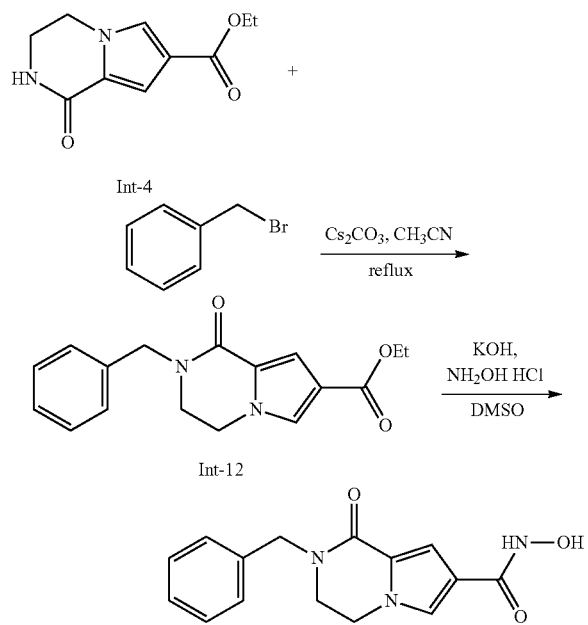

Step 1: ethyl 2-benzyl-1-oxo-1,2,3,4-tetrahydropyrrolo[1,2-a]pyrazine-7-carboxylate Intermediate 12

To a vial charged with ethyl 1-oxo-1,2,3,4-tetrahydropyrrolo[1,2-a]pyrazine-7-carboxylate (0.0298 g, 0.143 mmol) was added cesium carbonate (0.061 g, 0.186 mmol), benzyl bromide (0.037 g, 0.2145 mmol), and acetonitrile (1 mL). The vial was capped and was shaken at 70° C. overnight. The solids were removed by filtration and the solution was concentrated to give crude ethyl 2-benzyl-1-oxo-1,2,3,4-tetrahydropyrrolo[1,2-a]pyrazine-7-carboxylate Intermediate 12.

Step 2: 2-benzyl-N-hydroxy-1-oxo-1,2,3,4-tetrahydropyrrolo[1,2-a]pyrazine-7-carboxamide Compound I-42

To a vial was added potassium hydroxide (0.1 g, 2 mmol), hydroxylamine hydrochloride (0.05 g, 0.715 mmol), and DMSO (1 mL). The vial was sonicated until the hydroxylamine hydrochloride had gone into solution. This solution was then added to the vial containing the crude ethyl 2-benzyl-1-oxo-1,2,3,4-tetrahydropyrrolo[1,2-a]pyrazine-7-carboxylate prepared in Step 1 above. The resulting mixture was shaken overnight at room temperature. Purification via Gilson prep-HPLC afforded 2-benzyl-N-hydroxy-1-oxo-1,2,3,4-tetrahydropyrrolo[1,2-a]pyrazine-7-carboxamide (0.0049 g, 11.7%). LC-MS: (FA) ES+286; $^1$H NMR (Methanol-d$_4$, 400 MHz) δ7.39 (s, 1 H), (m, 5 H), 7.15 (s, 1 H), 4.74 (s, 2 H), 3.64 (t, J=5.8 Hz, 2 H), 4.18 (t, J=6.0 Hz, 2 H).

Example 8

2-benzyl-N-hydroxy-1-oxo-2,3,4,5-tetrahydro-1H-pyrrolo[1,2-a][1,4]diazepine-8-carboxamide Compound I-49

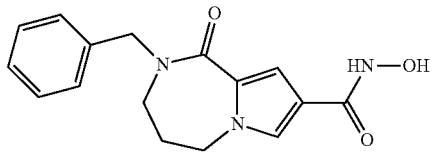 [SMILES: O=C(NO)c1cc2n(c1)CCCN(Cc1ccccc1)C2=O]

The title compound was prepared in an analogous fashion to that described in Example 7 starting from the appropriate starting materials. Yield: 9.5%. LC-MS (FA): ES+300; $^1$H NMR (Methanol-d$_4$, 400 MHz) δ7.40-7.28 (m, 6 H), 7.01 (s, 1H), 4.72 (s, 2 H), 4.14 (t, J=6.8 Hz, 2 H), 3.35 (t, J=6.5 Hz, 2 H), 1.95 (m, 2 H).

Example 9

N-hydroxy-2-(1-methyl-1H-pyrrole-2-carbonyl)-2,3,4,5-tetrahydro-1H-pyrrolo[1,2-a][1,4]diazepine-8-carboxamide Compound I-9

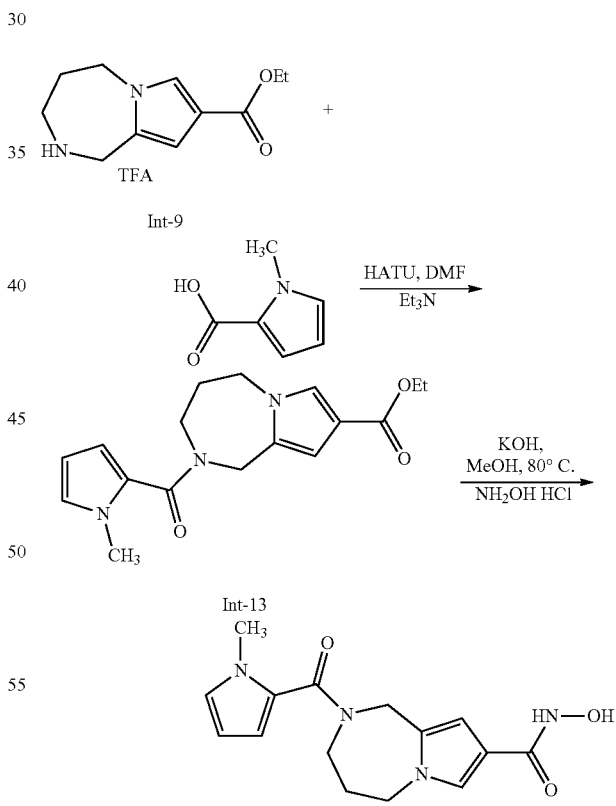

Step 1: ethyl 2-(1-methyl-1H-pyrrole-2-carbonyl)-2,3,4,5-tetrahydro-1H-pyrrolo[1,2-a][1,4]diazepine-8-carboxylate Intermediate 13

To a vial containing N-methylpyrrole-2-carboxylic acid (0.025 g, 0.2 mmol) was added HATU (0.076 g, 0.2 mmol), DCM (2 mL), and triethylamine (0.112 mL, 0.8 mmol). The solution was stirred at rt for 30 min then ethyl 2,3,4,5-tetrahydro-1H-pyrrolo[1,2-a][1,4]diazepine-8-carboxylate 2,2,2-trifluoroacetate (0.0644 g, 0.2 mmol) in DMF (0.5 mL) was added. The mixture was stirred at rt for 2 h. The reaction was quenched by addition of DCM (1 mL), sat. NaHCO$_3$ solution (0.5 mL), and water (1 mL). After separation, the aqueous layer was extracted with DCE (2×3 mL). The combined organic layers were concentrated to give crude ethyl 2-(1-methyl-1H-pyrrole-2-carbonyl)-2,3,4,5-tetrahydro-1H-pyrrolo[1,2-a][1,4]diazepine-8-carboxylate.

Step 2: N-hydroxy-2-(1-methyl-1H-pyrrole-2-carbonyl)-2,3,4,5-tetrahydro-1H-pyrrolo[1,2-a][1,4]diazepine-8-carboxamide Compound I-9

To a vial containing crude ethyl 2-(1-methyl-1H-pyrrole-2-carbonyl)-2,3,4,5-tetrahydro-1H-pyrrolo[1,2-a][1,4]diazepine-8-carboxylate from Step 1 above was added potassium hydroxide (0.112 g, 2 mmol), hydroxylamine hydrochloride (0.0417 g, 0.6 mmol), and methanol (2 mL). The mixture was shaken at 80° C. for 2 h then cooled to room temperature. Acetic acid (0.114 mL, 2 mmol) was added to quench the excess base. The solvent was then completely evaporated and to the residue was added DMSO (1.2 mL). After filtration, the solution was purified via Gilson prep-HPLC to give N-hydroxy-2-(1-methyl-1H-pyrrole-2-carbonyl)-2,3,4,5-tetrahydro-1H-pyrrolo[1,2-a][1,4]diazepine-8-carboxamide (0.004 g, 6.5%). LC-MS (FA): ES+303; $^1$H NMR (CD$_3$CN, 400 MHz) δ6.81 (s, 1 H), 6.40 (s, 1 H), 5.95 (m, 1 H), 5.81 (m, 1 H), 5.70 (m, 1 H), 4.27 (s, 2 H), 3.83 (m, 2 H), 3.51 (m, 2 H), 3.21 (s, 3 H), 1.85 (m, 2 H).

Example 10

The following compounds were prepared in an analogous fashion to that described in Example 9 starting from the intermediates which were prepared as described above and the corresponding carboxylic acids.

| Compound | LC-MS (FA) |
| --- | --- |
| I-7 | ES+ 380 |
| I-19 | ES+ 292 |
| I-74 | ES+ 320 |
| I-79 | ES+ 368 |
| I-95 | ES+ 332 |
| I-56 | ES+ 334 |
| I-18 | ES+ 356 |
| I-69 | ES+ 320 |
| I-43 | ES+ 314 |
| I-33 | ES− 366 |
| I-104 | ES+ 371 |
| I-65 | ES+ 360 |
| I-5 | ES− 485 |
| I-96 | ES+ 356 |
| I-25 | ES+ 351 |
| I-111 | ES+ 306 |
| I-78 | ES+ 321 |
| I-34 | ES+ 374 |
| I-59 | ES+ 294 |
| I-34 | ES+ 358 |
| I-80 | ES+ 390 |
| I-4 | ES+ 318 |

Example 11 ethyl 4,5,6,7-tetrahydropyrazolo[1,5-a]pyrazine-2-carboxylate Intermediate 17

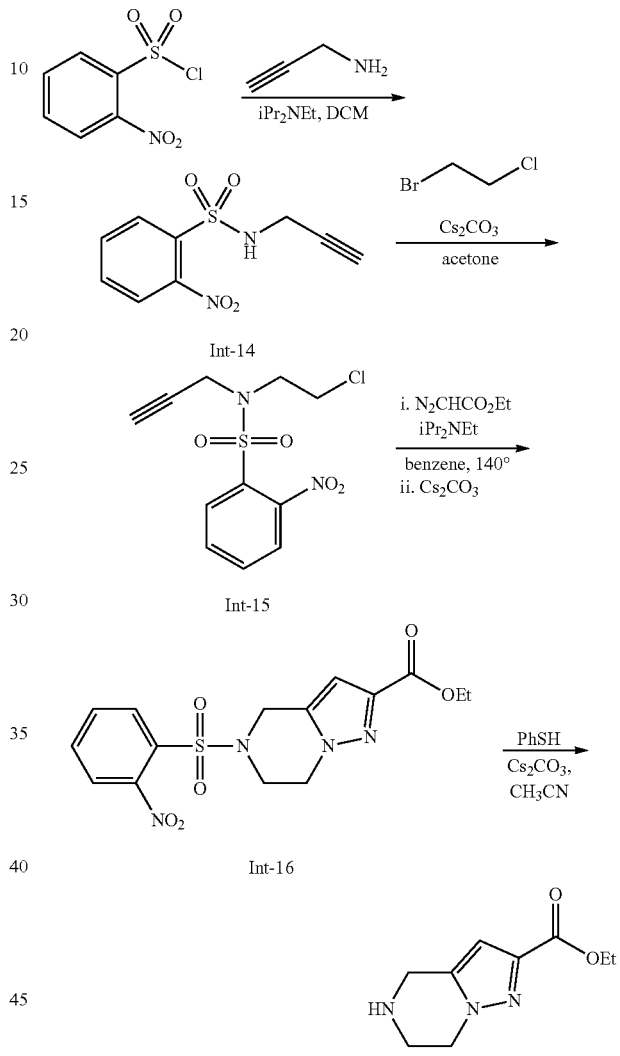

Step 1: 2-nitro-N-(prop-2-ynyl)benzenesulfonamide Intermediate 14

A solution of propargylamine (2 mL, 29 mmol) and N,N-diisopropylethylamine (10 mL, 57.4 mmol) in methylene chloride (100 mL) was cooled to 0° C. 2-nitrobenzenesulfonyl chloride (6.46 g, 29.2 mmol) was added portionwise. Upon complete addition, the solution was allowed to warm to room temperature and was further stirred at room temperature overnight. The reaction solution was concentrated in vacuo and the residue obtained was directly purified on silica chromatography (20-50% EtOAc/hexane) to afford Intermediate 14 as white solid (5.90 g, 84%). LC-MS: (FA) ES+241; $^1$H NMR (400 MHz, CDCl$_3$) δ 8.22-8.17 (m, 1H), 7.94-7.89 (m, 1H), 7.79-7.73 (m, 2H), 5.71 (s, 1H), 4.02 (dd, J=5.9, 2.4 Hz, 2H), 1.97 (t, J=2.5 Hz, 1H).

Step 2: N-(2-chloroethyl)-2-nitro-N-(prop-2-ynyl)benzenesulfonamide Intermediate 15

To a mixture of 2-nitro-N-(prop-2-yn-1-yl)benzenesulfonamide (0.448 g, 1.86 mmol) and cesium carbonate (1.75 g, 5.37 mmol) in acetone (10 mL) was added neat 1-bromo-2-chloroethane (0.775 mL, 9.31 mmol) dropwise. The reaction mixture was stirred at room temperature for 20 hours. The reaction mixture was concentrated and the residue partitioned between EtOAc (25 mL) and water (15 mL). The aqueous layer was extracted with additional EtOAc (20 mL), the combined organic layers dried over anhydrous MgSO4 and concentrated. Purification via silica chromatography (25-40% EtOAc/hexane) afforded an oil (0.540 g, 96%). LC-MS: (FA) ES+303. $^1$H NMR (400 MHz, CDCl$_3$) δ 8.08 (dt, J=8.2, 3.7 Hz, 1H), 7.77-7.64 (m, 3H), 4.30 (d, J=2.5 Hz, 2H), 3.78-3.68 (m, 4H), 2.23 (t, J=2.5 Hz, 1H).

Step 3: ethyl 5-(2-nitrophenylsulfonyl)-4,5,6,7-tetrahydropyrazolo[1,5-a]pyrazine-2-carboxylate Intermediate 16

A solution of N-(2-chloroethyl)-2-nitro-N-(prop-2-yn-1-yl)benzenesulfonamide (0.51 g, 1.69 mmol and ethyl diazoacetate (0.266 mL, 2.532 mmol) in benzene (2 mL) was heated in a microwave reactor at 140° C. for 1 hour. Upon cooling to room temperature, cesium carbonate (0.637 g, 1.95 mmol) along with tetrahydrofuran (1 mL) was added. The vial was again sealed and heated at 140° C. for 30 minutes in the microwave reactor. Upon cooling to room temperature, the solvents were then evaporated in vacuo and the residue obtained was partitioned between water (10 mL) and EtOAc (15 mL). The aqueous layer was washed with additional EtOAc (15 mL), the combined organic layers were dried over anhydrous MgSO4, concentrated and purified via silica chromatography (20-90% EtOAc/hexane) to afford Intermediate 16 as a semi solid (0.235 g, 37%). LC-MS: (FA) ES+381; $^1$H NMR (400 MHz, CDCl$_3$) δ 8.07 (dd, J=7.5, 1.7 Hz, 1H), 7.79-7.67 (m, 3H), 6.63 (s, 1H), 4.64 (s, 2H), 4.41-4.31 (m, 4H), 3.92-3.89 (m, 2H), 1.37 (t, J=7.1 Hz, 3H).

Step 4: ethyl 4,5,6,7-tetrahydropyrazolo[1,5-a]pyrazine-2-carboxylate Intermediate 17

To a mixture of ethyl 5-[(2-nitrophenyl)sulfonyl]-4,5,6,7-tetrahydropyrazolo[1,5-a]pyrazine-2-carboxylate (0.216 g, 0.568 mmol) and cesium carbonate (0.35 g, 1.1 mmol) was added a solution of benzenethiol (0.11 mL, 1.1 mmol) in acetonitrile (1 mL). The resulting reaction mixture was stirred at room temperature for 1 hour. The solvent was removed in vacuo and the residue applied directly to silica purification (5% MeOH/DCM with 1% Et$_3$N) to afford Intermediate 17 as a white solid (0.093 g, 84%). LC-MS: (FA) ES+196; $^1$H NMR (400 MHz, CDCl$_3$) δ 6.49 (s, 1H), 4.35 (q, J=7.1 Hz, 2H), 4.17-4.13 (m, 2H), 4.04 (s, 2H), 3.29-3.25 (m, 2H), 1.74 (s, 1H), 1.35 (t, J=7.1 Hz, 3H).

Example 12

N-(tetrahydro-2H-pyran-2-yloxy)-5,6,7,8-tetrahydro-4H-pyrazolo[1,5-a][1,4]diazepine-2-carboxamide Intermediate 22

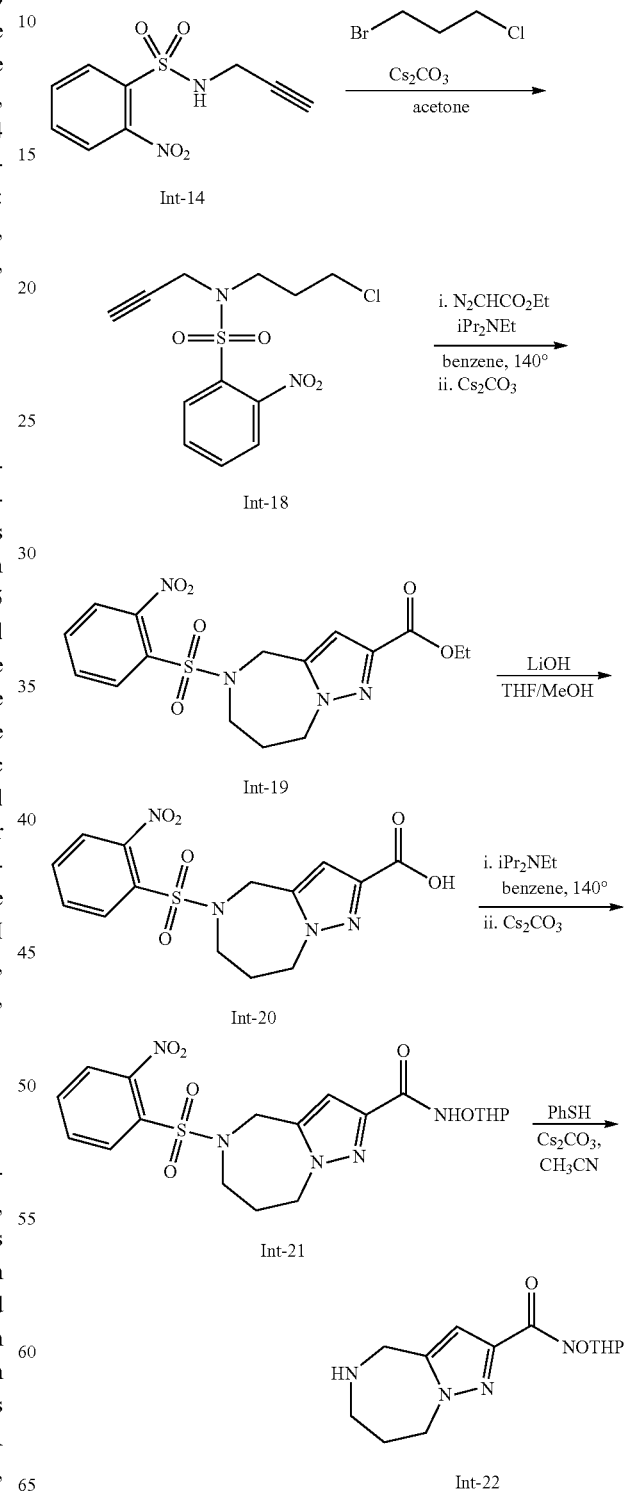

Step 1: N-(3-chloropropyl)-2-nitro-N-(prop-2-ynyl) benzenesulfonamide Intermediate 18

To a mixture of 2-nitro-N-(prop-2-yn-1-yl)benzenesulfonamide (1.08 g, 4.48 mmol) and cesium carbonate (7.30 g, 22.42 mmol) in acetone (40 mL) was added neat 1-bromo-3-chloropropane (6.5 mL, 66 mmol) dropwise. Upon complete addition, the reaction mixture was stirred at room temperature for 2 days. The reaction mixture was concentrated and the residue partitioned between EtOAc (25 mL) and water (15 mL). The aqueous layer was extracted with additional EtOAc (20 mL), the combined organic layers dried over anhydrous $MgSO_4$ and concentrated. Purification via silica chromatography (25-40% EtOAc/hexane) afforded Intermediate 18 as an oil (0.9764 g, 69%). $^1$H NMR (400 MHz, $CDCl_3$) δ 8.10-8.05 (m, 1H), 7.76-7.62 (m, 3H), 4.22 (d, J=2.5 Hz, 2H), 3.57 (td, J=6.6, 2.9 Hz, 4H), 2.21 (t, J=2.5 Hz, 1H), 2.14-2.06 (m, 2H).

Step 2: ethyl 5-(2-nitrophenylsulfonyl)-5,6,7,8-tetrahydro-4H-pyrazolo[1,5-a][1,4]diazepine-2-carboxylate Intermediate 19

To a solution of N-(3-chloropropyl)-2-nitro-N-(prop-2-yn-1-yl)benzenesulfonamide (0.5 g, 1.59 mmol) and ethyl diazoacetate (0.251 mL, 2.384 mmol) in benzene (1.5 mL) was added N,N-diisopropylethylamine (0.27 mL, 1.6 mmol). The resulting solution was heated in a microwave reactor at 140° C. for 1 hour. Upon cooling to room temperature, cesium carbonate (0.621 g, 1.91 mmol) and tetrahydrofuran (1 mL) was added and the reaction mixture again heated at 140° C. for 30 minutes. Upon cooling to room temperature, the solvents were evaporated and the residue obtained was partitioned between water (10 mL) and EtOAc (15 mL). The aqueous layer was washed with additional EtOAc (15 mL), the combined organic layers were dried over anhydrous $MgSO_4$, concentrated and purified via silica chromatography (20-90% EtOAc/hexane) to afford Intermediate 19 as a yellow oil (0.314 g, 50%). LC-MS: (FA) ES+395; $^1$H NMR (400 MHz, $CDCl_3$) δ 7.96 (dd, J=7.8, 1.5 Hz, 1H), 7.73-7.60 (m, 3H), 6.77 (s, 1H), 4.58 (s, 2H), 4.52-4.47 (m, 2H), 4.37 (q, J=7.1 Hz, 2H), 3.72-3.65 (m, 2H), 2.10-2.04 (m, 2H), 1.37 (t, J=7.1 Hz, 3H).

Step 3: 5-(2-nitrophenylsulfonyl)-5,6,7,8-tetrahydro-4H-pyrazolo[1,5-a][1,4]diazepine-2-carboxylic acid Intermediate 20

Ethyl 5-[(2-nitrophenyl)sulfonyl]-5,6,7,8-tetrahydro-4H-pyrazolo[1,5-a][1,4]diazepine-2-carboxylate (0.143 g, 0.362 mmol) was dissolved in a mixture of THF (4 mL) and methanol (1 mL) and to the solution was added 1.0 M of lithium hydroxide in water (1.5 mL, 1.5 mmol). The resulting mixture was stirred at room temperature for 2 hours. The mixture was concentrated, and the residue was dissolved in water (5 mL) and neutralized with 1.0 M hydrochloric acid in water (1.5 mL, 1.5 mmol). The resulting precipitate was collected via vacuum filtration to afford Intermediate 20 as a white solid (0.1166 g, 88%). LC-MS: (FA) ES+395.

Step 4: 5-(2-nitrophenylsulfonyl)-N-(tetrahydro-2H-pyran-2-yloxy)-5,6,7,8-tetrahydro-4H-pyrazolo[1,5-a][1,4]diazepine-2-carboxamide Intermediate 21

To a solution of 5-[(2-nitrophenyl)sulfonyl]-5,6,7,8-tetrahydro-4H-pyrazolo[1,5-a][1,4]diazepine-2-carboxylic acid (0.116 g, 0.316 mmol) and O-(tetrahydropyran-2-yl) hydroxylamine (0.0407 g, 0.347 mmol) in methylene chloride (2.5 mL) was added N,N,N',N'-tetramethyl-O-(7-azabenzotriazol-1-yl)uronium hexafluorophosphate (0.144 g, 0.379 mmol) and N-methylmorpholine (0.1 mL, 0.9 mmol). The resulting reaction mixture was stirred at room temperature overnight. The solvent was evaporated and the residue obtained purified via silica chromatography (80-100% EtOAc/hexane) to afford Intermediate 21 as a clear colorless oil (0.152 g, 100%). LC-MS: (FA) ES+466.

Step 5: N-(tetrahydro-2H-pyran-2-yloxy)-5,6,7,8-tetrahydro-4H-pyrazolo[1,5-a][1,4]diazepine-2-carboxamide Intermediate 22

To a mixture of 5-[(2-nitrophenyl)sulfonyl]-N-(tetrahydro-2H-pyran-2-yloxy)-5,6,7,8-tetrahydro-4H-pyrazolo[1,5-a][1,4]diazepine-2-carboxamide (0.15 g, 0.32 mmol) and cesium carbonate (0.2 g, 0.62 mmol) in acetonitrile (10 mL) was added a solution of benzenethiol (0.063 mL, 0.62 mmol) in acetonitrile (0.60 mL). The resulting reaction mixture was stirred at room temperature for 1 hour. The solvent was evaporated and the residue applied directly to silica purification (5% MeOH/DCM) to afford the title compound as a white solid (0.082 g, 91%). LC-MS: (FA) ES+281; $^1$H NMR (400 MHz, $CDCl_3$) δ 6.59 (s, 1H), 5.30 (s, 1H), 5.08 (s, 1H), 4.39-4.32 (m, 2H), 4.08-4.00 (m, 1H), 3.92 (q, J=15.7 Hz, 2H), 3.71-3.61 (m, 1H), 3.26-3.15 (m, 2H), 2.29 (s, 1H), 1.92-1.79 (m, 5H), 1.70-1.54 (m, 3H).

Example 13

N-hydroxy-5-(3-methylbenzo[b]thiophene-2-carbonyl)-4,5,6,7-tetrahydropyrazolo[1,5-a]pyrazine-2-carboxamide Compound I-97

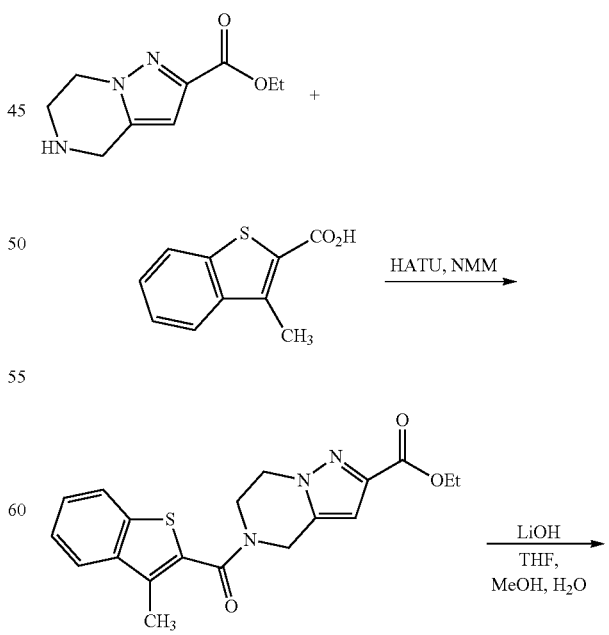

Int-23

-continued

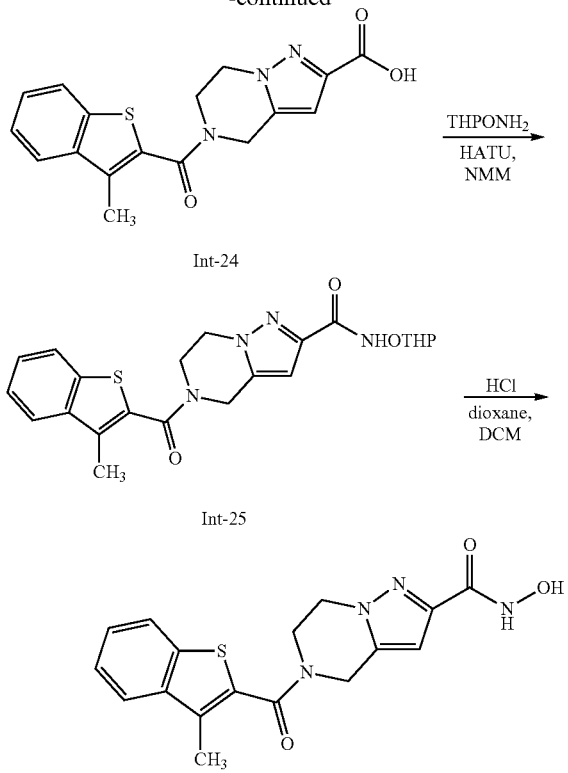

Int-24

Int-25

Step 1: ethyl 5-(3-methylbenzo[b]thiophene-2-carbonyl)-4,5,6,7-tetrahydropyrazolo[1,5-a]pyrazine-2-carboxylate Intermediate 23

To a mixture of ethyl 4,5,6,7-tetrandropyrazolo[1,5-a]pyrazine-2-carboxylate (0.029 g, 0.15 mmol) and 3-methylbenzo[b]thiophene-2-carboxylic acid (0.0314 g, 0.163 mmol) in methylene chloride (1.5 mL) was added N,N,N',N'-tetramethyl-O-(7-azabenzotriazol-1-yl)uronium hexafluorophosphate (0.0678 g, 0.178 mmol) and N-methylmorpholine (0.05 mL, 0.446 mmol). The reaction mixture was stirred at room temperature overnight. The reaction was diluted with additional methylene chloride (1.5 mL) and was washed with aqueous $NaHCO_3$ (2 mL). The layers were separated and the aqueous layer was extracted with additional methylene chloride (3 mL) and the combined organic layers evaporated to dryness to give crude ethyl 5-(3-methylbenzo[b]thiophene-2-carbonyl)-4,5,6,7-tetrahydropyrazolo[1,5-a]pyrazine-2-carboxylate Intermediate 23.

Step 2: 5-(3-methylbenzo[b]thiophene-2-carbonyl)-4,5,6,7-tetrahydropyrazolo[1,5-a]pyrazine-2-carboxylic acid Intermediate 24

The ethyl 5-(3-methylbenzo[b]thiophene-2-carbonyl)-4,5,6,7-tetrahydropyrazolo[1,5-a]pyrazine-2-carboxylate obtained in the previous step was dissolved in a mixture of tetrahydrofuran (1.8 mL) and methanol (0.3 mL). To the resulting solution was added 1M aqueous sodium hydroxide (0.4 mL, 0.4 mmol). The solution was stirred at room temperature for 4 hours whereupon the reaction was neutralized with the addition of 1M aqueous hydrochloric acid (0.4 mL). The solvents were evaporated under reduced pressure to afford crude Intermediate 24 as a white solid.

Step 3: 5-(3-methylbenzo[b]thiophene-2-carbonyl)-N-(tetrahydro-2H-pyran-2-yloxy)-4,5,6,7-tetrahydropyrazolo[1,5-a]pyrazine-2-carboxamide Intermediate 25

To a mixture of 5-(3-methylbenzo[b]thiophene-2-carbonyl)-4,5,6,7-tetrahydropyrazolo[1,5-a]pyrazine-2-carboxylic acid obtained in the previous step and O-(tetrahydropyran-2-yl)hydroxylamine (0.035 g, 0.3 mmol) in methylene chloride (1.5 mL) was added N,N,N',N'-tetramethyl-O-(7-azabenzotriazol-1-yl)uronium hexafluorophosphate (0.085 g, 0.22 mmol) and N-methylmorpholine (0.05 mL, 0.44 mmol). The resulting mixture was stirred overnight at room temperature. The reaction was then diluted with additional methylene chloride (1.5 mL) and washed with aqueous $NaHCO_3$ (2 mL). The separated aqueous layer was extracted with methylene chloride (3 mL) and the combined organic layers were concentrated to afford crude Intermediate 25.

Step 4: N-hydroxy-5-(3-methylbenzo[b]thiophene-2-carbonyl)-4,5,6,7-tetrahydropyrazolo[1,5-a]pyrazine-2-carboxamide Compound I-97

The crude intermediate 25 obtained in the previous step was taken up in tetrahydrofuran (1 mL) and to the solution was added 4M hydrochloric acid in 1,4-dioxane (0.50 mL, 2 mmol). The reaction was stirred at room temperature for 1.5 hours. The solution was evaporated to dryness, the residue dissolved in DMSO (1 mL) and purified on Gilson prep-HPLC to afford the title compound as a white solid (0.0043 g, 8%). LC-MS: (FA) ES+357; $^1$H NMR (400 MHz, DMSO) δ 10.95 (s, 1H), 8.91 (s, 1H), 8.05-7.95 (m, 1H), 7.90-7.82 (m, 1H), 7.51-7.45 (m, 2H), 6.49 (s, 1H), 4.84 (s, 2H), 4.21 (s, 2H), 4.04 (s, 2H), 2.38 (s, 3H).

Example 14

The following compounds were prepared in an analogous fashion to that described in Example 13 starting from the intermediates which were prepared as described above and the corresponding carboxylic acids.

| Compound | LC-MS (FA) |
|---|---|
| I-6 | ES+ 307 |
| I-97 | ES+ 357 |
| I-36 | ES+ 267 |

Example 15

N-hydroxy-5-(1H-indol-3-ylacetyl)-4,5,6,7-tetrahydropyrazolo[1,5-a]pyrazine-2-carboxamide Compound I-102

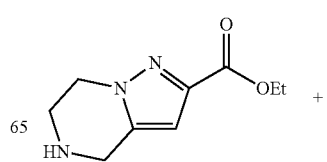

119

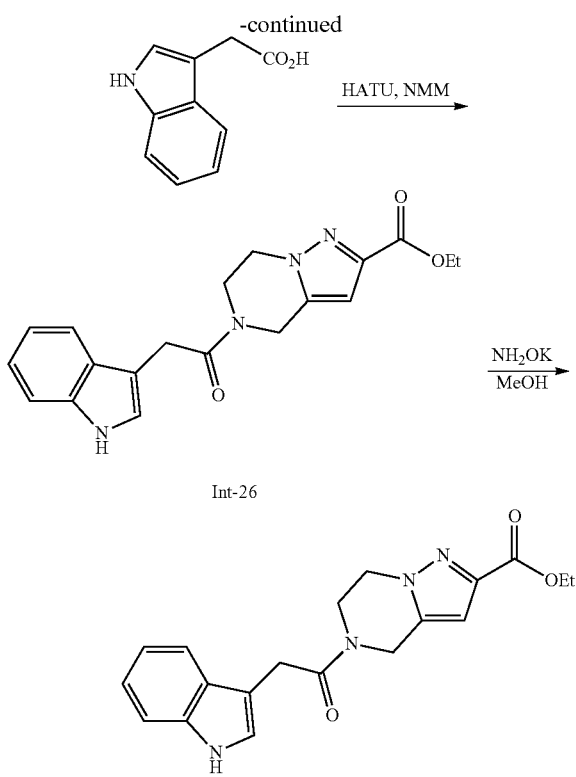

Int-26

Step 1: ethyl 5-(2-(1H-indol-3-yl)acetyl)-4,5,6,7-tetrahydropyrazolo[1,5-a]pyrazine-2-carboxylate Intermediate 26

To a mixture of ethyl 4,5,6,7-tetrandropyrazolo[1,5-a]pyrazine-2-carboxylate (0.02 g, 0.1 mmol) and indole-3-acetic acid (0.019 g, 0.11 mmol) in methylene chloride (1.5 mL) was added N,N,N',N'-tetramethyl-O-(7-azabenzotriazol-1-yl)uronium hexafluorophosphate (0.046 g, 0.12 mmol) and N-methylmorpholine (0.02 mL, 0.2 mmol). The reaction mixture was stirred at room temperature overnight. The reaction was diluted with additional methylene chloride (1.5 mL) and washed with aqueous $NaHCO_3$ (2 mL). The layers were separated and the aqueous layer was extracted with additional methylene chloride (3 mL) and the combined organic layers evaporated to dryness to give crude ethyl 5-(2-(1H-indol-3-yl)acetyl)-4,5,6,7-tetrahydropyrazolo[1,5-a]pyrazine-2-carboxylate.

Step 2: N-hydroxy-5-(1H-indol-3-ylacetyl)-4,5,6,7-tetrahydropyrazolo[1,5-a]pyrazine-2-carboxamide Compound I-102

To a solution of ethyl 5-(2-(1H-indol-3-yl)acetyl)-4,5,6,7-tetrahydropyrazolo[1,5-a]pyrazine-2-carboxylate obtained in the previous step in methanol (0.5 mL) was added 1.7 M hydroxylamine potassium salt in methanol (0.5 mL, 0.85 mmol; prepared as described in *Journal of Medicinal Chemistry* 2009, 52(21):6757). The reaction mixture was stirred at room temperature for 1 hour. Upon evaporation of the solvent, the resulting residue was dissolved in DMSO (1 mL) and purified using an Agilent 1100 LC/MSD instrument to afford the title compound as a white solid (11.0 mg, 32%). LC-MS: (FA) ES+340.

120

Example 16

The following compounds were prepared in an analogous fashion to that described in Example 15 starting from the intermediates which were prepared as described above and the corresponding carboxylic acids.

| Compound | LC-MS (FA) |
|---|---|
| I-90 | ES+ 322 |
| I-106 | ES+ 315 |
| I-107 | ES+ 338 |
| I-11 | ES+ 358 |
| I-37 | ES+ 363 |
| I-31 | ES+ 340 |
| I-8 | ES+ 319 |
| I-17 | ES+ 393 |
| I-93 | ES+ 354 |

Example 17

N-hydroxy-5-(4-methoxybenzoyl)-4,5,6,7-tetrahydropyrazolo[1,5-a]pyrazine-2-carboxamide Compound I-100

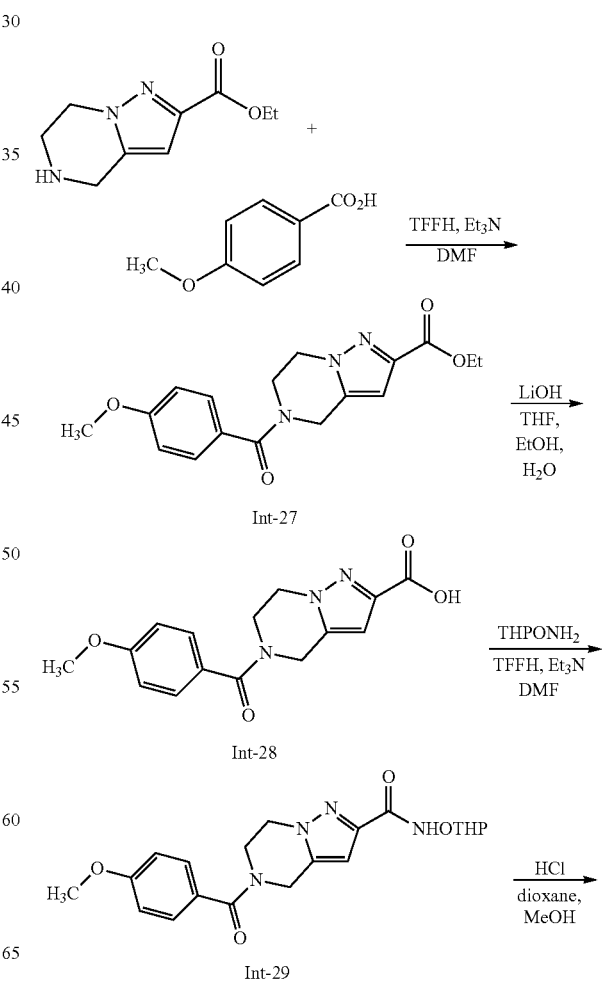

-continued

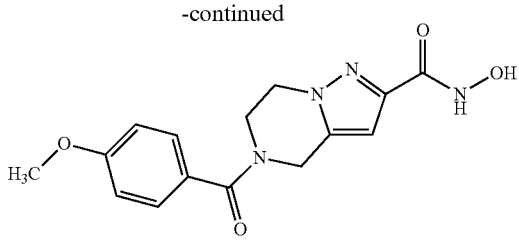

Step 1: ethyl 5-(4-methoxybenzoyl)-4,5,6,7-tetrahydropyrazolo[1,5-a]pyrazine-2-carboxylate Intermediate 27

To a solution of 4-methoxybenzoic acid (0.187 g, 1.23 mmol) dissolved in N,N-dimethylformamide (5 mL) and triethylamine (0.428 mL, 3.07 mmol) was added tetramethylfluoroformamidinium hexafluorophosphate (0.406 g, 1.54 mmol) and the reaction mixture was stirred for 15 minutes. Ethyl 4,5,6,7-tetrahydropyrazolo[1,5-a]pyrazine-2-carboxylate (0.2 g, 1.02 mmol) was added and the reaction continued to stir at room temperature for 5 hours. The reaction mixture was diluted with water and extracted with EtOAc (3×). The combined organic layers were washed with water, brine, dried over anhydrous $Na_2SO_4$, filtered and concentrated. The residue was purified via silica gel chromatography (0-90% EtOAc/hexane) to afford ethyl 5-(4-methoxybenzoyl)-4,5,6,7-tetrahydropyrazolo[1,5-a]pyrazine-2-carboxylate Intermediate 27 (0.359 g, 100%). LC-MS: (FA) ES+330.

Step 2: 5-(4-methoxybenzoyl)-4,5,6,7-tetrahydropyrazolo[1,5-a]pyrazine-2-carboxylic acid Intermediate 28

To a solution of ethyl 5-(4-methoxybenzoyl)-4,5,6,7-tetrahydropyrazolo[1,5-a]pyrazine-2-carboxylate (0.359 g, 1.09 mmol) obtained in the previous step dissolved in tetrahydrofuran (5 mL), ethanol (5 mL) and water (3 mL) was added lithium hydroxide (0.039 g, 1.64 mmol) and the reaction was stirred at room temperature for 2 hours. The solvent was then concentrated and the remaining aqueous solution was acidified with 1M aqueous hydrochloric acid to pH=1 resulting in the formation of a solid precipitate. EtOAc was added to dissolve the precipitate and the organic layer was separated and the aqueous layer was re-extracted with EtOAc (2×). The combined organic layers were then washed with water, brine, dried over $Na_2SO_4$, filtered and concentrated to afford 5-(4-methoxybenzoyl)-4,5,6,7-tetrahydropyrazolo[1,5-a]pyrazine-2-carboxylic acid Intermediate 28 (0.205 g, 62%). LC-MS: (FA) ES+302.

Step 3: 5-(4-methoxybenzoyl)-N-(tetrahydro-2H-pyran-2-yloxy)-4,5,6,7-tetrahydropyrazolo[1,5-a]pyrazine-2-carboxamide Intermediate 29

To a solution of 5-(4-methoxybenzoyl)-4,5,6,7-tetrahydropyrazolo[1,5-a]pyrazine-2-carboxylic acid obtained in the previous step (0.205 g, 0.68 mmol) dissolved in N,N-dimethylformamide (5 mL) and triethylamine (0.284 mL, 2.04 mmol) was added tetramethylfluoroformamidinium hexafluorophosphate (0.216 g, 0.816 mmol) and the reaction mixture was stirred for 15 minutes. Solid O-(tetrahydropyran-2-yl)hydroxylamine (0.096 g, 0.816 mmol) was added and the reaction continued to stir at room temperature for 4 hours. The reaction mixture was then diluted with water and extracted with EtOAc (3×). The combined organic layers were then washed with water, brine, dried using anhydrous $Na_2SO_4$, filtered and concentrated. The residue was purified via silica gel chromatography (0-10% MeOH/DCM) to afford 5-(4-methoxybenzoyl)-N-(tetrahydro-2H-pyran-2-yloxy)-4,5,6,7-tetrahydropyrazolo[1,5-a]pyrazine-2-carboxamide (0.167 g, 61%). LC-MS: (FA) ES+401.

Step 4: N-hydroxy-5-(4-methoxybenzoyl)-4,5,6,7-tetrahydropyrazolo[1,5-a]pyrazine-2-carboxamide Compound I-100

To a solution of 5-(4-methoxybenzoyl)-N-(tetrahydro-2H-pyran-2-yloxy)-4,5,6,7-tetrahydropyrazolo[1,5-a]pyrazine-2-carboxamide (0.167 g, 0.417 mmol) obtained in the previous step dissolved in methanol (4 mL) was added 4.0 M of hydrochloric acid in 1,4-dioxane (0.021 mL, 0.083 mmol) and the reaction was stirred at room temperature for 3 hours. The solvent was then concentrated to dryness and the residue was purified on a BioCAD 700E HPLC instrument using a Phenomenex (C18) Luna (21.2 mm×250 mm) column to afford N-hydroxy-5-(4-methoxybenzoyl)-4,5,6,7-tetrahydropyrazolo[1,5-a]pyrazine-2-carboxamide (0.018 g, 14%). LC-MS: (AA) ES+317.

Example 18

The following compound was prepared in an analogous fashion to that described in Example 17 starting from the intermediates which were prepared as described above and the corresponding carboxylic acid.

| Compound | LC-MS (AA) |
|---|---|
| I-76 | ES+ 290 |

Example 19

N-hydroxy-5-(4-methoxybenzoyl)-5,6,7,8-tetrahydro-4H-pyrazolo[1,5-a][1,4]diazepine-2-carboxamide Compound I-53

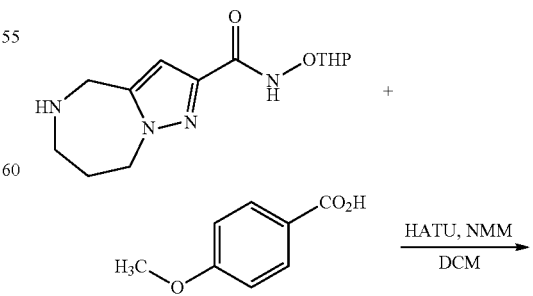

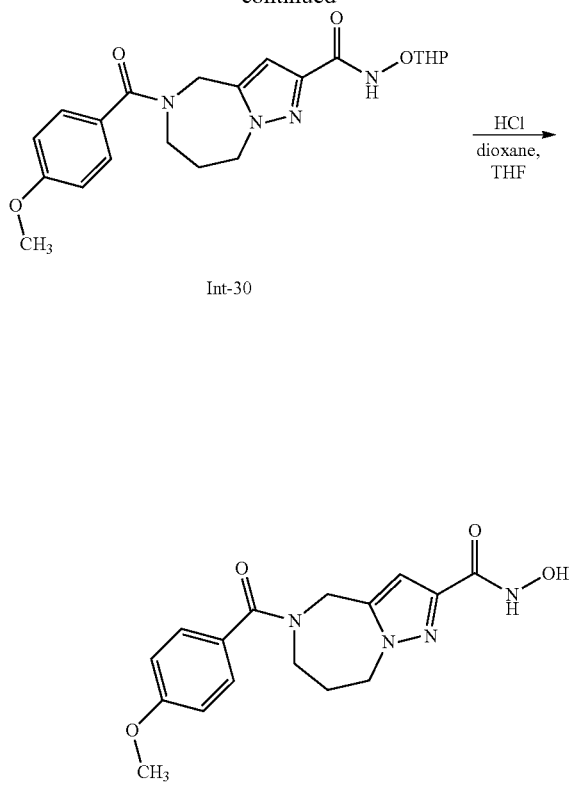

Int-30

J=7.9 Hz, 2H), 6.97 (d, J=8.4 Hz, 2H), 4.72 (s, 2H), 4.46-4.42 (m, 2H), 3.79 (s, 3H), 3.33 (s, 2H), 1.87 (s, 2H).

Example 20

N-hydroxy-5-[(5-pyridin-2-yl-2-thienyl)carbonyl]-5,6,7,8-tetrahydro-4H-pyrazolo[1,5-a][1,4]diazepine-2-carboxamide Compound I-70

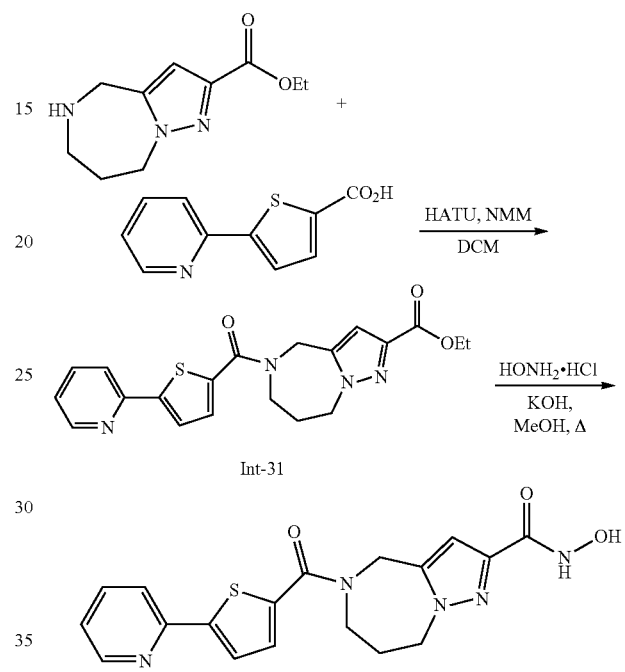

Int-31

Step 1: 5-(4-methoxybenzoyl)-N-(tetrahydro-2H-pyran-2-yloxy)-5,6,7,8-tetrahydro-4H-pyrazolo[1,5-a][1,4]diazepine-2-carboxamide Intermediate 30

To a mixture of N-(tetrahydro-2H-pyran-2-yloxy)-5,6,7,8-tetrahydro-4H-pyrazolo[1,5-a][1,4]diazepine-2-carboxamide (0.0283 g, 0.101 mmol) and 4-methoxybenzoic acid (0.016 g, 0.105 mmol) in methylene chloride (1 mL) was added N,N,N',N'-tetramethyl-O-(7-azabenzotriazol-1-yl)uronium hexafluorophosphate (0.0434 g, 0.114 mmol) and N-methylmorpholine (0.0333 mL, 0.303 mmol). The reaction mixture was stirred at room temperature overnight. The reaction mixture was diluted with methylene chloride (2 mL) and washed with aqueous NaHCO₃ (2 mL). The aqueous layer was extracted with additional methylene chloride (3 mL) and the combined organic layers concentrated to afford Intermediate 30 as a white solid.

Step 2: N-hydroxy-5-(4-methoxybenzoyl)-5,6,7,8-tetrahydro-4H-pyrazolo[1,5-a][1,4]diazepine-2-carboxamide Compound I-53

The material obtained in the previous step was taken up in tetrahydrofuran (1 mL) and to the resulting solution was added 4 M of hydrochloric acid in 1,4-dioxane (0.2 mL, 0.8 mmol). The reaction was stirred at room temperature for 1 hour, then evaporated to dryness, and the residue obtained was dissolved in DMSO (1 mL) and purified on Gilson prep-HPLC to afford the title compound as a white powder (19.3 mg, 58% over two steps). LC-MS: (FA) ES+331; ¹H NMR (400 MHz, DMSO) δ 10.87 (s, 1H), 8.92 (s, 1H), 7.29 (d,

Step 1: ethyl 5-(5-(pyridin-2-yl)thiophene-2-carbonyl)-5,6,7,8-tetrahydro-4H-pyrazolo[1,5-a][1,4]diazepine-2-carboxylate Intermediate 31

To a mixture of ethyl 5,6,7,8-tetrahydro-4H-pyrazolo[1,5-a][1,4]diazepine-2-carboxylate (0.033 g, 0.16 mmol) and 5-(2-pyridyl)thiophene-2-carboxylic acid (0.036 g, 0.18 mmol) in methylene chloride (1 mL) was added N,N,N',N'-tetramethyl-O-(7-azabenzotriazol-1-yl)uronium hexafluorophosphate (0.07 g, 0.184 mmol) and N-methylmorpholine (0.053 mL, 0.48 mmol). The reaction was stirred overnight at room temperature. The reaction was diluted with methylene chloride (3 mL) and washed with saturated aqueous NaHCO₃ (2 mL). The aqueous layer was extracted with additional methylene chloride (3 mL). The combined organic layers were dried over anhydrous Na₂SO₄, filtered and concentrated to dryness to afford Intermediate 31.

Step 2: N-hydroxy-5-(5-(pyridin-2-yl)thiophene-2-carbonyl)-5,6,7,8-tetrahydro-4H-pyrazolo[1,5-a][1,4]diazepine-2-carboxamide Compound I-70

A mixture of hydroxylamine hydrochloride (2.35 g, 33.8 mmol) and lithium hydroxide (1.43 g, 59.7 mmol) in anhydrous methanol (20 mL) was heated at 90° C. for 1 hour in a sealed 50 mL pressure flask. Upon cooling to room temperature 1 mL of the filtered solution was added to the material prepared in the previous step dissolved in methanol (0.5 mL). The resulting reaction solution was stirred at room temperature for 1 hour. Upon quenching with the addition of formic acid (0.1 mL, 2.6 mmol), the solvent was evaporated to dryness and the residue obtained was dissolved in DMSO (1 mL) and purified on an Agilent 1100 LC/MSD instrument to afford the title compound as a white solid (19.1 mg, 31%). LC-MS: (FA) ES+384; $^1$H NMR (400 MHz, DMSO) δ 10.89 (s, 1H), 8.88 (s, 11-1), 8.55 (ddd, J=4.9, 1.7, 0.9 Hz, 1H), 7.99 (d, J=8.0 Hz, 1H), 7.87 (td, J=7.8, 1.8 Hz, 1H), 7.79 (d, J=3.9 Hz, 1H), 7.43 (d, J=3.9 Hz, 1H), 7.33 (ddd, J=7.5, 4.9, 1.0 Hz, 1H), 6.54 (s, 1H), 4.84 (s, 2H), 4.52-4.43 (m, 2H), 3.99 (s, 2H), 2.00 (s, 2H).

Example 21

The following compounds were prepared in an analogous fashion to that described in Example 20 starting from the intermediates which were prepared as described above and the corresponding carboxylic acids.

| Compound | LC-MS (FA) |
|---|---|
| I-108 | ES+ 355 |
| I-72 | ES+ 359 |
| I-105 | ES+ 354 |
| I-98 | ES+ 357 |

Example 22

5-benzyl-N-hydroxy-4-oxo-4,5,6,7-tetrahydropyrazolo[1,5-a]pyrazine-2-carboxamide Compound I-81

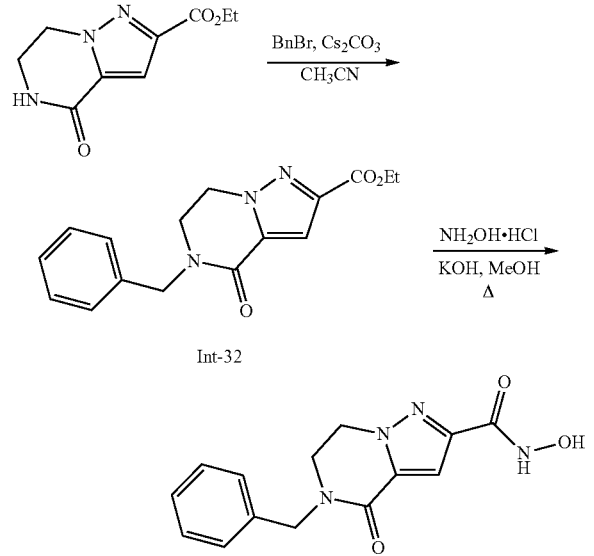

Int-32

Step 1: ethyl 5-benzyl-4-oxo-4,5,6,7-tetrahydropyrazolo[1,5-a]pyrazine-2-carboxylate Intermediate 32

To a solution of ethyl 4-oxo-4,5,6,7-tetrahydropyrazolo[1,5-a]pyrazine-2-carboxylate (30 mg, 0.143 mmol) in acetonitrile (1 mL) was added cesium carbonate (93.4 mg, 0.287 mmol) and benzyl bromide (25.6 μL, 0.215 mmol). The reaction mixture was stirred overnight at 70° C. Upon cooling to room temperature, the cesium carbonate was removed by filtration and the solvent evaporated under reduced pressure to afford crude Intermediate 32. LC-MS: (AA) ES+300.

Step 2: 5-benzyl-N-hydroxy-4-oxo-4,5,6,7-tetrahydropyrazolo[1,5-a]pyrazine-2-carboxamide Compound I-81

To a solution of the material obtained in the previous step in methanol (3 mL) was added solid potassium hydroxide (100 mg, 2 mmol) and hydroxylamine hydrochloride (50 mg, 0.72 mmol). The reaction mixture was heated at 80° C. for 30 minutes. Upon cooling to room temperature all solids were removed via filtration and the solvent evaporated to dryness. The residue was dissolved in DMSO (1 mL) and purified on an Agilent 1100 LC/MSD instrument to afford the title compound as a white solid (9.1 mg, 21%). $^1$H NMR (400 MHz, MeOD) δ 7.39-7.26 (m, 5H), 7.23 (s, 1H), 4.76 (s, 2H), 4.42-4.38 (m, 2H), 3.77 (dd, J=6.9, 5.5 Hz, 2H); LC-MS: (AA) ES+287.

Example 23

5-(cyclopropylmethyl)-N-hydroxy-4-oxo-4,5,6,7-tetrahydropyrazolo[1,5-a]pyrazine-2-carboxamide Compound I-83

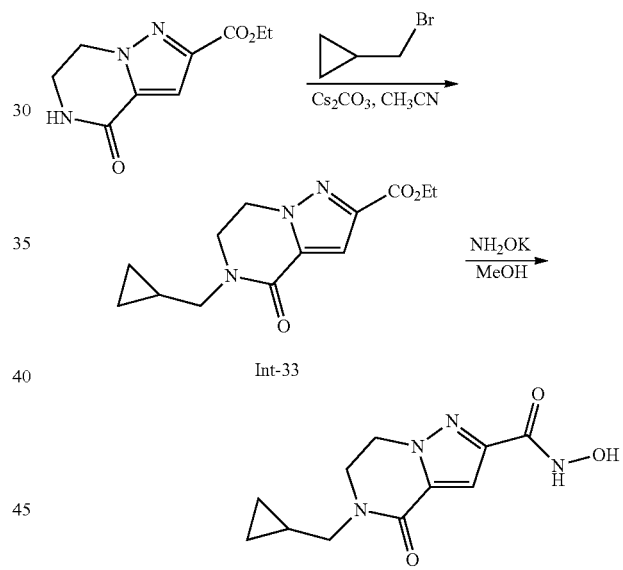

Int-33

Step 1: ethyl 5-(cyclopropylmethyl)-4-oxo-4,5,6,7-tetrahydropyrazolo[1,5-a]pyrazine-2-carboxylate Intermediate 33

To a solution of cyclopropylmethyl bromide (0.101 g, 0.75 mmol) and ethyl 4-oxo-4,5,6,7-tetrahydropyrazolo[1,5-a]pyrazine-2-carboxylate (31.4 mg, 0.150 mmol) in acetonitrile (2 mL) was added cesium carbonate (147 mg, 0.45 mmol). The reaction mixture was heated overnight at 70° C. Upon cooling to room temperature, the insolubles were removed by filtration and the solvent evaporated to dryness to afford crude Intermediate 33.

Step 2: 5-(cyclopropylmethyl)-N-hydroxy-4-oxo-4,5,6,7-tetrahydropyrazolo[1,5-a]pyrazine-2-carboxamide Compound I-83

To a solution of the material obtained in the previous step in methanol (1 mL) was added 1.7 M hydroxylamine potassium salt in methanol (1 mL, 1.7 mmol; prepared as described in *Journal of Medicinal Chemistry* 2009, 52(21):6757). The reaction mixture was stirred at room temperature for 1 hour. Upon evaporation of the solvent the residue was dissolved in DMSO (1 mL) and purified on a Agilent 1100 LC/MSD instrument to afford the title compound as a white solid (8.4 mg, 22%). LC-MS: (FA) ES+251.

Example 24

The following compounds were prepared in an analogous fashion to that described in Example 23 starting from the intermediates which were prepared as described above and the corresponding starting materials.

| Compound | LC-MS (FA) |
|---|---|
| I-103 | ES+ 355 |
| I-24 | ES+ 293 |
| I-77 | ES+ 367 |
| I-12 | ES+ 305 |
| I-88 | ES+ 269 |
| I-50 | ES+ 281 |
| I-110 | ES+ 321 |
| I-65 | ES+ 315 |
| I-48 | ES+ 317 |
| I-46 | ES+ 239 |
| I-67 | ES+ 343 |
| I-109 | ES+ 304 |

Example 25

2-benzyl-N-hydroxy-1-oxo-1,2,3,4-tetrahydropyrrolo[1,2-a]pyrazine-7-carboxamide Compound I-42

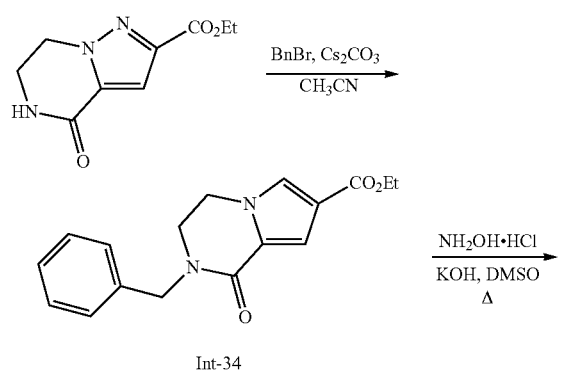

Int-34

Step 1: ethyl 2-benzyl-1-oxo-1,2,3,4-tetrahydropyrrolo[1,2-a]pyrazine-7-carboxylate Intermediate 34

To a solution of ethyl 1-oxo-1,2,3,4-tetrahydropyrrolo[1,2-a]pyrazine-7-carboxylate (29.8 mg, 0.143 mmol) in acetonitrile (1 mL) was added cesium carbonate (60.6 mg, 0.186 mmol) and benzyl bromide (36.7 mg, 0.215 mmol). The reaction mixture was heated at 70° C. overnight. Upon cooling to room temperature all insolubles were removed by filtration and the solvent evaporated to dryness to afforde crude Intermediate 34.

Step 2: 2-benzyl-N-hydroxy-1-oxo-1,2,3,4-tetrahydropyrrolo[1,2-a]pyrazine-7-carboxamide Compound I-42

A mixture of potassium hydroxide (100 mg, 2 mmol) and hydroxylamine hydrochloride (49.7 mg, 0.715 mmol) in dimethyl sulfoxide (1 mL) was sonicated until the hydroxylamine hydrochloride had gone into solution. After removal of insolubles, the solution was added to Intermediate 34 obtained in the previous step and the solution stirred at room temperature overnight. The solution was purified directly on an Agilent 1100 LC/MSD instrument to afford the title compound as a white solid (4.9 mg, 12%). $^1$H NMR (400 MHz, MeOD) δ 7.42-7.24 (m, 6H), 7.15 (s, 1H), 4.74 (s, 2H), 4.18 (dd, J=12.2, 6.1 Hz, 2H), 3.64 (dd, J=6.7, 5.1 Hz, 2H). LC-MS: (FA) ES+286.

Example 26

The following compound was prepared in an analogous fashion to that described in Example 25 starting from the intermediates which were prepared as described above and the corresponding starting material.

| Compound | LC-MS (FA) |
|---|---|
| I-49 | ES+ 300 |
| I-197 | ES+ 367 |
| I-240 | ES– 352 |
| I-241 | ES+ 250 |

Example 27

N-hydroxy-7-(1-methylcyclohexanecarbonyl)-5,6,7,8-tetrahydroimidazo[1,2-a]pyrazine-2-carboxamide Compound I-26

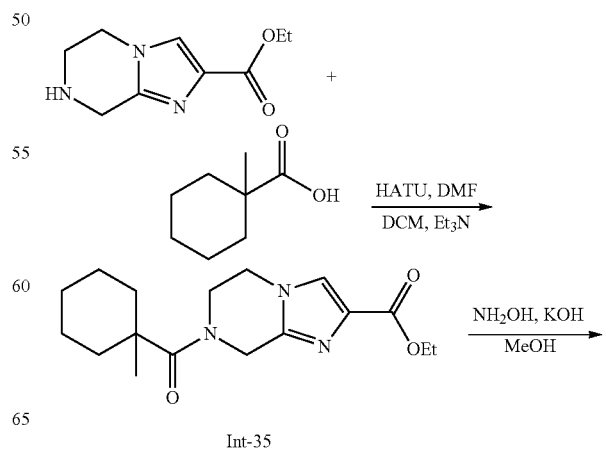

Int-35

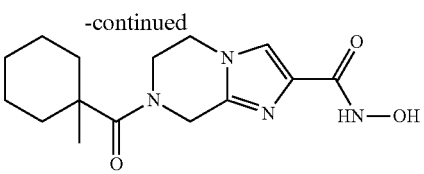

Step 1: ethyl 7-(1-methylcyclohexanecarbonyl)-5,6,7,8-tetrahydroimidazo[1,2-a]pyrazine-2-carboxylate Intermediate 35

To a vial was added 1-methyl-1-cyclohexanecarboxylic acid (0.024 g, 0.168 mmol), HATU (0.064 g, 0.168 mmol), triethylamine (0.134 mL, 0.96 mmol), DCM (2 mL), and DMF (0.2 mL). After shaking for 30 min, ethyl 5,6,7,8-tetrahydroimidazo[1,2-a]pyrazine-2-carboxylate (0.031 g, 0.16 mmol) was added. The mixture was shaken at rt for 16 h. To the vial was added water (1 mL) and DCE (1 mL). After separation, the aqueous layer was extracted with DCE twice (3 mL). The combined organic layers were concentrated to give crude ethyl 7-(1-methylcyclohexanecarbonyl)-5,6,7,8-tetrahydroimidazo[1,2-a]pyrazine-2-carboxylate as a solid.

Step 2: ethyl 7-(1-methylcyclohexanecarbonyl)-5,6,7,8-tetrahydroimidazo[1,2-a]pyrazine-2-carboxylate Compound I-26

Preparation of NH₂OK solution (1.76 M in methanol): A suspension of hydroxylamine hydrochloride (9.4 g, 135 mmol) in methanol (48 mL) was heated at 68° C. under argon until a clear solution was obtained. To this solution was added a solution of potassium hydroxide (13.4 g, 239 mmol) in methanol (28 mL). After refluxing at 80° C. for 30 min, the mixture was cooled to room temperature and the upper clear solution (approximately 1.76 M NH₂OH in methanol) was used directly in further reactions.

To the crude ethyl 7-(1-methylcyclohexanecarbonyl)-5,6,7,8-tetrahydroimidazo[1,2-a]pyrazine-2-carboxylate in a vial was added methanol (1 mL), and NH₂OK solution (1 mL, 1.76 M in methanol). The mixture was stirred at rt for 1 h. To the reaction was added acetic acid (0.182 mL, 3.2 mmol). After stirring for 5 min, the solvent was completely evaporated. The residue was dissolved in DMSO (1.2 mL), filtered, and purified by prep-HPLC to give ethyl 7-(1-methylcyclohexanecarbonyl)-5,6,7,8-tetrahydroimidazo[1,2-a]pyrazine-2-carboxylate (0.01 g, 32.6%) as a white solid. LC-MS (FA): ES+307; $^1$H NMR (Methanol-$d_4$, 400 MHz) δ7.58 (s, 1 H), 4.82 (s, 2 H), 4.10 (m, 4 H), 2.06 (m, 2 H), 1.60-1.35 (m, 8 H), 1.27 (s, 3 H).

Example 28

The following compounds were prepared in an analogous fashion to that described in Example 27 using the corresponding starting materials.

| Compound No | LC-MS (FA) |
|---|---|
| I-44 | ES+ 343 |
| I-41 | ES+ 267 |
| I-13 | ES+ 317 |
| I-14 | ES+ 290 |
| I-60 | ES+ 377 |
| I-57 | ES+ 321 |
| I-21 | ES+ 327 |
| I-2 | ES+ 363 |
| I-27 | ES+ 345 |
| I-45 | ES+ 343 |
| I-55 | ES+ 308 |
| I-101 | ES+ 385 |

Example 29

N-2-hydroxy-N-7-o-tolyl-5,6-dihydroimidazo[1,2-a]pyrazine-2,7(8H) dicarboxamide Compound I-117

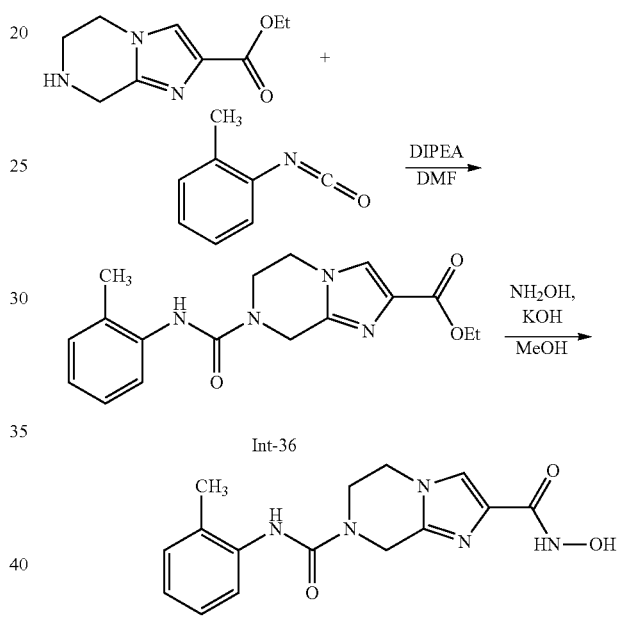

Step 1: ethyl 7-(o-tolylcarbamoyl)-5,6,7,8-tetrahydroimidazo[1,2-a]pyrazine-2-carboxylate Intermediate 36

To a vial containing 1-isocyanato-2-methylbenzene (0.0166 g, 0.125 mmol) was added ethyl 5,6,7,8-tetrahydroimidazo[1,2-a]pyrazine-2-carboxylate (0.024 g, 0.125 mmol), DIPEA (0.0762 mL, 0.438 mmol), and DMF (1.5 mL). The solution was shaken at room temperature for 16 h, then concentrated to give crude ethyl 7-(o-tolylcarbamoyl)-5,6,7,8-tetrahydroimidazo[1,2-a]pyrazine-2-carboxylate.

Step 2: N-2-hydroxy-N-7-o-tolyl-5,6-dihydroimidazo[1,2-a]pyrazine-2,7(8H) dicarboxamide Compound I-117

The NH₂OK solution was prepared as described above in Example 27. To crude ethyl 7-(o-tolylcarbamoyl)-5,6,7,8-tetrahydroimidazo[1,2-a]pyrazine-2-carboxylate from step 1 was added methanol (1 mL) and NH₂OK solution (1 mL, 1.76 M in MeOH). The solution was stirred at room temperature for 1 hour. Acetic acid (0.2 mL, 2.8 mmol) was added to neutralize the excess base. The solution was then concentrated, taken-up in DMSO (1.2 mL), filtered, and purified by prep-HPLC to give N-2-hydroxy-N-7-o-tolyl-5,6 dihydroimidazo[1,2-a]pyrazine-2,7(8H) dicarboxamide (0.096 g, 24.3%) as a white solid. LC-MS (FA): ES+316; $^1$H NMR (Methanol-$d_4$, 400 MHz) δ7.62 (s, 1 H), 7.24-7.12 (m, 4 H), 4.78 (s, 2 H), 4.20 (t, J=4.8 Hz, 2 H), 3.99 (t, J=5.8 Hz, 2 H), 2.22 (s, 3 H).

Example 30

The following compounds were prepared in an analogous fashion to that described in Example 29 using the corresponding starting materials.

| Compound | LC-MS (FA) |
|---|---|
| I-118 | ES+ 282 |
| I-122 | ES+ 383 |
| I-123 | ES+ 316 |
| I-113 | ES+ 360 |
| I-116 | ES+ 302 |
| I-115 | ES+ 358 |
| I-112 | ES+ 358 |
| I-120 | ES+ 330 |
| I-114 | ES+ 378 |
| I-119 | ES+ 282 |
| I-121 | ES+ 308 |

II. BIOLOGICAL DATA

Example 31

HDAC6 enzyme assay

To measure the inhibition of HDAC6 activity, purified human HDAC6 (BPS Bioscience; Cat. No. 5006) is incubated with substrate Ac-Arg-Gly-Lys(Ac)-AMC peptide (Bachem Biosciences; Cat. No. I-1925) for 1 hour at 30° C. in the presence of test compounds or vehicle DMSO control. The reaction is stopped with the HDAC inhibitor trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition ($IC_{50}$) values are determined from those curves.

Example 32

Nuclear Extract HDAC Assay

As a screen against Class I HDAC enzymes, HeLa nuclear extract (BIOMOL; Cat. No. KI-140) is incubated with Ac-Arg-Gly-Lys(Ac)-AMC peptide (Bachem Biosciences; Cat. No. 1-1925) in the presence of test compounds or vehicle DMSO control. The HeLa nuclear extract is enriched for Class I enzymes HDAC1, -2 and -3. The reaction is stopped with the HDAC inhibitor Trichostatin A (Sigma; Cat. No. T8552) and the amount of Arg-Gly-Lys-AMC generated is quantitated by digestion with trypsin (Sigma; Cat. No. T1426) and subsequent measurement of the amount of AMC released using a fluorescent plate reader (Pherastar; BMG Technologies) set at Ex 340 nm and Em 460 nm. Concentration response curves are generated by calculating the fluorescence increase in test compound-treated samples relative to DMSO-treated controls, and enzyme inhibition ($IC_{50}$) values are determined from those curves.

Example 33

Western Blot and Immunofluorescence Assays

Cellular potency and selectivity of compounds are determined using a published assay (Haggarty et al., *Proc. Natl. Acad. Sci. USA* 2003, 100 (8): 4389-4394) using Hela cells (ATCC cat#CCL-2™) which are maintained in MEM medium (Invitrogen) supplemented with 10% FBS; or multiple myeloma cells RPMI-8226 (ATCC cat#CCL-155™) which are maintained in RPMI 1640 medium (Invitrogen) supplemented with 10% FBS. Briefly, cells are treated with inhibitors for 6 or 24 h and either lysed for Western blotting, or fixed for immunofluorescence analyses. HDAC6 potency is determined by measuring K40 hyperacetylation of alpha-tubulin with an acetylation selective monoclonal antibody (Sigma cat#T7451) in IC50 experiments. Selectivity against Class I HDAC activity is determined similarly using an antibody that recognizes hyperacetylation of histone H4 (Upstate cat#06-866) in the Western blotting assay or nuclear acetylation (Abcam cat#ab21623) in the immunofluorescence assay.

Example 34

In vivo Tumor Efficacy Model

Female NCr-Nude mice (age 6-8 weeks, Charles River Labs) are aseptically injected into the subcutaneous space in the right dorsal flank with 1.0–5.0×10$^6$ cells (SKOV-3, HCT-116, BxPC3) in 100 µL of a 1:1 ratio of serum-free culture media (Sigma Aldrich) and BD Matrigel™ (BD Biosciences) using a 1 mL 26⅜ gauge needle (Becton Dickinson Ref#309625). Alternatively, some xenograft models require the use of more immunocompromised strains of mice such as CB-17 SCID (Charles River Labs) or NOD-SCID (Jackson Laboratory). Furthermore, some xenograft models require serial passaging of tumor fragments in which small fragments of tumor tissue (approximately 1 mm$^3$) are implanted subcutaneously in the right dorsal flank of anesthetized (3-5% isoflourane/oxygen mixture) NCr-Nude, CB-17 SCID or NOD-SCID mice (age 5-8 weeks, Charles River Labs or Jackson Laboratory) via a 13-ga trocar needle (Popper & Sons 7927). Tumor volume is monitored twice weekly with Vernier calipers. The mean tumor volume is calculated using the formula $V=W^2 \times L/2$. When the mean tumor volume is approximately 200 mm$^3$, the animals are randomized into treatment groups of ten animals each. Drug treatment typically includes the test compound as a single agent, and may include combinations of the test compound and other anticancer agents. Dosing and schedules are determined for each experiment based on previous results obtained from pharmacokinetic/pharmacodynamic and maximum tolerated dose studies. The control group will receive vehicle without any drug. Typically, test compound (100-200 µL) is administered via intravenous (27-ga needle), oral (20-ga gavage needle) or subcutaneous (27-ga needle) routes at various doses and schedules. Tumor size and body weight are measured twice a week and the study is terminated when the control tumors reach approximately 2000 mm$^3$, and/or if tumor volume exceeds 10% of the animal body weight or if the body weight loss exceeds 20%.

The differences in tumor growth trends over time between pairs of treatment groups are assessed using linear mixed effects regression models. These models account for the fact that each animal is measured at multiple time points. A separate model is fit for each comparison, and the areas under the curve (AUC) for each treatment group are calculated using the predicted values from the model. The percent decrease in AUC (dAUC) relative to the reference group is then calculated. A statistically significant P value suggests that the trends over time for the two treatment groups are different.

The tumor measurements observed on a date pre-specified by the researcher (typically the last day of treatment) are analyzed to assess tumor growth inhibition. For this analysis, a T/C ratio is calculated for each animal by dividing the tumor measurement for the given animal by the mean tumor measurement across all control animals. The T/C ratios across a treatment group are compared to the T/C ratios of the control group using a two-tailed Welch's t-test. To adjust for multiplicity, a False Discovery Rate (FDR) is calculated for each comparison using the approach described by Benjamini and Hochberg, *J.R. Stat. Soc. B* 1995, 57:289-300.

As detailed above, compounds of the invention inhibit HDAC6. In certain embodiments, compounds of the invention inhibit HDAC6 with an IC$_{50}$ value of less than 100 nM including compounds: I-2, I-10, I-17, I-20, I-22, I-28, I-31, I-32, I-35, I-42, I-44, I-47, I-51, I-68, I-75, I-85, I-87, I-89, I-91, I-94, I-99, I-116, I-197, I-240.

In certain embodiments, compounds of the invention inhibit HDAC6 with an IC$_{50}$ value of greater than 100 nM and less than 1 µM including compounds: I-1, I-11, I-12, I-13, I-14, I-21, I-23, I-24, I-29, I-30, I-40, I-45, I-48, I-50, I-52, I-57, I-58, I-60, I-61, I-62, I-65, I-66, I-67, I-70, I-76, I-81, I-92, I-93, I-97, I-100, I-101, I-102, I-103, I-104, I-107, I-110, I-112, I-113, I-114, I-117, I-119, I-120, I-121, I-241.

In certain embodiments, compounds of the invention inhibit HDAC6 with an IC50 value of greater than 1 µM and less than 10 µM including compounds: I-3, I-5, I-6, I-7, I-8, I-15, I-16, I-18, I-26, I-27, I-34, I-37, I-38, I-41, I-46, I-55, I-56, I-59, I-63, I-64, I-72, I-74, I-77, I-79, I-80, I-83, I-88, I-90, I-95, I-96, I-98, I-105, I-106, I-108, I-109, I-115, I-118, I-122, I-123.

In certain embodiments, compounds of the invention inhibit HDAC6 with an IC50 value of greater than 10 µM including compounds: I-4, I-19, I-36, I-53, I-54, I-69, I-71, I-73, I-82, I-84, I-86.

As detailed above, compounds of the invention are selective for HDAC6 over other Class I HDAC enzymes. In certain embodiments, the ratio of HDAC IC50 (as obtained in the nuclear extract assay described above) to HDAC6 IC50 is less than 5 (HDAC IC$_{50}$/HDAC6 IC$_{50}$). In certain embodiments, the ratio of HDAC IC$_{50}$ to HDAC6 IC$_{50}$ is between 5 and 10. In certain embodiments, the ratio of HDAC IC$_{50}$ to HDAC6 IC$_{50}$ is between 10 and 100.

While we have described a number of embodiments of this invention, it is apparent that our basic examples may be altered to provide other embodiments, which utilize the compounds and methods of this invention. Therefore, it will be appreciated that the scope of this invention is to be defined by the appended claims rather than by the specific embodiments, which have been represented by way of examples.

What is claimed is:

1. A compound of formula (I):

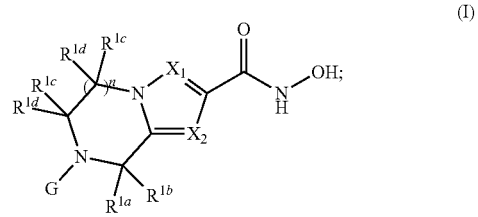

or a pharmaceutically acceptable salt thereof;
wherein:
$X_1$ is CH or N;
$X_2$ is CH or N;
n is 1;
$R^{1a}$ is hydrogen, fluoro, $C_{1-4}$ alkyl, or $C_{1-3}$ fluoroalkyl;
$R^{1b}$ is hydrogen, fluoro, $C_{1-4}$ alkyl, or $C_{1-3}$ fluoroalkyl; or $R^{1a}$ and $R^{1b}$ are taken together to form an oxo group;
each occurrence of $R^{1c}$ is independently hydrogen, fluoro, $C_{1-4}$ alkyl, or $C_{1-3}$ fluoroalkyl;
each occurrence of $R^{1d}$ is independently hydrogen, fluoro, $C_{1-4}$ alkyl, or $C_{1-3}$ fluoroalkyl;
G is —$R^3$, —$V_1$—$R^3$, —$V_1$-$L_1$-$R^3$, -$L_2$-$V_1$—$R^3$, -$L_2$-$V_2$—$R^3$, or -$L_1$-$R^3$; or when $R^{1a}$ and $R^{1b}$ are taken together to form an oxo group, G is —$R^3$, or -$L_1$-$R^3$;
$L_1$ is an unsubstituted or substituted $C_{1-3}$ alkylene chain;
$L_2$ is an unsubstituted or substituted $C_{2-3}$ alkylene chain;
$V_1$ is —C(O)—, —C(S)—, —C(O)—$CR^A$=$CR^A$—, —C(O)—N($R^{4a}$)—, —C(O)—O—, or —S(O)$_2$—;
$V_2$ is —N($R^{4a}$)—, —N($R^{4a}$)—C(O)—, —SO$_2$—N($R^{4a}$)—, —N($R^{4a}$)—SO$_2$—, —O—, —S—, —S(O)—, —N($R^{4a}$)—C(O)—N($R^{4a}$)—, —N($R^4$a)—C(O)—O—, —O—C(O)—N($R^{4a}$)—, or —N($R^{4a}$)—SO$_2$—N($R^{4a}$)—;
$R^3$ is unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each occurrence of $R^A$ is independently hydrogen, fluoro, or unsubstituted or substituted $C_{1-4}$ aliphatic; and
each occurrence of $R^{4a}$ is independently hydrogen, or unsubstituted or substituted $C_{1-4}$ aliphatic;
provided that the compound of formula (I) is other than:
N-hydroxy-5-(4-methoxybenzyl)-4-oxo-4,5,6,7-tetrahydropyrazolo[1,5-a]pyrazine-2-carboxamide; or
N-hydroxy-5-(3-(trifluoromethyl)benzyl)-4-oxo-4,5,6,7-tetrahydropyrazolo[1,5-a]pyrazine-2-carboxamide.

2. The compound of claim 1, represented by formula (I-a):

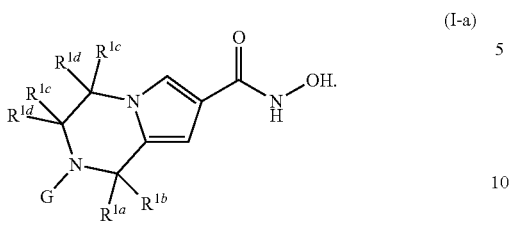

(I-a)

wherein:
each substitutable carbon chain atom in $R^3$ is unsubstituted or substituted with 1-2 occurrences of —$R^{5dd}$;
each substitutable saturated ring carbon atom in $R^3$ is unsubstituted or substituted with =O, =S, =C($R^5$)$_2$, =N—N($R^4$)$_2$, =N—O$R^5$, =N—NHC(O)$R^5$, =N—NHCO$_2R^6$, =N—NHSO$_2R^6$, =N—$R^5$ or —$R^{5a}$;
each substitutable unsaturated ring carbon atom in $R^3$ is unsubstituted or is substituted with —$R^{5a}$;
each substitutable ring nitrogen atom in $R^3$ is unsubstituted or substituted with —$R^{9b}$;
each $R^{5a}$ is independently halogen, —NO$_2$, —CN, —C($R^5$)=C($R^5$)$_2$, —C≡C—$R^5$, —O$R^5$, —S$R^6$, —S(O)$R^6$, —SO$_2R^6$, —SO$_2$N($R^4$)$_2$, —N($R^4$)$_2$, —N$R^4$C(O)$R^5$, —N$R^4$C(O)N($R^4$)$_2$, —N$R^4$CO$_2R^6$, —OC(O)N($R^4$)$_2$, —C(O)$R^5$, —C(O)N($R^4$)$_2$, —C(=N$R^4$)—N($R^4$)$_2$, —C(=N$R^4$)—O$R^5$, —N($R^4$)—N($R^4$)$_2$, —N($R^4$)C(=N$R^4$)—N($R^4$)$_2$, —N($R^4$)SO$_2R^6$, —N($R^4$)SO$_2$N($R^4$)$_2$, —P(O)($R^5$)$_2$, —P(O)(O$R^5$)$_2$, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^{5a}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur;
each occurrence of $R^{5dd}$ is independently fluoro, hydroxy, —O($C_{1-3}$ alkyl), cyano, —N($R^4$)$_2$, —C(O)($C_{1-3}$ alkyl), —CO$_2$H, —C(O)NH$_2$, —N—C(O)—($C_{1-3}$ alkyl), —N—C(O)—O—($C_{1-3}$ alkyl), or —C(O)NH($C_{1-3}$ alkyl);
each $R^4$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur;
each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each $R^6$ is independently unsubstituted or substituted $C_{1-6}$ aliphatic, or unsubstituted or substituted 6-10-membered aryl;
each $R^{9b}$ is independently —C(O)$R^5$, —C(O)N($R^4$)$_2$, —CO$_2R^6$, —SO$_2R^6$, —SO$_2$N($R^4$)$_2$, unsubstituted $C_{1-4}$ aliphatic, or $C_{1-4}$ aliphatic substituted with 1-2 occurrences of $R^7$ or $R^8$;
each $R^7$ is independently unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; and
each $R^8$ is independently halogen, —OH, —O($C_{1-3}$ alkyl), —CN, —N($R^4$)$_2$, —C(O)($C_{1-3}$ alkyl), —CO$_2$H, —CO$_2$($C_{1-3}$ alkyl), —C(O)NH$_2$, or —C(O)NH($C_{1-3}$ alkyl).

3. The compound of claim 2, wherein:
$R^{1a}$ is hydrogen, fluoro, or methyl;
$R^{1b}$ is hydrogen, fluoro, trifluoromethyl, methyl, ethyl, isopropyl, n-propyl, or tert-butyl; or $R^{1a}$ and $R^{1b}$ are taken together to form an oxo group;
each occurrence of $R^{1c}$ is independently hydrogen, fluoro, or methyl; and
each occurrence of $R^{1d}$ is independently hydrogen, fluoro, trifluoromethyl, methyl, ethyl, isopropyl, n-propyl, or tert-butyl.

4. The compound of claim 3, wherein
$R^{1a}$ and $R^{1b}$ are not taken together to form an oxo group;
G is —$V_1$—$R^3$, or —$V_1$-$L_1$-$R^3$;
$V_1$ is —C(O)—; and
$L_1$ is —CH$_2$—.

5. The compound of claim 4, wherein:
$R^{1a}$ is hydrogen;
$R^{1b}$ is hydrogen, fluoro, or methyl;
$R^{1c}$ is hydrogen; and
each occurrence of $R^{1d}$ is independently hydrogen, fluoro, or methyl.

6. The compound of claim 3, wherein $R^{1a}$ and $R^{1b}$ are taken together to form an oxo group; and
G is —$R^3$, or -$L_1$-$R^3$.

7. The compound of claim 6, wherein
$R^{1c}$ is hydrogen; and
each occurrence of $R^{1d}$ is independently hydrogen, fluoro, or methyl.

8. The compound of claim 3, wherein:
each substitutable saturated ring carbon atom in $R^3$ is unsubstituted or substituted with —$R^{5a}$;
the total number of $R^{5a}$ substituents is p;
p is 1-2;
each $R^{5a}$ is independently halogen, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —NHC(O)NH$C_{1-3}$ alkyl, —NHS(O)$_2$C$_{1-3}$ alkyl, —NHC$_{1-3}$ alkyl, —N(C$_{1-3}$ alkyl)$_2$, 3-10-membered cycloaliphatic substituted with 0-2 occurrences of —R$^{7a}$, 4-10-membered heterocyclyl having 1-4 heteroatoms independently selected from nitrogen, oxygen, and sulfur substituted with 0-2 occurrences of —R$^{7a}$, 6-10-membered aryl substituted with 0-2 occurrences of —R$^{7a}$, or 5-10-membered heteroaryl having 1-5 heteroatoms independently selected from nitrogen, oxygen, and sulfur substituted with 0-2 occurrences of —R$^{7a}$; and each occurrence of R$^{7a}$ independently halogen, C$_{1-4}$ alkyl, C$_{1-3}$ fluoroalkyl, —O—C$_{1-3}$ alkyl, —O—C$_{1-3}$ fluoroalkyl, cyano, hydroxy, —NHC(O)C$_{1-3}$ alkyl, —NHC$_{1-3}$ alkyl, —N(C$_{1-3}$alkyl)$_2$, —C(O)NHC$_{1-3}$ alkyl, —NHC(O)NHC$_{1-3}$ alkyl, or —NHS(O)$_2$C$_{1-3}$ alkyl.

9. The compound of claim 1, represented by formula (I-b):

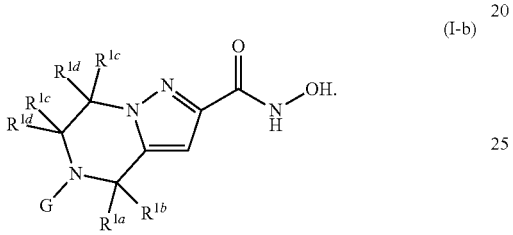

wherein:
each substitutable carbon chain atom in R$^3$ is unsubstituted or substituted with 1-2 occurrences of —R$^{5dd}$;

each substitutable saturated ring carbon atom in R$^3$ is unsubstituted or substituted with =O, =S, =C(R$^5$)$_2$, =N—N(R$^4$)$_2$, =N—OR$^5$, =N—NHC(O)R$^5$, =N—NHCO$_2$R$^6$, =N—NHSO$_2$R$^6$, =N—R$^5$ or —R$^{5a}$;

each substitutable unsaturated ring carbon atom in R$^3$ is unsubstituted or is substituted with —R$^{5a}$;

each substitutable ring nitrogen atom in R$^3$ is unsubstituted or substituted with —R$^{9b}$;

each R$^{5a}$ is independently halogen, —NO$_2$, —CN, —C(R$^5$)=C(R$^5$)$_2$, —C≡C—R$^5$, —OR$^5$, —SR$^6$, —S(O)R$^6$, —SO$_2$R$^6$, —SO$_2$N(R$^4$)$_2$, —N(R$^4$)$_2$, —NR$^4$C(O)R$^5$, —NR$^4$C(O)N(R$^4$)$_2$, —NR$^4$CO$_2$R$^6$, —OC(O)N(R$^4$)$_2$, —C(O)R$^5$, —C(O)N(R$^4$)$_2$, —C(=NR$^4$)—N(R$^4$)$_2$, —C(=NR$^4$)—OR$^5$, —N(R$^4$)—N(R$^4$)$_2$, —N(R$^4$)C(=NR$^4$)—N(R$^4$)$_2$, —N(R$^4$)SO$_2$R$^6$, —N(R$^4$)SO$_2$N(R$^4$)$_2$, —P(O)(R$^5$)$_2$, —P(O)(OR$^5$)$_2$, unsubstituted or substituted C$_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent R$^{5a}$, taken together with the intervening ring atoms, form an unsubstituted or substituted fused aromatic ring or an unsubstituted or substituted non-aromatic ring having 0-3 heteroatoms independently selected from nitrogen, oxygen, and sulfur;

each occurrence of R$^{5dd}$ is independently fluoro, hydroxy, —O(C$_{1-3}$ alkyl), cyano, —N(R$^4$)$_2$, —C(O)(C$_{1-3}$alkyl), —CO$_2$H, —C(O)NH$_2$, —N—C(O)—(C$_{1-3}$ alkyl), —N—C(O)—O—(C$_{1-3}$ alkyl), or —C(O)NH(C$_{1-3}$ alkyl);

each R$^4$ is independently hydrogen, unsubstituted or substituted C$_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two R$^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur;

each R$^5$ is independently hydrogen, unsubstituted or substituted C$_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;

each R$^6$ is independently unsubstituted or substituted C$_{1-6}$ aliphatic, or unsubstituted or substituted 6-10-membered aryl;

each R$^{9b}$ is independently —C(O)R$^5$, —C(O)N(R$^4$)$_2$, —CO$_2$R$^6$, —SO$_2$R$^6$, —SO$_2$N(R$^4$)$_2$, unsubstituted C$_{1-4}$ aliphatic, or C$_{1-4}$ aliphatic substituted with 1-2 occurrences of R$^7$or R$^8$;

each R$^7$ is independently unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; and each R$^8$ is independently halogen, —OH, —O(C$_{1-3}$ alkyl), —CN, —N(R$^4$)$_2$, —C(O)(C$_{1-3}$ alkyl), —CO$_2$H, —CO$_2$(C$_{1-3}$ alkyl), —C(O)NH$_2$, or —C(O) NH(C$_{1-3}$ alkyl).

10. The compound of claim 9, wherein:
R$^{1a}$ is hydrogen, fluoro, or methyl;
R$^{1b}$ is hydrogen, fluoro, trifluoromethyl, methyl, ethyl, isopropyl, n-propyl, or tert-butyl; or R$^{1a}$ and R$^{1b}$ are taken together to form an oxo group;
each occurrence of R$^{1c}$ is independently hydrogen, fluoro, or methyl; and
each occurrence of R$^{1d}$ is independently hydrogen, fluoro, trifluoromethyl, methyl, ethyl, isopropyl, n-propyl, or tert-butyl.

11. The compound of claim 10, wherein
R$^{1a}$ and R$^{1b}$ are not taken together to form an oxo group;
G is —V$_1$—R$^3$, or —V$_1$-L$_1$-R$^3$;
V$_1$ is —C(O)—; and
L$_1$ is —CH$_2$—.

12. The compound of claim 11, wherein
R$^{1a}$ is hydrogen;
R$^{1b}$ is hydrogen, fluoro, or methyl;
R$^{1c}$ is hydrogen; and each occurrence of $R^{1d}$ is independently hydrogen, fluoro, or methyl.

13. The compound of claim 10, wherein $R^{1a}$ and $R^{1b}$ are taken together to form an oxo group; and
G is $-R^3$, or $-L_1-R^3$.

14. The compound of claim 13, wherein:
$R^{1c}$ is hydrogen; and
each occurrence of $R^{1d}$ is independently hydrogen, fluoro, or methyl.

15. The compound of claim 10, wherein:
each substitutable saturated ring carbon atom in $R^3$ is unsubstituted or substituted with $-R^{5a}$;
the total number of $R^{5a}$ substituents is p;
p is 1-2;
each $R^{5a}$ is independently halogen, $C_{1-4}$ alkyl, $C_{1-3}$ fluoroalkyl, $-O-C_{1-3}$ alkyl, $-O-C_{1-3}$ fluoroalkyl, $-NHC(O)C_{1-3}$ alkyl, $-NHC(O)NHC_{1-3}$ alkyl, $-NHS(O)_2C_{1-3}$ alkyl, $-NHC_{1-3}$ alkyl, $-N(C_{1-3}$ alkyl$)_2$, 3-10-membered cycloaliphatic substituted with 0-2 occurrences of $-R^{7a}$, 4-10-membered heterocyclyl having 1-4 heteroatoms independently selected from nitrogen, oxygen, and sulfur substituted with 0-2 occurrences of $-R^{7a}$, 6-10-membered aryl substituted with 0-2 occurrences of $-R^{7a}$, or 5-10-membered heteroaryl having 1-5 heteroatoms independently selected from nitrogen, oxygen, and sulfur substituted with 0-2 occurrences of $-R^{7a}$; and
each occurrence of $R^{7a}$ is independently halogen, $C_{1-4}$ alkyl, $C_{1-3}$ fluoroalkyl, $-O-C_{1-3}$ alkyl, $-O-C_{1-3}$ fluoroalkyl, cyano, hydroxy, $-NHC(O)C_{1-3}$ alkyl, $-NHC_{1-3}$ alkyl, $-N(C_{1-3}$ alkyl$)_2$, $-C(O)NHC_{1-3}$ alkyl, $-NHC(O)NHC_{1-3}$ alkyl, or $-NHS(O)_2C_{1-3}$ alkyl.

16. The compound of claim 1, represented by formula (I-c):

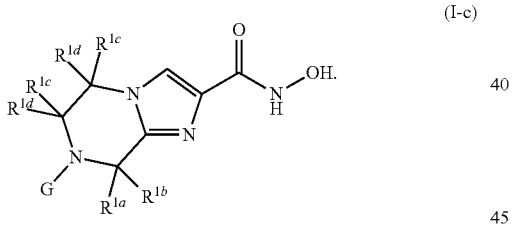

(I-c)

wherein:
each substitutable carbon chain atom in $R^3$ is unsubstituted or substituted with 1-2 occurrences of $-R_{5\,dd}$;
each substitutable saturated ring carbon atom in $R^3$ is unsubstituted or substituted with $=O$, $=S$, $=C(R^5)_2$, $=N-N(R^4)_2$, $=N-OR^5$, $=N-NHC(O)R^5$, $=N-NHCO_2R^6$, $=N-NHSO_2R^6$, $=N-R^5$ or $-R^{5a}$;
each substitutable unsaturated ring carbon atom in $R^3$ is unsubstituted or is substituted with $-R^{5a}$;
each substitutable ring nitrogen atom in $R^3$ is unsubstituted or substituted with $-R^{9b}$;
each $R^{5a}$ is independently halogen, $-NO_2$, $-CN$, $-C(R^5)=C(R^5)_2$;
$-C\equiv C-R^5$, $-SR^6$, $-S(O)R^6$, $-SO_2R^6$, $-SO_2N(R^4)_2$, $-N(R^4)_2$, $-NR^4C(O)R^5$, $-NR^4C(O)N(R^4)_2$, $-NR^4CO_2R_6$, $-OC(O)N(R^4)_2$, $-C(O)R^5$, $-C(O)N(R^4)_2$, $-C(=NR^4)-N(R^4)_2$, $-C(=NR^4)-OR^5$, $-N(R^4)-N(R^4)_2$, $-N(R^4)C(=NR^4)-N(R^4)_2-N(R^4)SO_2R^6$, $-N(R^4)SO_2N(R^4)_2$, $-P(O)(R^5)_2$, $-P(O)(OR^5)_2$, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two adjacent $R^ya$, taken together with the intervening ring atoms, form an unsubstituted or substituted fused aromatic ring or an unsubstituted or substituted non-aromatic ring having 0-3 heteroatoms independently selected from nitrogen, oxygen, and sulfur;
each occurrence of $R^{5dd}$ is independently fluoro, hydroxy, $-O(C_{1-3}$ alkyl$)$, cyano, $-N(R^4)_2$, $-C(O)(C_{1-3}$ alkyl$)$, $-CO_2H$, $-C(O)NH_2$, $-N-C(O)-(C_{1-3}$ alkyl$)$, $-N-C(O)-O-(C_{1-3}$ alkyl$)$, or $-C(O)NH(C_{1-3}$ alkyl$)$;
each $R^4$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; or two $R^4$ on the same nitrogen atom, taken together with the nitrogen atom, form an unsubstituted or substituted 5- to 6-membered heteroaryl or an unsubstituted or substituted 4- to 8-membered heterocyclyl having, in addition to the nitrogen atom, 0-2 ring heteroatoms selected from nitrogen, oxygen, and sulfur;
each $R^5$ is independently hydrogen, unsubstituted or substituted $C_{1-6}$ aliphatic, unsubstituted or substituted 3-10-membered cycloaliphatic, unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur;
each $R^6$ is independently unsubstituted or substituted $C_{1-6}$ aliphatic, or unsubstituted or substituted 6-10-membered aryl;
each $R^{9b}$ is independently $-C(O)R^5$, $-C(O)N(R^4)_2$, $-CO_2R^6$, $-SO_2R^6$, $-SO_2N(R^4)_2$, unsubstituted $C_{1-4}$ aliphatic, or $C_{1-4}$ aliphatic substituted with 1-2 occurrences of $R^7$ or $R^8$;
each $R^7$ is independently unsubstituted or substituted 4-10-membered heterocyclyl having 1-4 heteroatoms independently selected from nitrogen, oxygen, and sulfur, unsubstituted or substituted 6-10-membered aryl, or unsubstituted or substituted 5-10-membered heteroaryl having 1-5 heteroatoms independently selected from nitrogen, oxygen, and sulfur; and
each $R^8$ is independently halogen, $-OH$, $-O(C_{1-3}$ alkyl$)$, $-CN$, $-N(R^4)_2$, $-C(O)(C_{1-3}$ alkyl$)$, $-CO_2H$, $-CO_2(C_{1-3}$ alkyl$)$, $-C(O)NH_2$, or $-C(O)NH(C_{1-3}$ alkyl$)$.

17. The compound of claim 16, wherein:
$R^{1a}$ is hydrogen, fluoro, or methyl;
$R^{1b}$ is hydrogen, fluoro, trifluoromethyl, methyl, ethyl, isopropyl, n-propyl, or tert-butyl; or $R^{1a}$ and $R^{1b}$ are taken together to form an oxo group;

each occurrence of $R^{1c}$ is independently hydrogen, fluoro, or methyl; and each occurrence of $R^{1d}$ is independently hydrogen, fluoro, trifluoromethyl, methyl, ethyl, isopropyl, n-propyl, or tert-butyl.

18. The compound of claim 17, wherein
$R^{1a}$ and $R^{1b}$ are not taken together to form an oxo group;
G is —$V_1$—$R^3$, or —$V_1$-$L_1$-$R^3$;
$V_1$ is —C(O)—; and
$L_1$ is —$CH_2$—.

19. The compound of claim 18, wherein
$R^{1a}$ is hydrogen;
$R^{1b}$ is hydrogen, fluoro, or methyl;
$R^{1c}$ is hydrogen; and
each occurrence of $R^{1d}$ is independently hydrogen, fluoro, or methyl.

20. The compound of claim 17, wherein $R^{1a}$ and $R^{1b}$ are taken together to form an oxo group; and
G is —$R^3$, or -$L_1$-$R^3$.

21. The compound of claim 20, wherein:
$R^{1c}$ is hydrogen; and
each occurrence of $R^{1d}$ is independently hydrogen, fluoro, or methyl.

22. The compound of claim 17, wherein:
each substitutable saturated ring carbon atom in $R^3$ is unsubstituted or substituted with —$R^{5a}$;
the total number of $R^{5a}$ substituents is p;
p is 1-2;
each $R^{5a}$ is independently halogen, $C_{1-4}$ alkyl, $C_{1-3}$ fluoroalkyl, —O—$C_{1-3}$ alkyl, —O—$C_{1-3}$ fluoroalkyl, —NHC(O)$C_{1-3}$ alkyl, —NHC(O)NH$C_{1-3}$ alkyl, —NHS(O)$_2$$C_{1-3}$ alkyl, —NH$C_{1-3}$ alkyl, —N($C_{1-3}$ alkyl)$_2$, 3-10-membered cycloaliphatic substituted with 0-2 occurrences of —$R^{7a}$, 4-10-membered heterocyclyl having 1-4 heteroatoms independently selected from nitrogen, oxygen, and sulfur substituted with 0-2 occurrences of —$R^{7a}$, 6-10-membered aryl substituted with 0-2 occurrences of —$R^{7a}$, or 5-10-membered heteroaryl having 1-5 heteroatoms independently selected from nitrogen, oxygen, and sulfur substituted with 0-2 occurrences of —$R^{7a}$; and
each occurrence of $R^{7a}$ is independently halogen, $C_{1-4}$ alkyl, $C_{1-3}$ fluoroalkyl, —O—$C_{1-3}$ alkyl, —O—$C_{1-3}$ fluoroalkyl, cyano, hydroxy, —NHC(O)$C_{1-3}$ alkyl, —NH$C_{1-3}$ alkyl, —N($C_{1-3}$ alkyl)$_2$, —C(O)NH$C_{1-3}$ alkyl, —NHC(O)NH$C_{1-3}$ alkyl, or —NHS(O)$_2$$C_{1-3}$ alkyl.

23. The compound of claim 1, wherein the compound is:
2-(4-tert-butylbenzoyl)-N-hydroxy-1,2,3,4-tetrahydropyrrolo[1,2-a]pyrazine-7-carboxamide,
7-(biphenyl-4-ylcarbonyl)-N-hydroxy-5,6,7,8-tetrahydroimidazo[1,2-a]pyrazine-2-carboxamide,
N-hydroxy-2-(imidazo[1,2-a]pyridin-2-ylcarbonyl)-1,2,3,4-tetrahydropyrrolo[1,2-a]pyrazine-7-carboxamide,
N-hydroxy-5-[(1-methylcyclohexyl)carbonyl]-4,5,6,7-tetrahydropyrazolo[1,5-a]pyrazine-2-carboxamide,
N-hydroxy-5-{[1-(trifluoromethyl)cyclopropyl]carbonyl}-4,5,6,7-tetrahydropyrazolo[1,5-a]pyrazine-2-carboxamide,
2-(1-benzothien-3-ylcarbonyl)-N-hydroxy-1,2,3,4-tetrahydropyrrolo[1,2-a]pyrazine-7-carboxamide,
5-[(4,5-dichloro-1-methyl-1H-pyrrol-2-yl)carbonyl]-N-hydroxy-4,5,6,7-tetrahydropyrazolo[1,5-a]pyrazine-2-carboxamide,
5-(4-fluorobenzyl)-N-hydroxy-4-oxo-4,5,6,7-tetrahydropyrazolo[1,5-a]pyrazine-2-carboxamide,
N-hydroxy-7-(4-methoxybenzoyl)-5,6,7,8-tetrahydroimidazo[1,2-a]pyrazine-2-carboxamide,
N-hydroxy-7-[(1-methyl-1H-pyrrol-2-yl)carbonyl]-5,6,7,8-tetrahydroimidazo[1,2-a]pyrazine-2-carboxamide,
2-[(4-acetyl-3,5-dimethyl-1H-pyrrol-2-yl)carbonyl]-N-hydroxy-1,2,3,4-tetrahydropyrrolo[1,2-a]pyrazine-7-carboxamide,
5-(1-adamantylcarbonyl)-N-hydroxy-4,5,6,7-tetrahydropyrazolo[1,5-a]pyrazine-2-carboxamide,
5[4-(benzyloxy)benzoyl]-N-hydroxy-4,5,6,7-tetrahydropyrazolo[1,5-a]pyrazine-2-carboxamide,
N-hydroxy-2-[(1-methyl-1H-indol-2-yl)carbonyl]-1,2,3,4-tetrahydropyrrolo[1,2-a]pyrazine-7-carboxamide,
7-(1-benzofuran-2-ylcarbonyl)-N-hydroxy-5,6,7,8-tetrahydroimidazo[1,2-a]pyrazine-2-carboxamide,
N-hydroxy-2-[(5-methyl-1H-indol-2-yl)carbonyl]-1,2,3,4-tetrahydropyrrolo[1,2-a]pyrazine-7-carboxamide,
2-benzyl-N-hydroxy-1,2,3,4-tetrahydropyrrolo[1,2-a]pyrazine-7-carboxamide,
5-(cyclohexylmethyl)-N-hydroxy-4-oxo-4,5,6,7-tetrahydropyrazolo[1,5-a]pyrazine-2-carboxamide,
N-hydroxy-7-[(1-methylcyclohexyl)carbonyl]-5,6,7,8-tetrahydroimidazo[1,2-a]pyrazine-2-carboxamide,
7-[1-adamantylcarbonyl]-N-hydroxy-5,6,7,8-tetrahydroimidazo[1,2-a]pyrazine-2-carboxamide,
2-[(3,5-dimethyl-1H-indol-2-yl)carbonyl]-N-hydroxy-1,2,3,4-tetrahydropyrrolo[1,2-a]pyrazine-7-carboxamide,
N-hydroxy-2-(1H-indol-2-ylcarbonyl)-1,2,3,4-tetrahydropyrrolo[1,2-a]pyrazine-7-carboxamide,
N-hydroxy-2-(2-thienylcarbonyl)-1,2,3,4-tetrahydropyrrolo[1,2-a]pyrazine-7-carboxamide,
N-hydroxy-5-[(1-methyl-1H-indol-2-yl)carbonyl]-4,5,6,7-tetrahydropyrazolo[1,5-a]pyrazine-2-carboxamide,
N-hydroxy-2-[(1-methyl-1H-pyrrol-2-yl)carbonyl]-1,2,3,4-tetrahydropyrrolo[1,2-a]pyrazine-7-carboxamide,
2-{[2,5-dimethyl-1-(2-thienylmethyl)-1H-pyrrol-3-yl]carbonyl}-N-hydroxy-1,2,3,4-tetrahydropyrrolo[1,2-a]pyrazine-7-carboxamide,
5-(2,2-dimethylpropanoyl)-N-hydroxy-4,5,6,7-tetrahydropyrazolo[1,5-a]pyrazine-2-carboxamide,
5-[2-(4-chlorophenyl)-2-methylpropanoyl]-N-hydroxy-4,5,6,7-tetrahydropyrazolo[1,5-a]pyrazine-2-carboxamide,
N-hydroxy-2-[(1-methyl-1H-pyrazol-3-yl)carbonyl]-1,2,3,4-tetrahydropyrrolo[1,2-a]pyrazine-7-carboxamide,
2-[(3,5-dimethyl-1H-pyrrol-2-yl)carbonyl]-N-hydroxy-1,2,3,4-tetrahydropyrrolo[1,2-a]pyrazine-7-carboxamide,
7-(2,2-dimethylpropanoyl)-N-hydroxy-5,6,7,8-tetrahydroimidazo[1,2-a]pyrazine-2-carboxamide,
2-benzyl-N-hydroxy-1-oxo-1,2,3,4-tetrahydropyrrolo[1,2-a]pyrazine-7-carboxamide,
7-(1-benzothien-2-ylcarbonyl)-N-hydroxy-5,6,7,8-tetrahydroimidazo[1,2-a]pyrazine-2-carboxamide,
7-(4-tert-butylbenzoyl)-N-hydroxy-5,6,7,8-tetrahydroimidazo[1,2-a]pyrazine-2-carboxamide,
N-hydroxy-5-isopropyl-4-oxo-4,5,6,7-tetrahydropyrazolo[1,5-a]pyrazine-2-carboxamide,
2-{[5-(aminosulfonyl)-1-methyl-1H-pyrrol-2-yl]carbonyl}-N-hydroxy-1,2,3,4-tetrahydropyrrolo[1,2-a]pyrazine-7-carboxamide,
N-hydroxy-4-oxo-5-(2-phenoxyethyl)-4,5,6,7-tetrahydropyrazolo[1,5-a]pyrazine-2-carboxamide, or
N-hydroxy-5-(4-methylpentyl)-4-oxo-4,5,6,7-tetrahydropyrazolo[1,5-a]pyrazine-2-carboxamide.

24. The compound of claim 1, wherein the compound is:
2-(biphenyl-4-ylcarbonyl)-N-hydroxy-1,2,3,4-tetrahydropyrrolo[1,2-a]pyrazine-7-carboxamide,
2[(1,5-dimethyl-1H-pyrazol-3-yl)carbonyl]-N-hydroxy-1,2,3,4-tetrahydropyrrolo[1,2-a]pyrazine-7-carboxamide,
N-hydroxy-2-[3-(methylsulfonyl)benzoyl]-1,2,3,4-tetrahydropyrrolo[1,2-a]pyrazine-7-carboxamide,
N-hydroxy-7-[(2-methyl-1,3-thiazol-4-yl)carbonyl]-5,6,7,8-tetrahydroimidazo[1,2-a]pyrazine-2-carboxamide,
7-(4-chlorobenzoyl)-N-hydroxy-5,6,7,8-tetrahydroimidazo[1,2-a]pyrazine-2-carboxamide,
N-hydroxy-2[(1-methyl-1H-indol-3-yl)carbonyl]-1,2,3,4-tetrahydropyrrolo[1,2-a]pyrazine-7-carboxamide,
7-[(3-chloro-1-benzothien-2-yl)carbonyl]-N-hydroxy-5,6,7,8-tetrahydroimidazo[1,2-a]pyrazine -2-carboxamide,
2[(3,5-dimethylisoxazol-4-yl)carbonyl]-N-hydroxy-1,2,3,4-tetrahydropyrrolo[1,2-a]pyrazine-7-carboxamide,
2-[1-adamantylcarbonyl]-N-hydroxy-1,2,3,4-tetrahydropyrrolo[1,2-a]pyrazine-7-carboxamide,
N-hydroxy-2-{[1-phenyl-5-(trifluoromethyl)-1H-pyrazol-4-yl]-carbonyl}-1,2,3,4-tetrahydropyrrolo[1,2-a]pyrazine-7-carboxamide,
N-hydroxy-4-oxo-5-(3-phenylpropyl)-4,5,6,7-tetrahydropyrazolo[1,5-a]pyrazine-2-carboxamide,
N-hydroxy-2-[(2-methyl-4,5,6,7-tetrahydro-2H-indazol-3-yl)carbonyl]-1,2,3,4-tetrahydropyrrolo[1,2-a]pyrazine-7-carboxamide,
5-(4-tert-butylbenzyl)-N-hydroxy-4-oxo-4,5,6,7-tetrahydropyrazolo[1,5-a]pyrazine-2-carboxamide,
N-hydroxy-2-(4-methoxybenzoyl)-1,2,3,4-tetrahydropyrrolo[1,2-a]pyrazine-7-carboxamide,
N-hydroxy-2-[(2-methyl-1,3-thiazol-4-yl)carbonyl]-1,2,3,4-tetrahydropyrrolo[1,2-a]pyrazine-7-carboxamide,
N-hydroxy-2-(1H-indol-3-ylcarbonyl)-1,2,3,4-tetrahydropyrrolo[1,2-a]pyrazine-7-carboxamide,
N-hydroxy-5-[(1-methyl-1H-pyrrol-2-yl)carbonyl]-4,5,6,7-tetrahydropyrazolo[1,5-a]pyrazine-2-carboxamide,
N-hydroxy-5-(3-methylbutyl)-4-oxo-4,5,6,7-tetrahydropyrazolo[1,5-a]pyrazine-2-carboxamide, 5-benzyl-N-hydroxy-4-oxo-4,5,6,7-tetrahydropyrazolo[1,5-a]pyrazine-2-carboxamide,
N-hydroxy-2-[(5-methyl-2-phenyl-1,3-oxazol-4-yl)acetyl]-1,2,3,4-tetrahydropyrrolo[1,2-a]pyrazine-7-carboxamide,
5-(cyclopropylmethyl)-N-hydroxy-4-oxo-4,5,6,7-tetrahydropyrazolo[1,5-a]pyrazine-2-carboxamide,
N-hydroxy-2-(pyrazolo[1,5-a]pyrimidin-3-ylcarbonyl)-1,2,3,4-tetrahydropyrrolo[1,2-a]pyrazine -7-carboxamide,
2-(2,5-dimethyl-3-furoyl)-N-hydroxy-1,2,3,4-tetrahydropyrrolo[1,2-a]pyrazine-7-carboxamide,
2-butyl-N-hydroxy-1,2,3,4-tetrahydropyrrolo[1,2-a]pyrazine-7-carboxamide,
N-hydroxy-2-[(2-methyl-1,5-diphenyl-1H-pyrrol-3-yl)carbonyl]-1,2,3,4-tetrahydropyrrolo[1,2-a]pyrazine-7-carboxamide,
5-(2-ethoxyethyl)-N-hydroxy-4-oxo-4,5,6,7-tetrahydropyrazolo[1,5-a]pyrazine-2-carboxamide,
N-hydroxy-2-[(1-methyl-1H-indol-5-yl)carbonyl]-1,2,3,4-tetrahydropyrrolo[1,2-a]pyrazine-7-carboxamide,
N-hydroxy-5-[(2-methyl-1,3-thiazol-4-yl)acetyl]-4,5,6,7-tetrahydropyrazolo[1,5-a]pyrazine-2-carboxamide,
2-[(4,5-dichloro-1-methyl-1H-pyrrol-2-yl)carbonyl]-N-hydroxy-1,2,3,4-tetrahydropyrrolo[1,2-]pyrazine-7-carboxamide,
2-(cyclohexylcarbonyl)-N-hydroxy-1,2,3,4-tetrahydropyrrolo[1,2-a]pyrazine-7-carboxamide,
N-hydroxy-5-[(5-methyl-1H-indol-3-yl)acetyl]-4,5,6,7-tetrahydropyrazolo[1,5-a]pyrazine-2-carboxamide,
2-[(2,5-dimethyl-1H-pyrrol-3-yl)carbonyl]-N-hydroxy-1,2,3,4-tetrahydropyrrolo[1,2-a]pyrazine -7-carboxamide,
N-hydroxy-5-[(3-methyl-1-benzothien-2-yl)carbonyl]-4,5,6,7-tetrahydropyrazolo[1,5-a]pyrazin-2-carboxamide,
N-hydroxy-2-[(5-methyl-1-phenyl-1H-pyrazol-4-yl)carbonyl]-1,2,3,4-tetrahydropyrrolo[1,2-a]pyrazine-7-carboxamide,
N-hydroxy-5-(4-methoxybenzoyl)-4,5,6,7-tetrahydropyrazolo[1,5-a]pyrazine-2-carboxamide,
N-hydroxy-7-[(4-methyl-2-pyridin-2-yl-1,3-thiazol-5-yl)carbonyl]-5,6,7,8-tetrahydroimidazo[1,2-a]pyrazine-2-carboxamide, or
N-hydroxy-5-(1H-indol-3-ylacetyl)-4,5,6,7-tetrahydropyrazolo[1,5-a]pyrazine-2-carboxamide.

25. The compound of claim 1, wherein the compound is:
N-hydroxy-5-(3-phenylpropanoyl)-4,5,6,7-tetrahydropyrazolo[1,5-a]pyrazine-2-carboxamide,
N-hydroxy-5-(quinolin-8-ylcarbonyl)-4,5,6,7-tetrahydropyrazolo[1,5-a]pyrazine-2-carboxamide,
N-hydroxy-4-oxo-5-[3-(1H-pyrrol-1-yl)propyl]-4,5,6,7-tetrahydropyrazolo[1,5-a]pyrazine-2-carboxamide,
5-(3-chlorobenzyl)-N-hydroxy-4-oxo-4,5,6,7-tetrahydropyrazolo[1,5-a]pyrazine-2-carboxamide,
N7-(2-tert-butylphenyl)-N2-hydroxy-5,6-dihydroimidazo[1,2-a]pyrazine-2,7(8H)-dicarboxamide,
N7-[1-adamantyl]-N2-hydroxy-5,6-dihydroimidazo[1,2-a]pyrazine-2,7(8H)-dicarboxamide,
N7-biphenyl-2-yl-N2-hydroxy-5,6-dihydroimidazo[1,2-a]pyrazine-2,7(8H)-dicarboxamide,
N7-(2,6-diethylphenyl)-N2-hydroxy-5,6-dihydroimidazo[1,2-a]pyrazine-2,7(8H)-dicarboxamide,
N2-hydroxy-N7-phenyl-5,6-dihydroimidazo[1,2-a]pyrazine-2,7(8H)-dicarboxamide,
N2-hydroxy-N7-(2-methylphenyl)-5,6-dihydroimidazo[1,2-a]pyrazine-2,7(8H)-dicarboxamide,
N7-(sec-butyl)-N2-hydroxy-5,6-dihydroimidazo[1,2-a]pyrazine-2,7(8H)-dicarboxamide,
N7-(tert-butyl)-N2-hydroxy-5,6-dihydroimidazo[1,2-a]pyrazine-2,7(8H)-dicarboxamide,
N2-hydroxy-N7-(2-phenylethyl)-5,6-dihydroimidazo[1,2-a]pyrazine-2,7(8H)-dicarboxamide,
N7-cyclohexyl-N2-hydroxy-5,6-dihydroimidazo[1,2-a]pyrazine-2,7(8H)-dicarboxamide,
N2-hydroxy-N7-(5-methyl-3-phenylisoxazol-4-yl)-5,6-dihydroimidazo[1,2-a]pyrazine-2,7(8H)-dicarboxamide,
N7-benzyl-N2-hydroxy-5,6-dihydroimidazo[1,2-a]pyrazine-2,7(8H)-dicarboxamide,
1-ethyl-N-hydroxy-2-[(1-methylpiperidin-4-yl)carbonyl]-1,2,3,4-tetrahydropyrrolo[1,2-a]pyrazine-7-carboxamide,
N-hydroxy-3-methyl-2-[(1-methylpiperidin-4-yl)carbonyl]-1,2,3,4-tetrahydropyrrolo[1,2-a]pyrazine-7-carboxamide,
1-ethyl-N-hydroxy-2-[(1-methyl-1H-pyrrol-2-yl)carbonyl]-1,2,3,4-tetrahydropyrrolo[1,2-a]pyrazine-7-carboxamide,
N-hydroxy-1-isopropyl-2-{[4-(trifluoromethyl)phenyl]sulfonyl}-1,2,3,4-tetrahydropyrrolo[1,2-a]pyrazine-7-carboxamide, N-hydroxy-1-methyl-2-[(1-methylpiperidin-4-yl)carbonyl]-1,2,3,4-tetrahydropyrrolo[1,2-a]pyrazine-7-carboxamide, N2-1-adamantyl-N7-hydroxy-1-methyl-3,4-dihydropyrrolo[1,2-a]pyrazine-2,7(1H)-dicarboxamide, 2-cyclopropyl-N-hydroxy-1-oxo-1,2,3,4-tetrahydropyrrolo[1,2-a]pyrazine-7-carboxamide, N-hydroxy-1-methyl-2-[(1-methyl-1H-indol-2-yl)carbonyl]-1,2,3,4-tetrahydropyrrolo[1,2-a]pyrazine-7-carboxamide, 5-(1-adamantylcarbonyl)-N-hydroxy-4-methyl-4,5,6,7-tetrahydropyrazolo[1,5-a]pyrazine-2-carboxamide, 2-(3-cyanobenzyl)-N-hydroxy-1-oxo-1,2,3,4-tetrahydropyrrolo[1,2-a]pyrazine-7-carboxamide, 7-[(dimethylamino)acetyl]-N-hydroxy-8-methyl-5,6,7,8-tetrahydroimidazo[1,2-a]pyrazine-2-carboxamide, 5-(1-benzothien-2-ylcarbonyl)-N-hydroxy-4-methyl-4,5,6,7-tetrahydropyrazolo[1,5-a]pyrazine-2-carboxamide, N-hydroxy-7-[(1-methyl-1H-indol-2-yl)carbonyl]-5,6,7,8-tetrahydro[1,2,4]triazolo[1,5-a]pyrazine-2-carboxamide, N5-cyclohexyl-N2-hydroxy-4-methyl-6,7-dihydropyrazolo[1,5-a]pyrazine-2,5(4H)-dicarboxamide, N-hydroxy-3-methyl-1-oxo-2-[4-(1H-pyrazol-1-yl)benzyl]-1,2,3,4-tetrahydropyrrolo[1,2-a]pyrazine-7-carboxamide, 5-(2,2-dimethylpropanoyl)-N-hydroxy-4-methyl-4,5,6,7-tetrahydropyrazolo[1,5-a]pyrazine-2-carboxamide, 2-(1-adamantylcarbonyl)-N-hydroxy-3-methyl-1,2,3,4-tetrahydropyrrolo[1,2-a]pyrazine-7-carboxamide, 7-[(dimethylamino)acetyl]-N-hydroxy-8-isopropyl-5,6,7,8-tetrahydroimidazo[1,2-a]pyrazine-2-carboxamide, N2-(tert-butyl)-1-ethyl-N7-hydroxy-3,4-dihydropyrrolo[1,2-a]pyrazine-2,7(1H)-dicarboxamide, N-hydroxy-1-oxo-2-[4-(trifluoromethyl)benzyl]-1,2,3,4-tetrahydropyrrolo[1,2-a]pyrazine-7-carboxamide, 2-(cyclopentylacetyl)-N-hydroxy-1-methyl-1,2,3,4-tetrahydropyrrolo[1,2-a]pyrazine-7-carboxamide, or 1-ethyl-N-hydroxy-2-[(1-methyl-1H-indol-2-yl)carbonyl]-1,2,3,4-tetrahydropyrrolo[1,2-a]pyrazine-7-carboxamide.

26. The compound of claim 1, wherein the compound is:
N-hydroxy-7-[(1-methyl-1H-pyrrol-2-yl)carbonyl]-5,6,7,8-tetrahydro[1,2,4]triazolo[1,5-a]pyrazine-2-carboxamide, 2-(biphenyl-4-ylcarbonyl)-N-hydroxy-3-methyl-1,2,3,4-tetrahydropyrrolo[1,2-a]pyrazine-7-carboxamide, N-hydroxy-8-methyl-7-[(1-methylpiperidin-4-yl)carbonyl]-5,6,7,8-tetrahydroimidazo[1,2-a]pyrazine-2-carboxamide, 2-(1-adamantylcarbonyl)-N-hydroxy-1-methyl-1,2,3,4-tetrahydropyrrolo[1,2-a]pyrazine-7-carboxamide, 2-(1-benzothien-2-ylcarbonyl)-N-hydroxy-3-methyl-1,2,3,4-tetrahydropyrrolo[1,2-a]pyrazine-7-carboxamide, N-hydroxy-1-oxo-2-[3-(trifluoromethoxy)benzyl]-1,2,3,4-tetrahydropyrrolo[1,2-a]pyrazine-7-carboxamide, 1-ethyl-N-hydroxy-2-(propylsulfonyl)-1,2,3,4-tetrahydropyrrolo[1,2-a]pyrazine-7-carboxamide, N-hydroxy-8-methyl-7-[(1-methyl-1H-pyrrol-2-yl)carbonyl]-5,6,7,8-tetrahydroimidazo[1,2-a]pyrazine-2-carboxamide, 7-(biphenyl-4-ylcarbonyl)-N-hydroxy-5,6,7,8-tetrahydro[1,2,4]triazolo[1,5-a]pyrazine-2-carboxamide, N-hydroxy-8-isopropyl-7-[(1-methylpiperidin-4-yl)carbonyl]-5,6,7,8-tetrahydroimidazo[1,2-a]pyrazine-2-carboxamide, 7-(biphenyl-4-ylcarbonyl)-N-hydroxy-8-isopropyl-5,6,7,8-tetrahydroimidazo[1,2-a]pyrazine-2-carboxamide, N-hydroxy-3-methyl-1-oxo-2-[3-(trifluoromethyl)benzyl]-1,2,3,4-tetrahydropyrrolo[1,2-a]pyrazine-7-carboxamide, N-hydroxy-8-isopropyl-7-[(1-methyl-1H-pyrrol-2-yl)carbonyl]-5,6,7,8-tetrahydroimidazo[1,2-a]pyrazine-2-carboxamide, 7-(1-benzothien-2-ylcarbonyl)-N-hydroxy-8-methyl-5,6,7,8-tetrahydroimidazo[1,2-a]pyrazine-2-carboxamide, N-hydroxy-4-methyl-5-[(1-methylpiperidin-4-yl)carbonyl]-4,5,6,7-tetrahydropyrazolo[1,5-a]pyrazine-2-carboxamide, 2-(4-fluorobenzyl)-N-hydroxy-1-oxo-1,2,3,4-tetrahydropyrrolo[1,2-a]pyrazine-7-carboxamide, N-hydroxy-8-isopropyl-7-{[4-(trifluoromethyl)phenyl]sulfonyl}-5,6,7,8-tetrahydroimidazo[1,2-a]pyrazine-2-carboxamide, 7-(1-adamantylcarbonyl)-N-hydroxy-8-methyl-5,6,7,8-tetrahydroimidazo[1,2-a]pyrazine-2-carboxamide, 7-(cyclopentylacetyl)-N-hydroxy-8-isopropyl-5,6,7,8-tetrahydroimidazo[1,2-a]pyrazine-2-carboxamide, 7-(1-adamantylcarbonyl)-N-hydroxy-5,6,7,8-tetrahydro[1,2,4]triazolo[1,5-a]pyrazine-2-carboxamide, 2-(1-benzothien-2-ylcarbonyl)-N-hydroxy-1-methyl-1,2,3,4-tetrahydropyrrolo[1,2-a]pyrazine-7-carboxamide, N-hydroxy-1-oxo-2-(quinolin-8-ylmethyl)-1,2,3,4-tetrahydropyrrolo[1,2-a]pyrazine-7-carboxamide, N-hydroxy-3-methyl-2-[(1-methyl-1H-pyrrol-2-yl)carbonyl]-1,2,3,4-tetrahydropyrrolo[1,2-a]pyrazine-7-carboxamide, 2-[(dimethylamino)acetyl]-N-hydroxy-3-methyl-1,2,3,4-tetrahydropyrrolo[1,2-a]pyrazine-7-carboxamide, 2-[3-(4-fluorophenoxy)benzyl]-N-hydroxy-1-oxo-1,2,3,4-tetrahydropyrrolo[1,2-a]pyrazine-7-carboxamide, 7-(1-benzothien-2-ylcarbonyl)-N-hydroxy-8-isopropyl-5,6,7,8-tetrahydroimidazo[1,2-a]pyrazine-2-carboxamide, 2-(biphenyl-2-ylmethyl)-N-hydroxy-1-oxo-1,2,3,4-tetrahydropyrrolo[1,2-a]pyrazine-7-carboxamide, 7-(2,2-dimethylpropanoyl)-N-hydroxy-8-isopropyl-5,6,7,8-tetrahydroimidazo[1,2-a]pyrazine-2-carboxamide, 7-(2,2-dimethylpropanoyl)-N-hydroxy-5,6,7,8-tetrahydro[1,2,4]triazolo[1,5-a]pyrazine-2-carboxamide, N-hydroxy-2-[(1-methyl-1H-pyrrol-2-yl)carbonyl]-3-phenyl-1,2,3,4-tetrahydropyrrolo[1,2-a]pyrazine-7-carboxamide, 7-(cyclopentylacetyl)-N-hydroxy-8-methyl-5,6,7,8-tetrahydroimidazo[1,2-a]pyrazine-2-carboxamide, N-hydroxy-2-[(5-methyl-3-phenylisoxazol-4-yl)methyl]-1-oxo-1,2,3,4-tetrahydropyrrolo[1,2-a]pyrazine-7-carboxamide, 2-(cyclopropylmethyl)-N-hydroxy-3-methyl-1-oxo-1,2,3,4-tetrahydropyrrolo[1,2-a]pyrazine-7-carboxamide, 7-[(dimethylamino)acetyl]-N-hydroxy-5,6,7,8-tetrahydro[1,2,4]triazolo[1,5-a]pyrazine-2-carboxamide, 2-(2,2-dimethylpropanoyl)-1-ethyl-N-hydroxy-1,2,3,4-tetrahydropyrrolo[1,2-a]pyrazine-7-carboxamide, or N-hydroxy-4-methyl-5-[(1-methyl-1H-indol-2-yl)carbonyl]-4,5,6,7-tetrahydropyrazolo[1,5-a]pyrazine-2-carboxamide.

27. The compound of claim 3, wherein the compound is:
2-(2,2-dimethylpropanoyl)-N-hydroxy-3-methyl-1,2,3,4-tetrahydropyrrolo[1,2-a]pyrazine-7-carboxamide, N-hydroxy-7-[(1-methylpiperidin-4-yl)carbonyl]-5,6,7,8-tetrahydro[1,2,4]triazolo[1,5-a]pyrazine-2-carboxamide, 2-[(dimethylamino)acetyl]-1-ethyl-N-hydroxy-1,2,3,4-tetrahydropyrrolo[1,2-a]pyrazine-7-carboxamide, 7-(2,2-dimethylpropanoyl)-N-hydroxy-8-methyl-5,6,7,8-tetrahydroimidazo[1,2-a]pyrazine-2-carboxamide, N-hydroxy-8-isopropyl-7-[(1-methyl-1H-indol-2-yl)carbonyl]-5,6,7,8-tetrahydroimidazo[1,2-a]pyrazine-2-carboxamide, 2-ethyl-N-hydroxy-1-oxo-1,2,3,4-tetrahydropyrrolo[1,2-a]pyrazine-7-carboxamide, 2-[(5-chloro-1-benzothien-3-yl)methyl]-hydroxy-1-oxo-1,2,3,4-tetrahydropyrrolo[1,2-a]pyrazine-7-carboxamide, N-hydroxy-8-methyl-7-[(1-methyl-1H-indol-2-yl)carbonyl]-5,6,7,8-tetrahydroimidazo[1,2-a]pyrazine-2-carboxamide, N-hydroxy-7-{[4-(trifluoromethyl)phenyl]sulfonyl}-5,6,7,8-tetrahydro[1,2,4]triazolo[1,5-a]pyrazine-2-carboxamide, 5-(cyclopentylacetyl)-N-hydroxy-4-methyl-4,5,6,7-tetrahydropyrazolo[1,5-a]pyrazine-2-carboxamide, 2-(3-chlorobenzyl)-N-hydroxy-1-oxo-1,2,3,4-tetrahydropyrrolo[1,2-a]pyrazine-7-carboxamide, N-hydroxy-1-methyl-2-[(1-methyl-1H-pyrrol-2-yl)carbonyl]-1,2,3,4-tetrahydropyrrolo[1,2-a]pyrazine-7-carboxamide, N-hydroxy-7-(propylsulfonyl)-5,6,7,8-tetrahydro[1,2,4]triazolo[1,5-a]pyrazine-2-carboxamide, 2-(1-adamantylcarbonyl)-1-ethyl-N-hydroxy-1,2,3,4-tetrahydropyrrolo[1,2-a]pyrazine-7-carboxamide, N-hydroxy-4-methyl-5-[(1-methyl-1H-pyrrol-2-yl)carbonyl]-4,5,6,7-tetrahydropyrazolo[1,5-a]pyrazine-2-carboxamide, 7-(cyclopentylacetyl)-N-hydroxy-5,6,7,8-tetrahydro[1,2,4]triazolo[1,5-a]pyrazine-2-carboxamide, 2-(cyclopentylacetyl)-N-hydroxy-3-methyl-1,2,3,4-tetrahydropyrrolo[1,2-a]pyrazine-7-carboxamide, 2-(1-benzothien-2-ylcarbonyl)-1-ethyl-N-hydroxy-1,2,3,4-tetrahydropyrrolo[1,2-a]pyrazine-7-carboxamide, N-hydroxy-3-methyl-2-[(1-methyl-1H-indol-2-yl)carbonyl]-1,2,3,4-tetrahydropyrrolo[1,2-a]pyrazine-7-carboxamide, 2-(cyclopentylacetyl)-1-ethyl-N-hydroxy-1,2,3,4-tetrahydropyrrolo[1,2-a]pyrazine-7-carboxamide, 2-(biphenyl-4-ylcarbonyl)-1-ethyl-N-hydroxy-1,2,3,4-tetrahydropyrrolo[1,2-a]pyrazine-7-carboxamide, 7-(1-adamantylcarbonyl)-N-hydroxy-8-isopropyl-5,6,7,8-tetrahydroimidazo[1,2-a]pyrazine-2-carboxamide, 2-[(dimethylamino)acetyl]-N-hydroxy-1-methyl-1,2,3,4-tetrahydropyrrolo[1,2-a]pyrazine-7-carboxamide, 5-(biphenyl-4-ylcarbonyl)-N-hydroxy-4-methyl-4,5,6,7-tetrahydropyrazolo[1,5-a]pyrazine-2-carboxamide, 7-(1-benzothien-2-ylcarbonyl)-N-hydroxy-5,6,7,8-tetrahydro[1,2,4]triazolo[1,5-a]pyrazine-2-carboxamide, 5-[(dimethylamino)acetyl]-N-hydroxy-4-methyl-4,5,6,7-tetrahydropyrazolo[1,5-a]pyrazine-2-carboxamide, 2-(biphenyl-4-ylcarbonyl)-N-hydroxy-1-methyl-1,2,3,4-tetrahydropyrrolo[1,2-a]pyrazine-7-carboxamide, 2-(2,2-dimethylpropanoyl)-N-hydroxy-1-methyl-1,2,3,4-tetrahydropyrrolo[1,2-a]pyrazine-7-carboxamide, 7-(biphenyl-4-ylcarbonyl)-N-hydroxy-8-methyl-5,6,7,8-tetrahydroimidazo[1,2-a]pyrazine-2-carboxamide, N-hydroxy-7-{3-[(pyrrolidin-3-ylamino)carbonyl]benzyl}-5,6,7,8-tetrahydroimidazo[1,2-a]pyrazine-2-carboxamide, N-hydroxy-2-[(1-isopropylpiperidin-4-yl)methyl]-1,2,3,4-tetrahydropyrrolo[1,2-a]pyrazine-7-carboxamide, N-hydroxy-7-[(2-{[(4-methylpiperidin-4-yl)carbonyl]amino}pyridin-4-yl)methyl]-5,6,7,8-tetrahydroimidazo[1,2-a]pyrazine-2-carboxamide, N-hydroxy-2-(4-{[(1-methylpiperidin-4-yl)carbonyl]amino}benzyl)-1,2,3,4-tetrahydropyrrolo[1,2a]pyrazine-7-carboxamide, 2-[(1-ethylpiperidin-4-yl)methyl]-N-hydroxy-1,2,3,4-tetrahydropyrrolo[1,2-a]pyrazine-7-carboxamide, N-hydroxy-1-oxo-2-[4-(trifluoromethyl)benzyl]-1,2,3,4-tetrahydropyrrolo[1,2-a]pyrazine-7-carboxamide, or 2-(cyclopropylmethyl)-N-hydroxy-1-oxo-1,2,3,4-tetrahydropyrrolo[1,2-a]pyrazine-7-carboxamide.

28. A pharmaceutical composition comprising a compound of claim 1 and a pharmaceutically acceptable carrier.

\* \* \* \* \*